(12) United States Patent  (10) Patent No.: US 8,889,854 B2
Sin et al.  (45) Date of Patent: Nov. 18, 2014

(54) C-17 BICYCLIC AMINES OF TRITERPENOIDS WITH HIV MATURATION INHIBITORY ACTIVITY

(71) Applicant: Bristol-Myers Squibb Company, Princeton, NJ (US)

(72) Inventors: Ny Sin, East Hampton, CT (US); Zheng Liu, Beacon Falls, CT (US); Jacob Swidorski, Southington, CT (US); Sing-Yuen Sit, Meriden, CT (US); Jie Chen, Madison, CT (US); Yan Chen, Wallingford, CT (US); Nicholas A. Meanwell, East Hampton, CT (US); Alicia Regueiro-Ren, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 7 days.

(21) Appl. No.: 13/799,479

(22) Filed: Mar. 13, 2013

(65) Prior Publication Data

US 2013/0296554 A1  Nov. 7, 2013

Related U.S. Application Data

(60) Provisional application No. 61/643,483, filed on May 7, 2012.

(51) Int. Cl.
| | | |
|---|---|---|
| *C07J 53/00* | (2006.01) | |
| *C07D 498/08* | (2006.01) | |
| *C07D 495/08* | (2006.01) | |
| *C07D 495/10* | (2006.01) | |
| *C07D 487/10* | (2006.01) | |
| *C07J 63/00* | (2006.01) | |
| *C07D 491/08* | (2006.01) | |
| *C07D 209/52* | (2006.01) | |
| *C07D 487/08* | (2006.01) | |

(52) U.S. Cl.
CPC ............ *C07D 487/08* (2013.01); *C07D 498/08* (2013.01); *C07D 495/08* (2013.01); *C07D 495/10* (2013.01); *C07D 487/10* (2013.01); *C07J 63/008* (2013.01); *C07D 491/08* (2013.01); *C07D 209/52* (2013.01)
USPC ............................................. 540/47; 552/510

(58) Field of Classification Search
USPC ............................................. 552/510; 540/47
See application file for complete search history.

(56) References Cited

U.S. PATENT DOCUMENTS 5,679,828 A   10/1997 Lee et al.
7,354,924 B2   4/2008 Wang et al.

(Continued)

FOREIGN PATENT DOCUMENTS

WO    WO 98/51293    11/1998
WO    WO 98/51294    11/1998

(Continued)

OTHER PUBLICATIONS

Blair, W.S. et al., "HIV-1 entry—an expanding portal for drug discovery", Drug Discovery Today, vol. 5, No. 5, pp. 183-194 (2000).

(Continued)

*Primary Examiner* — Barbara P Badio
(74) *Attorney, Agent, or Firm* — John F. Levis

(57) ABSTRACT

Compounds having drug and bio-affecting properties, their pharmaceutical compositions and methods of use are set forth. In particular, C-17 bicyclic amines of triterpenoids that possess unique antiviral activity are provided as HIV maturation inhibitors, as represented by compounds of Formulas I, II and III:

Formula I

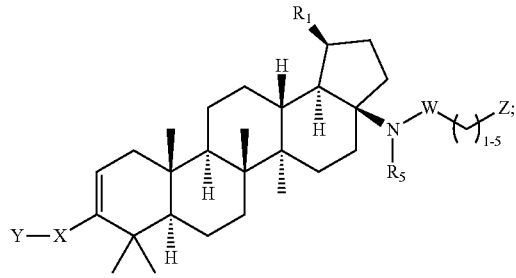

Formula II

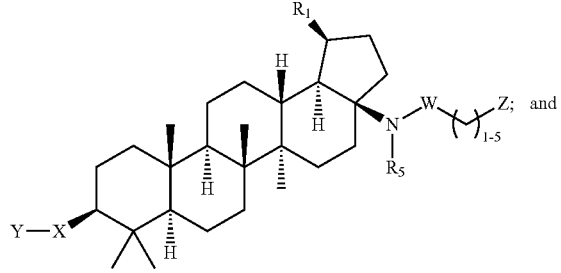

Formula III

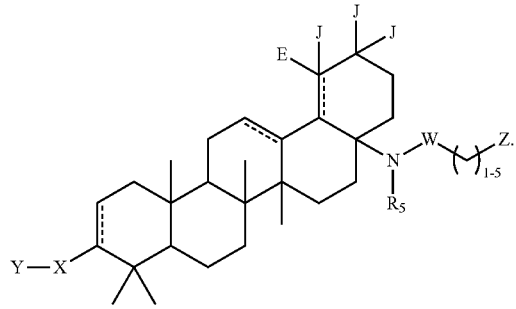

These compounds are useful for the treatment of HIV and AIDS.

18 Claims, No Drawings

(56) References Cited

U.S. PATENT DOCUMENTS

| | | |
|---|---|---|
| 7,365,221 B2 | 4/2008 | Allaway et al. |
| 7,745,625 B2 | 6/2010 | Ueda et al. |
| 8,748,415 B2 | 6/2014 | Regueiro-Ren et al. |
| 8,754,068 B2 | 6/2014 | Regueiro-Ren et al. |
| 8,754,069 B2 | 6/2014 | Liu et al. |
| 2005/0239748 A1 | 10/2005 | Power et al. |
| 2008/0207573 A1 | 8/2008 | Yager et al. |
| 2012/0142653 A1 | 6/2012 | Regueiro-Ren et al. |
| 2013/0035318 A1 | 2/2013 | Regueiro-Ren et al. |
| 2013/0210787 A1 | 8/2013 | Swidorski et al. |

FOREIGN PATENT DOCUMENTS

| | | |
|---|---|---|
| WO | WO 2004/089357 | 10/2004 |
| WO | WO 2006/053255 | 5/2006 |
| WO | WO 2008/127364 | 10/2008 |
| WO | WO 2009/100532 | 8/2009 |
| WO | WO 2011/007230 | 1/2011 |

OTHER PUBLICATIONS

Hotoda, H., "Small-molecule inhibitors of HIV-1 entry via chemokine receptors", Drugs of the Future, vol. 24, No. 12, pp. 1355-1362 (1999).

Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).

Meanwell, N.A. et al., "Inhibitors of the entry of HIV into host cells", Current Opinion in Drug Discovery & Development, vol. 6, No. 4, pp. 451-461 (2003).

Pokrovskii, A.G. et al., "Synthesis of derivatives of plant triterpenes and study of their antiviral and immunostimulating activity", Khimiya y lnteresakh Ustoichivogo Razvitiya, vol. 9, No. 3, pp. 485-491 (2001) (English abstract).

Sodroski, J.G., "HIV-1 Entry Inhibitors in the Side Pocket: Minireview", Cell, vol. 99, pp. 243-246 (1999).

Swidorski et al., U.S. Appl. No. 14/172,389, filed Feb. 4, 2014.

Swidorski et al., U.S. Appl. No. 14/186,533, filed Feb. 21, 2014.

C-17 BICYCLIC AMINES OF TRITERPENOIDS WITH HIV MATURATION INHIBITORY ACTIVITY

CROSS REFERENCE TO RELATED APPLICATION

This non-provisional application claims the benefit of U.S. Provisional Application Ser. No. 61/643,483 filed May 7, 2012.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC—EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA®(lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and US 2005/0209246 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., Gos. Nauchnyi Tsentr Virusol. Biotekhnol. "Vector", Koltsovo, Russia. Khimiya v Interesakh Ustoichivogo Razvitiya, 9:485-491 (2001)).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) 1up-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (US 2012-0142707) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (US 2012-0142653). Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012 (US 2013-0029954), as well as to the application entitled: "C-17 AND C-3 MODIFIED TRITERPENOIDS WITH HIV MATURATION INHIBITORY ACTIVITY" U.S. Ser. No. 13/359,727, filed on Jan. 27, 2012 (US 2013-0035318). Further reference is made to the application entitled "NOVEL BETULINIC ACID DERIVATIVES WITH ANTIVIRAL ACTIVITY" U.S. Ser. No. 61/537,099, filed on Sep. 21, 2011, as well as to the application entitled "C-3 CYCLOALKYENYL TRITERPERNOIDS WITH HIV MATURATION INHIBITORY ACTIVITY" U.S. Ser. No. 61/599,040, filed on Feb. 15, 2012.

What is now needed in the art are new compounds which are useful as HIV maturation inhibitors, as well as new pharmaceutical compositions containing these compounds.

SUMMARY OF THE INVENTION

The present invention provides compounds of Formulas I, II, and III below, including pharmaceutically acceptable salts thereof, their pharmaceutical formulations, and their use in patients suffering from or susceptible to a virus such as HIV. The compounds of Formulas I-III are effective antiviral agents, particularly as inhibitors of HIV. They are useful for the treatment of HIV and AIDS.

One embodiment of the present invention is directed to a compound, including pharmaceutically acceptable salts thereof, which is selected from the group of:
a compound of Formula I Formula I

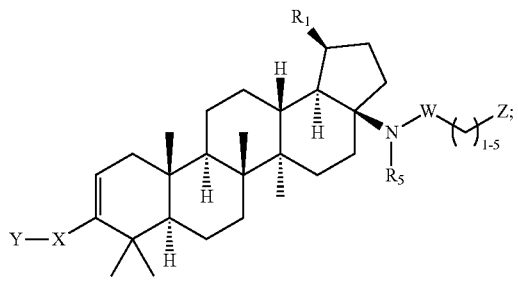

a compound of Formula II

Formula II

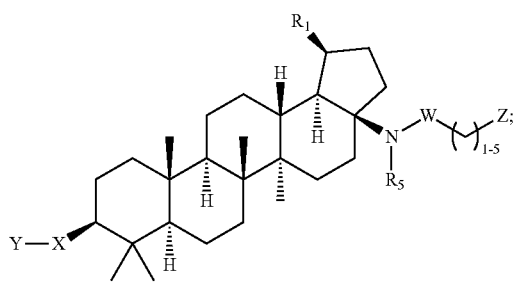

and
a compound of Formula III

Formula III

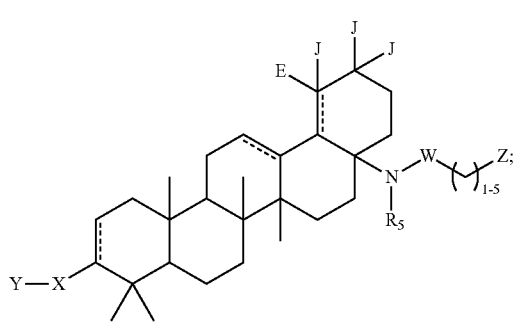

wherein $R_1$ is isopropenyl or isopropyl;
J and E are each independently —H or —$CH_3$, and E is absent when the double bond is present;

X is selected from the group of phenyl, heteroaryl ring, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring;

X can also be selected from the group of:

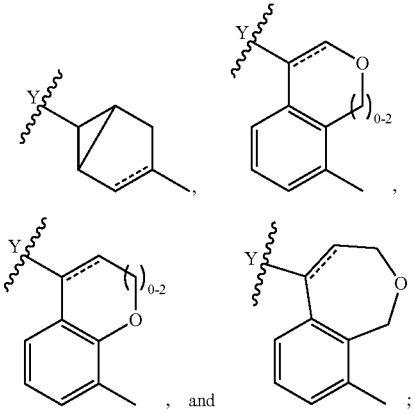

, and ;

and for compounds of formula II and III, X can also be

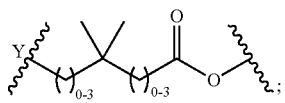

;

wherein X is substituted with A, and A is at least one member selected from the group of —H, -halo, -hydroxyl, —$C_{1-6}$ alkyl, —$C_{1-6}$ alkoxy, —$C_{1-6}$haloalkyl, —$NR_2R_2$, —$COOR_2$, —$C(O)NR_2R_2$, —$C(O)NR_2SO_2R_3$, —$SO_2NR_2R_2$, —$NR_2SO_2R_2$, —$SO_2NR_2R_2$, —$C_{1-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and -bicyclic heteroaryl-$COOR_2$;

Y is selected from the group of —$COOR_2$, —$C(O)NR_2SO_2R_3$, —$C(O)NHSO_2NR_2R_2$, —$NR_2SO_2R_3$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, tetrazole, and —CONHOH, wherein n=1-6;

W is —$CH_2$ or —CO;

Z is selected from the group of:

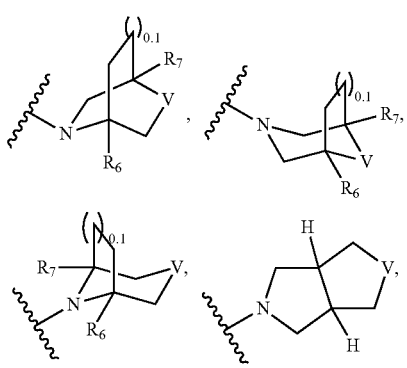

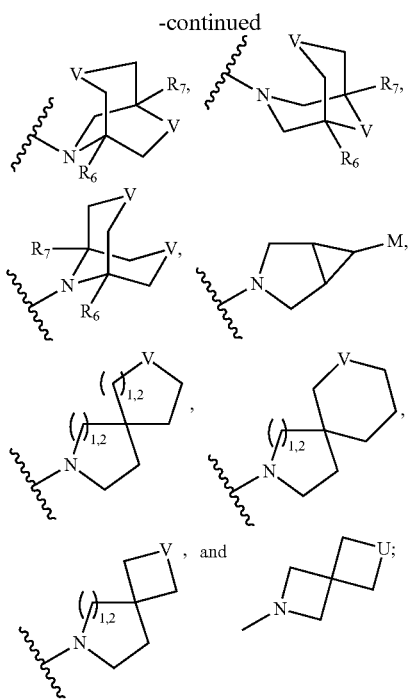

V is selected from the group of —CR$_8$R$_9$—, —SO$_2$—, —O— and —NR$_{10}$—;

U is selected from the group of —CR$_8$R$_9$—, —SO$_2$— and —NR$_{10}$—;

M is selected from the group of —CHR$_8$R$_9$, —SO$_2$R$_4$, —SO$_2$NR$_3$R$_3$, —OH and —NR$_{10}$R$_{11}$—;

R$_2$ is —H, —C$_{1-6}$ alkyl, -alkylsubstituted C$_{1-6}$ alkyl or -aryl-substituted C$_{1-6}$ alkyl;

R$_3$ is —C$_{1-6}$ alkyl or -alkylsubstituted C$_{1-6}$ alkyl;

R$_4$ is selected from the group of —C$_{1-6}$alkyl, -alkylsubstituted C$_{1-6}$ alkyl, —C$_{3-6}$ cycloalkl, -aryl and -heteroaryl;

R$_5$ is selected from the group of —H, —C$_{1-6}$ alkyl, -alkylsubstituted C$_{1-6}$ alkyl and —C$_{1-6}$ alkyl-OH;

R$_6$ and R$_7$ are each independently selected from the group of —H, —C$_{1-6}$ alkyl, -alkylsubstituted C$_{1-6}$ alkyl, —CO$_2$R$_2$, —CH$_2$OH, —CHF$_2$ and —CF$_3$;

R$_8$ and R$_9$ are each independently selected from the group of —H, —C$_{1-6}$ alkyl, -alkylsubstituted C$_{1-6}$ alkyl, —SO$_2$R$_3$, —SO$_2$NR$_2$R$_2$ or —OH, —NR$_2$R$_2$, —NR$_2$SO$_2$R$_3$, —NR$_2$COR$_3$ and —NR$_2$CONR$_2$R$_2$;

with the proviso that only one of R$_8$ and R$_9$ can be selected from the group of —OH, —NR$_2$R$_2$, —NR$_2$SO$_2$R$_3$, —NR$_2$COR$_3$ and —NR$_2$CONR$_2$R$_2$; and R$_{10}$ and R$_{11}$ are each independently selected from the group of —H, —C$_{1-6}$ alkyl, -alkylsubstituted C$_{1-6}$ alkyl, —C$_{1-3}$ alkylaryl, C$_{1-3}$alkylheteroaryl, —CO$_2$R$_2$ and —SO$_2$R$_3$;

with the proviso that only one of R$_{10}$ and R$_{11}$ can be selected from the group of —CO$_2$R$_2$ or —SO$_2$R$_3$.

In a further embodiment, there is provided a method for treating mammals infected with a virus, especially wherein the virus is HIV, comprising administering to said mammal an antiviral effective amount of a compound which is selected from the group of compounds of Formulas I, II, III above, and one or more pharmaceutically acceptable carriers, excipients or diluents. Optionally, the compound of Formulas I, II, and/or III can be administered in combination with an antiviral effective amount of another-AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II, and III, and one or more pharmaceutically acceptable carriers, excipients, and diluents; and optionally in combination with an antiviral effective amount of another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, and III herein.

Also provided herein are intermediate compounds useful in making the compounds of Formulas I, II, and III herein.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II and III, in addition to the mixtures thereof.

DEFINITIONS

Unless otherwise specifically set forth elsewhere in the application, one or more of the following terms may be used herein, and shall have the following meanings:

"H" refers to hydrogen, including its isotopes, such as deuterium.

The term "C$_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"C$_1$-C$_4$ fluoroalkyl" refers to F-substituted C$_1$-C$_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl, diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O— group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^x$R$^Y$, with R$^x$ and R$^Y$ independently being H or (C$_{1-6}$)alkyl.

A "N-Sulfonamido" group refers to a R"S(=O)$_2$NR$_x$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "amidino" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

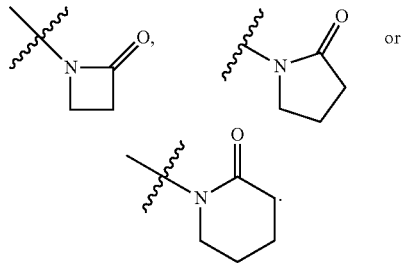

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from the group of:

a compound of Formula I

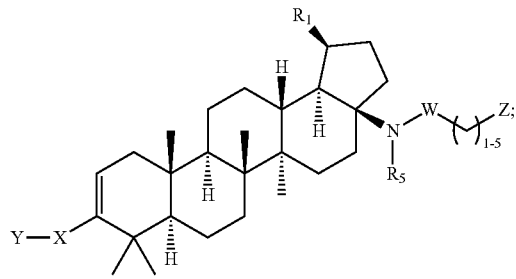

Formula I a compound of Formula II

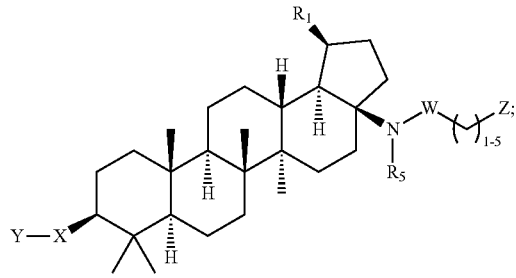

Formula II and
a compound of Formula III

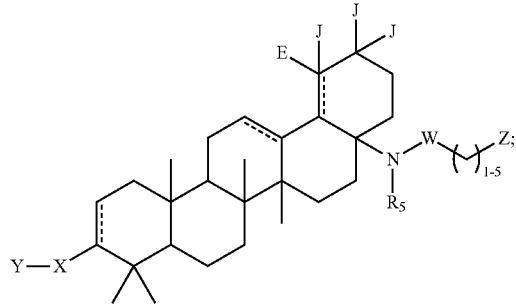

Formula III wherein R_1 is isopropenyl or isopropyl;

J and E are each independently —H or —CH_3, and E is absent when the double bond is present;

X is selected from the group of phenyl, heteroaryl ring, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring;

X can also be selected from the group of:

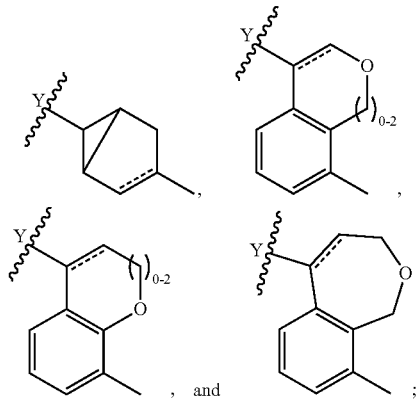

and for compounds of formula II and III, X can also be

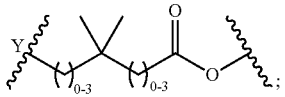

wherein X is substituted with A, and A is at least one member selected from the group of —H, -halo, -hydroxyl, —$C_{1-6}$ alkyl, —$C_{1-6}$ alkoxy, —$C_{1-6}$haloalkyl, —$NR_2R_2$, —$COOR_2$, —$C(O)NR_2R_2$, —$C(O)NR_2SO_2R_3$, —$SO_2NR_2R_2$, —$NR_2SO_2R_2$, —$SO_2NR_2R_2$, —$C_{1-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and -bicyclic heteroaryl-$COOR_2$;

Y is selected from the group of —$COOR_2$, —$C(O)NR_2SO_2R_3$, —$C(O)NHSO_2NR_2R_2$, —$NR_2SO_2R_3$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$alkyl-$COOR_2$, —$NHC(O)(CH_2)_n$—$COOR_2$, —$SO_2NR_2C(O)R_2$, tetrazole, and —CONHOH, wherein n=1-6;

W is —$CH_2$ or —CO;

Z is selected from the group of:

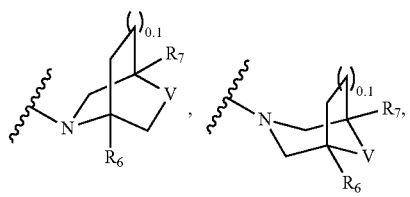

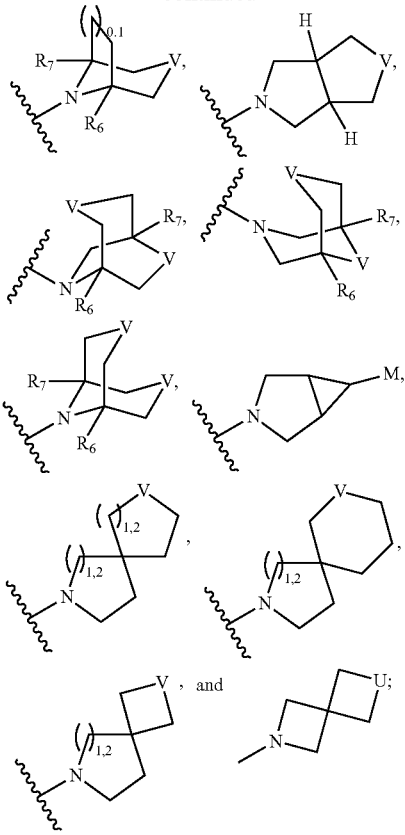

V is selected from the group of —$CR_8R_9$—, —$SO_2$—, —O— and —$NR_{10}$—;

U is selected from the group of —$CR_8R_9$—, —$SO_2$— and —$NR_{10}$—;

M is selected from the group of —$CHR_8R_9$, —$SO_2R_4$, —$SO_2NR_3R_3$, —OH and —$NR_{10}R_{11}$—;

$R_2$ is —H, —$C_{1-6}$ alkyl, -alkylsubstituted $C_{1-6}$ alkyl or -arylsubstituted $C_{1-6}$ alkyl;

$R_3$ is —$C_{1-6}$ alkyl or -alkylsubstituted $C_{1-6}$ alkyl;

$R_4$ is selected from the group of —$C_{1-6}$ alkyl, -alkylsubstituted $C_{1-6}$ alkyl, —$C_{3-6}$ cycloalkl, -aryl and -heteroaryl;

$R_5$ is selected from the group of —H, —$C_{1-6}$ alkyl, -alkylsubstituted $C_{1-6}$ alkyl and —$C_{1-6}$ alkyl-OH;

$R_6$ and $R_7$ are each independently selected from the group of —H, —$C_{1-6}$ alkyl, -alkylsubstituted $C_{1-6}$ alkyl, —$CO_2R_2$, —$CH_2OH$, —$CHF_2$ and —$CF_3$;

$R_8$ and $R_9$ are each independently selected from the group of —H, —$C_{1-6}$ alkyl, -alkylsubstituted $C_{1-6}$ alkyl, —$SO_2R_3$, —$SO_2NR_2R_2$ or —OH, —$NR_2R_2$, —$NR_2SO_2R_3$, —$NR_2COR_3$ and —$NR_2CONR_2R_2$;

with the proviso that only one of $R_8$ and $R_9$ can be selected from the group of —OH, —$NR_2R_2$, —$NR_2SO_2R_3$, —$NR_2COR_3$ and —$NR_2CONR_2R_2$; and $R_{10}$ and $R_{11}$ are each independently selected from the group of —H, —$C_{1-6}$ alkyl, -alkylsubstituted $C_{1-6}$ alkyl, —$C_{1-3}$ alkylaryl, $C_{1-3}$alkylheteroaryl, —$CO_2R_2$ and —$SO_2R_3$; with the proviso that only one of $R_{10}$ and $R_{11}$ can be selected from the group of —$CO_2R_2$ or —$SO_2R_3$.

More preferred compounds include those which are encompassed by Formula I. Of these, those wherein X is a phenyl ring are even more preferred. Also preferred are compounds of Formula I wherein X is a phenyl ring and Y is in the para position. Also preferred are compounds wherein X is —$C_{4-8}$ cycloalkenyl.

Also preferred are compounds of Formula I wherein A is at least one member selected from the group of —H, —OH, -halo, —C$_{1-3}$ alkyl, and —C$_{1-3}$alkoxy, wherein -halo is selected from the group of —Cl, —F and —Br, with —F being more preferred. In certain embodiments, it is preferred that A is —H.

Also preferred are compounds of Formula I wherein Y is —COOR$_2$, and more preferably —COOH.

It is also preferred that R$_5$ is —H.

In addition, it is preferred that R$_{10}$ is —C$_{1-3}$ alkylaryl. More preferably, alkylaryl is alkylphenyl. Even more preferably, alkylphenyl is methylphenyl.

It is also preferred that Z is

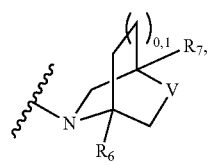

and more preferably wherein R$_6$ is —H and R$_7$ is —H. Preferably, V is —O—.

In another embodiment of the invention, it is preferred that the compound have the formula:

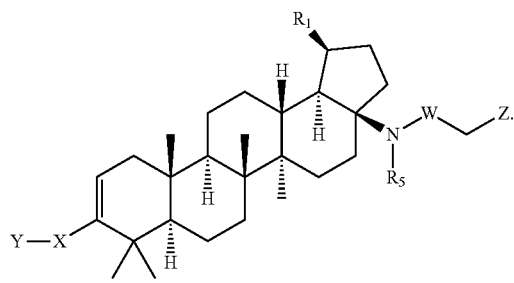

In a further embodiment of the invention, it is preferred that the compound have the formula:

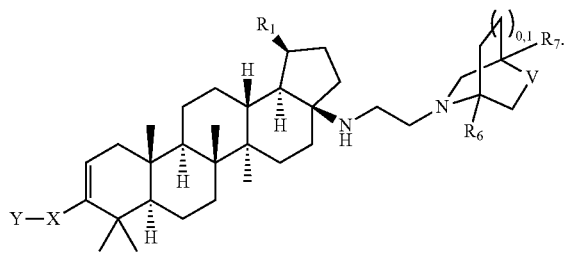

In yet another embodiment, the compound of the invention will have the following formula:

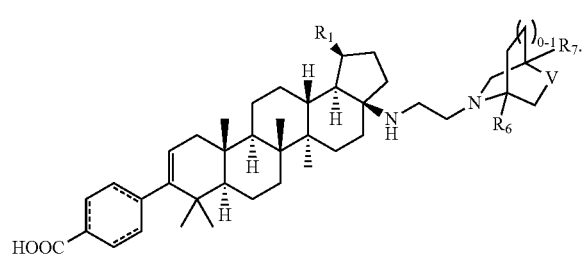

Other compounds, including pharmaceutically acceptable salts thereof, which are preferred as part of the invention include the following:

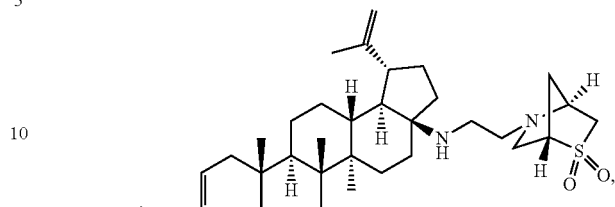

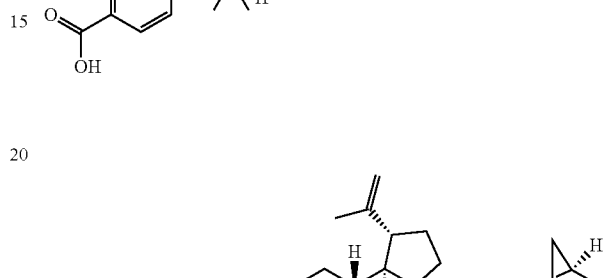

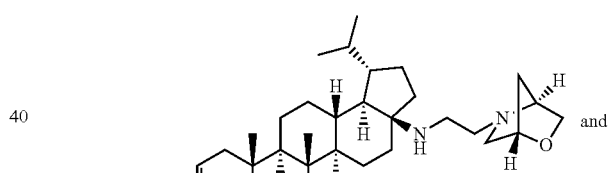

and

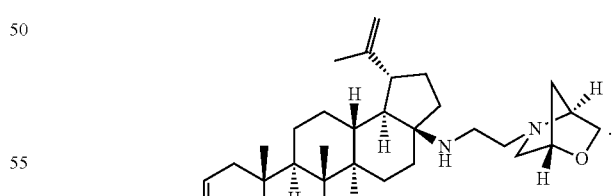

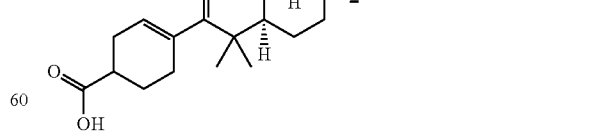

Also preferred are the following compounds, including pharmaceutically acceptable salts thereof:

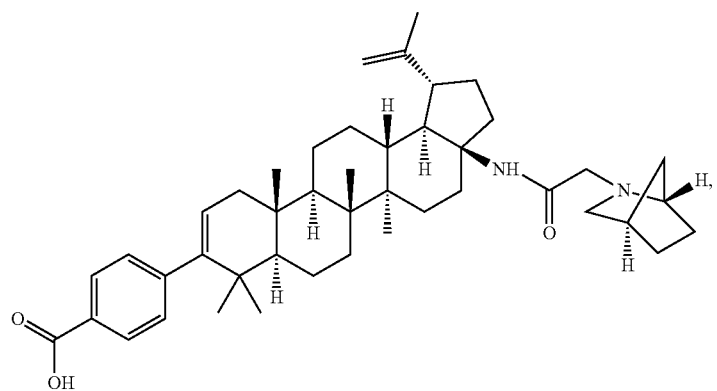
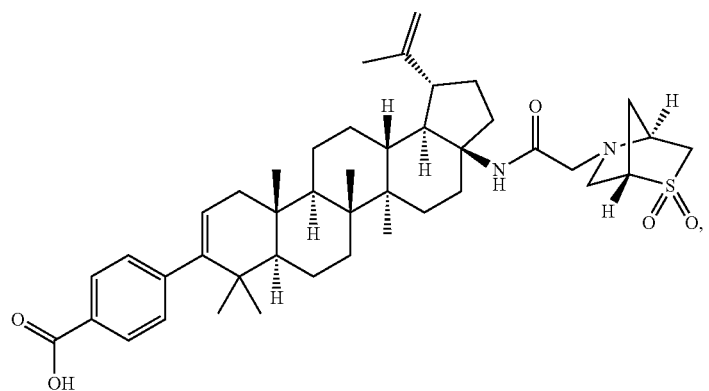
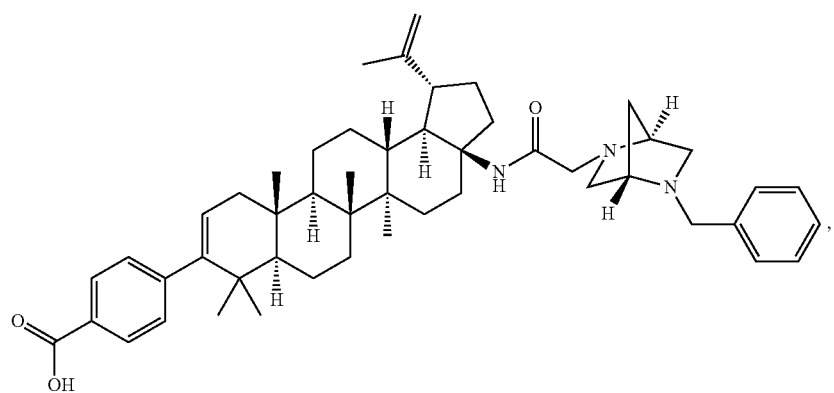
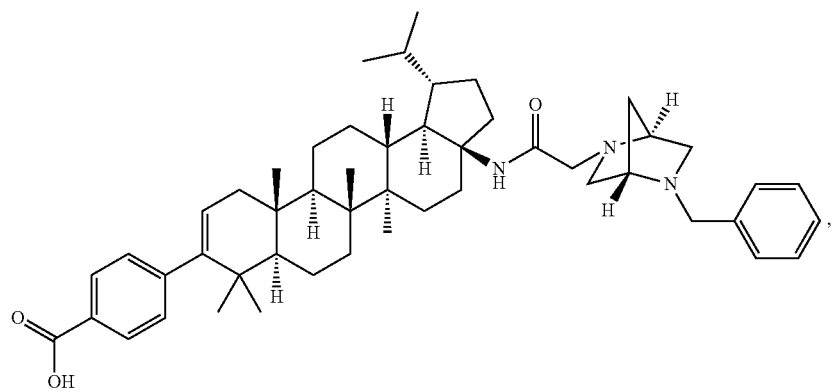

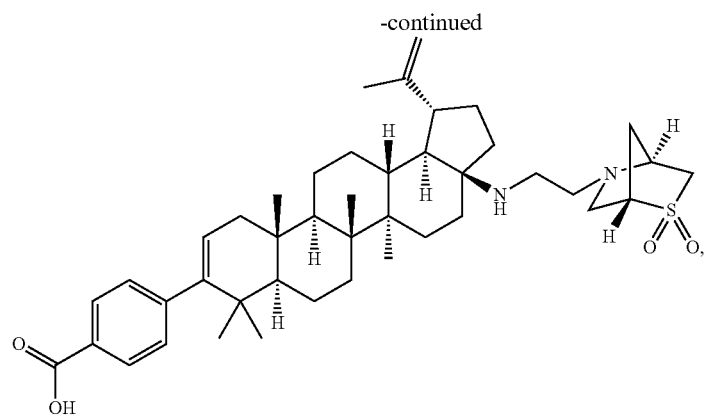
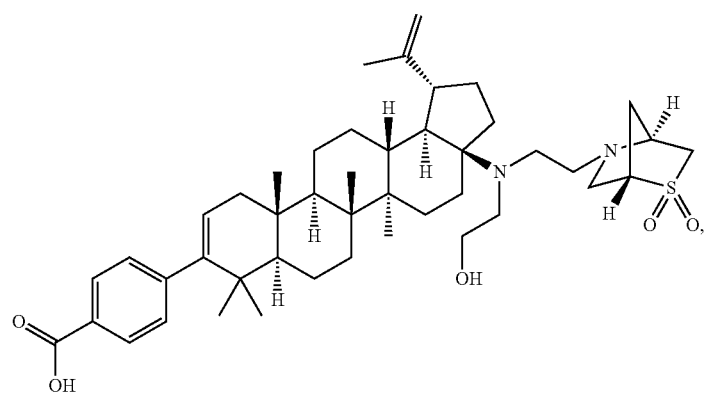
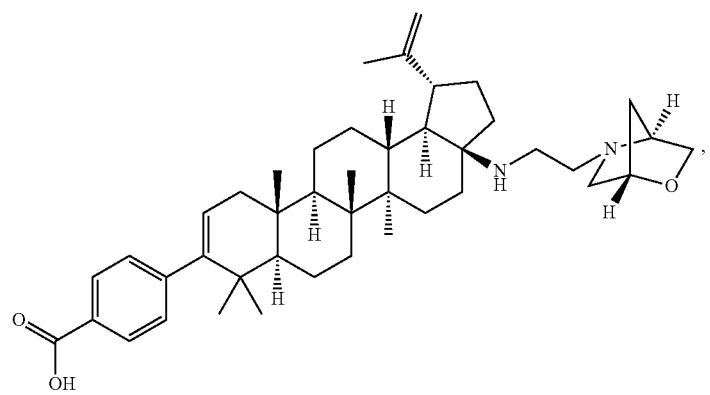
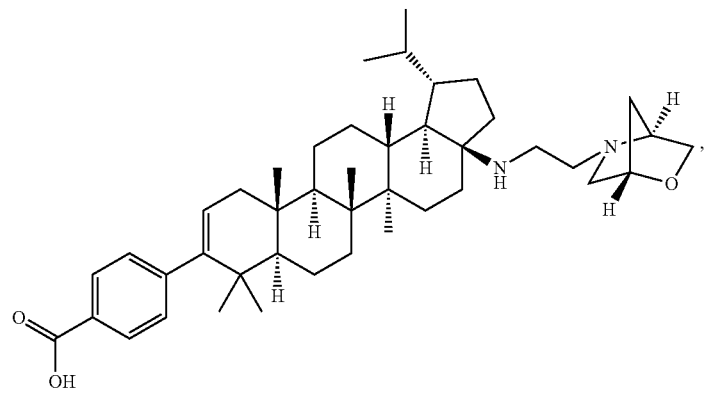

-continued
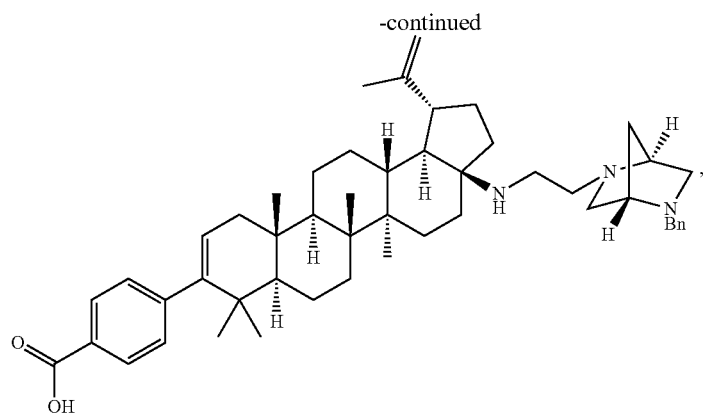
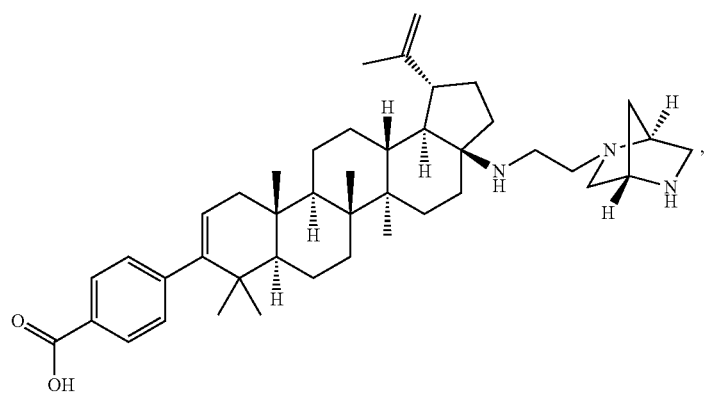
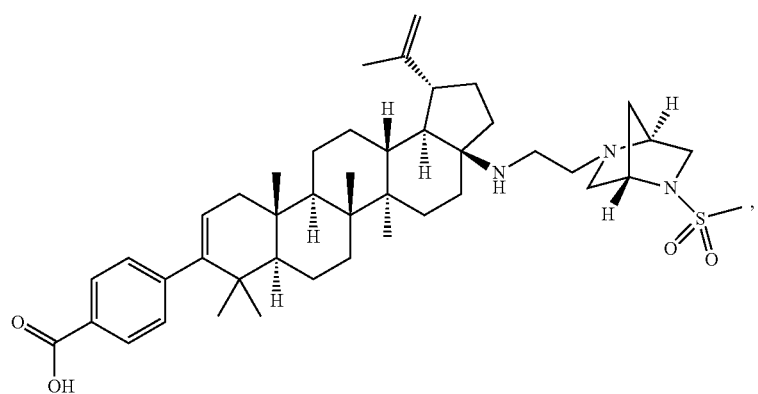
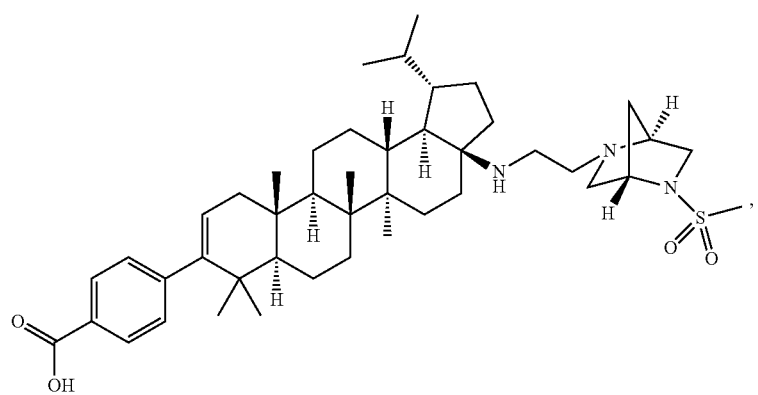

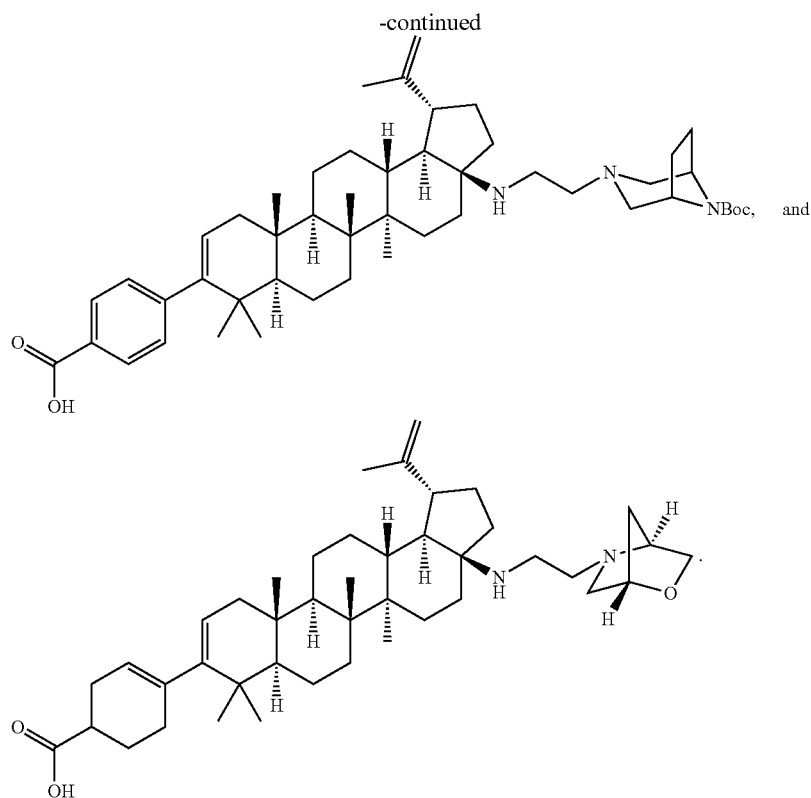
Other preferred compounds, including pharmaceutically acceptable salts thereof, include the following:
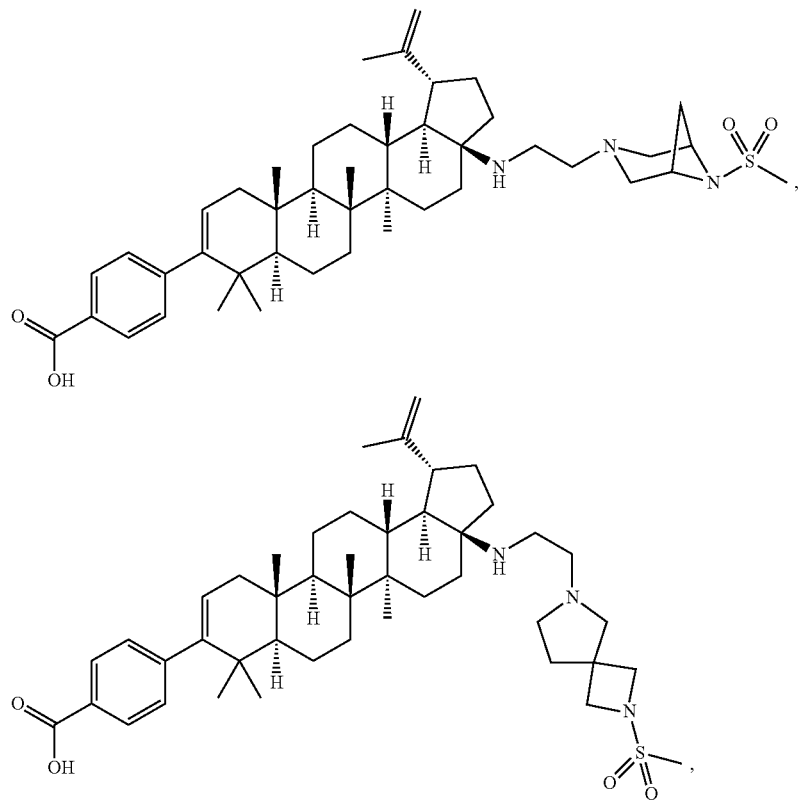

-continued
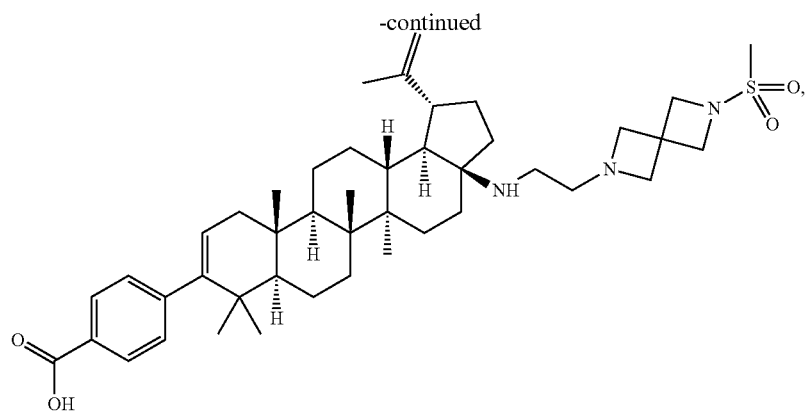
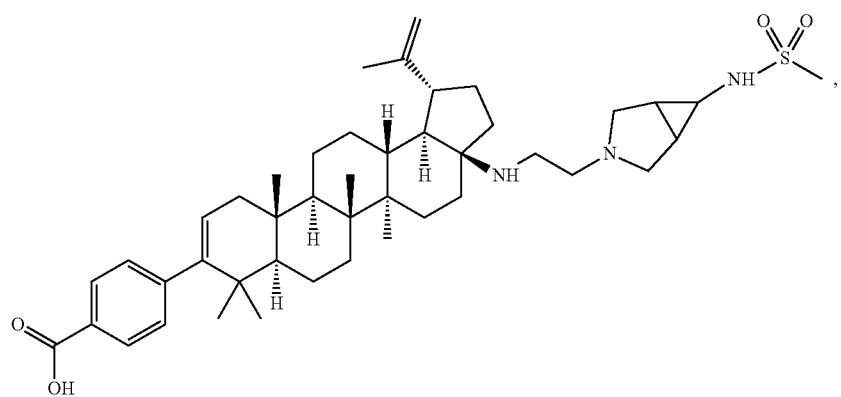
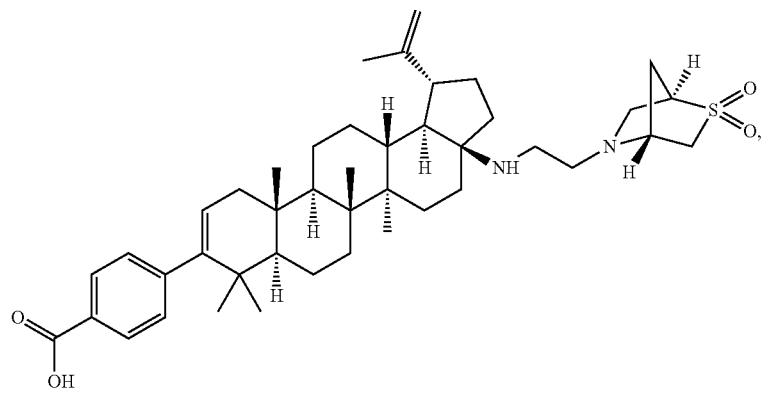
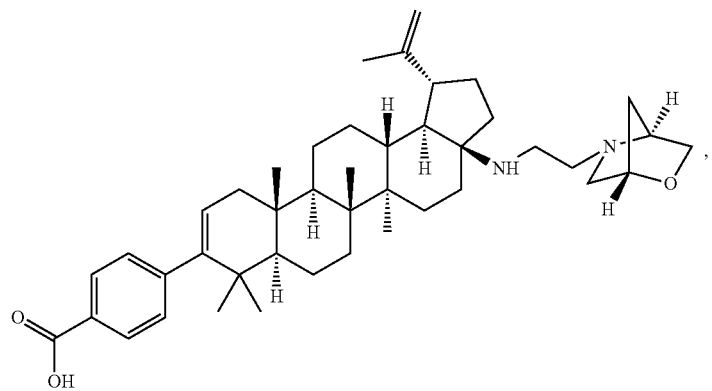

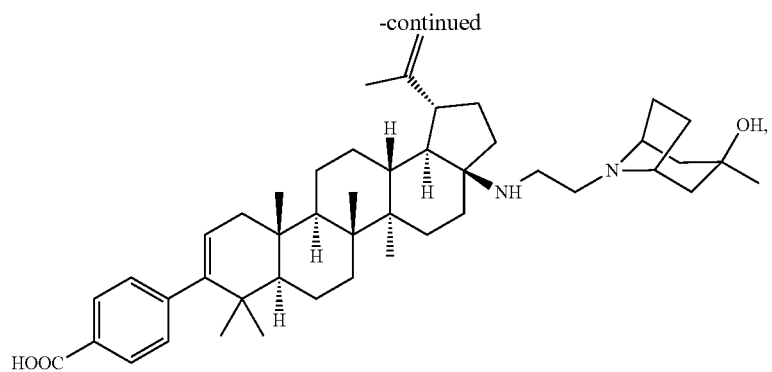
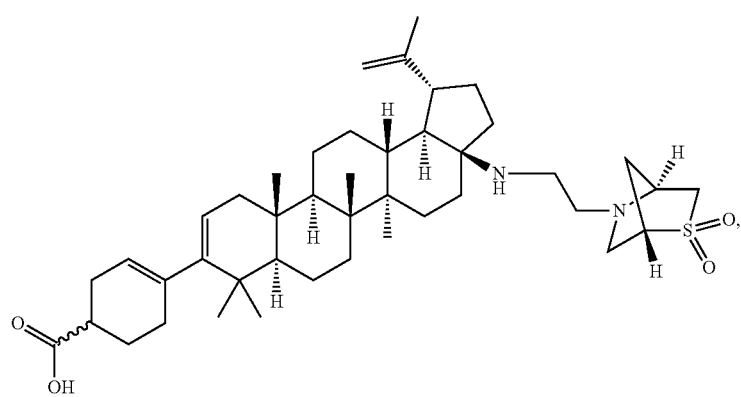
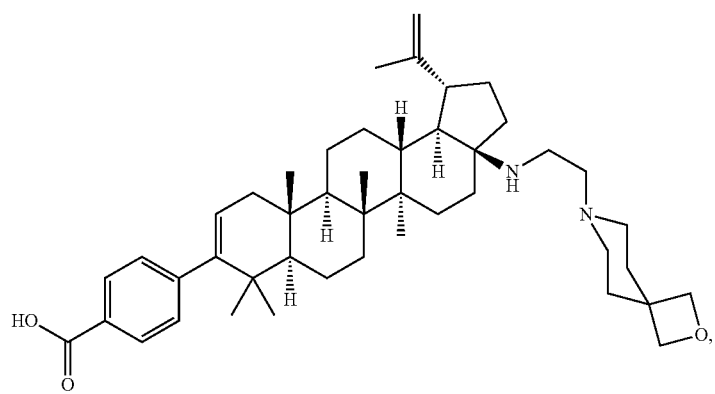
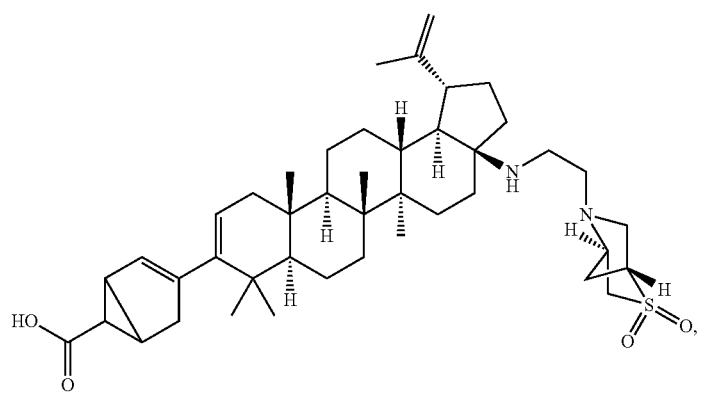
Isomer 1

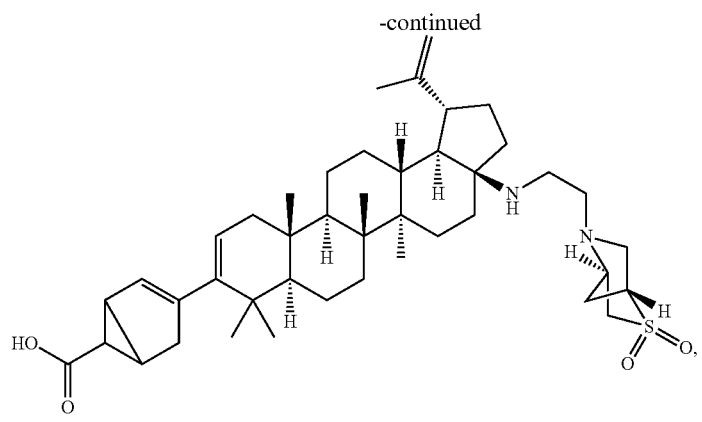
Isomer 2
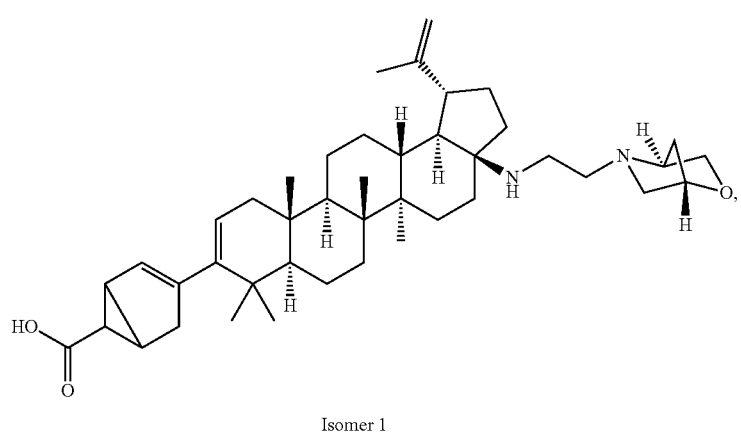
Isomer 1
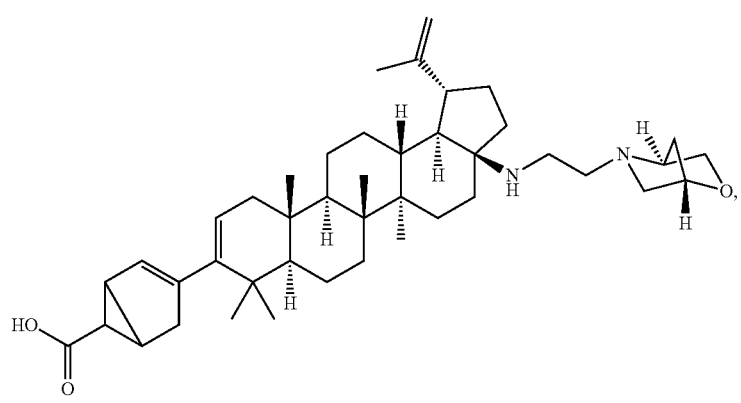
Isomer 2
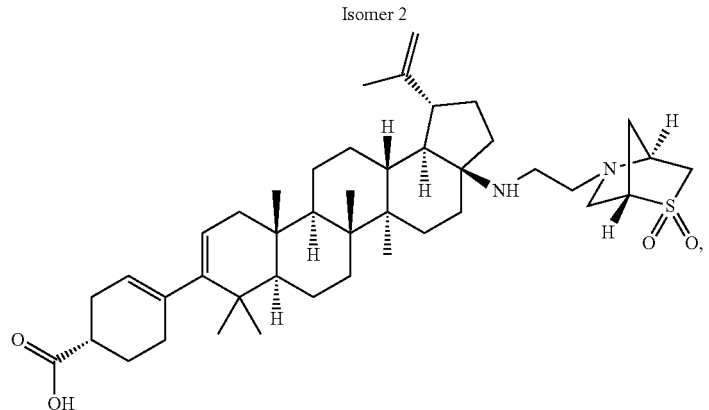

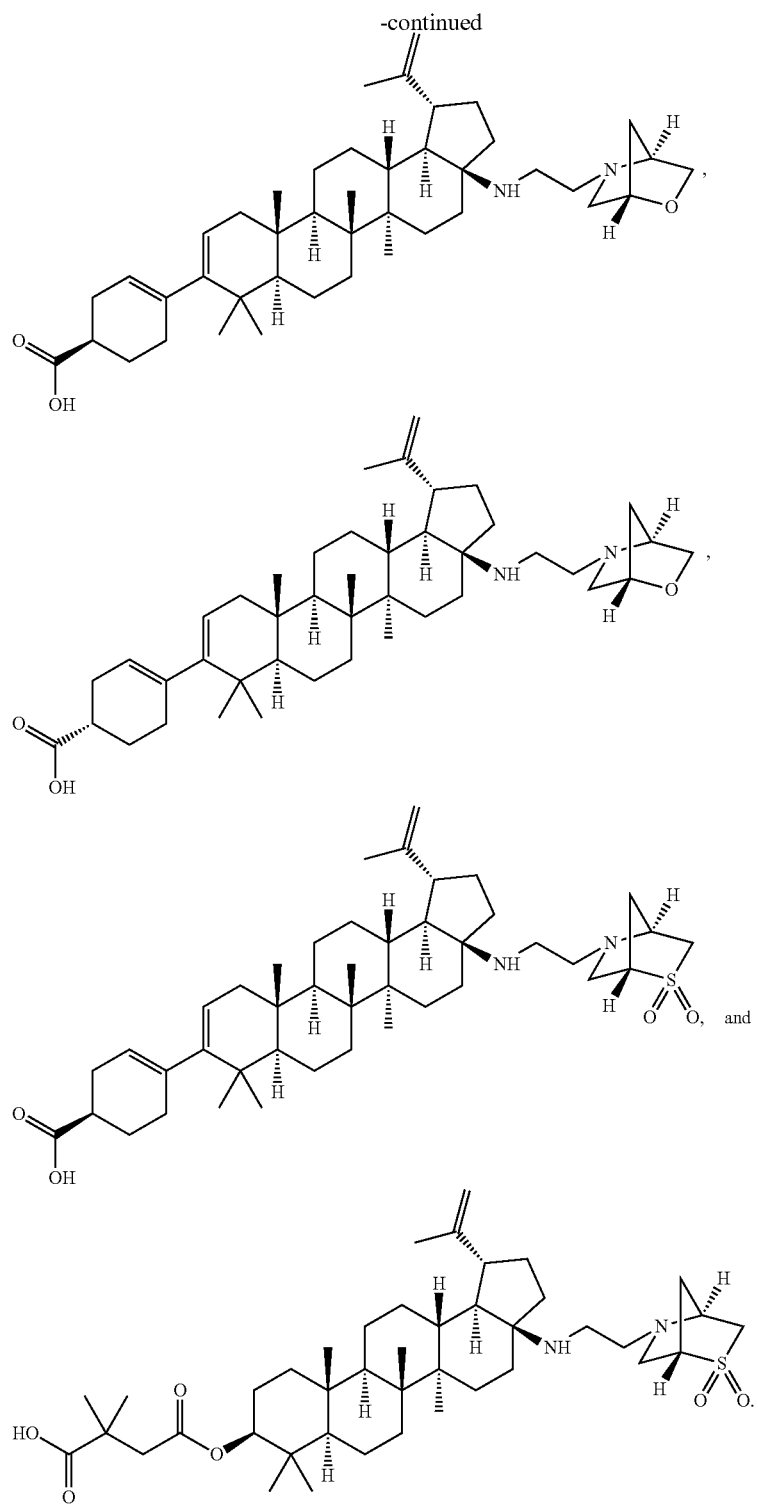

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, and/or III, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II, and/or III herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |

-continued

| Drug Name | Manufacturer | Indication |
|---|---|---|
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| Reyataz REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ® Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/ Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 | Cetus | AIDS, in combination |

-continued

| Drug Name | Manufacturer | Indication |
| --- | --- | --- |
| Interleukin-2 | | w/AZT |
| IL-2 | Hoffman-LaRoche | AIDS, ARC, HIV, in |
| Interleukin-2 | Immunex | combination w/AZT |
| IL-2 | Chiron | AIDS, increase in |
| Interleukin-2 (aldeslukin) | | CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*, Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

GENERAL CHEMISTRY

Methods of Synthesis

The present invention comprises compounds of Formulas I, II, and III, their pharmaceutical formulations, and their use in patients suffering from or susceptible to HIV infection. The compounds of Formulas I, II, and III also include pharmaceutically acceptable salts thereof. General procedures to construct compounds of Formulas I, II, and III and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:

Bz$_2$O=benzoic anhydride
TBTU=O-(benzotriazol-1-yl)-N,N,N',N'-tetramethyluronium tetrafluoroborate
HATU=2-(1H-7-azabenzotriazol-1-yl)-1,1,3,3-tetramethyluronium hexafluorophosphate methanaminium
DCE=dichloroethane
DCM=dichloromethane
CDI=carbonyl diimidazole
prep. HPLC=preparative high performance liquid chromatography
rt=room temperature
DIPEA=diisopropylethylamine
DMAP=4-dimethylaminopyridine
DMSO=dimethylsulfoxide
THF=tetrahydrofuran
KHMDS=potassium bis(trimethylsilyl)amide
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
µg=microgram(s)
µl=microliter(s)
µm=micrometer(s)
mm=millimeter(s)
HOAc=acetic acid
MeOH=methanol
DMF=N,N-dimethylformamide
TBAF=tetrabutylammonium fluoride
TBDMSCl=tert-butyldimethylsilyl chloride The terms "C-3" and "C-28" refer to certain positions of a triterpene core as numbered in accordance with IUPAC rules (positions depicted below with respect to an illustrative triterpene: betulin):

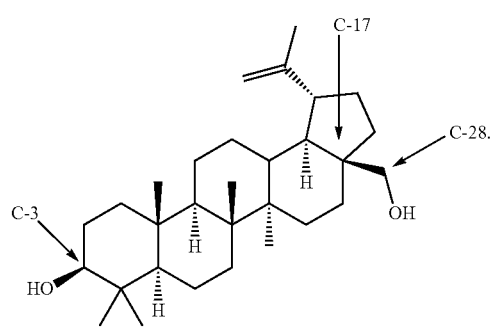

The same numbering is maintained when referring to the compound series in schemes and general descriptions of methods.

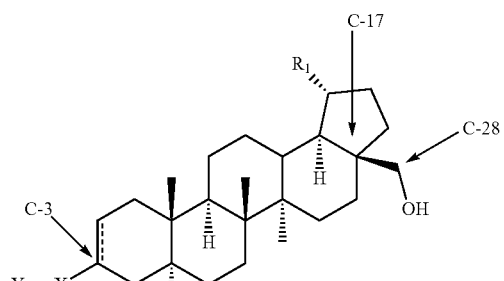

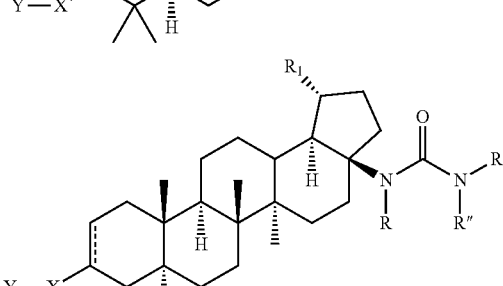

C-17 ureas

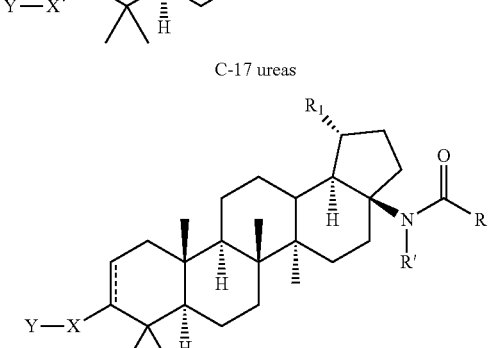

C-17 amides

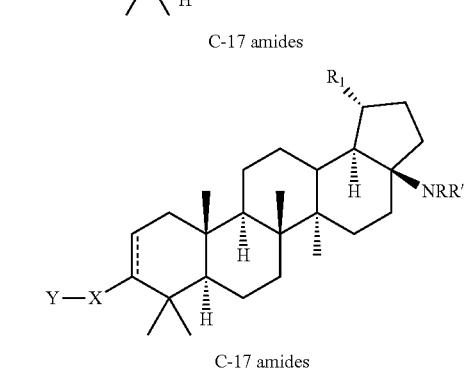

C-17 amides

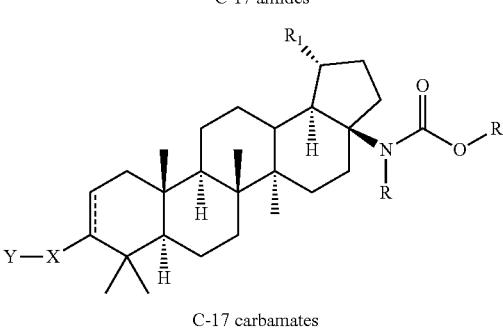

C-17 carbamates

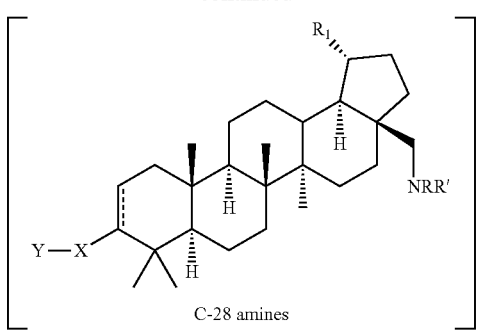
C-28 amines
Preparation of Compounds of Formulas I, II and III General Chemistry Schemes:
Compounds of Formula I can be prepared from commercially available (Aldrich, others) betulinic acid by chemistry described in the following schemes. Compounds of Formula II and III are described thereafter.
General Reaction Schemes are Set Forth as Follows:
Scheme 1
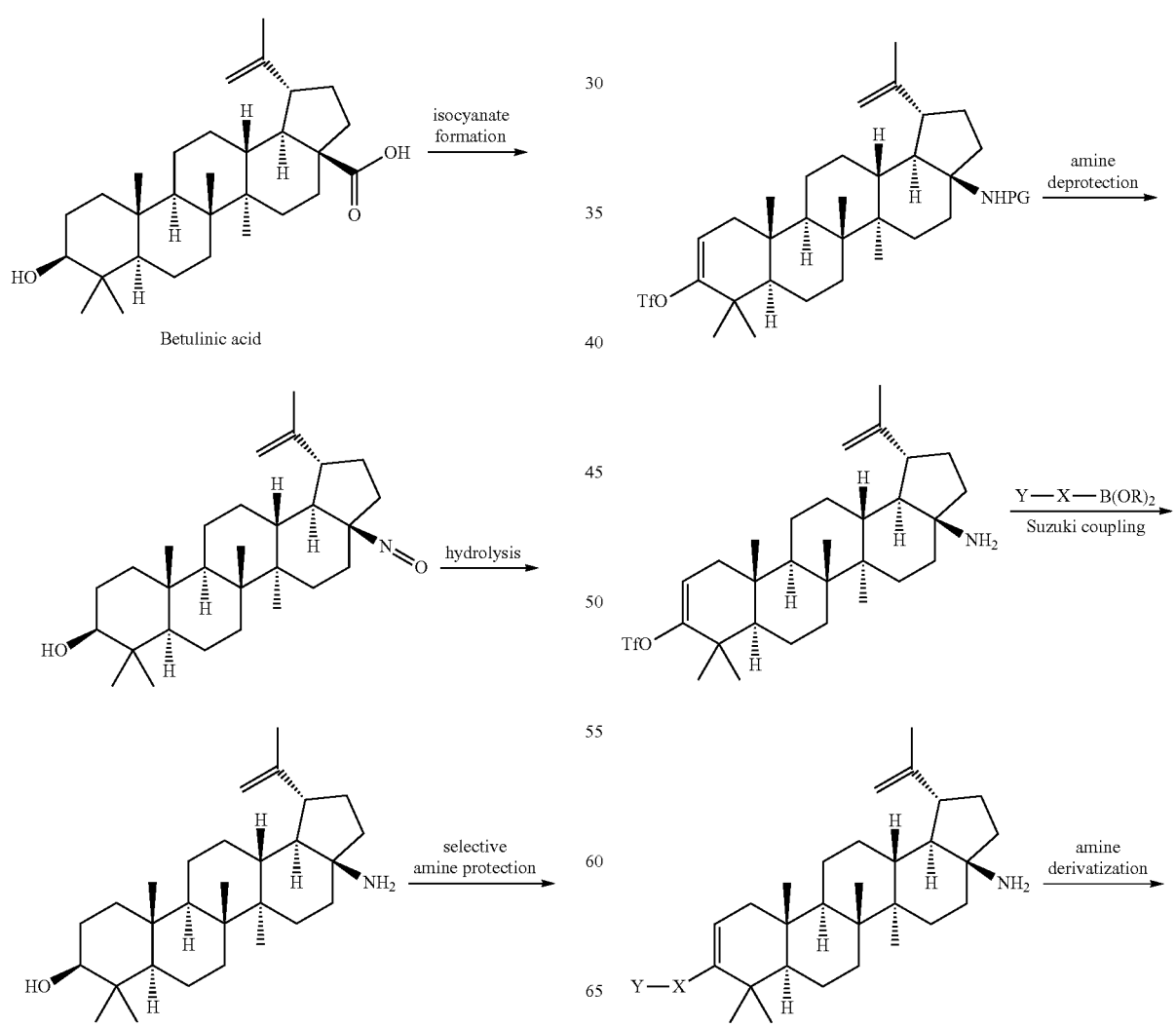

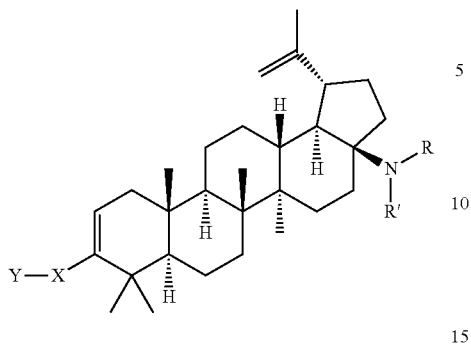

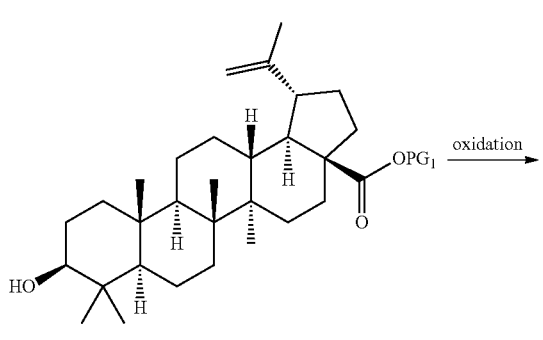

Compounds of formula I can be prepared from betulinic acid as described in Scheme 1. Curtis rearrangement of betulinic acid can be accomplished without protection of the C-3 hydroxyl group to render the C-17 isocyanate which upon acid hydrolysis affords the C-17 amine. The C-17 amine is selectively protected with an amine protective group (i.e F-moc, Boc) to then perform the oxidation of the C-3 hydroxy group to a ketone under standard conditions (i.e. PCC, Dess-Martin reagent, etc). In the case of the Boc protected C-17 amines it is possible to obtain it directly from the isocyanate, without isolation of the C-17 amine, by quenching the Curtius rearrangement with tert-butanol instead of water. Conversion of the ketone into its triflate can be accomplished by methods known to those skilled in the art. The protective group in the amino group is then taken off to produce the C-17 unsubstituted amine. Installation of the C-3 moiety is accomplished via Suzuki coupling of the triflate with the corresponding boronic acid or ester as described above. Alternatively, the triflate coupling with the corresponding boronic acid can be performed before the deprotection of the C-17 amine. Once deprotected, the C-17 amino group can then be further derivatized by methods know to those skilled in the art such as alkylation, reductive amination, acylation, etc. Several of these methods are described in the Schemes below (Scheme 3-7). In some cases, an additional step is needed to unmask any functional group that may be functionalized with a protective group (i.e. when Y is COOH, is always masked as the corresponding ester COOR until this last step).

Scheme 2

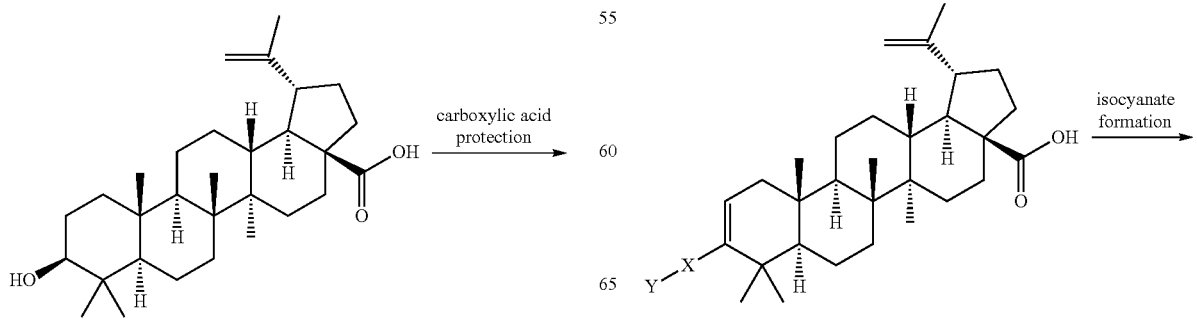

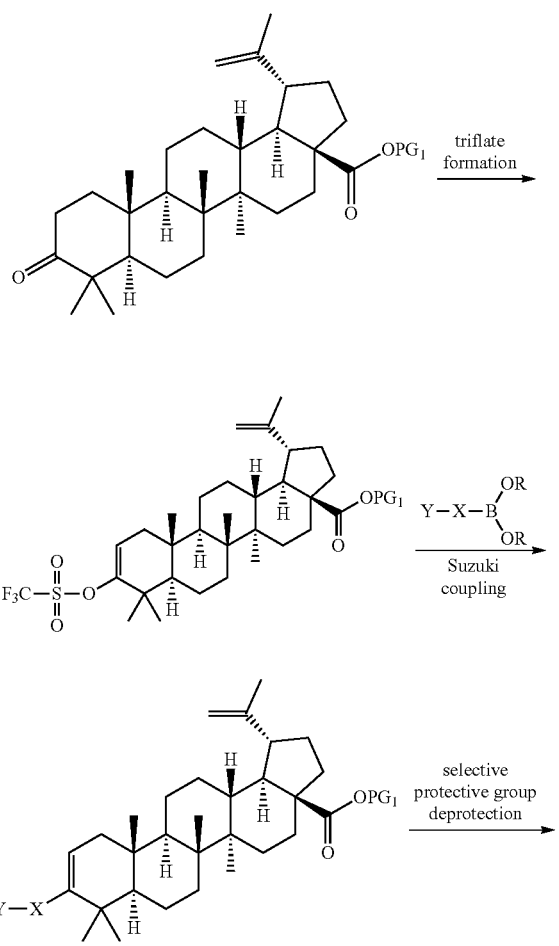

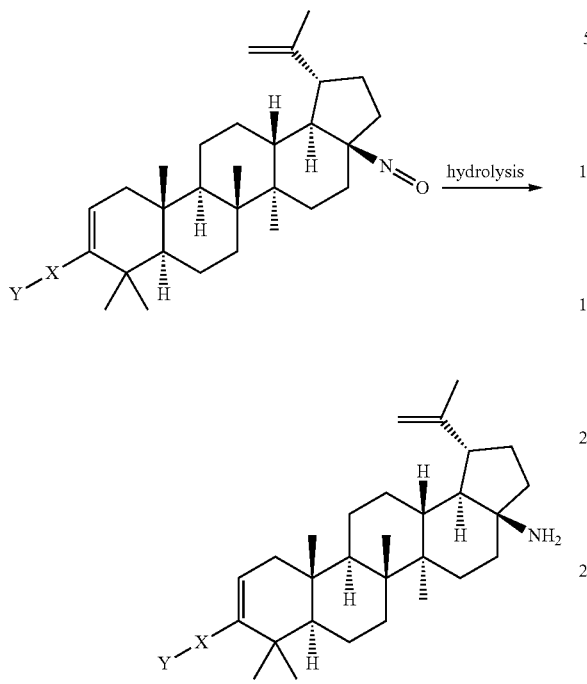

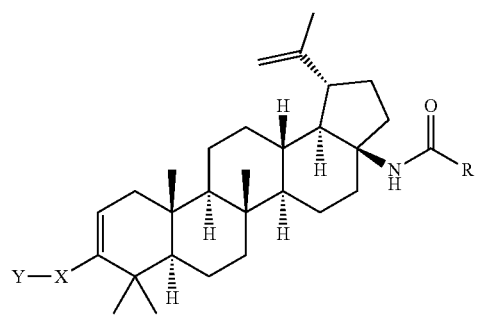

Alternatively, the key intermediate C-17 primary amine can be prepared from betulinic acid as described in Scheme 2. The carboxylic acid present in betulinic acid was protected with a suitable protective group. Standard oxidation (i.e. PCC, Dess-Martin) of the C-3 hydroxyl group produces the C-3 ketone which is then converted into the triflate using conditions know to those skilled in the art. Palladium-catalyzed cross coupling with a boronic acid derivative (Stille coupling using stannanes can also be used) afforded the corresponding C-3-modified betulinic acid derivatives. The C-28 carboxylic ester was then selectively deprotected and submitted to Curtius rearrangement conditions to afford the C-17 primary amine. This reaction can be carried out in one single step or stepwise via isolation of the isocyanate intermediate, as shown in Scheme 2.

The C-17 primary amine can be further modified using standard methods, known to those skilled in the art. Some examples are shown in the following schemes.

Scheme 3

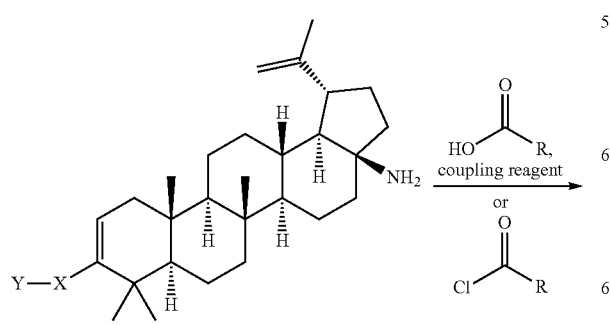

C-17 amides can be prepared by reacting a carboxylic acid with the C-17 primary amine in the presence of an adequate coupling reagent such as HATU, DCC, and others known to those skilled in the art, in the presence of a base such as Hunig's base, TEA, etc., in the appropriate solvent (DCM, THF, DMF, etc.). Hydrolysis of the carboxylic ester affords the benzoic acid. Alternatively, some amides can be prepared by treating the C-17 primary amine with the corresponding carboxylic acid chloride reagent instead of an acid. Similarly, sulfonamines and sulfonamides can be prepared from the C-17 primary amine by using a sulfonyl chloride as the sulfonylating agent.

Scheme 4

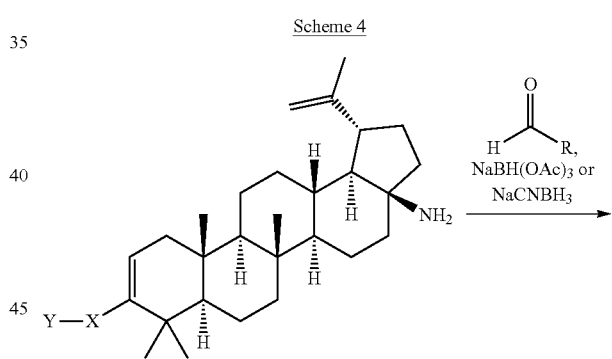

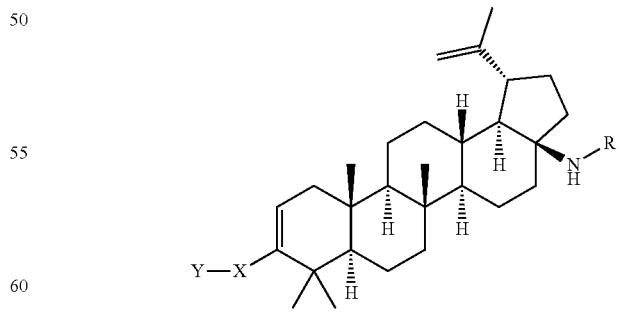

The C-17 primary amine can be treated with an aldehyde under reductive amination conditions (e.g. $NaBH(OAc)_3$) in the presence of AcOH/NaOAc or $Ti(OPr)_4$ in a solvent such as THF, 1,4-dioxane, DCE or DCM) to afford C-17 secondary amines Scheme 5

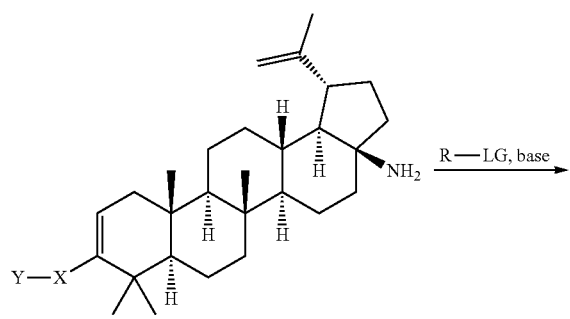

Some C-17 amines can be prepared by alkylation of the C-17 primary amine with an alkylating agent (R-LG), where LG is a leaving group such as, but not limited to Br, Cl, I, mesylate, tosylate or triflate in the presence of a base. Heating may be needed in some cases. Hydrolysis of the carboxylic ester renders the benzoic acid product.

Scheme 6

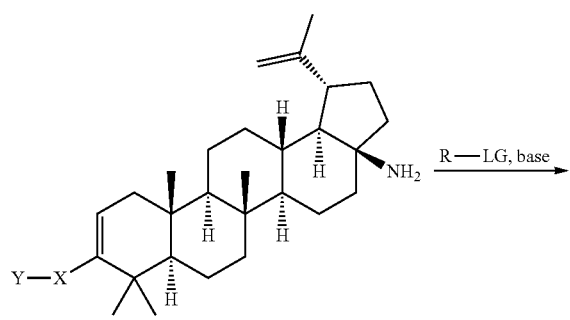

In some cases, by prolonging the reaction times and heating the reaction mixture, the dialkylated product can also be formed.

Scheme 7

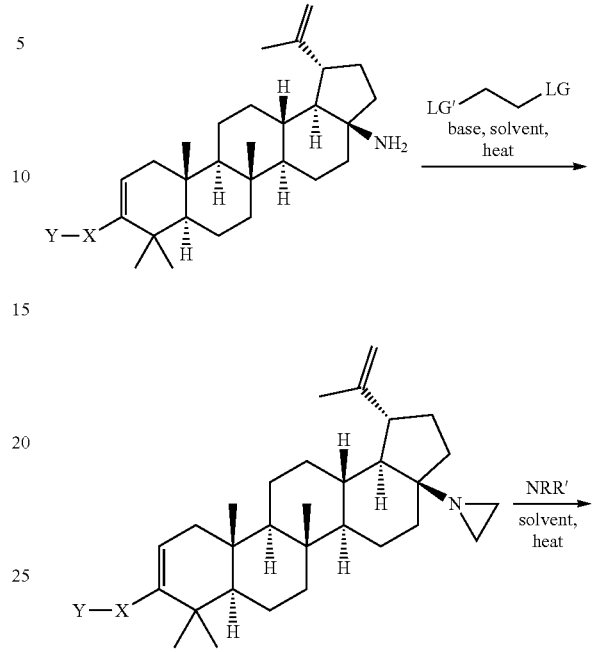

Alternatively, the C-17 amine can be converted into its aziridine via treatment with base and 1,2-disubstituted ethane (where the substituents are leaving groups such as Br, Cl, I, TsO, etc.) under heat. Further ring opening of the aziridine with an amine affords the corresponding substituted C-17 amine.

Scheme 8

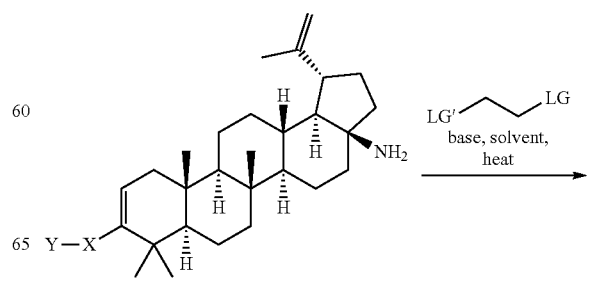

47
-continued

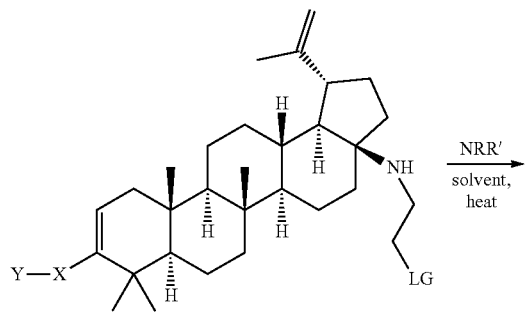

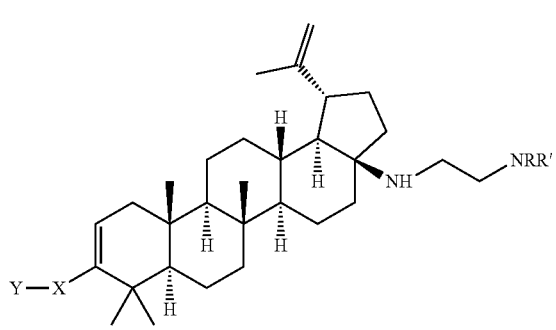

The C-17 amine can also be mono alkylated with the 1,2-disubstituted ethane as shown in Scheme 8. The remaining leaving group in the side chain can be displaced with an amine to afford the corresponding C-17 amine-ethyl-amine.

Substituents R, R' and R" may contain functional groups (i.e. COOH, COOR, OH, NHR) that can be further modified by methods know to those skilled in the art. The modification can be carried out before or after the final deprotection of the carboxylic acid is performed depending on the nature of the functional group.

Alternatively, the C-17 secondary amine can be further modified (i.e. alkylated, acylated, sulfonylated, etc.) using some of the methods described above or other standard methods known to those skilled in the art.

Compounds of formula II can be prepared using the chemistry methods described above for compounds of formula I, with one extra step which consists of saturation of the double bonds as shown in schemes 9 and 10.

Scheme 9

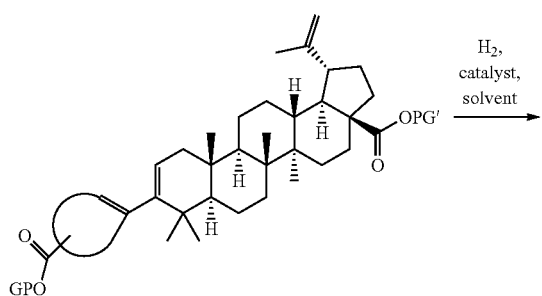

48
-continued

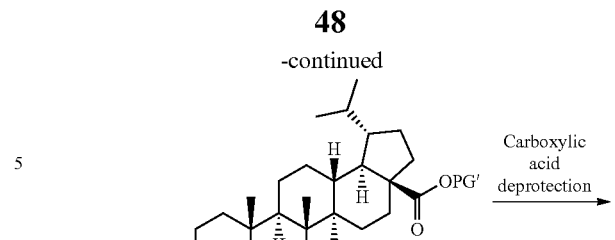

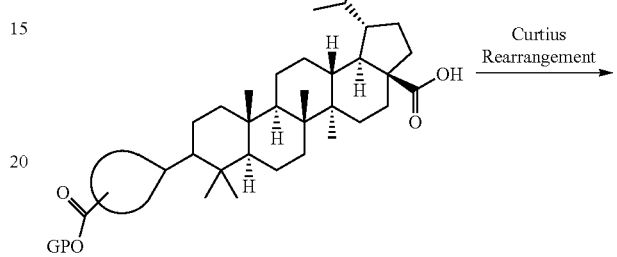

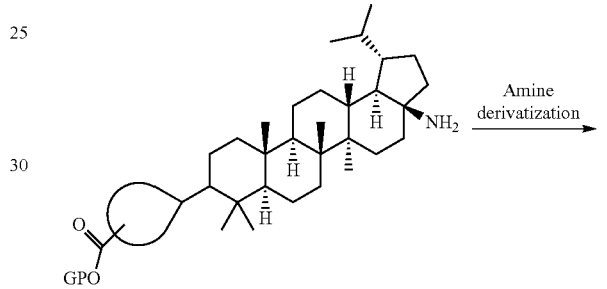

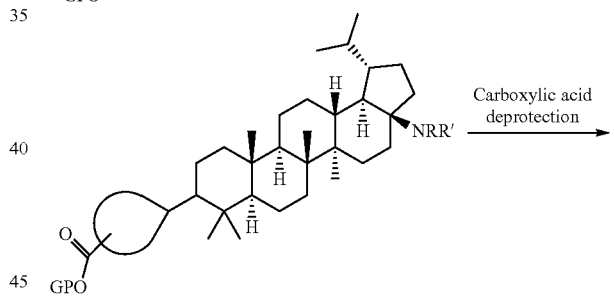

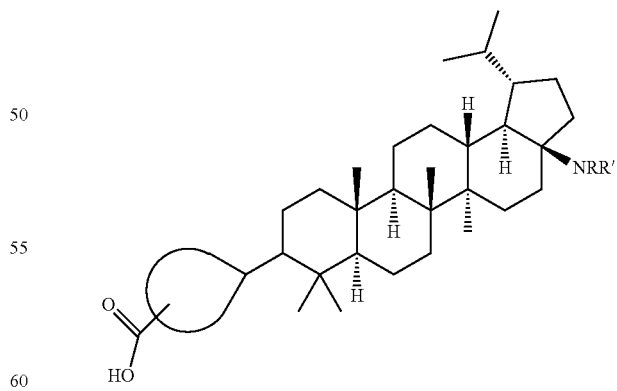

Alternatively, the hydrogenation of the olefins can be controlled to preserve the A-ring unsaturation as shown in scheme 10.

Scheme 10

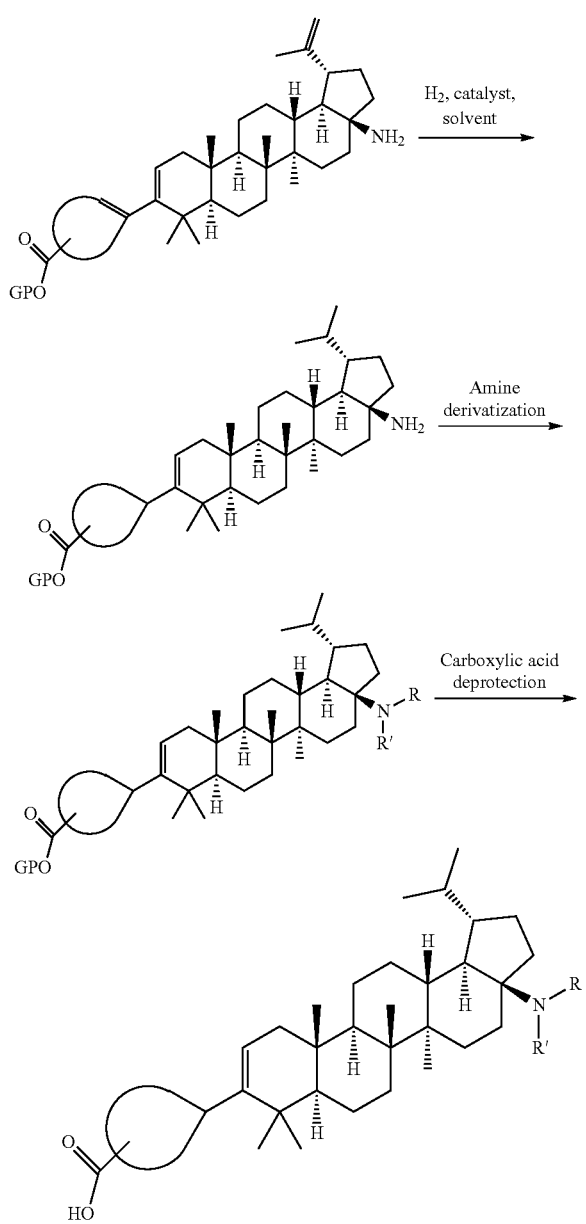

Compounds of formula III can be prepared in the same manner described above for compounds of formula I and II using oleanoic or ursolic acid as starting materials instead of betulinic acid.

EXAMPLES

The following examples illustrate typical syntheses of the compounds of Formulas I, II and III as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), Acetic-d4 (Acetic Acid d$_4$) ($\delta_H$ 11.6, 2.07), DMSO mix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods

Method 1
Start % B=0, Final % B=100 over 2 minute gradient, hold at 100% B
Flow Rate=4 mL/min
Wavelength=220 nm
Solvent A=95% water, 5% methanol, 10 mM ammonium acetate
Solvent B=5% water, 95% methanol, 10 mM ammonium acetate
Column=Phenomenex Luna C18, 5 μm, 3.0×50 mm
Method 2
Start % B=0, Final % B=100 over 2 minute gradient, hold at 100% B
Flow Rate=1 mL/min
Wavelength=220 nm
Solvent A=95% water, 5% acetonitrile, 10 mM ammonium acetate
Solvent B=5% water, 95% acetonitrile, 10 mM ammonium acetate
Column=Phenomenex Luna C18, 3 μm, 2.0×30 mm
Method 3
Start % B=0, Final % B=100 over 2 minute gradient, hold at 100% B
Flow Rate=1 mL/min
Wavelength=220 nm
Solvent A=90% water, 10% methanol, 0.1% TFA
Solvent B=10% water, 90% methanol, 0.1% TFA
Column=Phenomenex Luna C18, 3 μm, 2.0×30 mm
Method 4
Start % B=0, Final % B=100 over 2 minute gradient, hold at 100% B
Flow Rate=0.8 mL/min
Wavelength=220 nm
Solvent A=90% water, 10% acetonitrile, 0.1% TFA
Solvent B=10% water, 90% acetonitrile, 0.1% TFA
Column=Phenomenex LUNA C18, 3 μm, 2.0×50 mm
Method 5
Start % B=0, Final % B=100 over 2 minute gradient, hold at 100% B
Flow Rate=1 mL/min
Wavelength=220 nm
Solvent A=90% water, 10% methanol, 0.1% TFA
Solvent B=10% water, 90% methanol, 0.1% TFA
Column=Phenomenex LUNA C18, 3 μm, 2.0×30 mm Method 6
Start % B=20, Final % B=100 over 2 minute gradient, hold at 100% B
Flow Rate=0.8 mL/min
Wavelength=220 nm
Solvent A=90% water, 10% methanol, 0.1% TFA
Solvent B=10% water, 90% methanol, 0.1% TFA
Column=Xbridge Phenyl, 2.5 μm, 2.1×50 mm
Method 7
Start % B=20, Final % B=100 over 2 min gradient, hold at 100% B
Flow Rate=1 ml/min
Wavelength=220
Solvent A=90% Water-10% Methanol-0.1% TFA
Solvent B=10% Water-90% Methanol-0.1% TFA
Column 1=(1) PHENOMENEX-LUNA 2.0×30 mm 3 μm.
Method 8
Start % B=30, Final % B=100 over 4 min gradient, hold at 100% B
Flow Rate=0.8 ml/min
Wavelength=220
Solvent A=90% Water-10% Methanol-0.1% TFA
Solvent B=10% Water-90% Methanol-0.1% TFA
Column 2=(2) PHENOMENEX-LUNA 2.0×50 mm 3 μm
Method 9
Start % B=40, Final % B=100 over 4 min gradient, hold at 100% B
Flow Rate=0.8 ml/min
Wavelength=220
Solvent A=90% Water-10% Methanol-0.1% TFA
Solvent B=10% Water-90% Methanol-0.1% TFA
Column 2=(2) PHENOMENEX-LUNA 2.0×50 mm 3 μm
Prep HPLC Methods
Prep HPLC Method 1
Start % B=20, Final % B=100 over 8 min gradient, hold at 100% B for 10 min
Flow Rate=50 mL/min
Wavelength=220
Solvent A=5% ACN: 95% Water: 10 mM Ammonium Actetate
Solvent B=95% ACN: 5% Water: 10 mM Ammonium Actetate
Column=Waters Sunfire C18, 5 μm, 30×150 mm
Prep HPLC Method 2
Start % B=20% B to 100% B over 8 min. hold at 100% B for 10 min
Flow Rate=50 mL/min
Wavelength=220
Solvent A=90% $H_2O$+10% MeCN+0.1% TFA
Solvent B=10% $H_2O$+90% MeCN+0.1% TFA
Column=Waters Sunfire C18, 5 μm, 30×50 mm
Prep HPLC Method 3
Start % B=20, Final % B=100 over 10 min gradient, hold at 100% B for 15 min
Flow Rate=50 mL/min
Wavelength=220
Solvent A=90% Water-10% Methanol-0.1% TFA
Solvent B=10% Water-90% Methanol-0.1% TFA
Column=Waters Sunfire C18, 5 μm, 30×150 mm
Pep HPLC Method 4
Start % B=15, Final % B=100 over 10 min gradient, hold at 100% B for 4 min
Flow Rate=50 mL/min
Wavelength=220
Solvent A=90% Water-10% Methanol-0.1% TFA
Solvent B=10% Water-90% Methanol-0.1% TFA
Column=Waters Sunfire C18, 5 μm, 30×150 mm
Pep HPLC Method 5
Start % B=20, Final % B=100 over 15 min gradient, hold at 100% B for 5 min
Flow Rate=50 mL/min
Wavelength=220
Solvent A=90% Water-10% Methanol-0.1% TFA
Solvent B=10% Water-90% Methanol-0.1% TFA
Column=Waters Sunfire C18, 5 μm, 30×150 mm
Pep HPLC Method 6
Start % B=20, Final % B=100 over 15 min gradient, hold at 100% B for 10 min
Flow Rate=50 mL/min
Wavelength=220
Solvent A=90% Water-10% Acetonitrile-0.1% TFA
Solvent B=10% Water-90% Acetonitrile-0.1% TFA
Column=Waters Sunfire C18, 5 μm, 30×150 mm
Prep HPLC Method 7
Start % B=0, Final % B=100 over 15 min gradient, hold at 100% B for 4 min
Flow Rate=50 mL/min
Wavelength=220
Solvent A=90% Water-10% Methanol-0.1% TFA
Solvent B=10% Water-90% Methanol-0.1% TFA
Column=Waters Sunfire C18, 5 μm, 30×150 mm
Prep HPLC Method 8
Start % B=25 Final % B=100 over 15 minute gradient, hold at 100% B
Flow Rate=40 mL/min
Wavelength=220
Solvent A=10% MeCN-90% $H_2O$-0.1% TFA
Solvent B=90% MeCN-10% $H_2O$-0.1% TFA
Column=Waters Sunfire 30×100 mm S5
Prep HPLC Method 9
Start % B=20 Final % B=80 over 20 minute gradient, hold at 80% B
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm S5
Prep HPLC Method 10
Start % B=20 Final % B=75 over 25 minute gradient, hold at 75% B
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm S5
Prep HPLC Method 11
Start % B=10 Final % B=100 over 10 minute gradient, hold at 100% B for 5 min
Flow Rate=25 mL/min
Solvent A=5% ACN-95% $H_2O$-10 mM Ammonium Acetate
Solvent B=95% ACN-5% $H_2O$-10 mM Ammonium Acetate
Column=X-bridge OBD prep shield RP18 19×100 mm 5 μm
Prep HPLC Method 12
Start % B=10, Final % B=100 over 10 min gradient time
Flow Rate=40 mL/min
Wavelength=220
Solvent A=10% acetonitrile-90% $H_2O$ (0.1% TFA)
Solvent B=90% acetonitrile-10% $H_2O$ (0.1% TFA)
Column=WATERS-Sunfire 30×100 mm S5
Prep HPLC Method 13
Start % B=0, Final % B=100 over 15 min gradient, hold at 100% B for 4 min
Flow Rate=50 ml/min
Wavelength=220
Solvent A=90% Water-10% ACN-0.1% TFA
Solvent B=10% Water-90% ACN-0.1% TFA Column=Waters Sunfire C18, 5 μm, 30×150
Prep HPLC Method 14
Start % B=15, Final % B=100 over 10 min gradient, hold at 100% B for 4 min
Flow Rate=50 ml/min
Wavelength=220
Solvent Pair=Water-MeOH-ammonium bicarbonate
Solvent A=95% Water-5% MeOH-10 mm ammonium bicarbonate
Solvent B=5% Water-95% MeOH-10 mm ammonium bicarbonate
Column=Xbridge Phenyl C18, 5 μm, 30×100 mm
Prep-HPLC Method 15
Start % B=30, Final % B=100 over 12 min gradient, hold at 100% B for 6 min
Flow Rate=50 mL/min
Wavelength=220
Solvent A=10% ACN: 90% Water: 0.1% TFA
Solvent B=90% ACN: 10% Water: 0.1% TFA
Column=Waters Sunfire C18, 5 μm, 30×150 mm Preparation of Compounds Preparation of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

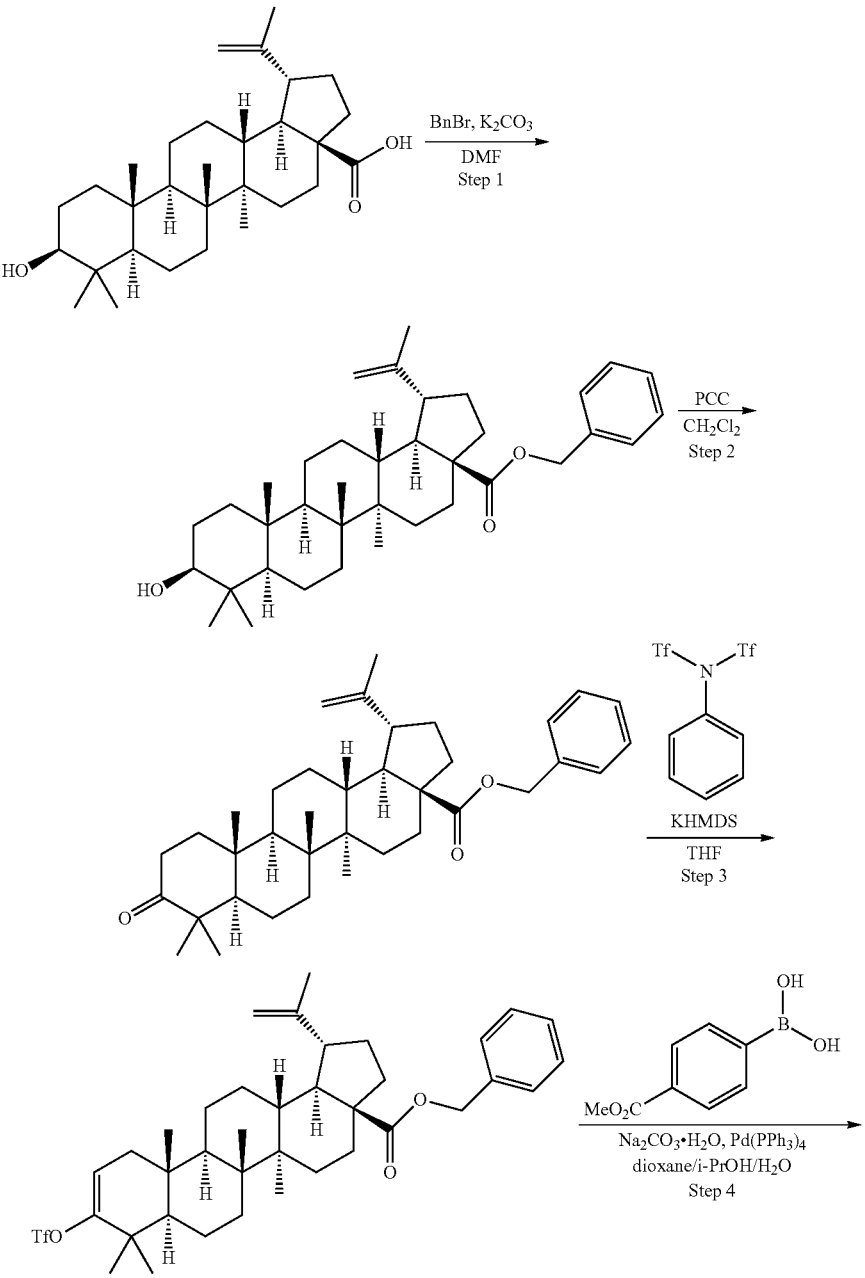

-continued
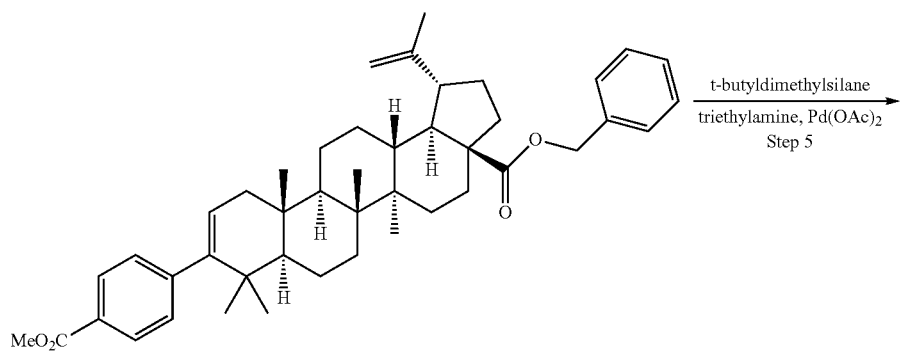
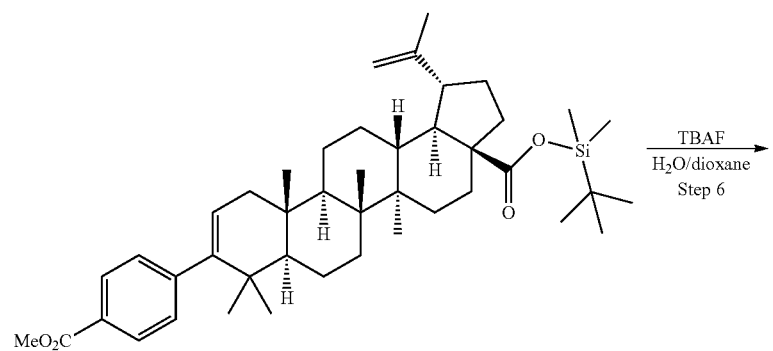
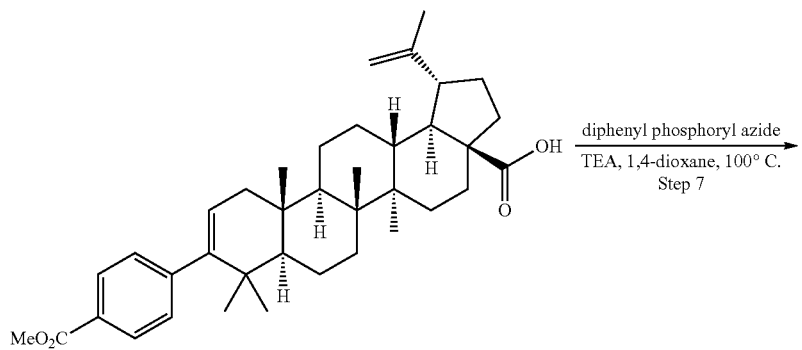
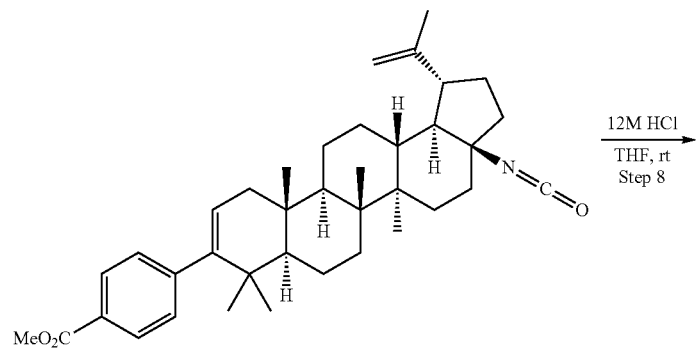

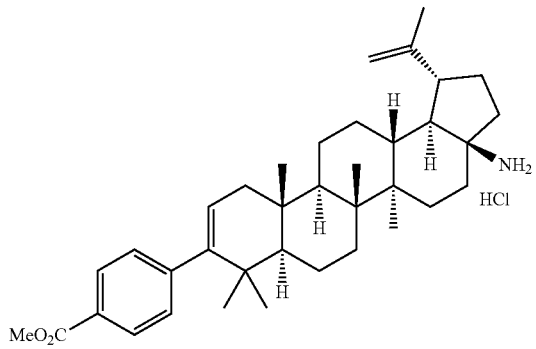

Step 1. Preparation of (1R,3aS,5aR,5bR,7aR,9S, 11aR,11bR,13aR,13bR)-benzyl 9-hydroxy-5a,5b,8,8, 11a-pentamethyl-1-(prop-1-en-2-yl)icosahydro-1H-cyclopenta[a]chrysene-3a-carboxylate

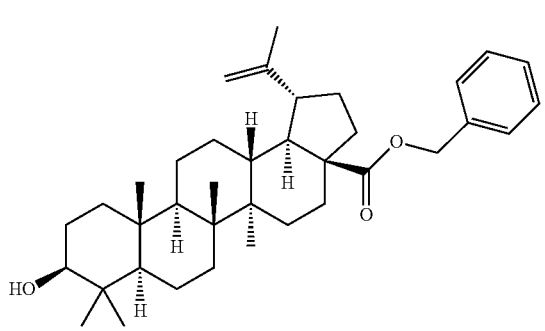

To a suspension of betulinic acid (12 g, 26.3 mmol) and potassium carbonate (7.26 g, 52.6 mmol) in DMF (150 mL) was added benzyl bromide (3.28 mL, 27.6 mmol). The mixture was heated to 60° C. for 3.5 h, and then it was cooled to rt. Solids started to precipitate upon cooling. The mixture was diluted with 200 mL of water and the solids that formed were collected by filtration to give (1R,3aS,5aR,5bR,7aR,9S, 11aR,11bR,13aR,13bR)-benzyl 9-hydroxy-5a,5b,8,8,11a-pentamethyl-1-(prop-1-en-2-yl)icosahydro-1H-cyclopenta[a]chrysene-3a-carboxylate (13.92 g, 97% yield) as a white solid. $^1$H NMR (500 MHz, CHLOROFORM-d) δ ppm 7.39-7.28 (m, 5H), 5.16-5.06 (m, 2H), 4.71 (d, J=1.83 Hz, 1H), 4.59 (s, 1H), 3.17 (ddd, J=11.44, 5.65, 5.49 Hz, 1H), 3.01 (td, J=10.99, 4.88 Hz, 1H), 2.27 (ddd, J=12.36, 3.20, 3.05 Hz, 1H), 2.21-2.13 (m, 1H), 1.93-1.81 (m, 2H), 1.67 (s, 3H), 0.95 (s, 3H), 0.93 (s, 3H), 1.71-0.82 (m, 20H), 0.79 (s, 3H), 0.75 (s, 3H), 0.74 (s, 3H).

Step 2. Preparation of (1R,3aS,5aR,5bR,7aR,11aR, 11bR,13aR,13bR)-benzyl 5a,5b,8,8,11a-pentamethyl-9-oxo-1-(prop-1-en-2-yl)icosahydro-1H-cyclopenta[a]chrysene-3a-carboxylate

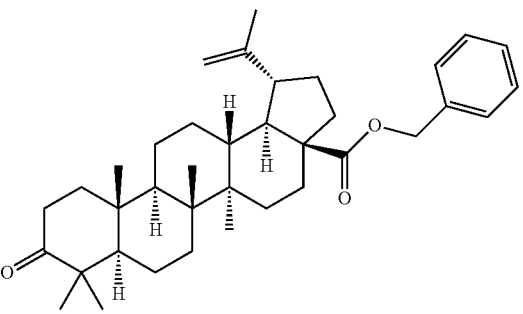

To a solution of (1R,3aS,5aR,5bR,7aR,9S,11aR,11bR, 13aR,13bR)-benzyl 9-hydroxy-5a,5b,8,8,11a-pentamethyl-1-(prop-1-en-2-yl)icosahydro-1H-cyclopenta[a]chrysene-3a-carboxylate (7.1 g, 12.98 mmol) in dichloromethane (100 mL) was added PCC (4.20 g, 19.48 mmol). After stirring for five minutes, the mixture turned a deep crimson color. The mixture was further stirred for 5.5 h. The mixture was filtered through a pad of celite and silica gel which was washed with dichloromethane and then with a 1:1 mixture of ethyl acetate: hexanes. The filtrate was concentrated under reduced pressure to give (1R,3aS,5aR,5bR,7aR,11aR,11bR,13aR,13bR)-benzyl 5a,5b,8,8,11a-pentamethyl-9-oxo-1-(prop-1-en-2-yl)icosahydro-1H-cyclopenta[a]chrysene-3a-carboxylate (6.92 g, 98% yield) as a white foam. $^1$H NMR (500 MHz, CHLOROFORM-d) δ ppm 7.38-7.28 (m, 5H), 5.17-5.06 (m, 2H), 4.72 (d, J=1.83 Hz, 1H), 4.59 (s, 1H), 3.01 (td, J=10.99, 4.88 Hz, 1H), 2.51-2.43 (m, 1H), 2.42-2.34 (m, 1H), 2.28 (dt, J=12.59, 3.17 Hz, 1H), 2.21 (td, J=12.28, 3.51 Hz, 1H), 1.94-1.82 (m, 3H), 1.67 (s, 3H), 1.05 (s, 3H), 1.01 (s, 3H), 1.73-0.95 (m, 17H), 0.94 (s, 3H), 0.89 (s, 3H), 0.78 (s, 3H).

Step 3. Preparation of (1R,3aS,5aR,5bR,7aR,11aR, 11bR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13, 13a,13b-octadecahydro-1H-cyclopenta[a]chrysene-3a-carboxylate Step 4. Preparation of (1R,3aS,5aR,5bR,7aR,11aS, 11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysene-3a-carboxylate

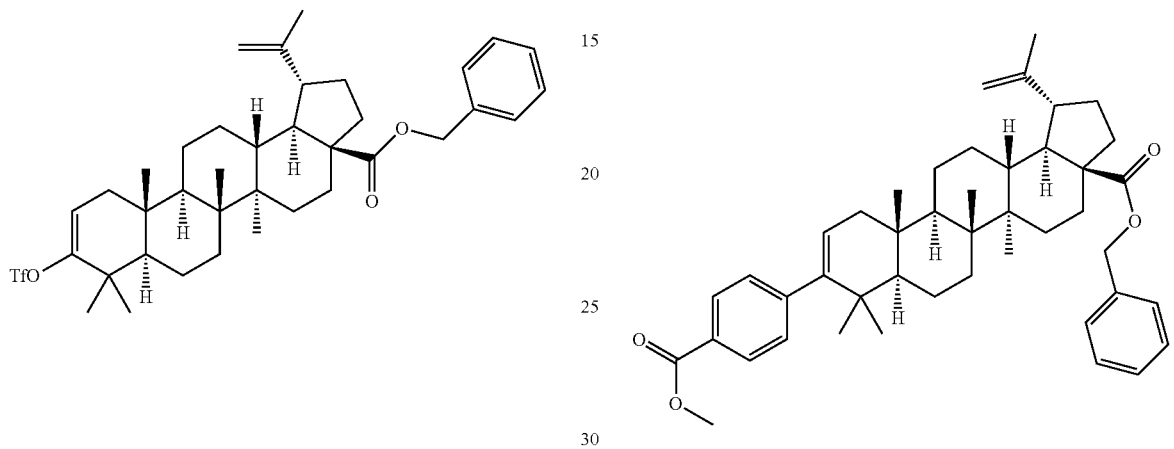

A solution of (1R,3aS,5aR,5bR,7aR,11aR,11bR,13aR, 13bR)-benzyl 5a,5b,8,8,11a-pentamethyl-9-oxo-1-(prop-1-en-2-yl)icosahydro-1H-cyclopenta[a]chrysene-3a-carboxylate (29.0 g, 53.2 mmol) in THF (Volume: 200 mL) was cooled to −78° C. To the solution was added KHMDS (0.5 M in toluene) (213 mL, 106 mmol). The yellow solution was stirred at −78° C. for 25 minutes and a solution of 1,1,1-trifluoro-N-phenyl-N-(trifluoromethyl)sulfonyl methanesulfonamide (20.92 g, 58.6 mmol) in THF (70 mL) and toluene (30 mL) was added via cannula. The solution was stirred at −78° C. for 3 h. TLC showed starting material still remained. Additional 1,1,1-trifluoro-N-phenyl-N-(trifluoromethyl)sulfonyl methanesulfonamide (1 g) was added and the mixture was stirred at −78° C. After 1 h of stirring, the mixture was quenched with water (300 mL) and the mixture was extracted with ethyl acetate (3×200 mL). The combined organic layers were dried with $MgSO_4$. The drying agent was removed by filtration, and the filtrate was concentrated under reduced pressure to give (1R,3aS,5aR,5bR,7aR,11aR,11bR, 13aR,13bR)-benzyl 5a,5b,8,8,11a-pentamethyl-1-(prop-1-en-2-yl)-9-(trifluoromethylsulfonyloxy)-2,3,3a,4,5,5a,5b,6, 7,7a,8,11,11a,11b,12,13,13a,13b-octadecahydro-1H-cyclopenta[a]chrysene-3a-carboxylate (40.0 g, 111% yield) as a yellow solid. Product Rf=0.57, 5% EtOAc in hexanes, visualized using Hanessian's stain. $^1$H NMR (500 MHz, CHLOROFORM-d) δ ppm 0.77 (s, 3H), 0.88 (s, 3H), 0.91-1.77 (m, 17H), 0.94 (s, 3H), 1.00 (s, 3H), 1.10 (s, 3H), 1.67 (s, 3H), 1.81-1.96 (m, 2H), 2.14 (dd, J=17.09, 6.71 Hz, 1H), 2.22 (td, J=12.21, 3.36 Hz, 1H), 2.25-2.31 (m, 1H), 3.02 (td, J=10.99, 4.58 Hz, 1H), 4.59 (s, 1H), 4.72 (d, J=1.53 Hz, 1H), 5.05-5.12 (m, 1H), 5.13-5.18 (m, 1H), 5.54 (dd, J=6.71, 1.53 Hz, 1H), 7.29-7.41 (m, 5H).

To a round bottom flask containing a solution of (1R,3aS, 5aR,5bR,7aR,11aR,11bR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (6.21 g, 9.18 mmol) in dioxane (25 mL) was added 2-propanol (25 mL) and water (15 mL) followed by sodium carbonate monohydrate (3.42 g, 27.5 mmol), 4-methoxycarbonylphenylboronic acid (2.478 g, 13.77 mmol), and tetrakis (triphenylphosphine)palladium(0) (0.318 g, 0.275 mmol). The flask was attached to a reflux condenser, was flushed with $N_2$, and was heated to reflux overnight. After heating the mixture for 14.5 h, it was cooled to rt and was diluted with water (75 mL). The mixture was extracted with ethyl acetate (3×75 mL) and washed with brine. The combined organic layers were dried with $MgSO_4$, filtered, and concentrated under reduced pressure. The residue was adsorbed to silica gel and was purified by flash chromatography using a 0-20% ethyl acetate in hexanes gradient. The fractions containing the expected product were combined and concentrated under reduced pressure to give the title compound, (1R,3aS,5aR, 5bR,7aR,11aS,11bR,13aR13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (4.16 g, 68.4% yield), as a white foam. $^1$H NMR (500 MHz, CHLOROFORM-d) δ ppm 7.92 (d, J=8.24 Hz, 2H), 7.40-7.29 (m, 5H), 7.19 (d, J=8.24 Hz, 2H), 5.28 (dd, J=6.10, 1.83 Hz, 1H), 5.19-5.07 (m, 2H), 4.73 (d, J=1.83 Hz, 1H), 4.60 (s, 1H), 3.90 (s, 3H), 3.04 (td, J=10.91, 4.73 Hz, 1H), 2.20-2.32 (m, 2H), 2.09 (dd, J=17.24, 6.26 Hz, 1H), 1.95-1.82 (m, 2H), 1.69 (s, 3H), 0.97 (s, 3H), 0.95 (s, 3H), 0.92 (s, 3H), 0.91 (s, 3H), 1.75-0.87 (m, 17H), 0.82 (s, 3H).

Step 5. Preparation of (1R,3aS,5aR,5bR,7aR,11aS, 11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate Step 6. Preparation of (1R,3aS,5aR,5bR,7aR,11aS, 11bR,13 aR,13bR)-9-(4-(methoxycarbonyl)phenyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysene-3a-carboxylic acid

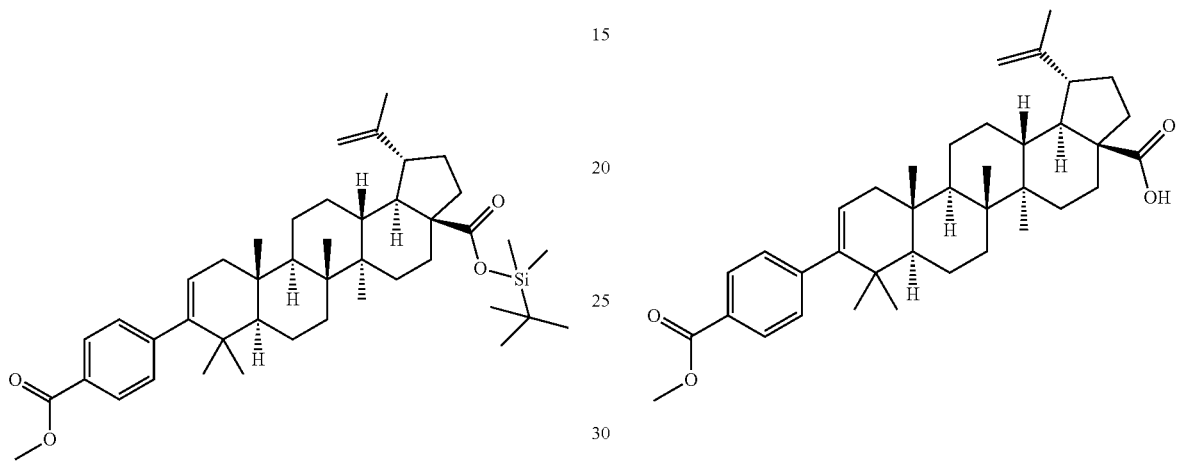

To a solution of (1R,3aS,5aR,5bR,7aR,11aS,11bR,13aR, 13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (3.82 g, 5.76 mmol) in dichloroethane (100 mL) was added triethylamine (1.285 mL, 9.22 mmol), tert-butyldimethylsilane (1.912 mL, 11.52 mmol), and palladium(II) acetate (0.647 g, 2.88 mmol). The mixture was flushed with $N_2$ and was heated to 60° C. After 2 h, the reaction was cooled to rt, was filtered through a pad of celite and silica gel to remove the solids which were washed with 25% EtOAc in hexanes. The filtrate was concentrated under reduced pressure and was treated with 20 mL of acetic acid, 10 mL of THF and 3 mL of water. After stirring for 1 h the solids that formed were collected by filtration and were washed with water to give (1R,3aS,5aR,5bR,7aR,11aS,11bR, 13aR,13bR)-tert-butyldimethylsilyl 9-(4-(methoxycarbonyl) phenyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysene-3a-carboxylate (3.62 g, 91% yield) as a white solid. $^1$H NMR (400 MHz, CHLOROFORM-d) δ ppm 7.94 (d, J=8.28 Hz, 2H), 7.21 (d, J=8.28 Hz, 2H), 5.30 (dd, J=6.15, 1.63 Hz, 1H), 4.75 (d, J=1.76 Hz, 1H), 4.62 (s, 1H), 3.92 (s, 4H), 3.08 (td, J=10.92, 4.27 Hz, 1H), 2.35-2.22 (m, 2H), 2.17-2.06 (m, 1H), 2.02-1.84 (m, 2H), 1.71 (s, 3H), 1.01 (s, 6H), 0.99 (br. s., 3H), 0.98 (s, 9H), 0.94 (s, 6H), 1.78-0.90 (m, 16H), 0.32-0.28 (m, 6H).

To solution of (1R,3aS,5aR,5bR,7aR,11aS,11bR,13aR, 13bR)-tert-butyldimethylsilyl 9-(4-(methoxycarbonyl)phenyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysene-3a-carboxylate (3.12 g, 4.54 mmol) in dioxane (25 mL) was added TBAF (75% wt in water) (2.375 g, 6.81 mmol). The mixture was stirred at rt for 4 h then was diluted with 1N HCl (25 mL) and water (5 mL) and extracted with dichloromethane (3×100 mL). The combined organic layers were dried with $Na_2SO_4$, filtered, and partially concentrated under reduced pressure to about 10 mL in volume. To the partially concentrated mixture was added 1N HCl (50 mL). The solids that formed were collected by filtration and were washed with water. The expected product, (1R,3aS,5aR,5bR,7aR,11aS,11bR,13 aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysene-3a-carboxylic acid (2.58 g, 99% yield), was isolated as a white solid. LCMS: m/e 571.47 (M−H)$^-$, 3.60 min (method 1). $^1$H NMR (500 MHz, CHLOROFORM-d) δ ppm 9.80 (br. s., 1H), 7.92 (d, J=8.24 Hz, 2H), 7.18 (d, J=8.24 Hz, 2H), 5.32-5.26 (m, 1H), 4.75 (s, 1H), 4.62 (br. s., 1H), 3.90 (s, 3H), 3.07-2.99 (m, 1H), 2.33-2.21 (m, 2H), 2.10 (dd, J=17.09, 6.10 Hz, 1H), 2.06-1.94 (m, 2H), 1.70 (s, 3H), 1.01 (br. s., 3H), 1.00 (br. s., 3H), 0.98 (s, 3H), 0.91 (s, 6H), 1.79-0.89 (m, 17H).

Step 7. Preparation of methyl 4-((1R,3aS,5aR,5bR, 7aR,11aS,11bR,13aR,13bR)-3a-isocyanato-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate

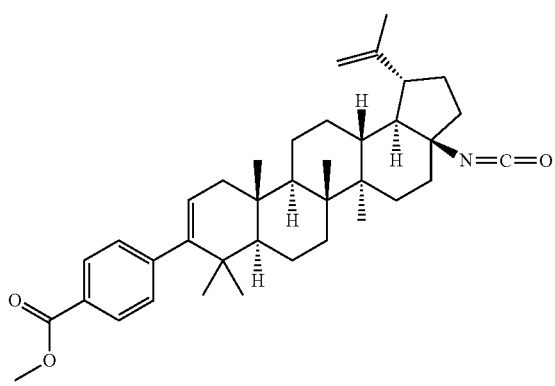

To a slurry of (1R,3aS,5aR,5bR,7aR,11aS,11bR,13aR, 13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysene-3a-carboxylic acid (10 g, 17.46 mmol) in 1,4-dioxane (200 mL) was added triethylamine (4.38 mL, 31.4 mmol) followed by diphenyl phosphoryl azide (5.82 mL, 26.2 mmol). The resulting white slurry was heated to 100° C. After 5 h, the reaction was allowed to cool to rt and was then diluted with EtOAc and washed with 1N NaOH (2×70 mL). The combined aqueous layer was extracted with EtOAc (2×150 mL). The combined organic layer was dried over $Na_2SO_4$, filtered and concentrated to slurry (about 75 mL) which was stored in a refrigerator overnight. The slurry was filtered and the white solid product was washed with $Et_2O$. The liquid filtrate was concentrated to yellow slurry which was filtered and washed with $Et_2O$ to give more white solid product. The two batches of white solid were combined and dried under reduced pressure to give methyl 4-((1R,3aS,5aR,5bR,7aR, 11aS,11bR,13aR,13bR)-3a-isocyanato-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (8.6 g, 86% yield) as a white solid. $^1$H NMR (500 MHz, CHLOROFORM-d) δ ppm 8.0 (2H, d, J=8.2 Hz), 7.2 (2H, d, J=8.2 Hz), 5.3 (1H, d, J=4.6 Hz), 4.8 (1H, s), 4.7 (1H, s), 3.9 (3H, s), 2.6 (1H, td, J=10.8, 5.8 Hz), 2.1-2.2 (2H, m), 1.8-2.0 (4H, m), 1.7-1.8 (1H, m), 1.7 (3H, s), 1.5-1.7 (5H, m), 1.4-1.5 (5H, m), 1.3-1.4 (2H, m), 1.2-1.3 (2H, m), 1.1 (3H, s), 1.1-1.1 (1H, m), 1.0 (3H, s), 1.0 (3H, s), 1.0 (3H, br. s.), 1.0 (3H, br. s.). $^{13}$C NMR (CHLOROFORM-d) δ ppm 14.2, 15.4, 16.2, 19.2, 19.5, 20.8, 21.0, 24.7, 27.4, 29.0, 29.2, 33.3, 36.0, 37.2, 39.0, 39.0, 40.3, 41.5, 41.8, 47.8, 49.0, 49.2, 51.7, 52.6, 66.8, 71.3, 110.2, 121.3, 123.7, 127.6, 128.2, 129.8, 146.0, 148.4, 148.6, 166.9.

Step 8. Preparation of methyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate

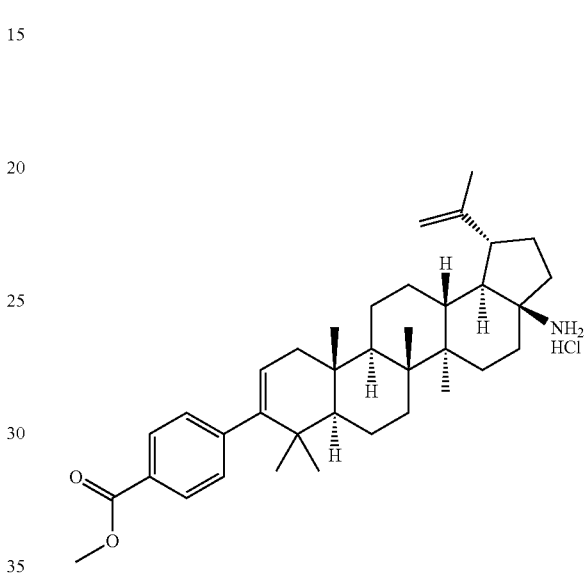

To a cloudy solution of methyl 4-((1R,3aS,5aR,5bR,7aR, 11aS,11bR,13aR,13bR)-3a-isocyanato-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (5.47 g, 9.60 mmol) in THF (100 mL) was added concentrated hydrochloric acid (19.83 mL, 240 mmol). The resulting homogeneous mixture was let stirred at rt. After 72 h, reaction mixture was concentrated to dryness to give methyl 4-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (4.98 g, 89% yield) as white solid. LCMS: m/e 544.5 (M+H)$^+$, 3.26 min (method 2). $^1$H NMR (500 MHz, 1:1 $CDCl_3$:MeOD) δ ppm 7.9 (2H, d, J=8.5 Hz), 7.3 (1H, t, J=7.8 Hz), 7.2 (2H, d, J=8.5 Hz), 7.1 (1H, t, J=7.3 Hz), 5.3 (1H, d, J=4.6 Hz), 4.8 (1H, s), 4.7 (1H, br. s.), 3.9 (2H, s), 3.6 (2H, dt, J=15.6, 6.6 Hz), 3.3 (1H, dt, J=3.1, 1.6 Hz), 2.6 (1H, td, J=11.0, 6.1 Hz), 2.1 (1H, dd, J=17.1, 6.4 Hz), 2.0 (1H, d, J=13.4 Hz), 1.9-2.0 (1H, m), 1.8-1.9 (2H, m), 1.7-1.7 (3H, m), 1.6-1.7 (3H, m), 1.5-1.6 (3H, m), 1.5-1.5 (2H, m), 1.4 (1H, br. s.), 1.3-1.4 (1H, m), 1.2-1.3 (1H, m), 1.1-1.2 (2H, m), 1.1-1.1 (1H, m), 1.0 (3H, s), 1.0 (3H, s), 0.9 (3H, s), 0.9 (3H, s).

Key intermediate 1 was prepared by the following methods:

Method 1

Intermediate 1

Preparation of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate

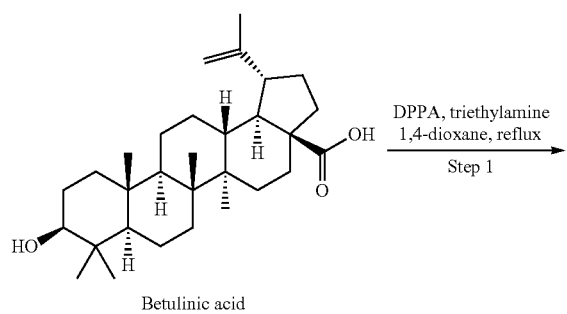

Betulinic acid

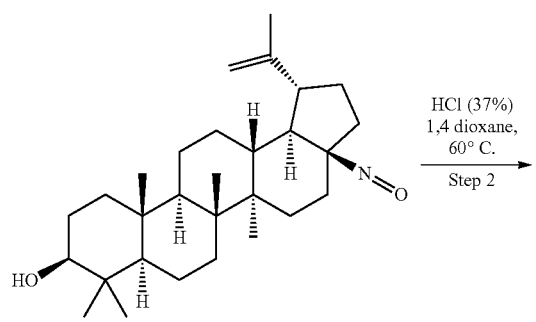

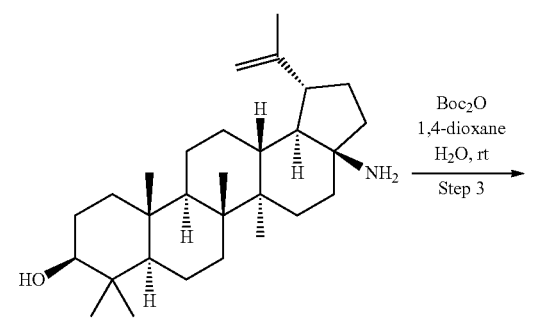

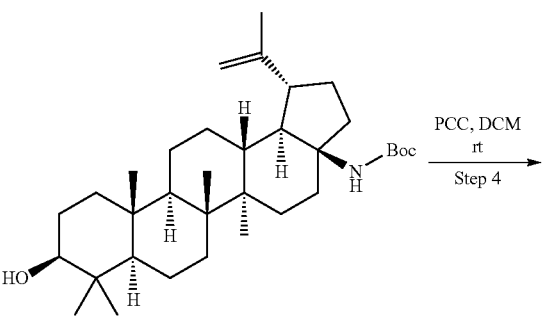

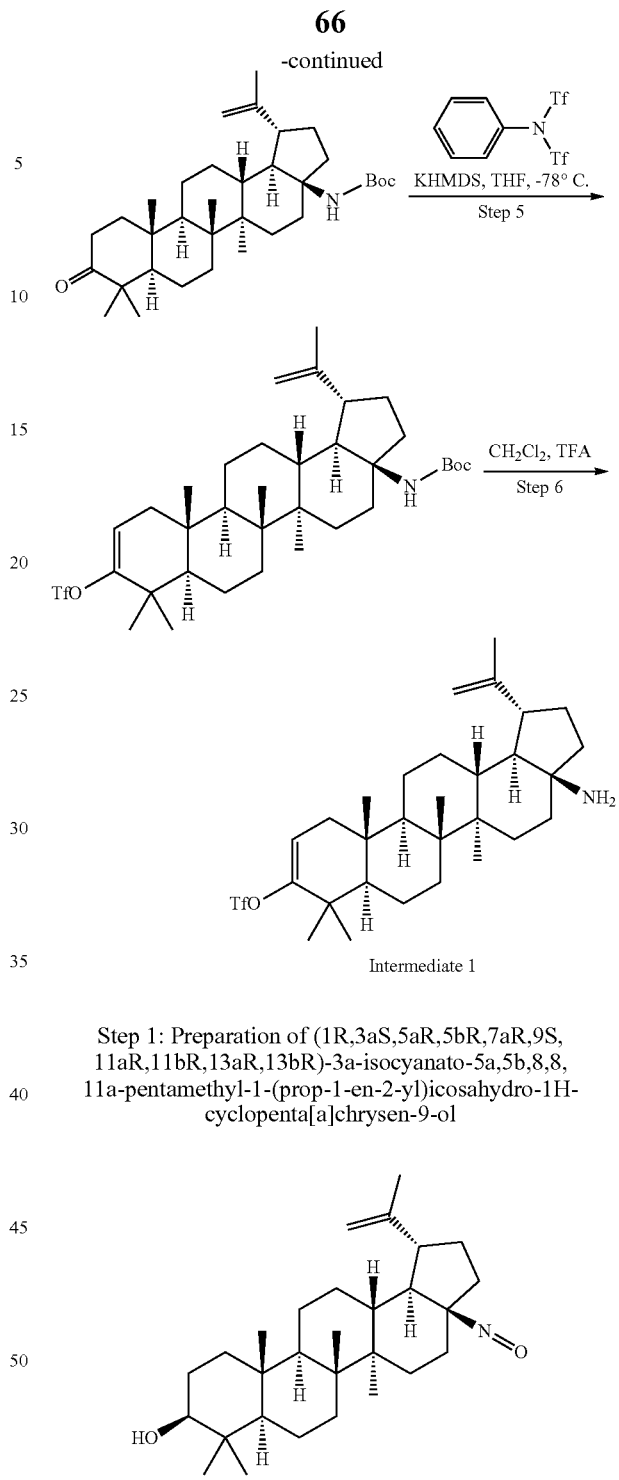

Intermediate 1

Step 1: Preparation of (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol To a suspension of betulinic acid (10 g, 21.90 mmol) in 1,4-dioxane (100 mL) was added triethylamine (9.16 mL, 65.7 mmol) and diphenyl phosphorazidate (7.08 mL, 32.8 mmol). The mixture was heated to reflux. Upon heating, all solids dissolved. After heating the mixture for 26 h, the mixture was cooled to rt and was concentrated under reduced pressure. The residue was diluted with 100 mL of water and was extracted with dichloromethane (3×100 mL). The combined organic layers were dried with sodium sulfate. The drying agent was removed by filtration and the filtrate was concentrated under reduced pressure. The residue was purified by flash chromatography using a 0-15% EtOAc in hexanes gradient and a Thomson 240 g silica gel column. The fractions containing the expected product were combined and concentrated under reduced pressure. A second batch of less-pure product was concentrated and was repurified using a Thomson 240 g column and the same gradient. The fractions containing the expected product were combined with the first-batch to give the title compound as a white solid (7.76 g, 17.10 mmol, 78% yield). ¹H NMR (400 MHz, chloroform-d) δ=4.75 (s, 1H), 4.67-4.62 (m, 1H), 3.20 (dt, J=11.3, 5.6 Hz, 1H), 2.55 (td, J=10.9, 5.9 Hz, 1H), 2.17-2.03 (m, 1H), 1.92-1.76 (m, 4H), 1.69 (s, 3H), 1.06 (s, 3H), 0.98 (s, 3H), 0.95 (s, 3H), 0.85 (s, 3H), 0.78 (s, 3H), 1.74-0.66 (m, 20H).

Step 2: Preparation of (1R,3aS,5aR,5bR,7aR,9S, 11aR,11bR,13aR,13bR)-3a-amino-5a,5b,8,8,11a-pentamethyl-1-(prop-1-en-2-yl)icosahydro-1H-cyclopenta[a]chrysen-9-ol, HCl

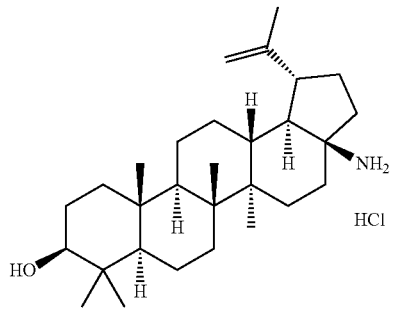

To a solution of (1R,3aS,5aR,5bR,7aR,9S,11aR,11bR, 13aR,13bR)-3a-isocyanato-5a,5b,8,8,11a-pentamethyl-1-(prop-1-en-2-yl)icosahydro-1H-cyclopenta[a]chrysen-9-ol (7.76 g, 17.10 mmol) in 1,4-dioxane (100 mL) was added HCl (37%) (21.07 mL, 257 mmol). The mixture was heated to 60° C. for 15 h, then was cooled to rt and concentrated under reduced pressure. The residue was dissolved in dichloromethane and methanol and was concentrated two additional times to give (1R,3aS,5aR,5bR,7aR,9S,11aR,11bR, 13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.7 mmol, 98% yield) as an off-white foam. The crude product was used in the next step with no purification.

Step 3: Preparation of tert-butyl((1R,3 aS,5aR,5bR, 7aR,9S,11aR,11bR,13 aR,13bR)-9-hydroxy-5a,5b,8, 8,11a-pentamethyl-1-(prop-1-en-2-yl)icosahydro-1H-cyclopenta[a]chrysen-3a-yl)carbamate

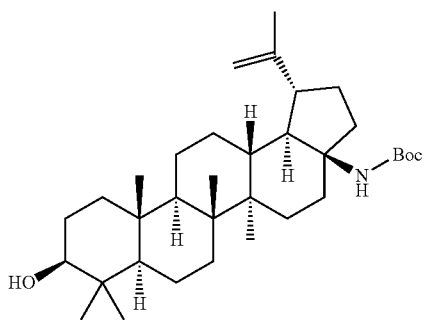

To a solution of (1R,3aS,5aR,5bR,7aR,9S,11aR,11bR, 13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.7 mmol) in 1,4-dioxane (100 mL) was added water (25 mL), sodium bicarbonate (4.21 g, 50.2 mmol) and Boc anhydride (5.82 mL, 25.08 mmol). The mixture was stirred at rt for 16 h then the mixture was diluted with 100 mL of water and was extracted with ethyl acetate (3×100 mL). The combined organic layers were washed with brine, dried over magnesium sulfate, filtered and concentrated under reduced pressure to give tert-butyl((1R,3aS,5aR,5bR,7aR,9S,11aR,11bR, 13aR,13bR)-9-hydroxy-5a,5b,8,8,11a-pentamethyl-1-(prop-1-en-2-yl)icosahydro-1H-cyclopenta[a]chrysen-3a-yl)carbamate as an off-white foam. ¹H NMR (500 MHz, chloroform-d) δ=4.74 (d, J=1.6 Hz, 1H), 4.64-4.62 (m, 1H), 4.34 (br. s., 1H), 3.24-3.18 (m, 1H), 2.63-2.35 (m, 3H), 2.06-1.93 (m, 1H), 1.71 (s, 3H), 1.46 (s, 9H), 1.04 (s, 3H), 0.99 (s, 3H), 0.98 (s, 3H), 0.86 (s, 3H), 0.79 (s, 3H), 1.77-0.68 (m, 22H).

Step 4: Preparation of tert-butyl((1R,3 aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate

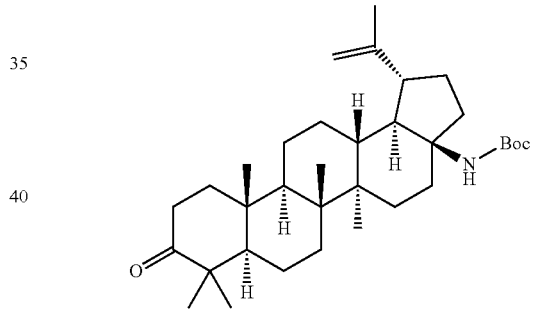

To a solution of the resulting tert-butyl ((1R,3aS,5aR,5bR, 7aR,9S,11aR,11bR,13aR,13bR)-9-hydroxy-5a,5b,8,8,11a-pentamethyl-1-(prop-1-en-2-yl)icosahydro-1H-cyclopenta [a]chrysen-3a-yl)carbamate in dichloromethane (100 mL) was added pyridinium chlorochromate (4.69 g, 21.74 mmol). The mixture was stirred at rt for 5 h then an additional 1.0 g of PCC was added and the mixture was stirred at rt for 1 h. The mixture was filtered through a plug of silica gel and celite which was washed with a solution of 25% ethyl acetate in hexanes. The filtrate was concentrated under reduced pressure to give tert-butyl ((1R,3 aS,5aR,5bR,7aR,11aR,11bR, 13aR,13bR)-5a,5b,8,8,11a-pentamethyl-9-oxo-1-(prop-1-en-2-yl)icosahydro-1H-cyclopenta[a]chrysen-3a-yl) carbamate as a light-yellow foam. ¹H NMR (500 MHz, chloroform-d) δ=4.74 (d, J=1.7 Hz, 1H), 4.63 (t, J=1.7 Hz, 1H), 4.34 (br. s., 1H), 2.65-2.34 (m, 5H), 2.05-1.88 (m, 2H), 1.71 (s, 3H), 1.47 (s, 9H), 1.10 (s, 3H), 1.08 (s, 3H), 1.05 (s, 3H), 0.99 (s, 3H), 0.96 (s, 3H), 1.76-0.93 (m, 18H).

Step 5: Preparation of (1R,3aS,5aR,5bR,7aR,11aR, 11bR,13aR,13bR)-3a-((tert-butoxycarbonyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate

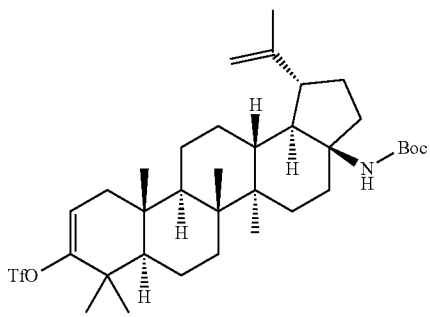

A solution of the resulting tert-butyl((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate in THF (100 mL) was cooled to −78° C. To the solution was added KHMDS (0.91M in THF) (40.4 mL, 36.8 mmol). The mixture was stirred for 20 minutes at −78° C. then a solution of 1,1,1-trifluoro-N-phenyl-N-(trifluoromethyl)sulfonyl methanesulfonamide (7.47 g, 20.90 mmol) in THF (100 mL) was added via canula. The mixture was stirred at −78° C. for 5 h, then was quenched with 100 mL of water and was extracted with ethyl acetate (3×75 mL). The combined organic layers were dried with magnesium sulfate. The drying agent was removed by filtration and the filtrate was concentrated under reduced pressure. The residue was taken up in a small amount of DCM and methanol and the yellow solids that formed were removed by filtration. The filtrate was again concentrated and treated with methanol and the solids that formed were again removed by filtration. The filtrate was concentrated and was adsorbed to silica gel and was then purified by flash chromatography using a 0-50% ethyl acetate in hexanes gradient and a Thomson 240 g silica gel column. The fractions containing the deprotected product were combined and were concentrated under reduced pressure to give a mixture of products. This mixture was repurified by flash chromatography using a 0-10% EtOAc in hexanes gradient and a 240 g Thomson silica gel column. The fractions containing the expected product were combined and concentrated under reduced pressure to give (1R,3aS,5aR, 5bR,7aR,11aR,11bR,13aR,13bR)-3a-((tert-butoxycarbonyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yltrifluoromethanesulfonate (1.31 g, 1.99 mmol, 11.9% over 3 steps). $^1$H NMR (500 MHz, CHLOROFORM-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 6: Preparation of (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl trifluoromethanesulfonate

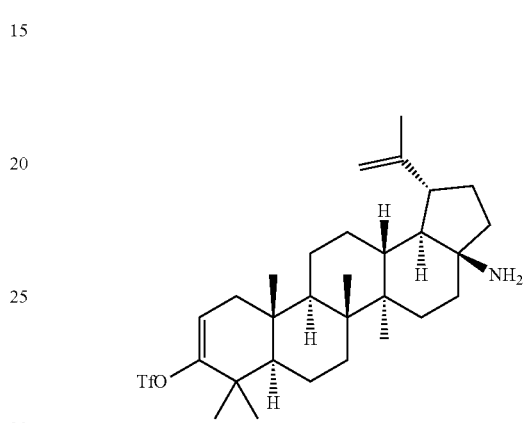

To a solution of (1R,3aS,5aR,5bR,7aR,11aR,11bR,13aR, 13bR)-3a-((tert-butoxycarbonyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl trifluoromethanesulfonate (0.2 g, 0.304 mmol) in dichloromethane (2 mL) was added trifluoroacetic acid (0.5 mL, 6.49 mmol). The mixture was stirred at rt for 1.5 h then was concentrated under reduced pressure. The residue was diluted with saturated aqueous sodium bicarbonate (20 mL) and extracted with dichloromethane (3×20 mL). The combined organic layers were dried with sodium sulfate. The drying agent was removed by filtration. The filtrate was concentrated and adsorbed to silica gel and purified using a 12-100% ethyl acetate in hexanes gradient and a 12 g Thomson silica gel column. The fractions containing the expected product were combined and were concentrated under reduced pressure to give (1R,3aS,5aR,5bR,7aR,11aR,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.109 g, 0.195 mmol, 64.3% yield) as an off-white solid. $^1$H NMR (500 MHz, chloroform-d) δ=5.57 (dd, J=6.8, 1.9 Hz, 1H), 4.73 (d, J=1.6 Hz, 1H), 4.63-4.60 (m, 1H), 2.54 (td, J=10.9, 5.3 Hz, 1H), 2.17 (dd, J=17.1, 6.9 Hz, 1H), 2.08-1.99 (m, 1H), 1.70 (s, 3H), 1.13 (s, 3H), 1.08 (s, 3H), 1.03 (s, 3H), 0.97 (s, 3H), 0.93 (s, 3H), 1.82-0.91 (m, 20H).

Method 2

Intermediate 1

Preparation of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate

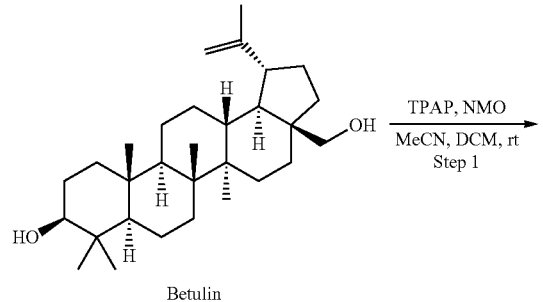

Betulin

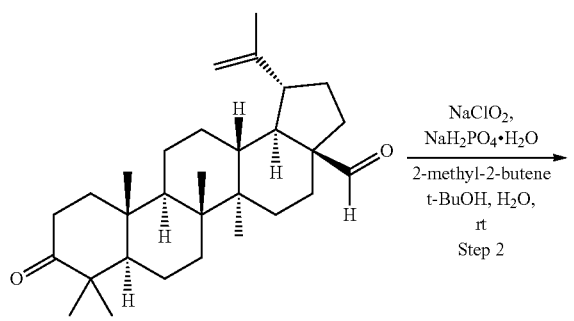

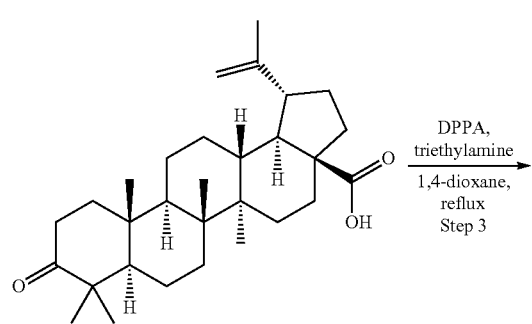

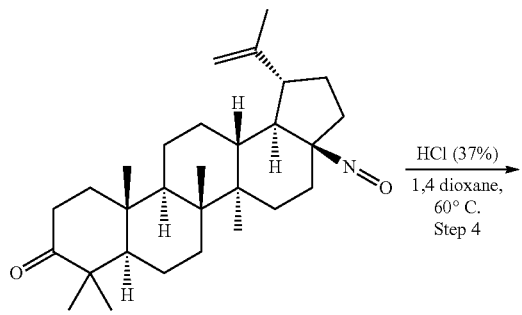

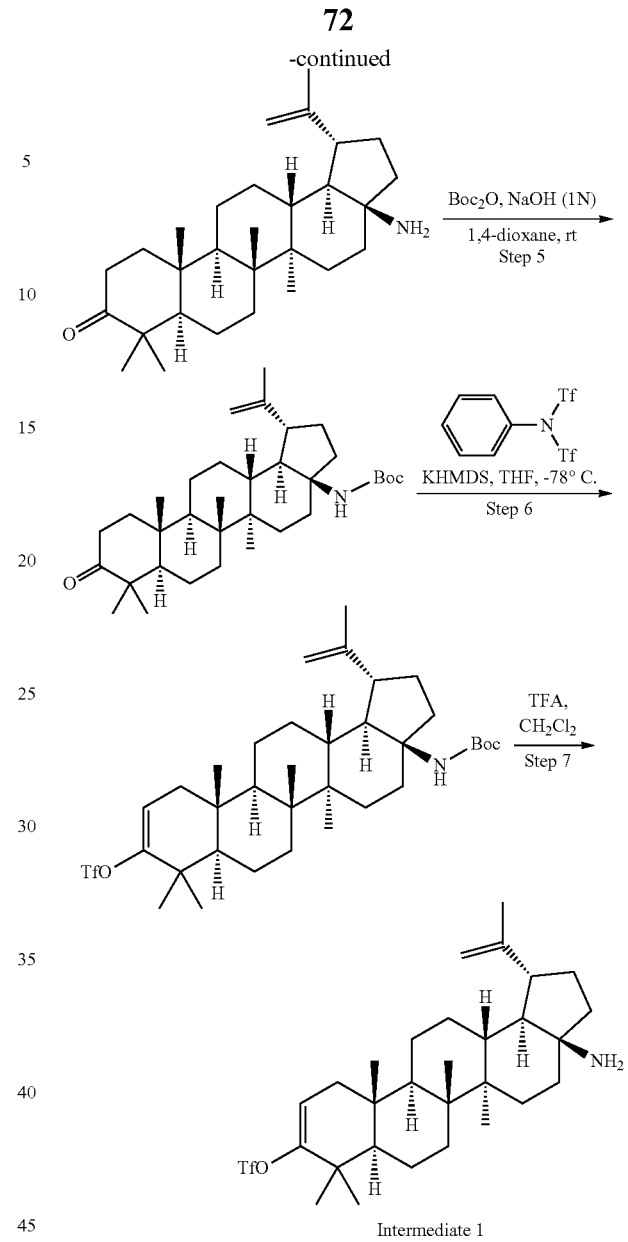

Intermediate 1

Step 1: Preparation of (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carbaldehyde To suspension of (1R,3aS,5aR,5bR,7aR,9S,11aR,11bR,13aR,13bR)-3a-(hydroxymethyl)-5a,5b,8,8,11a-pentamethyl-1-(prop-1-en-2-yl)icosahydro-1H-cyclopenta[a]chrysen-9-ol (20 g, 45.2 mmol) in acetonitrile (200 mL) and DCM (300 mL) was added 4 angstrom molecular sieves (5 g) and the mixture was stirred for 10 minutes at rt. To the mixture was then added NMO (15.88 g, 136 mmol) and TPAP (0.794 g, 2.259 mmol). The dark green mixture was stirred under nitrogen overnight. Additional NMO (2.0 g) and TPAP (0.08 g) were added and the mixture was stirred at rt for 7 h. The mixture was filtered through a pad of silica gel and celite which was washed with dichloromethane then 25% EtOAc in hexanes. The filtrate was concentrated under reduced pressure and purified using a Thomson 240 g silica gel column and a 15-20% ethyl acetate in hexanes gradient. The title product was isolated as a white foam (17.6 g, 40.1 mmol, 89%). $^1$H NMR (400 MHz, chloroform-d) δ=9.68 (d, J=1.5 Hz, 1H), 4.77 (d, J=2.0 Hz, 1H), 4.66-4.63 (m, 1H), 2.89 (td, J=11.2, 5.8 Hz, 1H), 2.56-2.36 (m, 2H), 2.16-2.03 (m, 2H), 1.97-1.84 (m, 2H), 1.71 (s, 3H), 1.08 (s, 3H), 1.03 (s, 3H), 1.00 (s, 3H), 0.97 (s, 3H), 0.94 (s, 3H), 1.83-0.87 (m, 18H).

Step 2: Preparation of (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carboxylic acid

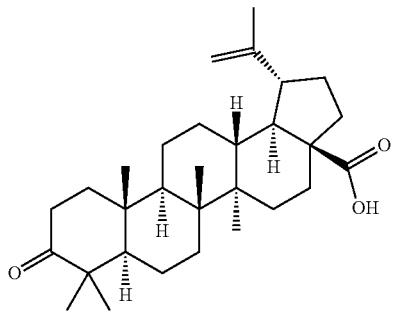

To a solution of (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carbaldehyde (17.6 g, 36.1 mmol) in t-BuOH (100 mL) was added 2-methyl-2-butene (40 mL, 476 mmol). A solution of sodium chlorite (15 g, 133 mmol) and sodium phosphate monobasic monohydrate (25 g, 181 mmol) in water (200 mL) was added drop wise over 1.25 h and the mixture was stirred at rt for an additional 45 minutes. The mixture was diluted with saturated aqueous ammonium chloride (100 mL) and extracted with ethyl acetate (3×125 mL). The combined organic layers were washed with brine and dried over sodium sulfate. The drying agent was removed by filtration and the filtrate was concentrated under reduced pressure. The residue was purified by using a 300 g Thomson silica gel column and a 10-50% ethyl acetate in hexanes gradient. The fractions containing the expected product were combined and concentrated under reduced pressure to give (1R,3aS,5aR,5bR,7aR,11aR,11bR,13 aR,13bR)-5a,5b,8,8,11a-pentamethyl-9-oxo-1-(prop-1-en-2-yl)icosahydro-1H-cyclopenta[a]chrysene-3a-carboxylic acid as a white foam (16.4 g, 36.1 mmol, 100%). LCMS: m/e 453.2 (M−H)$^-$, 2.61 min (method 3). $^1$H NMR (400 MHz, chloroform-d) δ=10.02 (br. s., 1H), 4.75 (d, J=1.8 Hz, 1H), 4.64-4.61 (m, 1H), 3.02 (td, J=10.8, 4.8 Hz, 1H), 2.55-2.36 (m, 3H), 2.33-2.19 (m, 2H), 2.08-1.86 (m, 4H), 1.70 (s, 3H), 1.08 (s, 3H), 1.02 (s, 3H), 1.00 (s, 3H), 0.98 (s, 3H), 0.93 (s, 3H), 1.82-0.90 (m, 15H).

Step 3: Preparation of (1R,3aS,5aR,5bR,7aR,11aR,11bR,13 aR,13bR)-3a-isocyanato-5a,5b,8,8,11a-pentamethyl-1-(prop-1-en-2-yl)octadecahydro-1H-cyclopenta[a]chrysen-9(5bH)-one

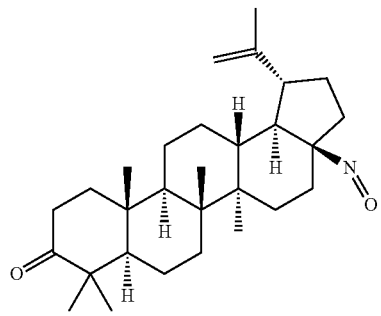

To a solution of (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carboxylic acid (16.41 g, 36.1 mmol) in 1,4-dioxane (200 mL) was added triethylamine (15.09 mL, 108 mmol) and diphenyl phosphorazidate (11.67 mL, 54.2 mmol). The mixture was heated to reflux for 18.5 h, then was cooled to rt and concentrated under reduced pressure. The residue was split into two portions and was purified using a 0-15% ethyl acetate in hexanes gradient and a Thomson 240 g silica gel column to purify each portion. The fractions containing the expected product were combined and concentrated under reduced pressure to give (1R,3aS,5aR,5bR,7aR,11aR,11bR,13aR,13bR)-3a-isocyanato-5a,5b,8,8,11a-pentamethyl-1-(prop-1-en-2-yl)octadecahydro-1H-cyclopenta[a]chrysen-9(5bH)-one (10.3 g, 22.80 mmol, 63.2% yield) as an off-white foam. $^1$H NMR (400 MHz, chloroform-d) δ=4.75 (d, J=2.0 Hz, 1H), 4.66-4.63 (m, 1H), 2.60-2.36 (m, 4H), 2.17-2.04 (m, 1H), 1.69 (s, 3H), 1.10 (s, 3H), 1.08 (s, 3H), 1.04 (s, 3H), 0.95 (s, 6H), 2.01-0.71 (m, 20H).

Step 4: Preparation of (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one, HCl

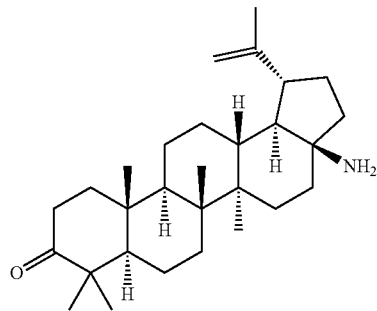

To a solution of (1R,3aS,5aR,5bR,7aR,11aR,11bR,13aR,13bR)-3a-isocyanato-5a,5b,8,8,11a-pentamethyl-1-(prop-1- en-2-yl)octadecahydro-1H-cyclopenta[a]chrysen-9(5bH)-one (10.3 g, 22.80 mmol) in 1,4-dioxane (100 mL) was added HCl (37%) (28.1 mL, 342 mmol). The mixture was heated to 60° C. for 15.5 h then was cooled to rt and was concentrated under reduced pressure. The residue was diluted with saturated aqueous sodium bicarbonate (150 mL) and was extracted with dichloromethane (3×100 mL). The combined organic layers were dried with sodium sulfate, filtered and concentrated under reduced pressure. The residue was purified by flash chromatography using a 20-60% ethyl acetate in hexanes gradient with 0.1% triethyl amine added to the mixture. The fractions containing the expected product were combined and concentrated under reduced pressure to give (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one, HCl (5.4 g, 11.68 mmol, 51.2% yield) as a yellow foam. LCMS: m/e 426.5 (M+H)$^+$, 1.59 min (method 1). $^1$H NMR (400 MHz, CHLOROFORM-d) δ=4.73 (d, J=2.3 Hz, 1H), 4.60 (dd, J=2.4, 1.4 Hz, 1H), 2.58-2.37 (m, 3H), 2.11-1.98 (m, 1H), 1.94-1.87 (m, 1H), 1.69 (d, J=0.5 Hz, 3H), 1.09 (s, 3H), 1.08 (s, 3H), 1.03 (s, 3H), 0.97 (s, 3H), 0.94 (s, 3H), 1.79-0.91 (m, 20H).

Step 5: Preparation of tert-butyl((1R,3aS,5aR,5bR,7aR,11aR,11bR,13 aR,13bR)-5a,5b,8,8,11a-pentamethyl-9-oxo-1-(prop-1-en-2-yl)icosahydro-1H-cyclopenta[a]chrysen-3a-yl)carbamate

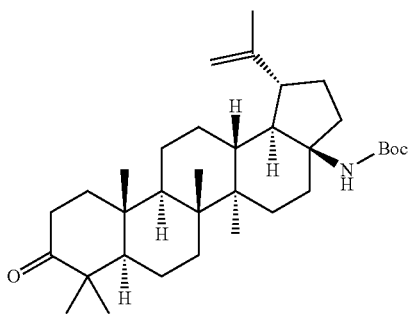

To a solution of (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one (5.25 g, 12.33 mmol) in 1,4-dioxane (50 mL) was added sodium hydroxide (1N) (24.67 mL, 24.67 mmol) followed by di-tert-butyl dicarbonate (3.15 mL, 13.57 mmol). The mixture was stirred at rt for 2 h then 30 mL of methanol, 50 mL of dichloromethane and 20 mL of water were added to help solubilize the mixture. After stirring for 1.5 h at rt, the reaction was not complete, so di-tert-butyl dicarbonate (0.3 g) was added and the mixture stirred at rt for 3 h. Again di-tert-butyl dicarbonate (0.3 g) was added and the mixture was stirred at rt for 16 h. Since traces of starting material were still present, di-tert-butyl dicarbonate (1 g) was added to the mixture and the stirring was continued for 6 h at which point TLC showed no starting material remaining. The mixture was diluted with water (75 mL) and extracted with dichloromethane (3×100 mL). The combined organic layers were washed with water (100 mL) then were dried with sodium sulfate, filtered and concentrated under reduced pressure. The residue was purified using a 0-10% ethyl acetate in hexanes gradient and a 240 g silica gel column. The fractions containing the expected product were combined and concentrated under reduced pressure to give tert-butyl((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate (5.85 g, 11.13 mmol, 90% yield) as a white foam. $^1$H NMR (400 MHz, chloroform-d) δ=4.72 (s, 1H), 4.62 (s, 1H), 4.33 (br. s., 1H), 2.64-2.32 (m, 5H), 2.06-1.84 (m, 2H), 1.69 (s, 3H), 1.45 (s, 9H), 1.08 (s, 3H), 1.06 (s, 3H), 1.03 (s, 3H), 0.97 (s, 3H), 0.94 (s, 3H), 1.74-0.86 (m, 18H).

Step 6: Preparation of (1R,3aS,5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate

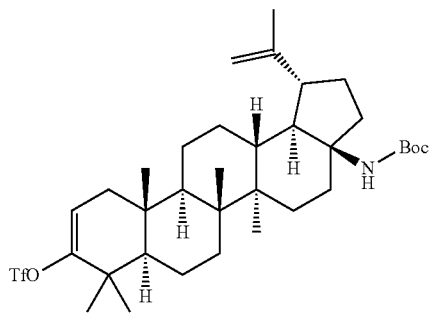

A flask containing a solution of tert-butyl ((1R,3 aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate (1.2 g, 2.282 mmol) and 1,1,1-trifluoro-N-phenyl-N-(trifluoromethyl)sulfonyl methanesulfonamide (1.019 g, 2.85 mmol) in THF (20 mL) was cooled to −78° C. To the solution was added KHMDS (0.91 M in THF) (5.52 mL, 5.02 mmol). The mixture was stirred at −78° C. for 1 h then warmed to rt and stirred for 1 h. The reaction was then quenched with saturated aqueous ammonium chloride (30 mL) and extracted with ethyl acetate (3×30 mL). The combined organic layers were dried over magnesium sulfate. The drying agent was removed by filtration and the filtrate was concentrated under reduced pressure. The crude material was purified using a 0-12% ethyl acetate in hexanes gradient and a Thomson 80 g silica gel column. The fractions containing the expected product were combined and concentrated under reduced pressure to give (1R,3aS,5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.9 g, 1.368 mmol, 59.9% yield) as a white foam. $^1$H NMR (500 MHz, chloroform-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 7: Same Experimental Procedure Described for Step 6 in Method 1 Above

Alternatively, the intermediate (1R,3aS,5aR,5bR,7aR,11aR,11bR,13aR,13bR)-3a-isocyanato-5a,5b,8,8,11a-pentamethyl-1-(prop-1-en-2-yl)octadecahydro-1H-cyclopenta

[a]chrysen-9(5bH)-one can be prepared from betulinic acid following the scheme shown below:

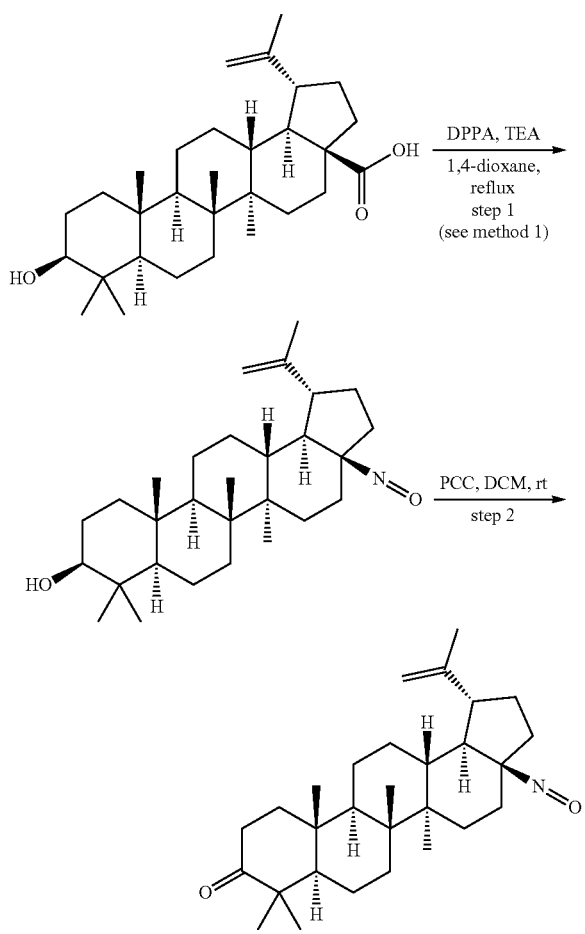

Step 1: Preparation of (1R,3aS,5aR,5bR,7aR,9S, 11aR,11bR,13aR,13bR)-3a-isocyanato-5a,5b,8,8, 11a-pentamethyl-1-(prop-1-en-2-yl)icosahydro-1H-cyclopenta[a]chrysen-9-ol The title compound was prepared using the same conditions described above in Step 1, method 1 using betulinic acid as starting material.

Step 2

To a solution of 24 g of crude (1R,3aS,5aR,5bR,7aR,9S, 11aR,11bR,13aR,13bR)-3a-isocyanato-5a,5b,8,8,11a-pentamethyl-1-(prop-1-en-2-yl)icosahydro-1H-cyclopenta[a]chrysen-9-ol in dichloromethane (200 mL) was added PCC (11.80 g, 54.8 mmol) in three portions over 45 minutes. The mixture was stirred at rt for 4 h, then an additional 1 g of PCC was added and the mixture was further stirred at rt for 2 h. The mixture was filtered through a plug of silica gel and celite and the plug was washed with a 1:1 solution of ethyl acetate: hexanes. The filtrate was concentrated under reduced pressure to give the crude product which was used in the next step with no additional purification. $^1$H NMR (500 MHz, Chloroform-d) δ=4.76-4.74 (m, 1H), 4.65-4.63 (m, 1H), 2.62-2.36 (m, 3H), 2.16-2.03 (m, 1H), 1.69 (s, 3H), 1.10 (s, 3H), 1.08 (s, 3H), 1.04 (s, 3H), 0.96 (s, 6H), 1.95-0.91 (m, 21H).

Preparation and purification of (R)- and (S)-benzyl 4-(4,4,5,5-tetramethyl-1,3,2-dioxaborolan-2-yl)cyclohex-3-enecarboxylate

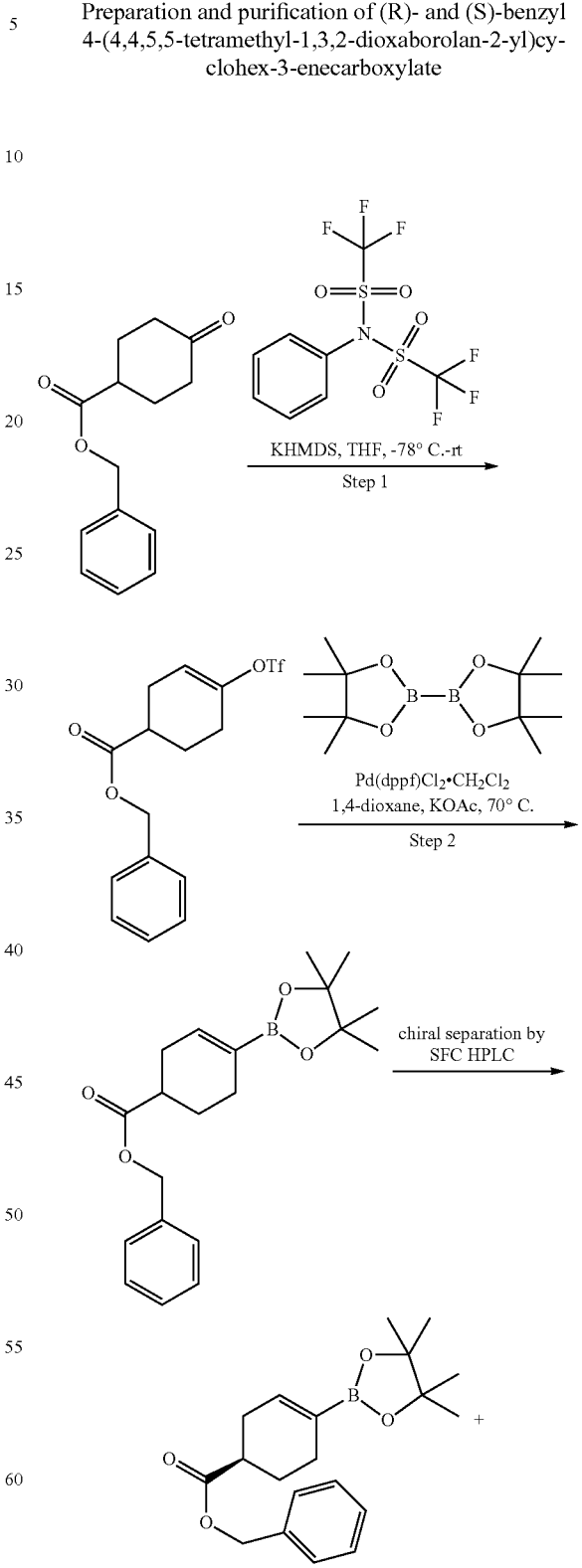

(R)-benzyl 4-(4,4,5,5-tetramethyl-1,3,2-dioxaborolan-2-yl)cyclohex-3-enecarboxylate

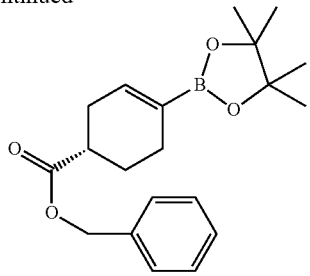

(S)-benzyl 4-(4,4,5,5-tetramethyl-1,3,2-
dioxaborolan-2-yl)cyclohex-3-
enecarboxylate

Step 1. Preparation of benzyl 4-(((trifluoromethyl)sulfonyl)oxy)cyclohex-3-enecarboxylate A rbf containing benzyl 4-oxocyclohexanecarboxylate (6.0 g, 25.8 mmol) (see *Bioorg. Med. Chem. Lett.* 2008, 18, 5107-5110. for the preparation) and 1,1,1-trifluoro-N-phenyl-N-((trifluoromethyl)sulfonyl)methanesulfonamide (10.15 g, 28.4 mmol) was evacuated and backfilled with nitrogen three times. The mixture was diluted with THF (100 mL) and was cooled to −78° C. To the mixture was added KHMDS (0.5M in toluene) (64.6 mL, 32.3 mmol) slowly over 20 minutes. The mixture was stirred at −78° C. for 30 minutes then the ice bath was removed and it was stirred for 1.5 h at rt. The mixture was diluted with water (150 mL) and was extracted with ethyl acetate (3×150 mL). The combined organic layers were washed with brine, dried over magnesium sulfate, filtered, and concentrated under reduced pressure to give the crude benzyl 4-(((trifluoromethyl)sulfonyl)oxy)cyclohex-3-enecarboxylate as a light-red oil. The crude product was used in the next step with no additional purification. ¹H NMR (500 MHz, CHLOROFORM-d) δ=7.42-7.29 (m, 5H), 5.79-5.76 (m, 1H), 5.18-5.13 (m, 2H), 2.70-2.61 (m, 1H), 2.52-2.34 (m, 4H), 2.20-2.13 (m, 1H), 1.99-1.90 (m, 1H).

Step 2. Preparation of benzyl 4-(4,4,5,5-tetramethyl-1,3,2-dioxaborolan-2-yl)cyclohex-3-enecarboxylate To a flask containing the crude benzyl 4-(((trifluoromethyl)sulfonyl)oxy)cyclohex-3-enecarboxylate (9.40 g, 25.8 mmol) was added bis(pinacolato)diboron (6.88 g, 27.1 mmol), potassium acetate (6.33 g, 64.5 mmol), and 1,1'-bis(diphenylphosphino)ferrocenepalladium(II) dichloride (0.637 g, 0.774 mmol). The mixture was evacuated and filled with nitrogen 3 times, then was diluted with 1,4-dioxane (100 mL) and was heated to 70° C. for 21.5 h. The mixture was cooled to rt, diluted with water (100 mL), and extracted with ethyl acetate (3×100 mL). The organic layers were washed with brine, dried over magnesium sulfate, filtered, and concentrated under reduced pressure. The residue was purified by flash chromatography using a 0-30% ethyl acetate in hexanes gradient and a 300 g silica gel column. The fractions containing the expected product were combined and concentrated under reduced pressure to give 4.26 g of the product as a clear, colorless oil. The sample was divided and one portion (1.0 g) was purified a second time by flash chromatography using a 0-7% acetone in hexanes gradient. The fractions containing the product were combined and concentrated under reduced pressure to give 0.7 g of benzyl 4-(4,4,5,5-tetramethyl-1,3,2-dioxaborolan-2-yl)cyclohex-3-enecarboxylate as a clear, colorless oil. A second portion (2.9 g), was purified by chiral SFC (chiral SFC method 2) to give the two separate enantiomers: enantiomer 1: (R)-benzyl 4-(4,4,5,5-tetramethyl-1,3,2-dioxaborolan-2-yl)cyclohex-3-enecarboxylate: 0.883 g; and enantiomer 2: (S)-benzyl 4-(4,4,5,5-tetramethyl-1,3,2-dioxaborolan-2-yl)cyclohex-3-enecarboxylate: 0.932 g. ¹H NMR (500 MHz, chloroform-d) δ=7.42-7.32 (m, 5H), 6.59-6.55 (m, 1H), 5.15 (s, 2H), 2.65-2.58 (m, 1H), 2.42-2.37 (m, 2H), 2.34-2.26 (m, 1H), 2.20-2.03 (m, 2H), 1.71-1.59 (m, 1H), 1.28 (s, 12H).

Preparation of (R)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

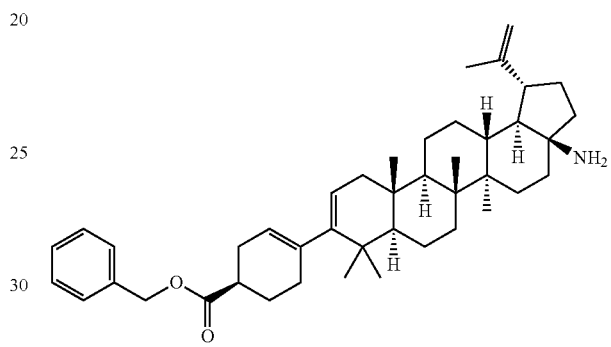

To a vial containing (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (0.65 g, 1.165 mmol) was added phosphoric acid, potassium salt (0.742 g, 3.50 mmol), (R)-benzyl 4-(4,4,5,5-tetramethyl-1,3,2-dioxaborolan-2-yl)cyclohex-3-enecarboxylate (0.8 g, 2.338 mmol) (enantiomer 1 prepared above), 2-dicyclohexylphosphino-2',6'-dimethoxy-1,1'-biphenyl (S-phos) (0.072 g, 0.175 mmol) and palladium (II) acetate (0.026 g, 0.117 mmol). The mixture was diluted with 1,4-dioxane (10 mL) and water (1 mL), flushed with nitrogen, then the vial was sealed and heated to 75° C. After 6 h of heating, the mixture was cooled to rt, diluted with water (20 mL) and brine (20 mL), and was extracted with dichloromethane (5×40 mL). The organic layers were dried with sodium sulfate, filtered, and concentrated under reduced pressure. The residue was purified by flash chromatography using a 10-60% ethyl acetate in hexanes gradient and a 40 g silica gel column. The fractions containing the expected product were combined and were concentrated under reduced pressure to give (R)-benzyl 4-((1R,3 aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.488 g, 0.782 mmol, 67.1% yield) as an off-white solid. LCMS: m/e 624.65 (M+H)⁺, 2.18 min (method 1). ¹H NMR (500 MHz, chloroform-d) δ=7.40-7.30 (m, 5H), 5.35 (br. s., 1H), 5.18 (dd, J=6.2, 1.8 Hz, 1H), 5.14 (s, 2H), 4.73 (d, J=2.0 Hz, 1H), 4.60 (s, 1H), 2.65-2.50 (m, 2H), 2.38-2.30 (m, 2H), 2.25-1.94 (m, 5H), 1.70 (s, 3H), 1.07 (s, 3H), 0.96 (s, 3H), 0.94 (s, 3H), 0.92 (s, 3H), 0.86 (s, 3H), 1.80-0.83 (m, 23H).

Preparation of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

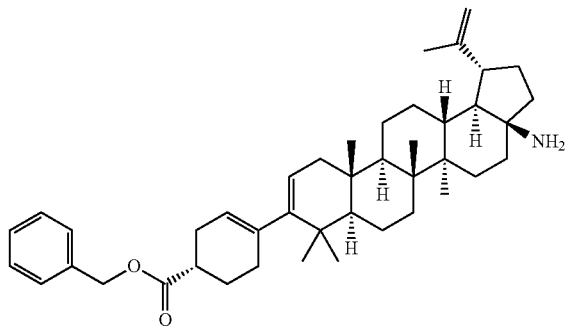

To a vial containing (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.05 g, 0.090 mmol) was added phosphoric acid, potassium salt (0.057 g, 0.269 mmol), (S)-benzyl 4-(4,4,5,5-tetramethyl-1,3,2-dioxaborolan-2-yl)cyclohex-3-enecarboxylate (0.062 g, 0.181 mmol) (enantiomer 2 prepared above), 2-dicyclohexylphosphino-2',6'-dimethoxy-1,1'-biphenyl (S-phos) (5.52 mg, 0.013 mmol), and palladium(II) acetate (2.013 mg, 8.96 μmol). The mixture was diluted with 1,4-dioxane (1 mL) and water (0.1 mL), was flushed with nitrogen, then was sealed and heated to 75° C. After 6 h of heating, the mixture was cooled to rt, was diluted with dichloromethane, and was dried with sodium sulfate. The drying agent was removed by filtration and the filtrate was concentrated under reduced pressure. The residue was purified by flash chromatography using a 10-60% ethyl acetate in hexanes gradient and a 12 g silica gel column. The fractions containing the expected product were combined and concentrated under reduced pressure to give (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.042 g, 0.067 mmol, 75% yield) as an off-white solid. $^1$H NMR (500 MHz, chloroform-d) δ=7.42-7.31 (m, 5H), 5.37 (br. s., 1H), 5.21-5.17 (m, 1H), 5.16 (s, 2H), 4.75 (d, J=1.9 Hz, 1H), 4.62 (s, 1H), 2.65-2.52 (m, 2H), 2.39-2.32 (m, 2H), 2.22-2.15 (m, 2H), 2.10-1.96 (m, 3H), 1.71 (s, 3H), 1.09 (s, 3H), 0.98 (s, 6H), 0.91 (s, 3H), 0.88 (s, 3H), 1.82-0.83 (m, 23H).

Example 1

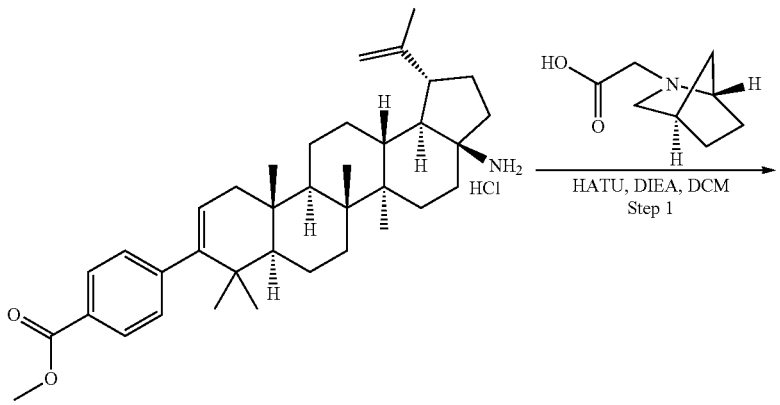

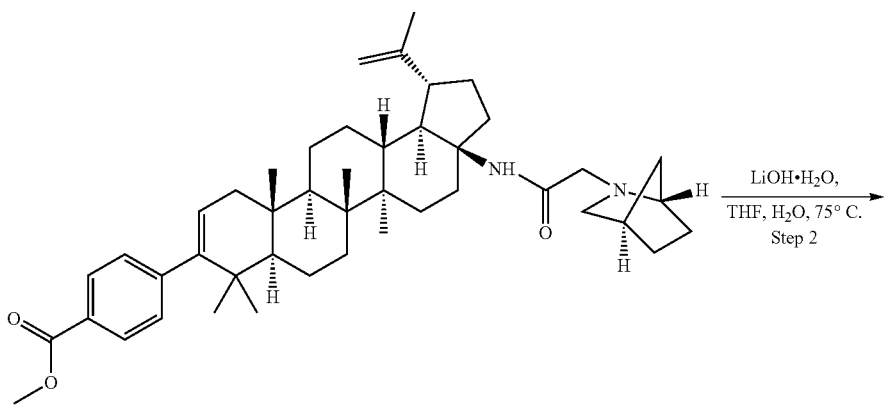

-continued

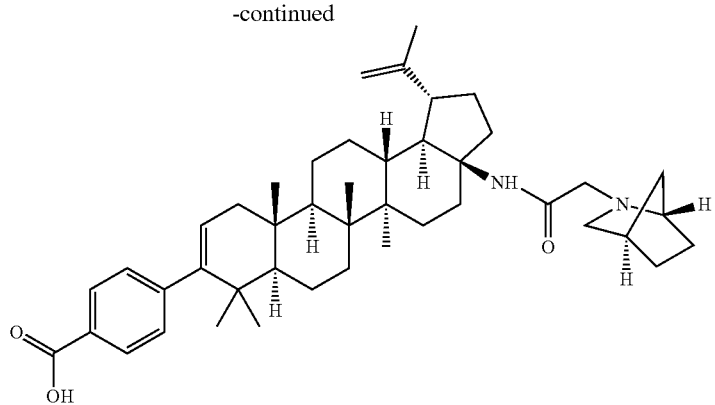

Example 1

Step 1. Preparation of methyl 4-((1R,3aS,5aR,5bR, 7aR,11aS,11bR,13 aR,13bR)-3a-(2-((1S,4R)-2-azabicyclo[2.2.1]heptan-2-yl)acetamido)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate Step 2. Preparation of 4-((1R,3aS,5aR,5bR,7aR, 11aS,11bR,13aR,13bR)-3a-(2-((1S,4R)-2-azabicyclo [2.2.1]heptan-2-yl)acetamido)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid

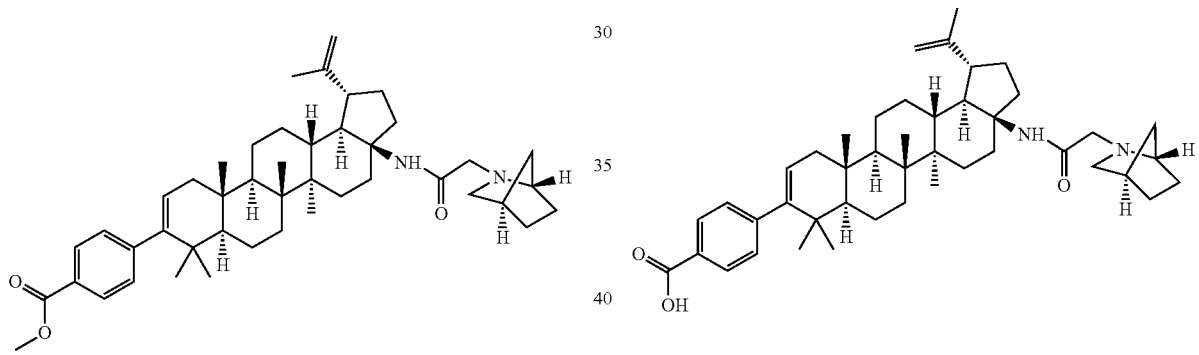

Example 1

To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate, HCl (100 mg, 0.172 mmol) and N,N-diisopropylethylamine (0.120 mL, 0.689 mmol) in DCM (3 mL) was added 2-((1S,4R)-2-azabicyclo[2.2.1]heptan-2-yl) acetic acid (40.1 mg, 0.258 mmol) and 2-(3H-[1,2,3]triazolo [4,5-β]pyridin-3-yl)-1,1,3,3-tetramethylisouronium hexafluorophosphate(V) (111 mg, 0.293 mmol). The reaction mixture was stirred at rt overnight. The reaction mixture was concentrated, dissolved in a mixture of THF (1 mL) and MeOH (0.5 mL) and purified by reverse phase HPLC using HPLC conditions 7 and dried under vacuum to give methyl 4-((1R,3aS,5aR,5bR,7aR,11aS,11bR,13aR,13bR)-3a-(2-((1S,4R)-2-azabicyclo[2.2.1]heptan-2-yl)acetamido)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoate, TFA (80.6 mg, 58.8% yield) as a white solid. LCMS: m/e 681.7 (M+H)$^+$, 3.65 min (method 2).

To a solution of methyl 4-((1R,3aS,5aR,5bR,7aR,11aS, 11bR,13aR,13bR)-3a-(2-((1S,4R)-2-azabicyclo[2.2.1]heptan-2-yl)acetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (69.6 mg, 0.102 mmol) in THF (5 mL) was added a 0.753 molar solution of LiOH.H$_2$O (17.16 mg, 0.409 mmol) in H$_2$O. The reaction was heated to 75° C. for 6.5 h. The reaction was concentrated to dryness and the crude residue was dissolved in a mixture of THF (1.0 mL) and MeOH (0.5 mL), filtered and purified using HPLC method 2 and dried under vacuum to give 4-((1R,3aS,5aR,5bR,7aR,11aS,11bR,13aR, 13bR)-3a-(2-((1S,4R)-2-azabicyclo[2.2.1]heptan-2-yl)acetamido)-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)benzoic acid, TFA (51.3 mg, 61.1% yield) as a white solid. LCMS: m/e 667.6 (M+H)$^+$, 2.68 min (method 2). $^1$H NMR (500 MHz, 1:1 CDCl$_3$:MeOD) δ=7.92 (d, J=8.2 Hz, 2H), 7.38 (s, 1H), 7.20 (d, J=8.2 Hz, 2H), 5.29 (d, J=4.6 Hz, 1H), 4.76 (br. s., 1H), 4.65 (br. s., 1H), 4.00-3.84 (m, 2H), 3.52-3.41 (m, 1H), 2.98 (t, J=12.1 Hz, 1H), 2.76 (br. s., 1H), 2.71-2.61 (m, 2H), 2.36 (dd, J=7.8, 12.1 Hz, 1H), 2.13 (dd, J=6.4, 17.1 Hz, 1H), 2.06-1.95 (m, 2H), 1.94-1.83 (m, 4H), 1.78 (d, J=13.4 Hz, 1H), 1.74 (br. s., 1H), 1.72 (s, 3H), 1.70-1.65 (m, 1H), 1.59-1.31 (m, 12H), 1.26 (br. s., 1H), 1.19-1.12 (m, 1H), 1.10 (s, 3H), 1.09 (br. s., 1H), 1.03 (s, 3H), 1.01 (s, 3H), 0.95 (br. s., 3H), 0.94 (br. s., 3H).
Example 2
Preparation of 4-((1R,3 aS,5aR,5bR,7aR,11aS,11bR, 13aR,13bR)-3a-(2-((1S,4S)-2,2-dioxido-2-thia-5-azabicyclo[2.2.1]heptan-5-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid
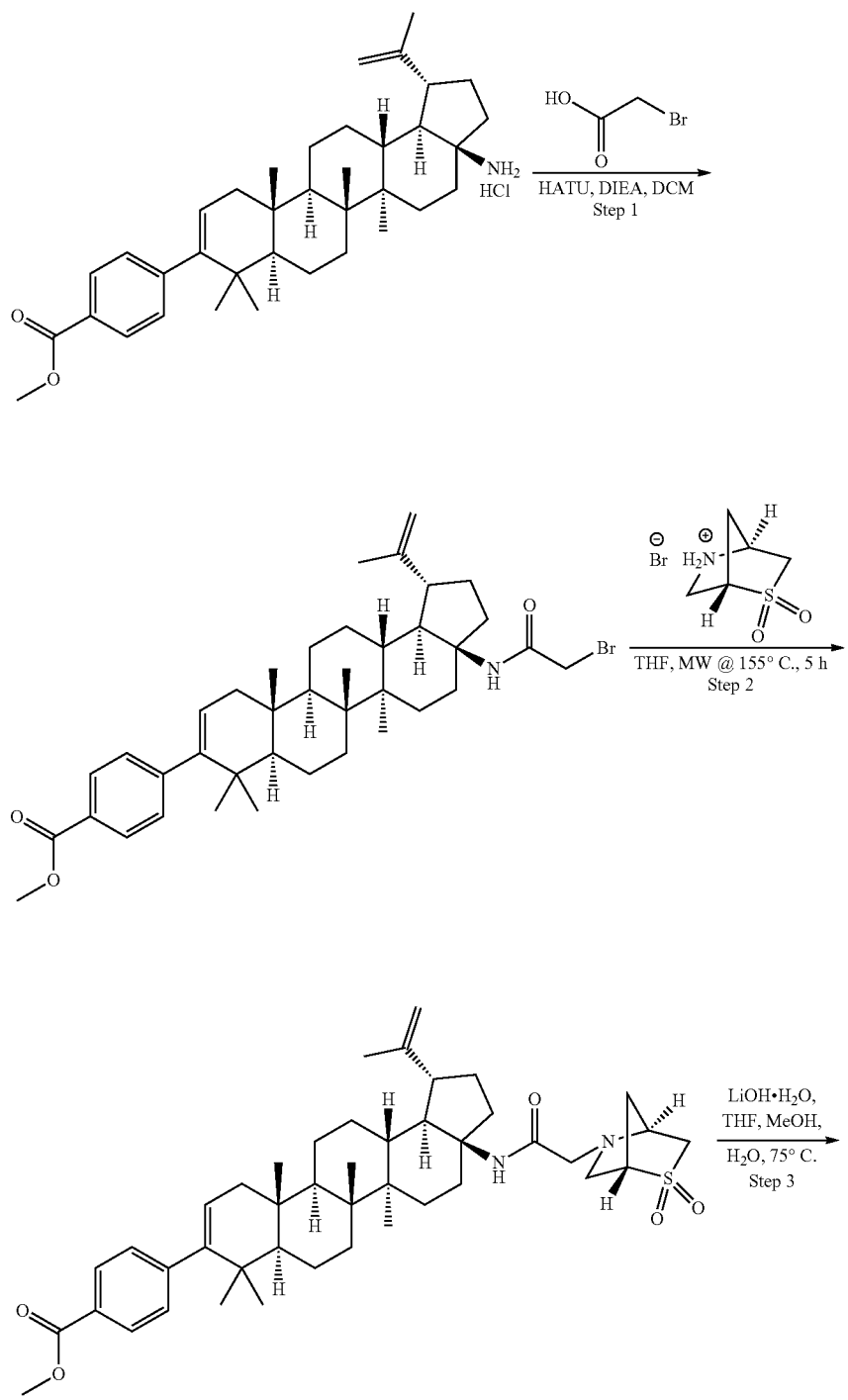

-continued

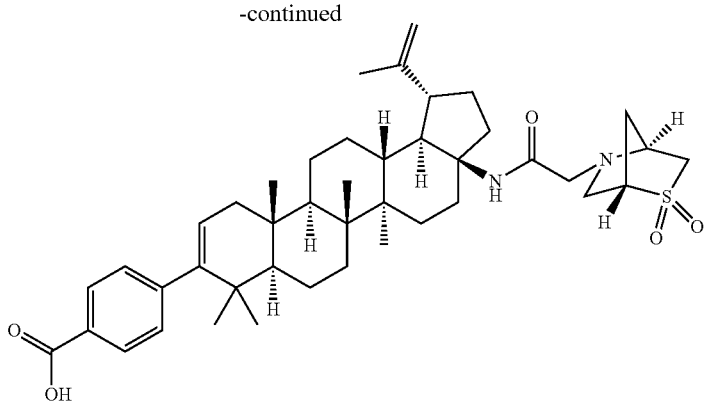

Example 2

Step 1. Preparation of methyl 4-((1R,3aS,5aR,5bR, 7aR,11aS,11bR,13aR,13bR)-3a-(2-bromoacetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate Step 2. Preparation of methyl 4-((1R,3aS,5aR,5bR, 7aR,11aS,11bR,13aR,13bR)-3a-(2-((1S,4S)-2,2-dioxido-2-thia-5-azabicyclo[2.2.1]heptan-5-yl)acetamido)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate

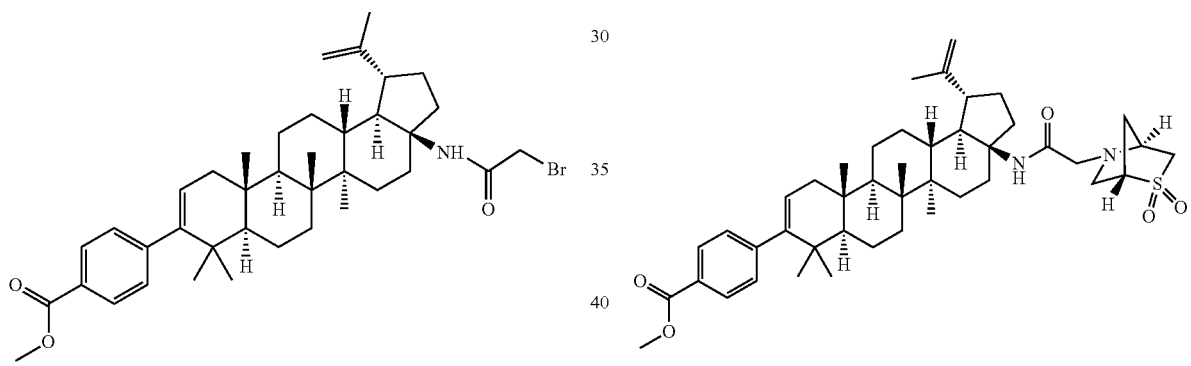

To a solution of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoate, HCl (403 mg, 0.694 mmol) in DCM (10 mL) was added N,N-diisopropylethylamine (0.484 mL, 2.78 mmol), bromoacetic acid (106 mg, 0.764 mmol) and 2-(3H-[1,2,3]triazolo[4,5-13]pyridin-3-yl)-1,1,3,3-tetramethylisouronium hexafluorophosphate(V) (317 mg, 0.833 mmol). The reaction mixture was stirred at rt for 15 h. Then, the reaction was concentrated and the crude residue was dissolved in THF (3.0 mL) filtered and purified by reverse phase preparative HPLC using HPLC method 2 to give methyl 4-((1R,3aS,5aR,5bR, 7aR,11aS,11bR,13aR,13bR)-3a-(2-bromoacetamido)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoate (148.9 mg, 32.3% yield) as a white solid. LCMS: m/e 664.6 (M+H)$^+$, 2.41 min (method 3).

To a solution of methyl 4-((1R,3aS,5aR,5bR,7aR,11aS, 11bR,13aR,13bR)-3a-(2-bromoacetamido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate (95 mg, 0.143 mmol) in THF (2 mL) in a microwave reaction tube was added N,N-di-iso-propylethylamine (0.125 mL, 0.715 mmol) followed by (1S,4S)-2-thia-5-azabicyclo[2.2.1]heptane 2,2-dioxide, hydrobromide (98 mg, 0.429 mmol). The resulting slurry was heated to 155° C. in a microwave. After 5 h, the reaction mixture was diluted with MeOH (1 mL), filtered and purified by a reverse phase prep-HPLC using Prep HPLC method 1 to give methyl 4-((1R,3 aS,5aR,5bR,7aR,11aS,11bR,13aR,13bR)-3a-(2-((1S,4S)-2,2-dioxido-2-thia-5-azabicyclo[2.2.1]heptan-5-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as a white solid (65.5 mg, 61% yield) after drying in a vacuum oven overnight at 50° C. LC/MS: m/e 731.3 (M+H)$^+$, 2.88 min (method 1). $^1$H NMR (400 MHz, CHLOROFORM-d) δ 7.92 (d, J=8.3 Hz, 2H), 7.19 (d, J=8.3 Hz, 2H), 6.93 (s, 1H), 5.29 (d, J=4.9 Hz, 1H), 4.80 (s, 1H), 4.65 (s, 1H), 3.90 (s, 3H), 3.81 (br. s., 1H), 3.64 (br. s., 1H), 3.59 (d, J=11.2 Hz, 1H), 3.45 (d, J=16.1 Hz, 1H), 3.29 (d, J=12.7 Hz, 1H), 3.23 (d, J=16.1 Hz, 1H), 3.07 (dd, J=12.5, 2.9 Hz, 2H), 2.72-2.58 (m, 2H), 2.56-2.38 (m, 3H), 2.11 (dd, J=17.1, 6.4 Hz, 1H), 1.92-1.75 (m, 2H), 1.71 (s, 3H), 1.65 (d, J=5.6 Hz, 2H), 1.59-1.40 (m, 8H), 1.40-1.20 (m, 4H), 1.13 (d, J=13.0 Hz, 2H), 1.03 (s, 3H), 1.01 (s, 3H), 0.98 (s, 3H), 0.92 (s, 6H). $^{13}$C NMR (101 MHz, CHLOROFORM-d) δ168.0, 167.1, 148.9, 148.5, 146.2, 130.0, 128.4, 127.9, 123.9, 110.6, 64.4, 62.2, 61.0, 59.8, 59.4, 54.3, 52.6, 51.9, 49.2, 49.0, 48.0, 42.0, 41.6, 40.5, 38.5, 37.4, 36.2, 35.1, 34.5, 33.2, 29.6, 29.4, 28.7, 27.2, 25.0, 21.3, 21.0, 19.6, 19.1, 16.4, 15.7, 14.4

Step 3. Preparation of 4-((1R,3aS,5aR,5bR,7aR, 11aS,11bR,13aR,13bR)-3a-(2-((1S,4S)-2,2-dioxido-2-thia-5-azabicyclo[2.2.1]heptan-5-yl)acetamido)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

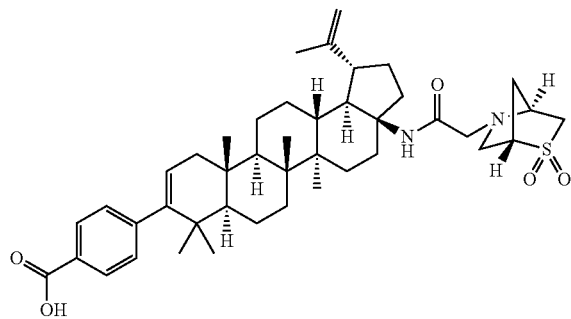

To a solution of methyl 4-((1R,3aS,5aR,5bR,7aR,11aS, 11bR,13aR,13bR)-3a-(2-((1S,4S)-2,2-dioxido-2-thia-5-azabicyclo[2.2.1]heptan-5-yl)acetamido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate (60 mg, 0.082 mmol) in THF (3 mL) and MeOH (1.00 mL) was added a solution of lithium hydroxide monohydrate (6.84 µl, 0.246 mmol) in water (0.50 mL). The reaction mixture was heated to 75° C. After 4 h, the reaction was concentrated to dryness. The material was redissolved in a mixture of THF (1.75 mL), MeOH (1 mL) and 1 N HCl (0.250 mL) and purified by reverse phase prep-HPLC using Prep HPLC method 4. The combined prep HPLC fractions were treated with 1N HCl (1 mL), concentrated and dried under reduce pressure to give 4-((1R,3 aS,5aR,5bR, 7aR,11aS,11bR,13 aR,13bR)-3a-(2-((1S,4S)-2,2-dioxido-2-thia-5-azabicyclo[2.2.1]heptan-5-yl)acetamido)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid, HCl (50.2 mg, 79% yield) as a white solid. LC/MS: m/e 717.5 (M+H)$^+$, 1.88 min (method 1). $^1$H NMR (400 MHz, 1:1 CDCl$_3$:METHANOL-d$_4$) δ 7.90 (d, J=8.1 Hz, 2H), 7.42 (br. s., 1H), 7.18 (d, J=8.1 Hz, 2H), 5.27 (d, J=4.9 Hz, 1H), 4.76 (br. s., 1H), 4.63 (br. s., 1H), 4.47 (br. s., 1H), 4.05 (br. s., 1H), 3.68 (br. s., 1H), 3.53-3.45 (m, 1H), 3.42-3.34 (m, 1H), 2.84-2.56 (m, 4H), 2.42-2.32 (m, 1H), 2.11 (dd, J=17.0, 6.2 Hz, 1H), 2.00-1.74 (m, 4H), 1.70 (s, 3H), 1.68-1.64 (m, 1H), 1.60-1.29 (m, 12H), 1.24 (br. s., 1H), 1.08 (br. s., 3H), 1.01 (br. s., 3H), 0.99 (br. s., 3H), 0.92 (br. s., 3H), 0.92 (br. s., 3H). $^{13}$C NMR (101 MHz, 1:1 CDCl$_3$:METHANOL-d$_4$) δ 209.8, 169.8, 150.0, 149.5, 147.1, 130.8, 129.5, 129.1, 124.7, 111.0, 78.65-78.52, 66.7, 66.6, 65.4, 60.4, 55.7, 53.7, 50.2, 49.9, 47.8, 42.7, 42.5, 41.4, 41.21-41.02, 38.4, 38.2, 37.0, 35.4, 34.3, 30.1, 30.0, 29.4, 28.0, 26.0, 22.1, 21.6, 20.5, 19.5, 17.1, 16.4, 14.9.

Example 3

Preparation of 4-((1R,3aS,5aR,5bR,7aR,11aS,11bR, 13aR,13bR)-3a-(2-((1S,4S)-5-benzyl-2,5-diazabicyclo[2.2.1]heptan-2-yl)acetamido)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid

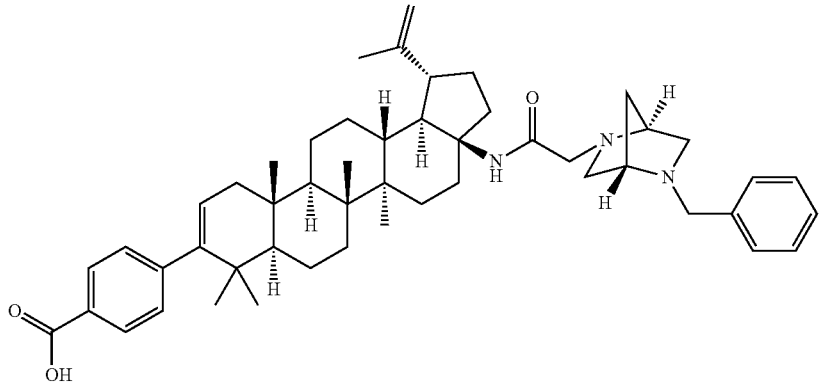

Step 1

To a solution of methyl 4-((1R,3aS,5aR,5bR,7aR,11aS, 11bR,13aR,13bR)-3a-(2-bromoacetamido)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (150 mg, 0.226 mmol) in THF (3 mL) in a 5 mL microwave tube was added N-ethyl-N-isopropylpropan-2-amine (0.197 mL, 1.128 mmol) and (1S,4S)-2-benzyl-2,5-diazabicyclo[2.2.1]heptane, hydrobromide (121 mg, 0.451 mmol). Reaction mixture was heated to 150° C. in a microwave for 8 h. The reaction was filtered and crude liquid filtrate was purified by reverse phase prep-HPLC using HPLC method 4 to give methyl 4-((1R,3aS,5aR,5bR,7aR,11aS, 11bR,13aR,13bR)-3a-(2-((1S,4S)-5-benzyl-2,5-diazabicyclo[2.2.1]heptan-2-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, 2 TFA (68.7 mg, 29.8% yield) as light brown foam. LC/MS: m/e 772.4 (M+H)+, 2.53 min (method 3). $^1$H NMR (400 MHz, CHLOROFORM-d) δ 7.94 (d, J=8.3 Hz, 2H), 7.54 (br. s., 2H), 7.49 (br. s., 3H), 7.20 (d, J=8.1 Hz, 2H), 6.73 (br. s., 1H), 5.30 (d, J=4.6 Hz, 1H), 4.76 (br. s., 1H), 4.65 (s, 1H), 4.46-4.27 (m, 4H), 4.09 (br. s., 2H), 3.92 (s, 4H), 3.82-3.76 (m, 1H), 3.57 (br. s., 1H), 3.36 (br. s., 1H), 2.58 (d, J=11.7 Hz, 3H), 2.44-2.34 (m, 1H), 2.11 (dd, J=17.2, 6.2 Hz, 1H), 1.89 (dt, J=6.7, 3.2 Hz, 1H), 1.72 (br. s., 2H), 1.70 (s, 3H), 1.65 (br. s., 1H), 1.58-1.20 (m, 13H), 1.15-1.05 (m, 2H), 0.99 (s, 3H), 0.97 (s, 6H), 0.94 (br. s., 3H), 0.93 (br. s., 3H).

Step 2

To a solution of methyl 4-((1R,3aS,5aR,5bR,7aR,11aS,11bR,13aR,13bR)-3a-(2-((1S,4S)-5-benzyl-2,5-diazabicyclo[2.2.1]heptan-2-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (56 mg, 0.073 mmol) in THF (3 mL) and MeOH (1 mL) was added a solution of lithium hydroxide monohydrate (8.06 µl, 0.290 mmol) in water (1 mL). The reaction mixture was heated to 75° C. for 6 h and concentrated to dryness. Material was dissolved in 2 mL THF, 2 ML H$_2$O, 0.5 mL 1N HCl and the mixture was extracted 2×15 mL OF 1:1 THF:EtOAc. The combined organic layer was dried over MgSO$_4$ filtered and concentrated and dried to give 4-((1R,3 aS,5aR,5bR,7aR,11aS,11bR,13 aR,13bR)-3a-(2-((1S,4S)-5-benzyl-2,5-diazabicyclo[2.2.1]heptan-2-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 HCl (37.1 mg, 61.6% yield) as white solid. LC/MS: m/e 758.4 (M+H)+, 2.40 min (method 3). $^1$H NMR (400 MHz, 1:1 CDCl$_3$:METHANOL-d$_4$) δ 7.90 (d, J=8.1 Hz, 2H), 7.56 (dd, J=6.5, 3.1 Hz, 2H), 7.48-7.41 (m, 3H), 7.21 (br. s., 1H), 7.18 (d, J=8.1 Hz, 2H), 5.27 (d, J=4.9 Hz, 1H), 4.75 (br. s., 1H), 4.62 (s, 1H), 4.46-4.40 (m, 1H), 4.31 (d, J=13.2 Hz, 1H), 4.28 (br. s., 1H), 4.13 (br. s., 1H), 3.83 (d, J=15.9 Hz, 1H), 3.75-3.61 (m, 3H), 3.37 (d, J=12.2 Hz, 2H), 2.58 (dd, J=9.8, 3.7 Hz, 2H), 2.52-2.45 (m, 1H), 2.41-2.31 (m, 2H), 2.10 (dd, J=17.0, 6.2 Hz, 1H), 1.95-1.82 (m, 1H), 1.75 (d, J=11.0 Hz, 2H), 1.69 (s, 3H), 1.67-1.62 (m, 1H), 1.51-1.38 (m, 8H), 1.37-1.28 (m, 3H), 1.27-1.20 (m, 3H), 1.16-1.06 (m, 2H), 1.00 (s, 3H), 1.00 (s, 3H), 0.97 (s, 3H), 0.92 (br. s., 3H), 0.91 (br. s., 3H). $^{13}$C NMR (101 MHz, 1:1 CDCl$_3$:METHANOL-d$_4$) δ 169.8, 167.3, 150.0, 149.5, 147.1, 131.3, 130.9, 130.8, 130.4, 130.2, 129.4, 129.0, 124.7, 110.9, 78.56-78.52, 66.3, 64.1, 63.5, 57.3, 56.3, 53.6, 50.1, 49.9, 47.9, 42.7, 42.4, 41.3, 38.6, 38.2, 37.0, 35.3, 34.2, 33.5, 30.8, 30.3, 30.1, 29.9, 29.4, 28.0, 26.0, 22.0, 21.6, 20.4, 19.6, 17.0, 16.3, 14.9.

Example 4

Preparation of 4-((1S,3aS,5aR,5bR,7aR,11aS,11bR,13aR,13bR)-3a-(2-((1S,4S)-2,2-dioxido-2-thia-5-azabicyclo[2.2.1]heptan-5-yl)acetamido)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

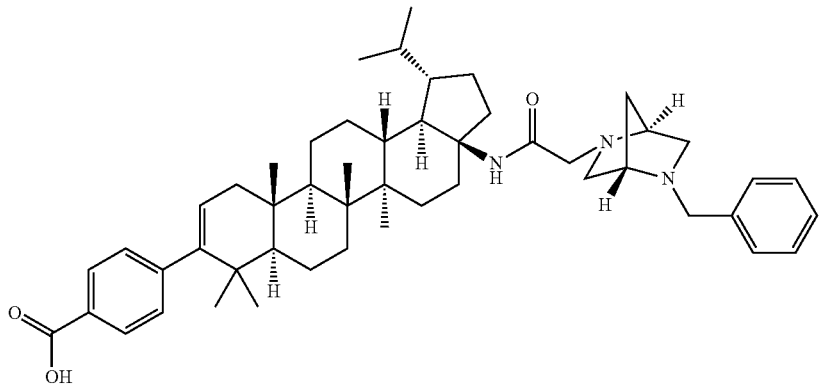

To a solution of 4-((1R,3aS,5aR,5bR,7aR,11aS,11bR,13aR,13bR)-3a-(2-((1S,4S)-2,2-dioxido-2-thia-5-azabicyclo[2.2.1]heptan-5-yl)acetamido)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (15 mg, 0.021 mmol) in a mixture of THF (4 mL) and MeOH (1 mL) under a N$_2$ (g) atmosphere was added palladium hydroxide on carbon (3.67 mg, 5.23 µmol). The reaction mixture was purged with H$_2$ (g) and was stirred under a H$_2$ (g) atmosphere. After 6 h, the reaction mixture was filtered and washed with DCM and concentrated to give brown solid. The material was then plugged through a silica gel column (3 g), eluted with 90:10 DCM:MeOH, concentrated and dried to give 4-((1S,3 aS,5aR,5bR,7aR,11aS,11bR,13 aR,13bR)-3a-(2-((1S,4S)-2,2-dioxido-2-thia-5-azabicyclo[2.2.1]heptan-5-yl)acetamido)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid (11.5 mg, 76% yield) as a light brown solid. LC/MS: m/e 719.3 (M+H)+, 2.61 min (method 3). $^1$H NMR (400 MHz, 1:1 CDCl$_3$:METHANOL-d$_4$) δ 7.90 (d, J=7.3 Hz, 2H), 7.30-7.21 (m, 1H), 7.18 (d, J=7.3 Hz, 2H), 5.28 (d, J=4.9 Hz, 1H), 4.09 (br. s., 1H), 3.77 (br. s., 1H), 3.65 (d, J=6.6 Hz, 2H), 2.59 (d, J=12.7 Hz, 4H), 2.32 (d, J=11.2 Hz, 1H), 2.13 (dd, J=17.0, 5.7 Hz, 1H), 1.97-1.82 (m, 3H), 1.78-1.67 (m, 3H), 1.60-1.42 (m, 12H), 1.39 (br. s., 1H), 1.24 (br. s., 4H), 1.13 (br. s., 1H), 1.07 (br. s., 3H), 1.00 (br. s., 6H), 0.92 (br. s., 6H), 0.88 (d, J=6.4 Hz, 3H), 0.78 (d, J=6.4 Hz, 3H).

Examples 5 and 6

Preparation of 4-((1R,3 aS,5aR,5bR,7aR,11aS,11bR, 13 aR,13bR)-3a-((2-((1S,4S)-2,2-dioxido-2-thia-5-azabicyclo[2.2.1]heptan-5-yl)ethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid and 4-((1R,3 aS,5aR,5bR,7aR,11aS, 11bR,13 aR,13bR)-3a-((2-((1S,4S)-2,2-dioxido-2-thia-5-azabicyclo[2.2.1]heptan-5-yl)ethyl)(2-hydroxyethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid, 2 HCl

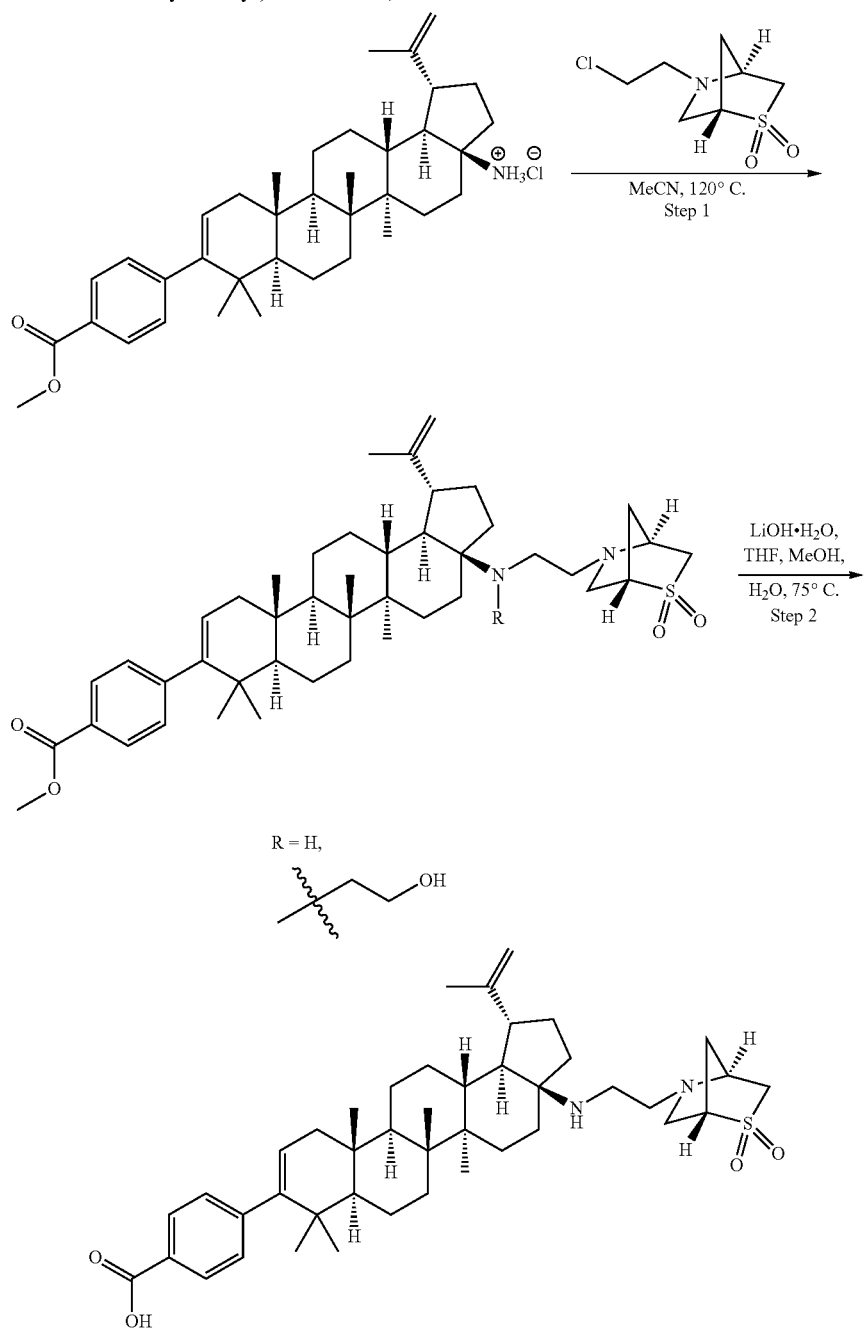

Example 5

-continued

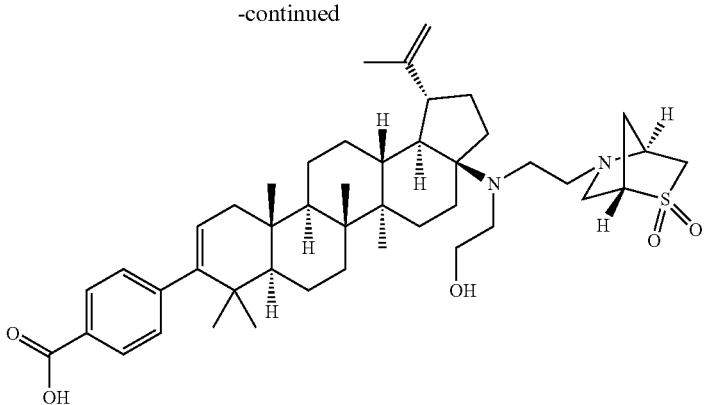

Example 6

Step 1. Preparation of methyl 4-((1R,3aS,5aR,5bR, 7aR,11aS,11bR,13aR,13bR)-3a-((2-((1S,4S)-2,2-dioxido-2-thia-5-azabicyclo[2.2.1]heptan-5-yl)ethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate, TFA and methyl 4-((1R,3 aS,5aR,5bR, 7aR,11aS,11bR,13aR,13bR)-3a-((2-((1S,4S)-2,2-dioxido-2-thia-5-azabicyclo[2.2.1]heptan-5-yl)ethyl) (2-hydroxyethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate, TFA

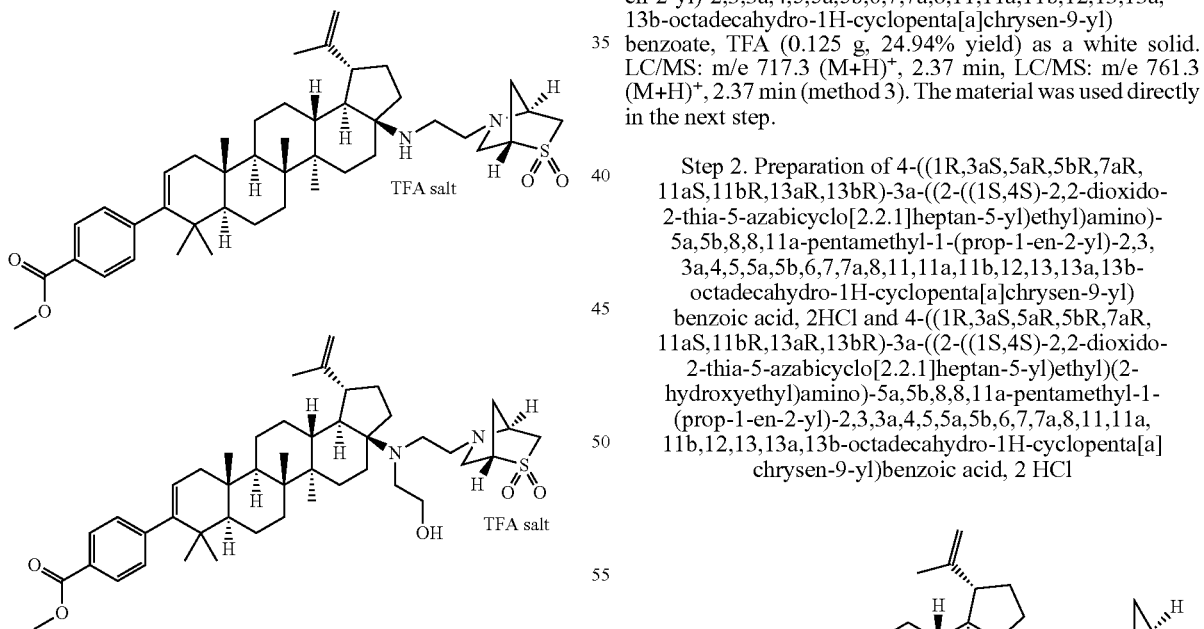

To a slurry of methyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate, HCl (0.350 g, 0.603 mmol) in acetonitrile (5 mL) in a 75 mL medium pressure flask was added phosphoric acid, potassium salt (0.563 g, 2.65 mmol), KI (0.270 g, 1.629 mmol) followed by a solution of (1S,4S)-5-(2-chloroethyl)-2-thia-5-azabicyclo[2.2.1]heptane 2,2-dioxide (0.152 g, 0.724 mmol) (prepared as described below) in acetonitrile (5 mL). The reaction mixture was purged with $N_2$ (g) and heated to 120° C. for 24 h. The reaction was allowed to cool to rt. Solid was removed by filtration and washed with DCM. The liquid filtrate was concentrated to a white paste. The crude material was dissolved in a mixture of THF/MeOH and purified by reverse phase prep-HPLC using Prep HPLC method 3 to give a mixture of methyl 4-((1R,3 aS,5aR,5bR,7aR,11aS, 11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate, TFA and methyl 4-((1R,3 aS,5aR, 5bR,7aR,11aS,11bR,13aR,13bR)-3a-((2-((1S,4S)-2,2-dioxido-2-thia-5-azabicyclo[2.2.1]heptan-5-yl)ethyl)(2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate, TFA (0.125 g, 24.94% yield) as a white solid. LC/MS: m/e 717.3 (M+H)$^+$, 2.37 min, LC/MS: m/e 761.3 (M+H)$^+$, 2.37 min (method 3). The material was used directly in the next step.

Step 2. Preparation of 4-((1R,3aS,5aR,5bR,7aR, 11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid, 2HCl and 4-((1R,3aS,5aR,5bR,7aR, 11aS,11bR,13aR,13bR)-3a-((2-((1S,4S)-2,2-dioxido-2-thia-5-azabicyclo[2.2.1]heptan-5-yl)ethyl)(2-hydroxyethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid, 2 HCl

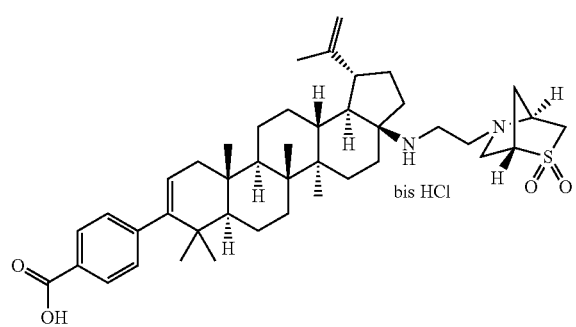

Example 5

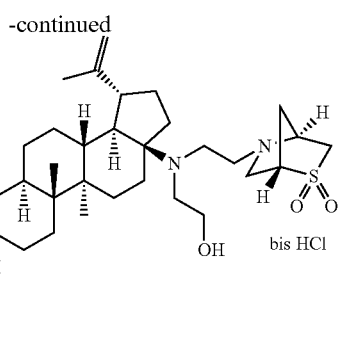

Example 6

To a solution of methyl 4-((1R,3aS,5aR,5bR,7aR,11aS,311bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA and methyl 4-((1R,3 aS,5aR,5bR,7aR,11aS,11bR,13aR,13bR)-3a-((2-((1S,4S)-2,2-dioxido-2-thia-5-azabicyclo[2.2.1]heptan-5-yl)ethyl)(2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (122 mg, 0.170 mmol) in THF (5 mL) and MeOH (2 mL) was added a solution of lithium hydroxide monohydrate (0.014 mL, 0.510 mmol) in water (1 mL). The reaction mixture was heated to 75° C. for 8 h. The mixture was then concentrated to dryness. The material was redissolved in THF (1.75 mL), MeOH (1 mL), 0.250 mL 1N HCl and purified using Prep HPLC method 1. The combined HPLC fractions were concentrated and the material was dissolved in a mixture of THF (2 mL) and H$_2$O (2 mL) and extracted with a mixture of 1:1 THF:EtOAc (2×20 mL). The combined organic layer was washed with brine, dried over MgSO$_4$, filtered and concentrated. The crude mixture was purified by reverse phase prep-HPLC using HPLC method 1. The combined HPLC fractions for each peak was treated with 1N HCl and concentrated and dried under vacuum to give 4-((1R,3 aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2HCl (20.5 mg, 15.0% yield) and 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)(2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 HCl (36.9 mg, 26.7% yield) both as a white solids. LC/MS: m/e 703.6 (M+H)$^+$, 1.84 min (method 2). $^1$H NMR (400 MHz, 1:1 CDCl3:METHANOL-d$_4$) δ 7.90 (d, J=8.1 Hz, 2H), 7.18 (d, J=8.1 Hz, 2H), 6.93 (s, 1H), 5.28 (d, J=4.9 Hz, 1H), 4.85 (br. s., 1H), 4.15 (br. s., 1H), 3.69 (br. s., 1H), 3.40 (br. s., 2H), 3.25 (br. s., 2H), 3.07 (d, J=13.0 Hz, 3H), 2.60 (d, J=12.0 Hz, 1H), 2.45 (d, J=10.8 Hz, 1H), 2.22 (s, 1H), 2.12 (dd, J=17.0, 6.2 Hz, 2H), 2.06-1.95 (m, 2H), 1.92-1.77 (m, 2H), 1.73 (s, 3H), 1.66-1.43 (m, 10H), 1.41-1.37 (m, 6H), 1.24 (br. s., 2H), 1.15 (br. s., 4H), 1.09 (s, 3H), 1.01 (s, 3H), 0.94 (br. s., 3H), 0.93 (br. s., 3H). $^{13}$C NMR (101 MHz, 1:1 CDCl3:METHANOL-d$_4$) δ 169.8, 149.4, 148.2, 147.1, 137.8, 130.8, 129.5, 129.2, 126.0, 124.6, 112.2, 61.5, 53.8, 53.6, 50.0, 49.4, 46.2, 42.9, 42.4, 41.6, 38.2, 38.1, 37.0, 35.0, 34.4, 33.1, 30.8, 30.0, 28.9, 27.8, 26.9, 25.9, 21.8, 21.6, 21.5, 20.5, 19.6, 17.1, 16.8, 14.9. LC/MS: m/e 747.3 (M+H)$^+$, 2.22 min (method 3). $^1$H NMR (400 MHz, 1:1 CDCl3:METHANOL-d$_4$) δ 7.90 (d, J=8.1 Hz, 2H), 7.18 (d, J=8.3 Hz, 2H), 5.27 (d, J=4.6 Hz, 1H), 4.71 (s, 1H), 4.59 (br. s., 1H), 4.33-4.22 (m, 2H), 4.11-3.95 (m, 1H), 3.81 (br. s., 1H), 3.61 (dd, J=11.1, 3.8 Hz, 1H), 3.28-3.13 (m, 2H), 2.94-2.74 (m, 2H), 2.69-2.55 (m, 2H), 2.43 (d, J=11.5 Hz, 1H), 2.11 (dd, J=17.2, 6.5 Hz, 1H), 1.98-1.77 (m, 4H), 1.72 (br. s., 2H), 1.69 (s, 3H), 1.64 (br. s., 2H), 1.63-1.51 (m, 3H), 1.49 (br. s., 2H), 1.43 (d, J=11.7 Hz, 2H), 1.40-1.29 (m, 3H), 1.28-1.22 (m, 2H), 1.18 (dd, J=12.7, 10.0 Hz, 2H), 1.11 (br. s., 3H), 1.10-1.06 (m, 1H), 1.01 (s, 3H), 1.00 (s, 3H), 0.94 (s, 3H), 0.93 (s, 3H).

Preparation of (1S,4S)-5-(2-chloroethyl)-2-thia-5-azabicyclo[2.2.1]heptane 2,2-dioxide

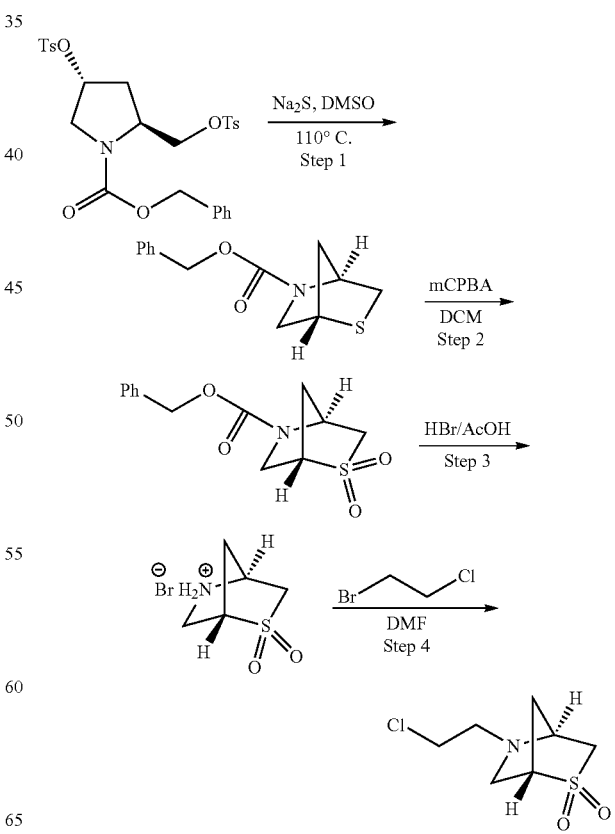

Step 1. Preparation of (1S,4S)-benzyl 2-thia-5-azabicyclo[2.2.1]heptane-5-carboxylate

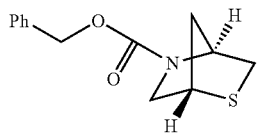 [SMILES: O=C(OCc1ccccc1)N1C[C@@H]2C[C@H]1CS2]

(2S,4R)-benzyl 4-(tosyloxy)-2-((tosyloxy)methyl)pyrrolidine-1-carboxylate (10 g, 17.87 mmol) and sodium sulfide (1.125 mL, 26.8 mmol) were combined in DMSO (80 mL) in a 150 mL medium pressure flask. The reaction mixture was purged with $N_2$ (g) and the resulting slurry was heated to 110° C. under a $N_2$ (g) atmosphere. The reaction became deep blue immediately. After 17 h, the resulting black reaction mixture was cooled to rt, diluted with 1:1 EtOAc:$Et_2O$ (150 mL) and washed with $H_2O$ (100 mL). The aqueous layer was extracted with 1:1 EtOAc:$Et_2O$ (100 mL). The combined organic layer was washed with 1N HCl (100 mL), brine, dried over $MgSO_4$, filtered and concentrated to give dark red viscous oil. The crude material was loaded onto a silica gel column (60 g) and eluted with 3:1 hex:EtOAc to give (1S,4S)-benzyl 2-thia-5-azabicyclo[2.2.1]heptane-5-carboxylate (2.7 g, 61% yield) as red viscous oil. LC/MS: m/e 250.0 $(M+H)^+$, 2.22 min (method 3). $^1$H NMR (400 MHz, CHLOROFORM-d) δ 7.39-7.31 (m, 5H), 5.18-5.06 (m, 2H), 4.79-4.65 (m, 1H), 3.64 (d, J=7.8 Hz, 2H), 3.59 (br. s., 1H), 3.22-3.04 (m, 1H), 3.04-2.96 (m, 1H), 2.16 (t, J=10.0 Hz, 1H), 1.88 (d, J=10.3 Hz, 1H).

Step 2. Preparation of (1S,4S)-benzyl 2-thia-5-azabicyclo[2.2.1]heptane-5-carboxylate 2,2-dioxide

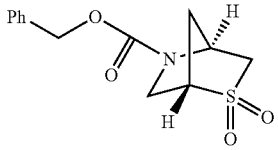 [SMILES: O=C(OCc1ccccc1)N1C[C@@H]2C[C@H]1CS2(=O)=O]

To a solution of (1S,4S)-benzyl 2-thia-5-azabicyclo[2.2.1]heptane-5-carboxylate (2.7 g, 10.83 mmol) in DCM (50 mL) was added m-chloroperbenzoic acid (4.67 g, 27.1 mmol) portion wise to control gas evolution. The reaction was slightly exothermic to the touch. The reaction mixture was stirred at rt for 24 h. The reaction was slowly quenched with 10% $Na_2SO_3$ (50 mL). The aqueous layer was extracted with DCM (2×50 mL). The combined organic layer was washed with 10% $NaHCO_3$, $H_2O$ (25 mL), brine, dried over $MgSO_4$, filtered and concentrated to brown viscous oil. The material was purified by flash column chromatography ($SiO_2$, 90 g), eluted with 1:2 hex:EtOAc to give (1S,4S)-benzyl 2-thia-5-azabicyclo[2.2.1]heptane-5-carboxylate 2,2-dioxide (1.52 g, 49.9% yield) as a white foam. $^1$H NMR (400 MHz, CHLOROFORM-d) δ 7.36-7.19 (m, 5H), 5.15-4.99 (m, 2H), 4.69-4.51 (m, 1H), 3.99-3.89 (m, 1H), 3.57 (br. s., 1H), 3.50-3.40 (m, 1H), 3.24-3.05 (m, 1H), 3.04-2.94 (m, 1H), 2.43 (d, J=12.2 Hz, 1H), 2.30-2.17 (m, 1H).

Step 3. Preparation of (1S,4S)-2-thia-5-azabicyclo[2.2.1]heptane 2,2-dioxide, hydrobromide

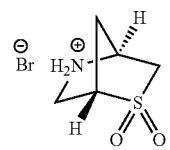

(1S,4S)-benzyl 2-thia-5-azabicyclo[2.2.1]heptane-5-carboxylate 2,2-dioxide (1.4 g, 4.98 mmol) was treated with hydrobromic acid (33% in acetic acid) (20 mL, 116 mmol) and stirred at rt. After 18 h, a white precipitate was filtered, washed with glacial acetic acid (5 mL), and dried under reduced pressure to give (1S,4S)-2-thia-5-azabicyclo[2.2.1]heptane 2,2-dioxide, hydrobromide (1.01 g, 85% yield) as a white solid. $^1$H NMR (400 MHz, DMSO-$d_6$) δ 9.49 (br. s., 2H), 4.60 (br. s., 1H), 4.15 (br. s., 1H), 3.67-3.51 (m, 2H), 3.49-3.32 (m, 2H), 2.34 (d, J=13.2 Hz, 1H). $^{13}$C NMR (101 MHz, DMSO-$d_6$) δ 57.7, 56.7, 55.3, 44.2, 33.5.

Step 4. Preparation of (1S,4S)-5-(2-chloroethyl)-2-thia-5-azabicyclo[2.2.1]heptane 2,2-dioxide

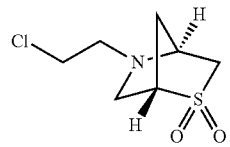

To a solution of (1S,4S)-2-thia-5-azabicyclo[2.2.1]heptane 2,2-dioxide, hydrobromide (0.5 g, 2.192 mmol) in DMF (25 mL) was added potassium carbonate (0.397 mL, 6.58 mmol) followed by 1-bromo-2-chloroethane (0.927 mL, 10.96 mmol). The reaction mixture was stirred at rt. After 30 h, the reaction mixture was poured into water (20 mL) and extracted with EtOAc (2×50 mL). The combined organic layer was washed with brine, dried over $MgSO_4$, filtered and concentrated to viscous light brown oil. The crude material was loaded onto a silica gel column, eluted with 1:2 hex: EtOAc to give (1S,4S)-5-(2-chloroethyl)-2-thia-5-azabicyclo[2.2.1]heptane 2,2-dioxide (150 mg, 32.6% yield) of a clear glass material. LC/MS: m/e 210.0 $(M+H)^+$, 0.240 min (method 3).

Example 7

Preparation of 4-((1R,3aS,5aR,5bR,7aR,11aS,11bR, 13aR,13bR)-3a-((2-((1S,4S)-2-oxa-5-azabicyclo [2.2.1]heptan-5-yl)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid and methyl 4-((1R,3aS,5aR,5bR,7aR,11aS,11bR,13 aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoate Step 1. Preparation of (1S,4S)-5-(2-chloroethyl)-2-oxa-5-azabicyclo[2.2.1]heptane

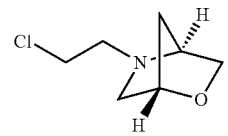

The solid mixture of (1S,4S)-2-oxa-5-azabicyclo[2.2.1] heptane, HCl (0.5 g, 3.69 mmol) and cesium carbonate (4.25 g, 12.91 mmol) was dried in a vacuum oven at 50° C. for 20 mins and the flask was back filled with a $N_2$ (g). THF (45 mL) was added to the mixture, followed by 1-bromo-2-chloroethane (0.936 mL, 11.06 mmol). The resulting slurry was stirred at 50° C. for 19 h. Then, the excess cesium carbonate was filtered and washed with EtOAc (2×25 mL). The liquid filtrate was concentrated and the light yellow crude was purified by flash column chromatography ($SiO_2$, 25 g, eluted with

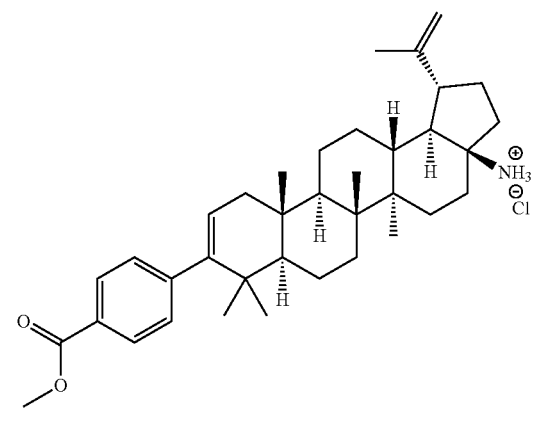

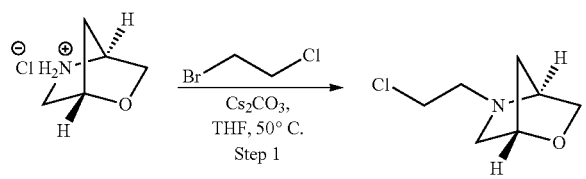

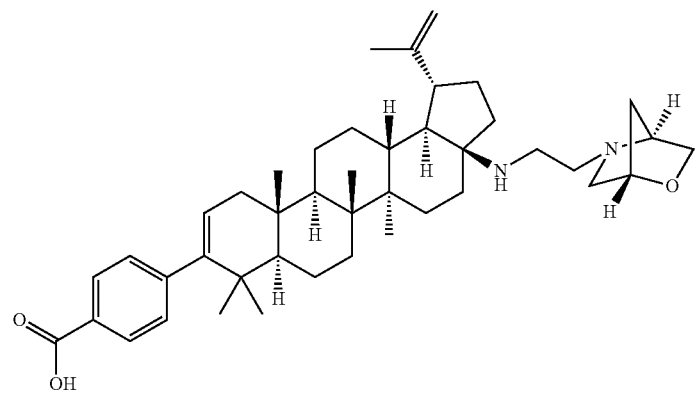

Example 7

95:5 DCM:MeOH) and dried under reduced pressure briefly to give (1S,4S)-5-(2-chloroethyl)-2-oxa-5-azabicyclo[2.2.1]heptane (129 mg, 19.48% yield) as clear viscous oil. $^1$H NMR (400 MHz, CHLOROFORM-d) δ 4.33 (s, 1H), 3.93 (d, J=8.1 Hz, 1H), 3.57 (dd, J=8.1, 1.7 Hz, 1H), 3.46 (d, J=6.8 Hz, 3H), 2.92 (dd, J=10.1, 1.6 Hz, 1H), 2.90-2.79 (m, 2H), 2.50 (dd, J=9.8, 1.0 Hz, 1H), 1.79 (dd, J=9.8, 2.0 Hz, 1H), 1.71-1.63 (m, 1H). $^{13}$C NMR (101 MHz, CHLOROFORM-d) δ 76.6, 69.1, 61.8, 61.0, 55.5, 42.8, 35.6.

Step 2. Preparation of 4-((1R,3aS,5aR,5bR,7aR,11aS,11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 HCl and methyl 4-((1R,3aS,5aR,5bR,7aR,11aS,11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, 2HCl

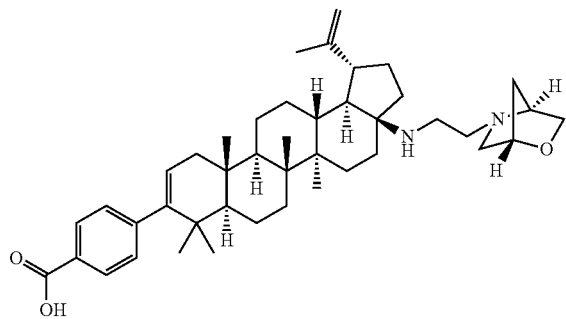

Methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (434 mg, 0.798 mmol), potassium iodide (530 mg, 3.19 mmol) and potassium phosphate (847 mg, 3.99 mmol) were placed in a 75 mL medium pressure flask, crushed, dried in a 50° C. vacuum oven for 30 mins and back filled with $N_2$ (g). The solid mixture was charged with a solution of (1S,4S)-5-(2-chloroethyl)-2-oxa-5-azabicyclo[2.2.1]heptane (129 mg, 0.798 mmol) in MeCN (10 mL) and heated to 120° C. After 48 h, the reaction was let cooled to rt, treated with $H_2O$ (10 mL) and stirred at rt for 15 mins. The off-white solid was filtered and washed with $H_2O$ (10 mL). The crude product was purified by reverse phase HPLC using HPLC method 5 to give 4-((1R,3aS,5aR,5bR,7aR,11aS,11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 HCl (35.6 mg, 0.048 mmol, 6.1% yield) as a white solid. $^1$H NMR (400 MHz, 1:1 CHLOROFORM-d:METHANOL-$d_4$) δ 7.91 (d, J=8.1 Hz, 2H), 7.19 (d, J=8.1 Hz, 2H), 5.29 (d, J=4.9 Hz, 1H), 4.87 (s, 1H), 4.74-4.64 (m, 4H), 4.49 (br. s., 1H), 4.30 (br. s., 1H), 3.84 (d, J=9.8 Hz, 2H), 3.48 (br. s., 2H), 2.85 (br. s., 1H), 2.30 (br. s., 1H), 2.24-1.97 (m, 7H), 1.88 (d, J=13.7 Hz, 1H), 1.81-1.76 (m, 1H), 1.74 (s, 3H), 1.70 (br. s., 1H), 1.65 (d, J=8.3 Hz, 2H), 1.62-1.46 (m, 7H), 1.45-1.35 (m, 3H), 1.27 (d, J=9.0 Hz, 2H), 1.23 (s, 3H), 1.09 (s, 3H), 1.03 (s, 3H), 0.95 (s, 3H), 0.94 (br. s., 3H). LC/MS: m/e 669.6 (M+H)$^+$, 2.40 min (method 3).

Example 8

Preparation of 4-((1S,3aS,5aR,5bR,7aR,11aS,11bR,13aR,13bR)-3a-((2-((1S,4S)-2-oxa-5-azabicyclo[2.2.1]heptan-5-yl)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

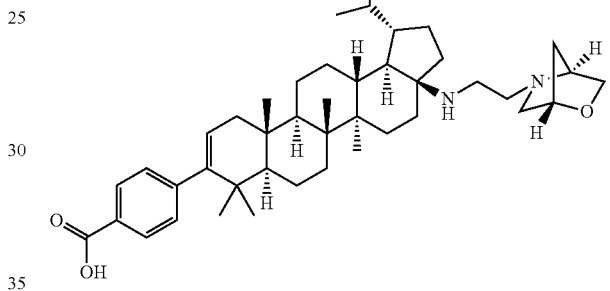

To a solution of 4-((1R,3aS,5aR,5bR,7aR,11aS,11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (12 mg, 0.018 mmol) in a mixture of THF (1 mL) and MeOH (1 mL) was added palladium(II) hydroxide (6.43 mg, 9.16 μmol). The reaction mixture was purged with a $H_2$ (g) and stirred at rt under a $H_2$ (g) atmosphere for 18 h. The catalyst was removed by filtration and washed with DCM. The filtrate was concentrated and dried to give 4-((1S,3aS,5aR,5bR,7aR,11aS,11bR,13aR,13bR)-3a-((2-((1S,4S)-2-oxa-5-azabicyclo[2.2.1]heptan-5-yl)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid, 2 HCl (11 mg, 76% yield) as a white foam. LC/MS: m/e 657.6 (M+H)$^+$, 2.30 min (method 3). $^1$H NMR (400 MHz, 1:1 CDCl$_3$:METHANOL-$d_4$) δ 7.91 (d, J=8.1 Hz, 2H), 7.19 (d, J=8.3 Hz, 2H), 5.29 (d, J=4.6 Hz, 1H), 4.36 (t, J=7.0 Hz, 1H), 4.26 (t, J=6.4 Hz, 1H), 3.79 (ddd, J=19.0, 9.1, 4.4 Hz, 2H), 3.68-3.60 (m, 1H), 3.12-3.06 (m, 1H), 2.87 (s, 1H), 2.54-2.47 (m, 1H), 2.26 (dd, J=16.4, 8.6 Hz, 1H), 2.15 (dd, J=16.8, 6.0 Hz, 2H), 2.01 (d, J=5.4 Hz, 3H), 1.89-1.85 (m, 1H), 1.84-1.67 (m, 7H), 1.63-1.53 (m, 5H), 1.50-1.43 (m, 3H), 1.42-1.36 (m, 2H), 1.31-1.23 (m, 4H), 1.21 (br. s., 3H), 1.07 (s, 3H), 1.03 (s, 3H), 0.94 (br. s., 3H), 0.93 (br. s., 3H), 0.92 (br. s., 3H), 0.83 (d, J=6.8 Hz, 3H).

Example 9
Preparation of 4-((1R,3aS,5aR,5bR,7aR,11aS,11bR, 13aR,13bR)-3a-((2-(((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
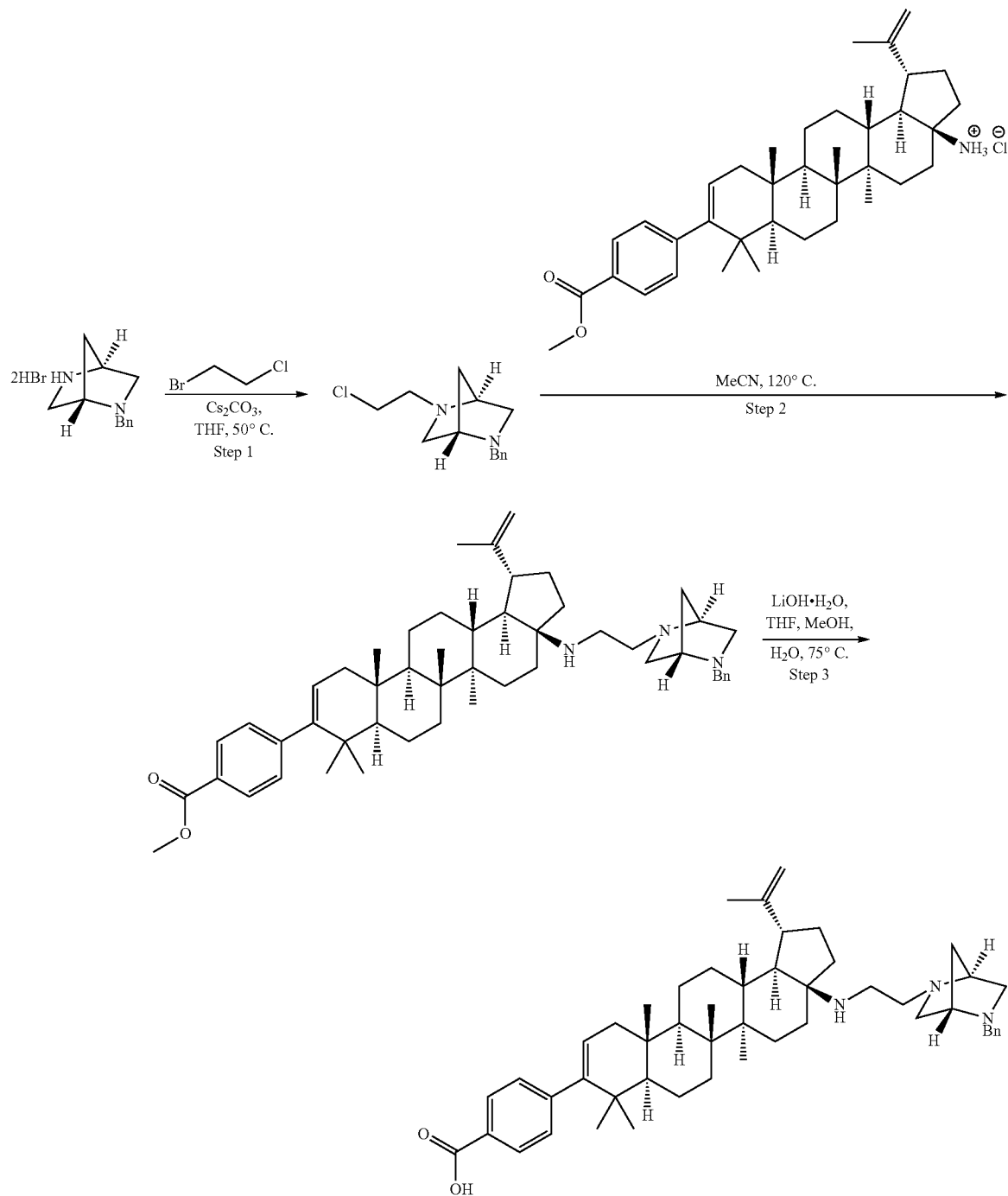
Example 9

Step 1. Preparation of (1S,4S)-2-benzyl-5-(2-chloro-ethyl)-2,5-diazabicyclo[2.2.1]

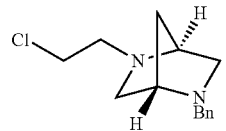 [SMILES: ClCCN1C[C@@H]2C[C@H]1CN2Cc1ccccc1]

The solid mixture of (1S,4S)-2-benzyl-2,5-diazabicyclo[2.2.1]heptane, 2HBr (0.973 g, 2.78 mmol) and cesium carbonate (3.20 g, 9.73 mmol) was dried in a vacuum oven for 15 mins and the flask was filled with a $N_2$ (g). THF (50 mL) was added to the mixture, followed by 1-bromo-2-chloroethane (0.705 mL, 8.34 mmol). The resulting cloudy mixture was stirred at rt for 24 h and then heated at 52° C. for 26 h. The reaction mixture was filtered and the solid formed was washed with EtOAc. The liquid filtrate was concentrated to a clear viscous oil which was purified by column chromatography ($SiO_2$, 40 g cartridge, eluted with 95:5 DCM:MeOH), dried under reduced pressure to give (1S,4S)-2-benzyl-5-(2-chloroethyl)-2,5-diazabicyclo[2.2.1]heptane (275 mg, 35.5% yield) as clear viscous oil. LC/MS: m/e 251.1 $(M+H)^+$, 0.45 min (method 3). $^1$H NMR (400 MHz, CHLOROFORM-d) δ 7.40-7.29 (m, 4H), 7.28-7.20 (m, 1H), 3.82-3.65 (m, 2H), 3.58-3.50 (m, 2H), 3.41-3.28 (m, 2H), 3.03-2.92 (m, 1H), 2.90-2.77 (m, 4H), 2.68 (dd, J=10.0, 2.4 Hz, 1H), 1.84-1.69 (m, 2H). $^{13}$C NMR (101 MHz, CHLOROFORM-d) δ 139.6, 128.4, 128.2, 126.8, 62.8, 61.4, 58.3, 57.1, 56.2, 56.0, 43.1, 34.1.

Step 2. Preparation of methyl 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

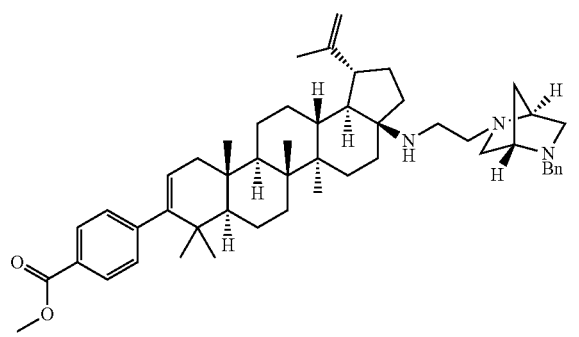

Methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, HCl (579 mg, 0.998 mmol), phosphoric acid, potassium salt (1059 mg, 4.99 mmol) and potassium iodide (0.212 mL, 3.99 mmol) were combined in a 75 mL medium pressure tube. The solid mixture was dried under vacuum at 50° C. for 10 min then placed under $N_2$ (g) atmosphere. The solid mixture was treated with a solution of (1S,4S)-2-benzyl-5-(2-chloroethyl)-2,5-diazabicyclo[2.2.1]heptane (250 mg, 0.998 mmol) in MeCN (10 mL). The resulting slurry was heated to 120° C. for 19 h. The reaction mixture was cooled to rt, treated $H_2O$ (15 mL) and stirred at rt for 15 mins. The brown solid formed was crushed, filtered, washed with $H_2O$ (15 mL) and saved for analysis. The liquid filtrate was extracted with 3×25 mL DCM. The combined organic layer was washed with brine, dried over $MgSO_4$, filtered and concentrated. LC/MS showed the brown solid (1 g) to be a mixture of product and sm. The liquid filtrated produced about 100 mg of product and sm. 50 mg of the crude material was purified by reverse phase prep-HPLC using HPLC method 6 to give 23 mg of methyl 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, bis-TFA salt as white solid which was used for characterization. The rest of the brown solid from above was purified by column chromatography ($SiO_2$, 90 g cartridge) and eluted with 95:5 DCM:MeOH to recover the starting material left and then eluted with 90:10 DCM:MeOH to give methyl 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (172 mg, 0.206 mmol, 57.2% yield base on recovered sm) as a light yellow oil.

LC/MS: m/e 758.7 $(M+H)^+$, 2.30 min (method 3). $^1$H NMR (400 MHz, CHLOROFORM-d) δ 7.94 (d, J=8.1 Hz, 2H), 7.53-7.42 (m, 5H), 7.20 (d, J=8.3 Hz, 2H), 5.30 (d, J=4.6 Hz, 1H), 4.77 (s, 1H), 4.68 (s, 1H), 4.30-4.18 (m, 2H), 4.14-4.04 (m, 2H), 3.91 (s, 3H), 3.35-3.08 (m, 4H), 3.08-2.84 (m, 3H), 2.78 (br. s., 1H), 2.24-2.05 (m, 4H), 1.98-1.87 (m, 4H), 1.70 (s, 3H), 1.65 (br. s., 2H), 1.59-1.41 (m, 7H), 1.40-1.31 (m, 4H), 1.24 (dd, J=11.5, 6.6 Hz, 2H), 1.14 (s, 3H), 1.05 (s, 3H), 1.00 (s, 3H), 0.93 (s, 6H).

Step 3. Preparation of 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

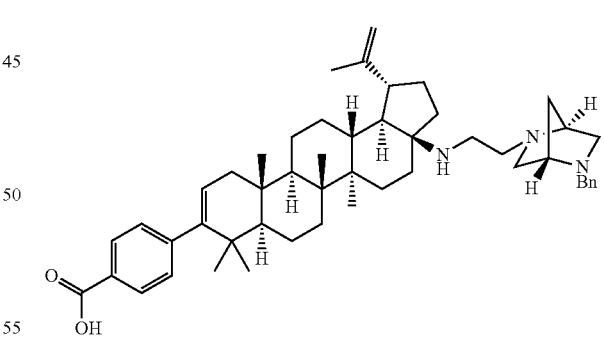

To a solution of methyl 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, 2 TFA (22 mg, 0.022 mmol) in a mixture of THF (1 mL) and MeOH (0.5 mL) was added a solution of lithium hydroxide monohydrate (4.68 mg, 0.112 mmol) in water (0.5 mL). The resulting mixture was heated to 75° C. for 3 h. The reaction mixture was concentrated to give a white paste. The crude product was dissolved in a mixture of THF (0.5 mL), MeOH (0.4 mL) and 1N HCl (0.1 mL) and purified using HPLC method 6. The combined HPLC fraction was treated with 1 mL 1.0N HCl, concentrated and dried under reduced pressure to give 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 3 HCl (8 mg, 38.7% yield) as a white solid. LC/MS: m/e 744.7 (M+H)$^+$, 2.18 min (method 3) $^1$H NMR (400 MHz, 1:1 CDCl3:METHANOL-d$_4$) δ 7.91 (d, J=8.3 Hz, 2H), 7.57 (dd, J=6.5, 2.8 Hz, 2H), 7.48-7.41 (m, 3H), 7.18 (d, J=8.1 Hz, 2H), 5.28 (d, J=4.6 Hz, 1H), 4.81 (s, 1H), 4.38-4.23 (m, 2H), 4.08 (br. s., 1H), 3.93 (s, 1H), 3.77-3.65 (m, 1H), 3.22-3.10 (m, 5H), 3.08-2.83 (m, 3H), 2.31 (d, J=11.5 Hz, 1H), 2.18-2.07 (m, 3H), 2.06-1.94 (m, 3H), 1.88-1.75 (m, 2H), 1.72 (s, 3H), 1.68 (d, J=5.4 Hz, 1H), 1.63-1.49 (m, 6H), 1.48-1.33 (m, 6H), 1.26 (d, J=12.5 Hz, 2H), 1.13 (s, 3H), 1.08 (s, 3H), 1.01 (s, 3H), 0.99-0.96 (m, 1H), 0.94 (br. s., 3H), 0.93 (br. s., 3H).

Example 10

Preparation of 4-((1R,3aS,5aR,5bR,7aR,11aS,11bR,13aR,13bR)-3a-((2-((1S,4S)-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid To a solution of 4-((1R,3aS,5aR,5bR,7aR,11aS,11bR,13aR,13bR)-3a-((2-((1S,4S)-5-benzyl-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 3 HCl (6 mg, 7.03 µmol) in a mixture of THF (1 mL) and MeOH (1 mL) was added palladium(II) hydroxide (4.94 mg, 7.03 µmol). The reaction mixture was purged with H$_2$ (g) and stirred at rt under a H$_2$ (g) atmosphere for 16 h. The catalyst was removed by filtration and washed with DCM and the liquid filtrate was concentrated. The crude product was purified by reverse phase prep-HPLC using HPLC method 6. HPLC fraction for the product was treated with 1N HCl (0.5 mL), concentrated and dried under vacuum to give 4-((1R,3aS,5aR,5bR,7aR,11aS,11bR,13aR,13bR)-3a-((2-((1S,4S)-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 3 HCl (2.5 mg, 42.9% yield) as a white solid. LC/MS: m/e 654.6 (M+H)$^+$, 2.15 min (method 3). $^1$H NMR (400 MHz, 1:1 CDCl3:METHANOL-d$_4$) δ 7.90 (d, J=8.3 Hz, 2H), 7.18 (d, J=8.3 Hz, 2H), 5.28 (d, J=4.6 Hz, 1H), 4.85 (s, 1H), 4.74 (br. s., 1H), 4.40 (br. s., 1H), 3.84-3.65 (m, 1H), 3.50 (d, J=17.1 Hz, 2H), 3.41-3.34 (m, 2H), 3.28-3.22 (m, 1H), 2.93 (br. s., 1H), 2.35 (br. s., 1H), 2.24-2.08 (m, 4H), 2.07-1.98 (m, 2H), 1.98-1.79 (m, 3H), 1.73 (s, 4H), 1.69 (br. s., 1H), 1.66-1.34 (m, 12H), 1.26 (d, J=9.8 Hz, 2H), 1.18 (s, 3H), 1.14 (br. s., 1H), 1.09 (s, 3H), 1.02 (s, 3H), 0.94 (s, 3H), 0.93 (br. s., 3H).

Example 11

Preparation of 4-((1R,3aS,5aR,5bR,7aR,11aS,11bR,13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

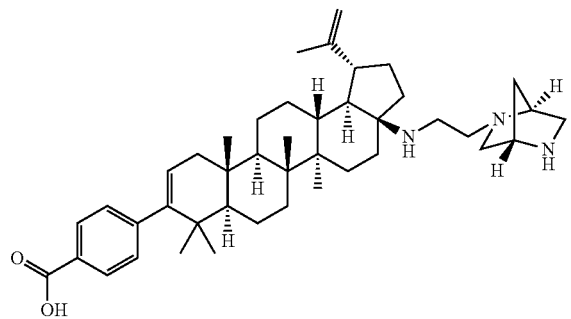

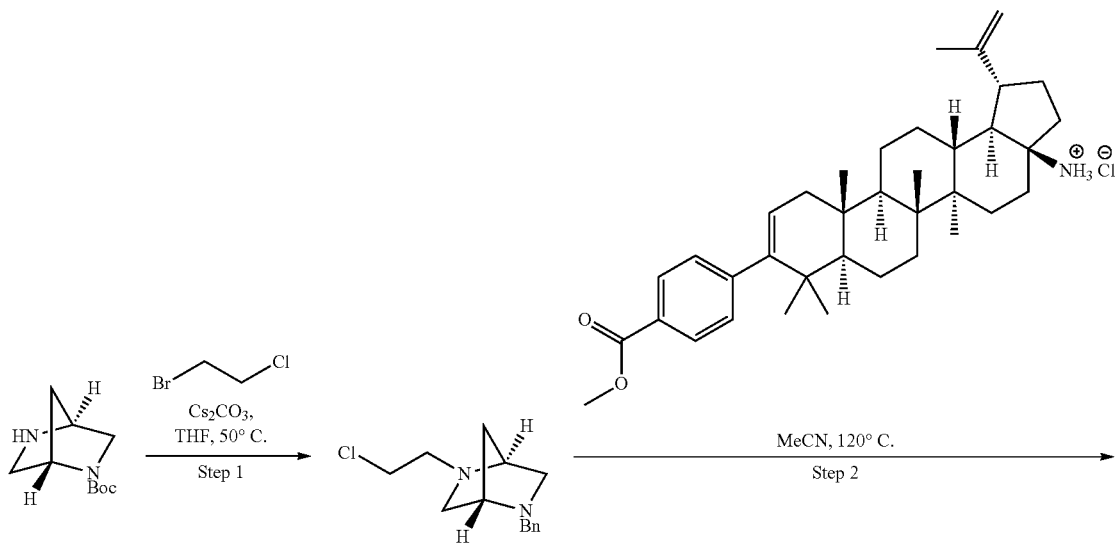

-continued
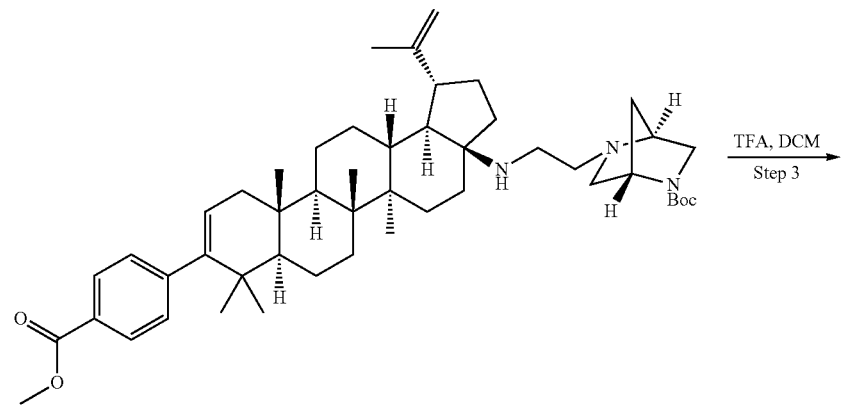
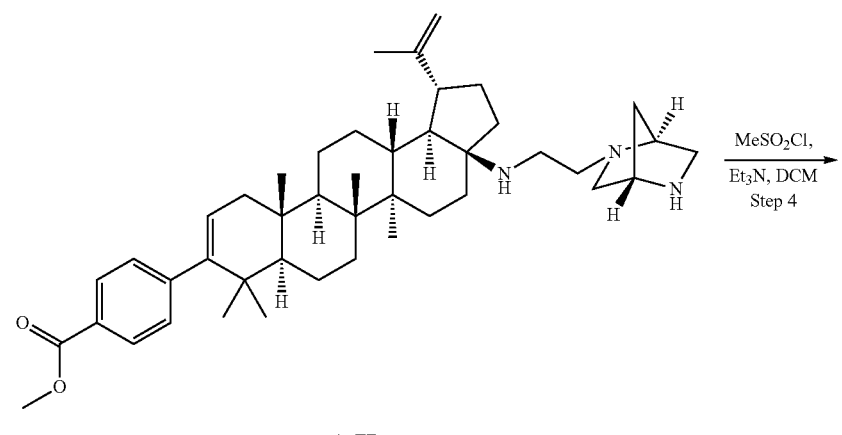
tris-TFA
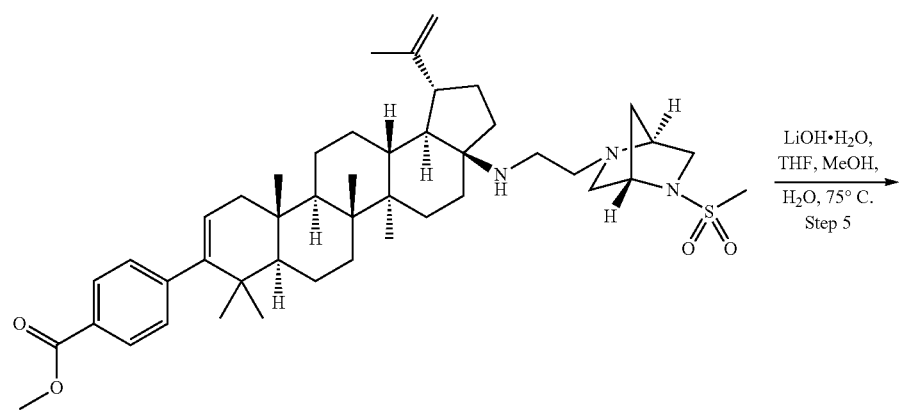

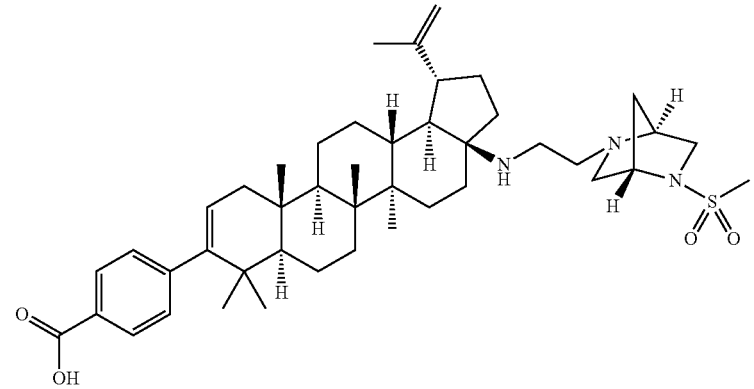

Example 11

Step 1. Preparation of (1S,4S)-tert-butyl 5-(2-chloroethyl)-2,5-diazabicyclo[2.2.1]heptane-2-carboxylate

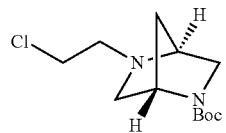

(1S,4S)-tert-butyl 2,5-diazabicyclo[2.2.1]heptane-2-carboxylate (525 mg, 2.65 mmol) and potassium phosphate (1686 mg, 7.94 mmol) were combined in a 75 mL medium pressure flask and purged in a 50° C. vacuum oven for 10 mins and placed under $N_2$ (g) atmosphere. THF (30 mL) was added, followed by 1-bromo-2-chloroethane (1.124 mL, 13.24 mmol) and the mixture was heated to 55° C. for 18 h. The reaction mixture was cooled to rt, treated with more 1-bromo-2-chloroethane (0.043 mL, 0.517 mmol) and heated back up to 55° C. for 68 h. The reaction was filtered and washed with DCM. The liquid filtrate was concentrated to viscous brown oil which was purified by column chromatography ($SiO_2$, 40 g cartridge, eluted with 95:5 DCM:MeOH), dried under vacuum with stirring to give (1S,4S)-tert-butyl 5-(2-chloroethyl)-2,5-diazabicyclo[2.2.1]heptane-2-carboxylate (465 mg, 1.783 mmol, 67.3% yield) as viscous light brown oil. $^1$H NMR (400 MHz, CHLOROFORM-d) δ 7.37 (s, 1H), 4.36 (br. s., 1H), 4.24 (br. s., 1H), 3.44 (d, J=9.5 Hz, 1H), 3.17 (t, J=8.8 Hz, 1H), 3.08-2.94 (m, 1H), 2.93-2.85 (m, 2H), 2.67 (d, J=9.5 Hz, 1H), 2.53 (d, J=9.5 Hz, 1H), 1.82 (d, J=6.4 Hz, 1H), 1.71 (dd, J=15.9, 9.8 Hz, 1H), 1.46 (s, 9H).

Step 2. Preparation of (1S,4S)-tert-butyl 5-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)-2,5-diazabicyclo[2.2.1]heptane-2-carboxylate

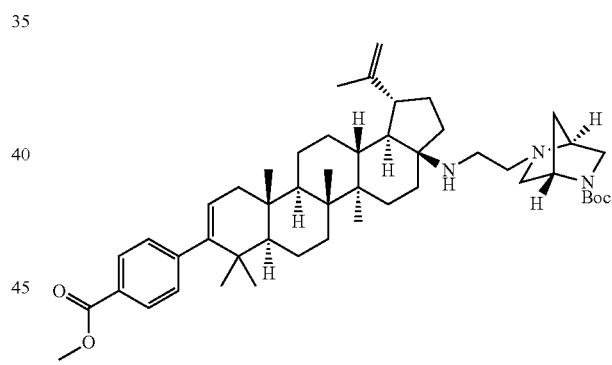

Methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (500 mg, 0.919 mmol), potassium phosphate (683 mg, 3.22 mmol) and potassium iodide (458 mg, 2.76 mmol) were combined in a 100 mL medium pressure flask, purged in a 50° C. vacuum oven for 30 mins and placed under an atmosphere of $N_2$ (g). DMSO (5 mL) was added to the solid followed by a solution of (1S,4S)-tert-butyl 5-(2-chloroethyl)-2,5-diazabicyclo[2.2.1]heptane-2-carboxylate (455 mg, 1.745 mmol) in DMSO (10 mL). The resulting reaction mixture was stirred at 110° C. overnight. The solid particles formed were removed by filtration and washed with DCM. The liquid filtrate was concentrated (at 60° C.) to give dark brown viscous oil. A small amount of crude material was subjected to purification by reverse phase HPLC for characterization. The rest of the crude was purified by flash column chromatography (SiO$_2$, 80 g cartridge, eluted with 97:3 DCM:MeOH) to give 419 mg mixture of (1S,4S)-tert-butyl 5-(2-(((1R,3 aS,5 aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)-2,5-diazabicyclo[2.2.1]heptane-2-carboxylate and methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate which was taken to the next step without further purification.

Alternatively, (1S,4S)-tert-butyl 5-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)-2,5-diazabicyclo[2.2.1]heptane-2-carboxylate can be prepared in two steps from methyl 4-((1R,3 aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as described below:

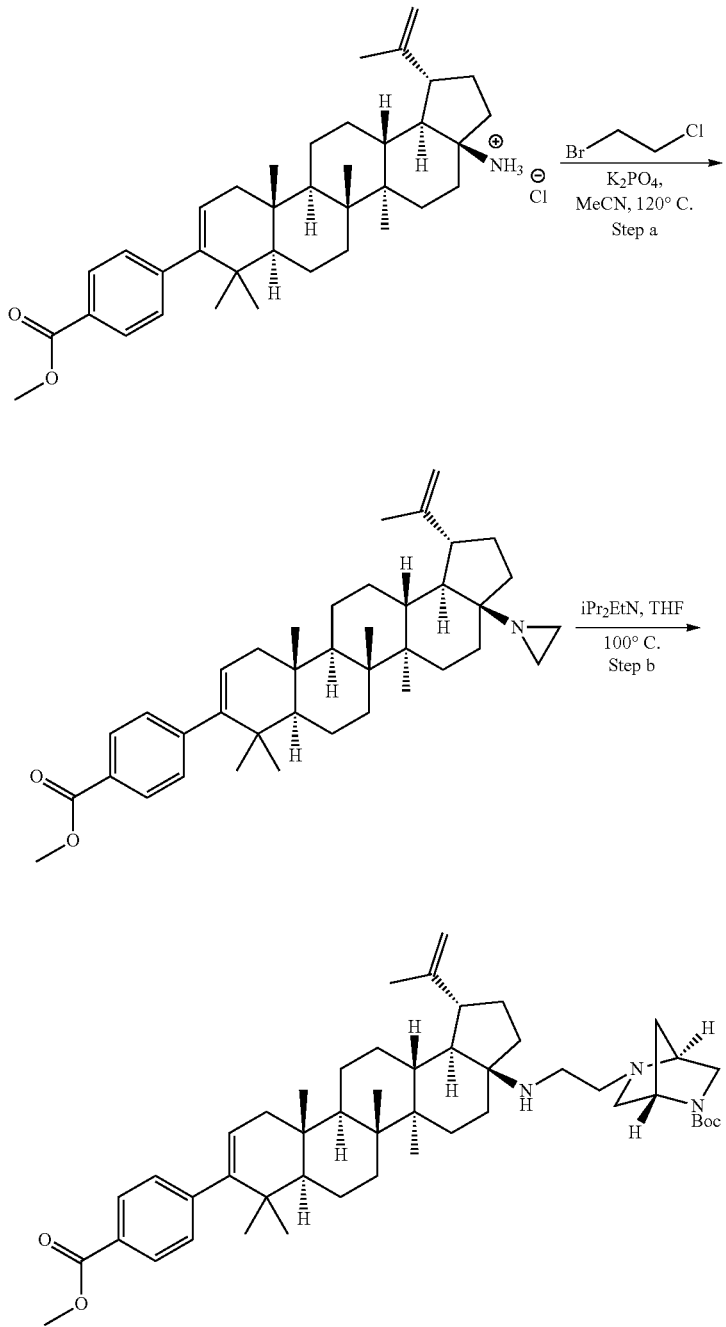

Step a. Preparation of methyl 4-((1R,3aS,5aR,5bR, 7aR,11aS,11bR,13aR,13bR)-3a-(aziridin-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoate To a solid mixture of methyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate, HCl (500 mg, 0.862 mmol) and potassium phosphate (914 mg, 4.31 mmol) was added acetonitrile (25 mL), followed by 1-bromo-2-chloroethane (0.717 mL, 8.62 mmol). The reaction mixture was heated to 120° C. for 24 h. The reaction was cooled to rt and the solid was removed by vacuum filtration and washed with DCM (2×25 mL). The liquid filtrate was concentrated to give methyl 4-((1R,3 aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (486 mg, 99% yield) as a light yellow solid. LC/MS: m/e 570.5 (M+H)$^+$, 2.38 min (method 3). $^1$H NMR (400 MHz, CHLOROFORM-d) δ 7.93 (d, J=8.1 Hz, 2H), 7.21 (d, J=8.1 Hz, 2H), 5.34-5.25 (m, 1H), 4.78 (br. s., 1H), 4.62 (br. s., 1H), 3.91 (s, 3H), 2.74-2.55 (m, 2H), 2.18-2.01 (m, 2H), 1.81 (d, J=11.7 Hz, 1H), 1.69 (s, 3H), 1.67 (br. s., 1H), 1.62-1.34 (m, 18H), 1.26-1.21 (m, 1H), 1.15 (br. s., 2H), 1.09 (s, 3H), 1.00 (br. s., 3H), 0.99 (br. s., 3H), 0.94 (s, 6H).

Step b

Methyl 4-((1R,3aS,5aR,5bR,7aR,11aS,11bR,13aR, 13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (82 mg, 0.144 mmol) and (1S,4S)-tert-butyl 2,5-diazabicyclo[2.2.1]heptane-2-carboxylate (86 mg, 0.432 mmol) were combined in a one dram vial, THF (1 mL) followed y N,N-di-iso-propylethylamine (0.175 mL, 1.007 mmol) were added and the reaction mixture was heated to 100° C. for 14 h. The reaction was cooled to rt and the crude material was purified by reverse phase HPLC using HPLC method 7 to give (1S,4S)-tert-butyl 5-(2-(((1R,3aS,5aR,5bR, 7aR,11aS,11bR,13aR,13bR)-9-(4-(methoxycarbonyl)phenyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysen-3a-yl)amino) ethyl)-2,5-diazabicyclo[2.2.1]heptane-2-carboxylate, 2 TFA (51.9 mg, 36.2% yield) as a white solid. LC/MS: m/e 768.7 (M+H)$^+$, 2.43 min (method 3). $^1$H NMR (400 MHz, CHLOROFORM-d) δ 8.14 (br. s., 2H), 7.93 (d, J=8.1 Hz, 2H), 7.19 (d, J=8.3 Hz, 2H), 5.29 (d, J=4.6 Hz, 1H), 4.78 (s, 1H), 4.70 (s, 1H), 4.65-4.49 (m, 1H), 4.28 (br. s., 1H), 3.91 (s, 3H), 3.70 (d, J=11.7 Hz, 3H), 3.55-3.35 (m, 4H), 2.78-2.62 (m, 1H), 2.23-1.97 (m, 6H), 1.94 (d, J=12.0 Hz, 1H), 1.86 (t, J=12.0 Hz, 1H), 1.80-1.71 (m, 2H), 1.69 (s, 3H), 1.67-1.61 (m, 2H), 1.54 (dd, J=15.5, 3.5 Hz, 5H), 1.46 (s, 9H), 1.43-1.28 (m, 4H), 1.27-1.17 (m, 1H), 1.10 (s, 3H), 1.04 (s, 3H), 0.99 (s, 3H), 0.93 (br. s., 3H), 0.93 (br. s., 3H). $^{13}$C NMR (101 MHz, CHLOROFORM-d) δ 167.3, 148.6, 146.6, 146.3, 130.0, 128.5, 127.9, 123.8, 117.2, 114.3, 112.1, 81.5, 77.2, 73.5, 52.8, 52.0, 49.3, 48.9, 45.4, 42.0, 41.7, 40.7, 38.6, 37.5, 37.4, 36.2, 33.4, 32.4, 29.4, 28.2, 28.0, 27.5, 26.3, 25.0, 21.0, 20.8, 19.6, 18.8, 16.4, 15.4, 14.5

Step 3. Preparation of 4-((1R,3aS,5aR,5bR,7aR, 11aS,11bR,13aR,13bR)-3a-((2-((1S,4S)-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate, 3 TFA

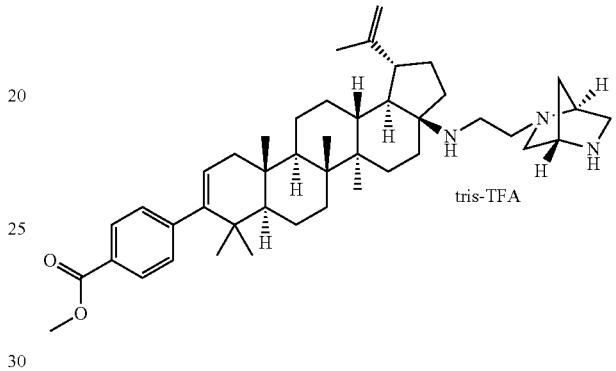

To a solution of (1S,4S)-tert-butyl 5-(2-(((1R,3aS,5aR, 5bR,7aR,11aS,11bR,13aR,13bR)-9-(4-(methoxycarbonyl) phenyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-3a-yl)amino) ethyl)-2,5-diazabicyclo[2.2.1]heptane-2-carboxylate (419 mg, 0.545 mmol) in DCM (10 mL) was added TFA (2 mL, 26.0 mmol) and the mixture was stirred at rt for 3 h. The reaction mixture was concentrated and dark brown viscous oil was dried to remove all TFA. The material was purified by reverse phase HPLC using HPLC method 6 and dried under vacuum to give methyl 4-((1R,3aS,5aR,5bR,7aR,11aS,11bR, 13aR,13bR)-3a-((2-((1S,4S)-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, 3 TFA (75.2 mg, 12.28% yield) as a light brown solid. LC/MS: m/e 668.7 (M+H)$^+$, 2.36 min (method 3). $^1$H NMR (400 MHz, CHLOROFORM-d) δ 9.77 (br. s., 1H), 9.49 (br. s., 1H), 7.92 (d, J=8.1 Hz, 2H), 7.19 (d, J=8.1 Hz, 2H), 5.28 (d, J=4.4 Hz, 1H), 4.76 (br. s., 1H), 4.69 (br. s., 1H), 4.31 (br. s., 1H), 3.96 (br. s., 1H), 3.90 (s, 3H), 3.66 (br. s., 1H), 3.40-3.10 (m, 5H), 3.09-2.89 (m, 2H), 2.81 (br. s., 1H), 2.23-2.06 (m, 4H), 2.05-1.91 (m, 3H), 1.85 (br. s., 1H), 1.78-1.73 (m, 1H), 1.69 (br. s., 3H), 1.65 (br. s., 1H), 1.62-1.30 (m, 11H), 1.26-1.17 (m, 2H), 1.11 (br. s., 3H), 1.05 (br. s., 3H), 0.99 (br. s., 3H), 0.93 (br. s., 6H). $^{13}$C NMR (101 MHz, CHLOROFORM-d) 167.2, 148.5, 147.1, 146.2, 130.0, 128.5, 127.9, 123.8, 114.8, 111.6, 77.24-77.18, 71.3, 65.8, 60.9, 57.7, 54.4, 52.7, 52.0, 49.2, 48.7, 48.62-48.49, 46.3, 45.0, 42.0, 41.6, 40.6, 37.4, 37.0, 36.2, 33.6, 32.5, 29.4, 28.0, 27.3, 25.8, 25.0, 20.9, 20.8, 19.5, 19.1, 16.3, 15.9, 15.2, 14.4.

119

Step 4. Preparation of methyl 4-((1R,3aS,5aR,5bR, 7aR,11aS,11bR,13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

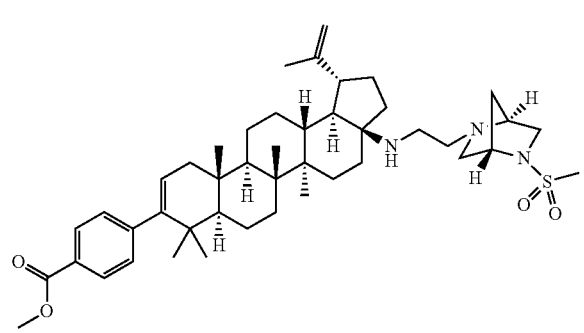

To a solution of methyl 4-((1R,3aS,5aR,5bR,7aR,11aS,11bR,13aR,13bR)-3a-((2-((1S,4S)-2,5-diazabicyclo[2.2.1]heptan-2-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (75.2 mg, 0.113 mmol) and triethyl amine (0.078 mL, 0.563 mmol) in DCM (3 mL) was added methanesulfonyl chloride (10.67 µl, 0.135 mmol). The reaction mixture was stirred at rt. After 1.5 h, the reaction mixture was diluted with DCM (25 mL) and washed with H$_2$O (2 mL). The aqueous layer was extracted with DCM (15 mL). The combined organic layer was washed with brine, dried over MgSO$_4$, filtered and concentrated to give methyl 4-((1R,3 aS,5aR,5bR,7aR,11aS,11bR,13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as a light brown solid (69.0 mg, 78% yield). LC/MS: m/e 746.8 (M+H)$^+$, 246 min (method 3). $^1$H NMR (400 MHz, CHLOROFORM-d) δ 7.88 (d, J=8.1 Hz, 2H), 7.15 (d, J=8.1 Hz, 2H), 5.25 (d, J=4.6 Hz, 1H), 4.71 (s, 1H), 4.57 (s, 1H), 4.26 (s, 1H), 3.86 (s, 3H), 3.69 (br. s., 1H), 3.58 (d, J=9.5 Hz, 1H), 3.19 (dd, J=9.4, 1.8 Hz, 1H), 2.97 (dd, J=9.8, 2.0 Hz, 1H), 2.85 (s, 3H), 2.80 (dd, J=8.3, 4.2 Hz, 2H), 2.65 (d, J=9.8 Hz, 1H), 2.61-2.44 (m, 2H), 2.07 (dd, J=17.1, 6.4 Hz, 2H), 1.95-1.68 (m, 6H), 1.66 (s, 3H), 1.65-1.37 (m, 9H), 1.31-1.06 (m, 7H), 1.04 (s, 3H), 0.96 (s, 3H), 0.94 (s, 3H), 0.89 (s, 6H).

120

Step 5. Preparation of 4-((1R,3aS,5aR,5bR,7aR,11aS,11bR,13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 TFA

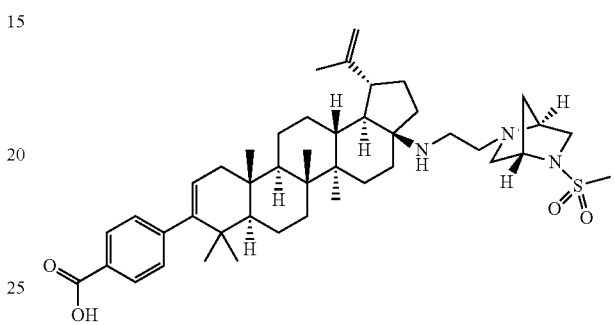

To a solution of methyl 4-((1R,3aS,5aR,5bR,7aR,11aS,11bR,13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (65 mg, 0.087 mmol) in THF (2 mL) and MeOH (1 mL) was added a solution of lithium hydroxide monohydrate (14.62 mg, 0.348 mmol). The reaction mixture was then stirred at 75° C. After 1 h, the reaction mixture was concentrated and redissolved in a mixture of THF (1.5 mL) and MeOH (0.5 mL) and purified by reverse phase prep-HPLC using HPLC method 6 to give 4-((1R,3aS,5aR,5bR,7aR,11aS,11bR,13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 TFA (46.6 mg, 54.6% yield) as white solid. LC/MS: m/e 732.7 (M+H)$^+$, 2.22 min (method 3). $^1$H NMR (400 MHz, 1:1 CDC$_{l3}$:METHANOL-d$_4$) δ 7.90 (d, J=8.3 Hz, 2H), 7.18 (d, J=8.1 Hz, 2H), 5.27 (d, J=4.9 Hz, 1H), 4.82 (s, 1H), 4.71 (br. s., 1H), 4.45 (br. s., 1H), 4.14 (br. s., 1H), 3.72 (d, J=10.5 Hz, 1H), 3.56 (dt, J=9.8, 6.5 Hz, 1H), 3.41 (d, J=10.0 Hz, 3H), 3.29-3.09 (m, 3H), 2.97 (s, 3H), 2.85 (td, J=11.0, 5.1 Hz, 1H), 2.22-1.96 (m, 7H), 1.93-1.75 (m, 3H), 1.72 (s, 3H), 1.68 (br. s., 1H), 1.66-1.47 (m, 8H), 1.47-1.32 (m, 4H), 1.26 (d, J=10.5 Hz, 1H), 1.16 (s, 3H), 1.08 (s, 3H), 1.01 (s, 3H), 0.93 (br. s., 3H), 0.92 (br. s., 3H). $^{13}$C NMR (101 MHz, 1:1 CDC$_{l3}$:METHANOL-d$_4$) δ 169.8, 149.4, 148.2, 147.2, 130.8, 129.5, 129.1, 124.6, 112.3, 78.7, 73.1, 64.9, 61.7 (br. s., 1C), 60.1, 53.6, 50.1, 46.4, 42.9, 42.5, 41.6, 38.8, 38.2, 38.2, 37.0, 34.4, 33.1, 30.5, 30.0, 28.9, 27.9, 27.0, 25.9, 21.8, 21.6, 20.4, 19.4, 17.1, 16.7, 15.0.

Example 12

Preparation of 4-((1S,3aS,5aR,5bR,7aR,11aS,11bR, 13aR,13bR)-1-isopropyl-5a,5b,8,8,11a-pentamethyl-3a-((2-((1S,4S)-5-(methylsulfonyl)-2,5-diazabicyclo[2.2.1]heptan-2-yl)ethyl)amino)-2,3,3a,4,5,5a,5b,6,7,7a,8,11,11a,11b,12,13,13a,13b-octadecahydro-1H-cyclopenta[a]chrysen-9-yl)benzoic acid

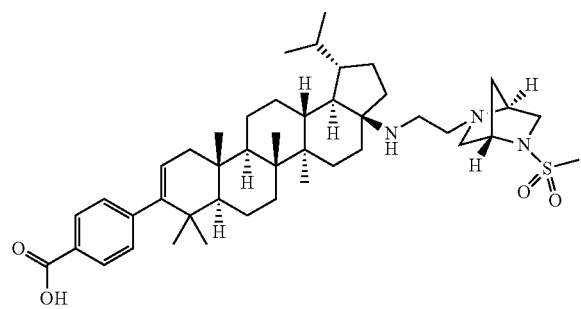

To a solution of 4-((1R,3aS,5aR,5bR,7aR,11aS,11bR, 13aR,13bR)-5a,5b,8,8,11a-pentamethyl-3a-((2-((1S,4S)-5-(methylsulfonyl)-2,5-diazabicyclo[2.2.1]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 TFA (10 mg, 10.42 µmol) in a mixture of THF (1.5 mL) and MeOH (0.5 mL) was added palladium hydroxide on carbon (14.63 mg, 0.021 mmol). The resulting slurry was purged with $H_2$ (g) and stirred under a $H_2$ (g) atmosphere for 16 h. The mixture was treated with celite (15 mg), filtered, washed with THF and concentrated. A grey residue was dissolved in THF (1 mL) and MeOH (0.5 mL), purified by reverse phase prep-HPLC using HPLC methods 6 and dried under vacuum to give 4-((1S,3aS,5aR,5bR,7aR, 11aS,11bR,13aR,13bR)-1-isopropyl-5a,5b,8,8,11a-pentamethyl-3a-((2-((1S,4S)-5-(methylsulfonyl)-2,5-diazabicyclo[2.2.1]heptan-2-yl)ethyl)amino)-2,3,3a,4,5,5a,5b,6,7,7a,8, 11,11a,11b,12,13,13a,13b-octadecahydro-1H-cyclopenta[a]chrysen-9-yl)benzoic acid, 2 TFA (6.2 mg, 60.6% yield) as white solid. LC/MS: m/e 734.6 (M+H)$^+$, 2.25 min (method 3). $^1$H NMR (400 MHz, 1:1 CDCl$_3$:METHANOL-d$_4$) δ 7.91 (d, J=8.3 Hz, 2H), 7.19 (d, J=8.3 Hz, 2H), 5.29 (d, J=4.6 Hz, 1H), 4.35 (s, 1H), 3.82 (s, 1H), 3.61 (d, J=10.3 Hz, 1H), 3.28 (d, J=1.7 Hz, 1H), 3.15 (d, J=11.7 Hz, 1H), 3.10-3.00 (m, 3H), 2.92 (s, 3H), 2.82 (d, J=10.0 Hz, 1H), 2.14 (dd, J=17.1, 6.4 Hz, 1H), 2.09-2.03 (m, 1H), 2.02-1.86 (m, 5H), 1.85-1.64 (m, 7H), 1.57 (dd, J=17.4, 11.7 Hz, 5H), 1.51-1.40 (m, 4H), 1.39-1.21 (m, 4H), 1.15 (s, 3H), 1.07 (s, 3H), 1.02 (s, 3H), 0.94 (s, 3H), 0.93 (s, 3H), 0.90 (d, J=6.8 Hz, 3H), 0.81 (d, J=6.6 Hz, 3H).

Example 13

Preparation of dried to give 4-((1R,3aS,5aR,5bR, 7aR,11aS,11bR,13aR,13bR)-3a-((2-((1R,5S)-8-(tert-butoxycarbonyl)-3,8-diazabicyclo[3.2.1]octan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

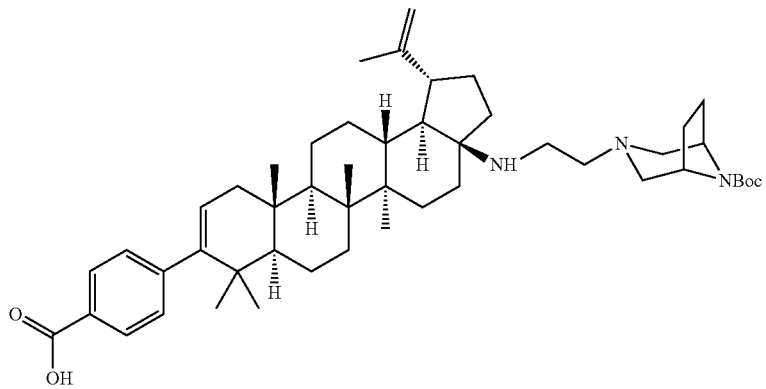

Methyl 4-((1R,3aS,5aR,5bR,7aR,11aS,11bR,13aR, 13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (95.0 mg, 0.167 mmol) and (1R,5S)-tert-butyl 3,8-diazabicyclo[3.2.1]octane-8-carboxylate (53.1 mg, 0.250 mmol) were combined in a one dram vial and charged with THF (1 mL) and N,N-di-iso-propylethylamine (0.145 mL, 0.834 mmol). The reaction mixture was heated at 100° C. for 2.5 h. Additional (1R,5S)-tert-butyl 3,8-diazabicyclo[3.2.1]octane-8-carboxylate (53.1 mg, 0.250 mmol) was added to the mixture and the stirring was continued at 100° C. for 23 h. The reaction mixture was purified by reverse phase prep-HPLC using HPLC method 7 and dried under vacuum to give (1R,5S)-tert-butyl 3-(2-(((1R,3aS,5aR,5bR,7aR,11aS,11bR, 13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-3a-yl)amino)ethyl)-3,8-diazabicyclo[3.2.1]octane-8-carboxylate, 2 TFA (108.5 mg, 63.1% yield) as a white solid. LC/MS: m/e 782.8 (M+H)$^+$, 2.48 min (method 3). $^1$H NMR (400 MHz, CHLOROFORM-d) δ 7.94 (d, J=8.3 Hz, 2H), 7.20 (d, J=8.3 Hz, 2H), 5.29 (d, J=4.6 Hz, 1H), 4.79 (s, 1H), 4.71 (s, 1H), 4.37 (br. s., 2H), 3.92 (s, 3H), 3.57-3.29 (m, 6H), 2.94 (d, J=10.8 Hz, 2H), 2.72 (br. s., 1H), 2.18-1.90 (m, 9H), 1.87 (d, J=12.0 Hz, 1H), 1.75 (d, J=12.7 Hz, 1H), 1.71-1.68 (m, 3H), 1.64 (br. s., 1H), 1.61-1.51 (m, 4H), 1.49 (s, 9H), 1.47-1.43 (m, 3H), 1.42-1.34 (m, 3H), 1.32 (d, J=4.6 Hz, 1H), 1.25-1.18 (m, 1H), 1.12 (s, 3H), 1.04 (s, 3H), 1.00 (s, 3H), 0.94 (s, 3H), 0.93 (br. s., 3H).

To a solution of (1R,5S)-tert-butyl 3-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)-3,8-diazabicyclo[3.2.1]octane-8-carboxylate, 2 TFA (30 mg, 0.030 mmol) in THF (0.75 mL) and MeOH (0.25 mL) was added a solution of lithium hydroxide (1N) (0.148 mL, 0.148 mmol). The reaction mixture was stirred at 75° C. After 1 h, the reaction mixture was cooled to rt and purified by reverse phase prep-HPLC using HPLC method 7 and dried to give 4-((1R,3 aS,5aR,5bR,7aR,11aS,11bR,13aR,13bR)-3a-((2-((1R,5S)-8-(tert-butoxycarbonyl)-3,8-diazabicyclo[3.2.1]octan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, 2 TFA (22.2 mg, 0.021 mmol, 69.0% yield) as pale yellow solid. LC/MS: m/e 768.8 (M+H)+, 2.34 min (method 3). ¹H NMR (400 MHz, CHLOROFORM-d) δ 7.96 (d, J=8.1 Hz, 2H), 7.21 (d, J=8.3 Hz, 2H), 5.13 (d, J=5.4 Hz, 1H), 4.84 (br. s., 1H), 4.68 (s, 1H), 4.36 (br. s., 2H), 3.68-3.32 (m, 6H), 2.98 (d, J=10.3 Hz, 2H), 2.70 (br. s., 1H), 2.08 (br. s., 7H), 1.97-1.82 (m, 2H), 1.70 (d, J=5.9 Hz, 1H), 1.66 (s, 3H), 1.63-1.51 (m, 5H), 1.49 (s, 9H), 1.47-1.39 (m, 5H), 1.39-1.27 (m, 4H), 1.27-1.15 (m, 3H), 1.11 (s, 3H), 1.02 (s, 3H), 0.98 (s, 3H), 0.97-0.94 (m, 3H), 0.89 (s, 4H).

Example 14

Preparation of 4-((1R,3aS,5aR,5bR,7aR,11aS,11bR,13aR,13bR)-5a,5b,8,8,11a-pentamethyl-3a-((2-((1R,5S)-6-(methylsulfonyl)-3,6-diazabicyclo[3.1.1]heptan-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

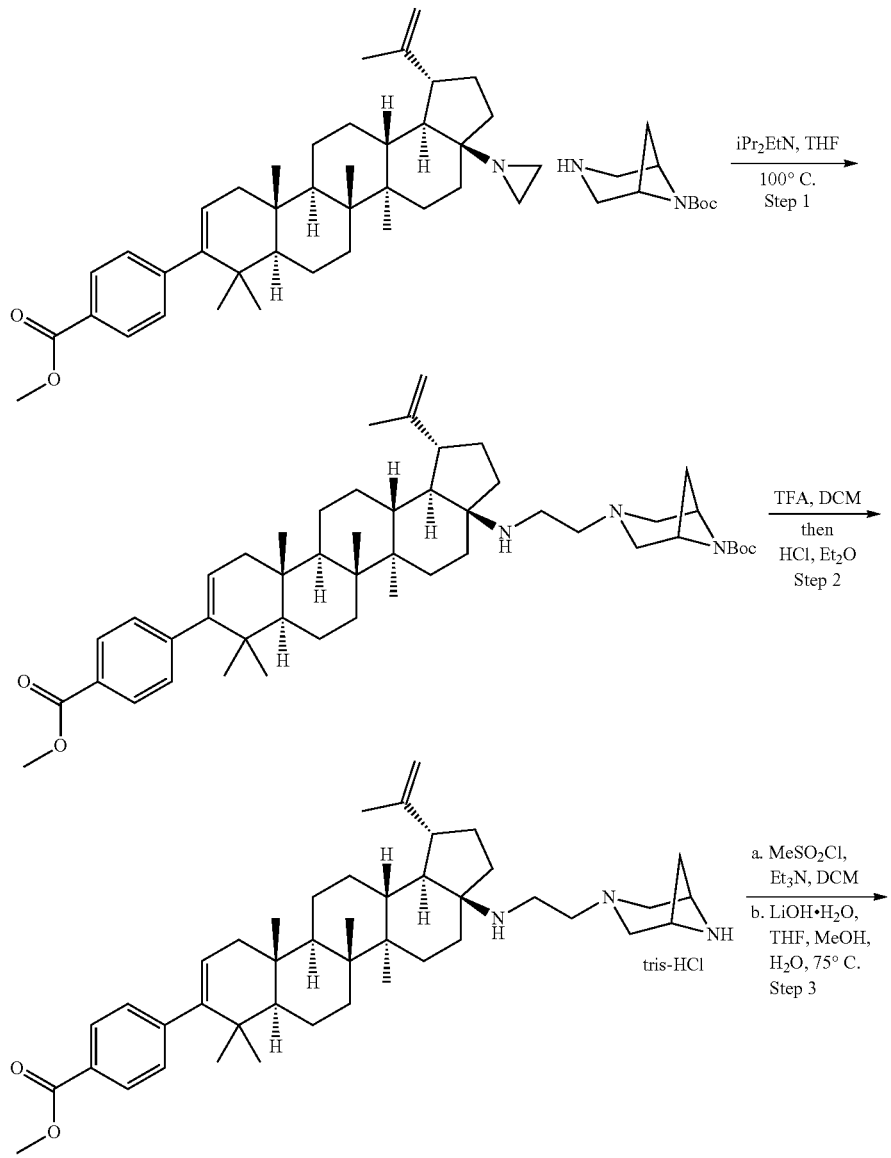

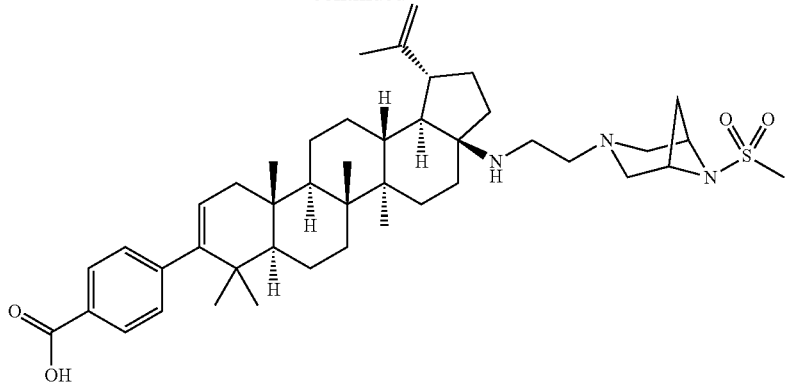

Example 14

Step 1. Preparation of (1R,5S)-tert-butyl 3-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)-3,6-diazabicyclo[3.1.1]heptane-6-carboxylate

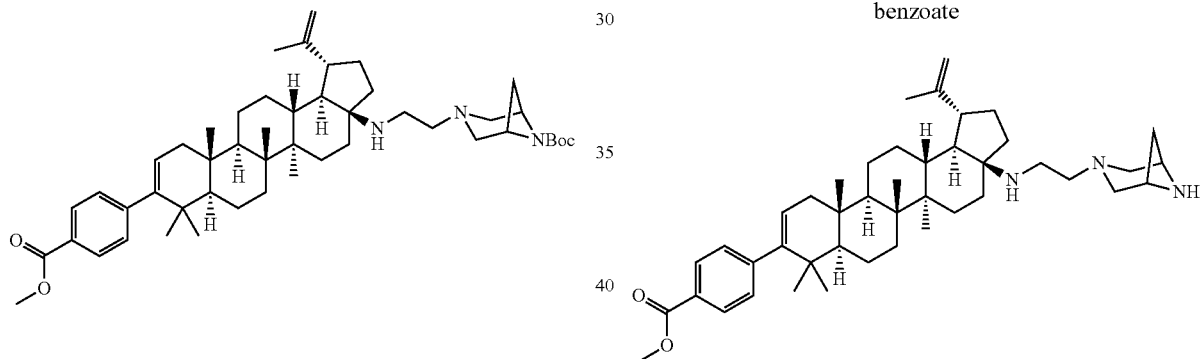

Methyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (250 mg, 0.439 mmol) and (1R,5S)-tert-butyl 3,6-diazabicyclo[3.1.1]heptane-6-carboxylate (435 mg, 2.194 mmol) were combined in a 20 mL scintillation vial, dissolved in THF (5 mL) and treated with N,N-di-iso-propylethylamine (0.764 mL, 4.39 mmol). The reaction mixture was heated to 100° C. After 112 h, the reaction mixture was cooled to rt, purified by reverse phase HPLC using prep-HPLC method 13 and dried under vacuum to give the title compound (126.6 mg, 0.127 mmol, 29.0% yield) as a white solid. LC/MS: m/e 768.5 (M+H)+, 2.41 min (method 7). $^1$H NMR (400 MHz, CHLOROFORM-d) δ 7.94 (d, J=8.6 Hz, 2H), 7.20 (d, J=8.3 Hz, 2H), 5.30 (d, J=4.4 Hz, 1H), 4.79 (s, 1H), 4.70 (s, 1H), 4.17 (d, J=5.9 Hz, 2H), 3.92 (s, 3H), 3.62 (d, J=11.7 Hz, 1H), 3.56-3.44 (m, 3H), 3.43-3.31 (m, 5H), 2.85-2.72 (m, 1H), 2.66-2.56 (m, 1H), 2.12 (dd, J=17.0, 6.5 Hz, 2H), 2.07-1.89 (m, 5H), 1.75 (d, J=11.5 Hz, 1H), 1.70 (s, 3H), 1.65 (br. s., 1H), 1.60-1.50 (m, 5H), 1.48 (s, 9H), 1.46-1.34 (m, 5H), 1.26-1.19 (m, 1H), 1.13 (s, 3H), 1.05 (s, 3H), 1.00 (s, 3H), 0.94 (s, 3H), 0.94 (br. s., 3H). $^{13}$C NMR (101 MHz, CHLOROFORM-d) δ 167.2, 154.9, 148.6, 146.9, 146.3, 130.0, 128.5, 128.0, 123.9, 111.8, 81.7, 77.2, 72.4, 58.3, 53.9, 52.8, 52.0, 49.4, 49.0, 45.3, 42.1, 41.8, 40.7, 37.9, 37.5, 37.2, 36.2, 33.5, 32.6, 29.4, 28.3, 28.3, 27.8, 26.3, 25.4, 25.1, 21.0, 20.9, 19.6, 19.1, 16.5, 15.8, 14.6.

Step 2. Preparation of methyl 4-((1R,3aS,5aR,5bR,7aR,11aS,11bR,13aR,13bR)-3a-((2-((1R,5S)-3,6-diazabicyclo[3.1.1]heptan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

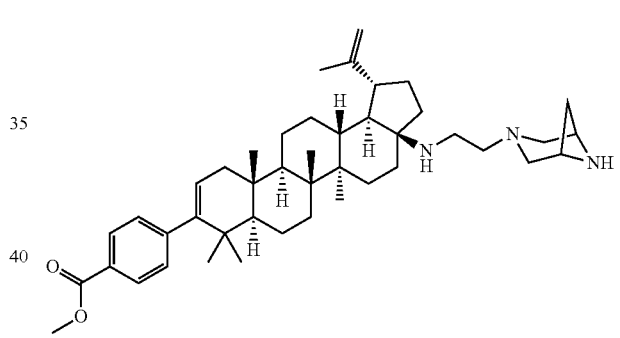

To a solution of (1R,5S)-tert-butyl 3-(2-(((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)-3,6-diazabicyclo[3.1.1]heptane-6-carboxylate (123 mg, 0.160 mmol) in DCM (3 mL) was added TFA (0.5 mL, 6.49 mmol) and the mixture was stirred at rt for 1 h. The resulting brown reaction mixture was diluted with DCE (3 mL) and concentrated to a light brown foam. The material was dissolved in DCM (2 mL) and DCE (2 mL) and treated with 2N HCl in Et$_2$O (0.5 mL, 1.0 mmol). The resulting slurry was concentrated and dried under vacuum to give the title compound (108.1 mg, 0.139 mmol, 87% yield) as light grey solid. LC/MS: m/e 668.5 (M+H)+, 2.28 min (method 3). $^1$H NMR (400 MHz, 1:1 CDCl$_3$:METHANOL-d$_4$) δ 7.89 (d, J=8.3 Hz, 2H), 7.18 (d, J=8.6 Hz, 2H), 5.27 (d, J=4.4 Hz, 1H), 4.85 (s, 1H), 4.71 (s, 1H), 4.39 (d, J=5.4 Hz, 2H), 3.88 (s, 3H), 3.76 (br. s., 1H), 3.59 (br. s., 1H), 3.48 (q, J=7.1 Hz, 3H), 3.40-3.33 (m, 2H), 3.07-2.91 (m, 2H), 2.37 (d, J=10.3 Hz, 1H), 2.25-1.89 (m, 7H), 1.83 (d, J=12.0 Hz, 1H), 1.77 (br. s., 1H), 1.73-1.71 (m, 3H), 1.67 (br. s., 1H), 1.65-1.58 (m, 2H), 1.57-1.38 (m, 8H), 1.37-1.29 (m, 1H), 1.27-1.22 (m, 1H), 1.13 (s, 3H), 1.08 (s, 3H), 1.00 (s, 3H), 0.92 (s, 3H), 0.91 (s, 3H).

Step 3

To a solution of methyl 4-((1R,3aS,5aR,5bR,7aR,11aS,11bR,13aR,13bR)-3a-((2-((1R,5S)-3,6-diazabicyclo[3.1.1]heptan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate (108 mg, 0.139 mmol) in DCM (3 mL) was added triethyl amine (0.097 mL, 0.695 mmol) and methanesulfonyl chloride (0.032 mL, 0.417 mmol). The reaction mixture was stirred at rt for 1 h before it was quenched with MeOH (0.5 mL), concentrated and dried under vacuum for 15 mins. LC/MS: m/e 746.6 (M+H)$^+$, 4.30 min (method 8).

The resulting brown residue from the above was dissolved in THF (2.5 mL) and MeOH (0.5 mL), treated with 3N lithium hydroxide (0.463 mL, 1.389 mmol) and stirred at 75° C. After 2.5 h, the reaction was cooled to rt. The reaction mixture was purified by reverse phase HPLC using prep-HPLC method 13 and dried under vacuum to give the title compound (81.7 mg, 0.083 mmol, 60.0% yield) as a white solid. LC/MS: m/e 632.5 (M+H)$^+$, 3.91 min (method 8). $^1$H NMR (400 MHz, 1:1 CDCl$_3$:METHANOL-d$_4$) δ 7.90 (d, J=8.6 Hz, 2H), 7.17 (d, J=8.3 Hz, 2H), 5.27 (d, J=4.6 Hz, 1H), 4.79 (s, 1H), 4.70 (s, 1H), 4.32 (d, J=4.6 Hz, 2H), 3.41-3.32 (m, 2H), 3.23-3.06 (m, 6H), 2.98 (s, 3H), 2.89-2.73 (m, 2H), 2.17-1.94 (m, 5H), 1.92-1.85 (m, 2H), 1.81-1.74 (m, 2H), 1.71 (s, 3H), 1.67 (s, 1H), 1.64-1.37 (m, 10H), 1.33 (dd, J=12.5, 3.7 Hz, 1H), 1.24 (d, J=10.0 Hz, 1H), 1.11 (s, 3H), 1.07 (s, 3H), 0.99 (s, 3H), 0.93 (s, 3H), 0.92 (s, 3H). $^{13}$C NMR (101 MHz, 1:1 CDCl$_3$:METHANOL-d$_4$) δ 169.0, 148.5, 147.2, 146.3, 129.9, 128.7, 128.3, 123.7, 111.6, 77.6, 72.0, 63.0, 62.9, 53.7, 53.6, 52.7, 52.69-52.62 (m, 1C), 49.2, 45.3, 42.1, 41.6, 41.2, 40.7, 39.7, 37.4, 37.1, 36.2, 33.6, 32.4, 30.9, 29.2, 28.0, 27.5, 26.4, 25.0, 20.9, 20.8, 19.6, 18.6, 16.3, 15.9, 14.2.

Example 15

Preparation of 4-((1R,3aS,5aR,5bR,7aR,11aS,11bR,13aR,13bR)-5a,5b,8,8,11a-pentamethyl-3a-((2-(2-(methylsulfonyl)-2,6-diazaspiro[3.4]octan-6-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid 4-((1R,3aS,5aR,5bR,7aR,11aS,11bR,13aR,13bR)-5a,5b,8,8,11a-Pentamethyl-3a-((2-(2-(methylsulfonyl)-2,6-diazaspiro[3.4]octan-6-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid was prepared in 24% yield from methyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the method used for the preparation of 4-((1R,3aS,5aR,5bR,7aR,11aS,11bR,13aR,13bR)-5a,5b,8,8,11a-pentamethyl-3a-((2-((1R,5S)-6-(methylsulfonyl)-3,6-diazabicyclo[3.1.1]heptan-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid; except in step 1 tert-butyl 2,6-diazaspiro[3.4]octane-2-carboxylate, HCl was used instead of (1R,5S)-tert-butyl 3,6-diazabicyclo[3.1.1]heptane-6-carboxylate. LC/MS: m/e 746.5 (M+H)$^+$, 3.91 min (method 8). $^1$H NMR (400 MHz, 1:1 CDCl$_3$:METHANOL-d$_4$) δ 7.90 (d, J=8.3 Hz, 2H), 7.18 (d, J=8.3 Hz, 2H), 5.27 (d, J=4.6 Hz, 1H), 4.79 (s, 1H), 4.70 (s, 1H), 3.99-3.91 (m, 2H), 3.90-3.85 (m, 2H), 3.29 (d, J=1.7 Hz, 1H), 3.25-3.14 (m, 3H), 3.08 (d, J=4.6 Hz, 2H), 2.91 (s, 3H), 2.77-2.66 (m, 1H), 2.33-2.24 (m, 2H), 2.18-1.98 (m, 4H), 1.98-1.92 (m, 1H), 1.89-1.82 (m, 1H), 1.80-1.75 (m, 1H), 1.71 (s, 3H), 1.68-1.65 (m, 1H), 1.64-1.30 (m, 11H), 1.25 (d, J=9.3 Hz, 1H), 1.20-1.13 (m, 1H), 1.10 (s, 3H), 1.07 (s, 3H), 1.00 (s, 3H), 0.94 (s, 3H), 0.92 (s, 3H). $^{13}$C NMR (101 MHz, 1:1 CDCl$_3$:METHANOL-d$_4$) δ 169.8, 149.4, 148.1, 147.1, 130.7, 129.4, 129.0, 124.5, 112.3, 78.5, 64.1, 61.6, 61.5, 54.3, 53.6, 52.2, 50.0, 46.4, 42.8, 42.4, 41.5, 40.4, 39.5, 38.2, 38.1, 36.9, 36.8, 36.2, 34.3, 33.1, 29.9, 28.8, 28.1, 27.1, 25.8, 21.7, 21.6, 20.4, 19.3, 17.0, 16.3, 15.0.

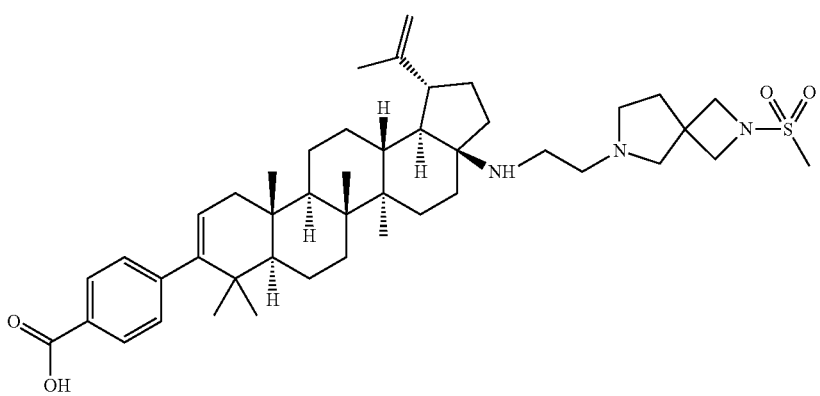

Example 16

Preparation of 4-((1R,3aS,5aR,5bR,7aR,11aS,11bR, 13aR,13bR)-5a,5b,8,8,11a-pentamethyl-3a-((2-(6-(methylsulfonyl)-2,6-diazaspiro[3.3]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

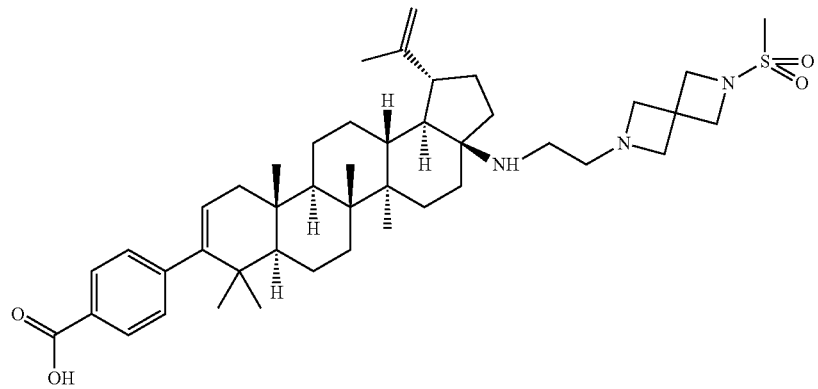

4-((1R,3aS,5aR,5bR,7aR,11aS,11bR,13aR,13bR)-5a,5b,8,8,11a-Pentamethyl-3a-((2-(6-(methylsulfonyl)-2,6-diazaspiro[3.3]heptan-2-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid was prepared in 5% yield from methyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the method used for the preparation of 4-((1R,3aS,5aR,5bR,7aR,11aS,11bR,13aR,13bR)-5a,5b,8,8,11a-pentamethyl-3a-((2-((1R,5S)-6-(methylsulfonyl)-3,6-diazabicyclo[3.1.1]heptan-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid; except in step 1 tert-butyl 2,6-diazaspiro[3.3]heptane-2-carboxylate (261 mg, 1.316 mmol) was used instead of (1R,5S)-tert-butyl 3,6-diazabicyclo[3.1.1]heptane-6-carboxylate. LC/MS: m/e 732.5 (M+H)$^+$, 3.92 min (method 8). $^1$H NMR (400 MHz, 1:1 CDCl$_3$: METHANOL-d$_4$) δ 7.90 (d, J=8.6 Hz, 2H), 7.18 (d, J=8.3 Hz, 2H), 5.28 (d, J=4.6 Hz, 1H), 4.78 (s, 1H), 4.69 (s, 1H), 4.11-4.00 (m, 3H), 3.84 (br. s., 4H), 3.79-3.74 (m, 1H), 3.13 (br. s., 1H), 3.10-3.01 (m, 2H), 2.98-2.92 (m, 1H), 2.89 (s, 3H), 2.70 (dt, J=11.0, 5.7 Hz, 1H), 2.12 (dd, J=17.1, 6.4 Hz, 1H), 2.07-1.88 (m, 4H), 1.86-1.74 (m, 2H), 1.71 (s, 3H), 1.68 (br. s., 1H), 1.64-1.30 (m, 12H), 1.25 (d, J=10.0 Hz, 1H), 1.14 (s, 3H), 1.07 (s, 3H), 1.01 (s, 3H), 0.94 (s, 3H), 0.93 (s, 3H).

Example 17

Preparation of 4-((1R,3aS,5aR,5bR,7aR,11aS,11bR, 13aR,13bR)-5a,5b,8,8,11a-pentamethyl-3a-((2-(6-(methylsulfonamido)-3-azabicyclo[3.1.0]hexan-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

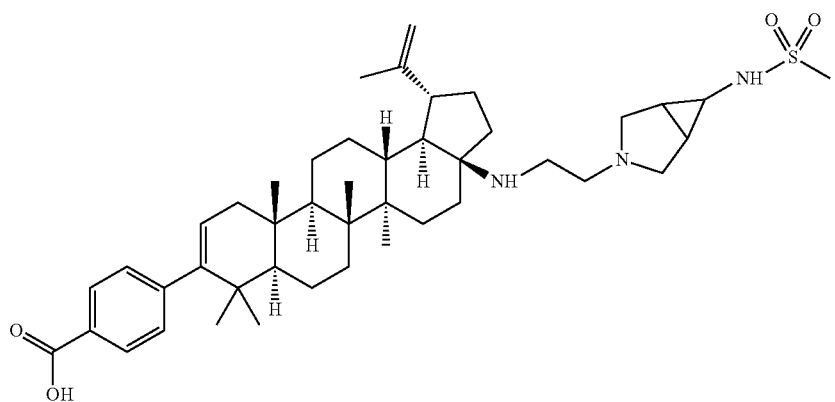

4-((1R,3aS,5aR,5bR,7aR,11aS,11bR,13aR,13bR)-5a,5b,8,8,11a-Pentamethyl-3a-((2-(6-(methylsulfonamido)-3-azabicyclo[3.1.0]hexan-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid was prepared in 12% yield over three steps from methyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate following the method used in the preparation of 4-((1R,3aS,5aR,5bR,7aR,11aS,11bR,13aR,13bR)-5a,5b,8,8,11a-pentamethyl-3a-((2-((1R,5S)-6-(methylsulfonyl)-3,6-diazabicyclo[3.1.1]heptan-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid; except in step 1 tert-butyl 3-azabicyclo[3.1.0]hexan-6-ylcarbamate was used instead of (1R,5S)-tert-butyl 3,6-diazabicyclo[3.1.1]heptane-6-carboxylate. LC/MS: m/e 732.5 (M+H)+, 3.86 min (method 8). ¹H NMR (400 MHz, 1:1 CDCl₃:METHANOL-d₄) δ 7.90 (d, J=8.3 Hz, 2H), 7.18 (d, J=8.3 Hz, 2H), 5.28 (d, J=4.9 Hz, 1H), 5.23 (s, 1H), 5.13 (s, 1H), 4.85 (s, 1H), 4.72 (br. s., 1H), 3.85 (br. s., 2H), 3.72 (br. s., 2H), 3.48 (br. s., 4H), 3.09 (br. s., 1H), 3.03 (s, 3H), 2.81 (d, J=10.3 Hz, 1H), 2.25-1.97 (m, 8H), 1.87 (d, J=11.5 Hz, 1H), 1.79-1.60 (m, 6H), 1.53 (d, J=16.1 Hz, 6H), 1.44-1.33 (m, 4H), 1.30-1.23 (m, 2H), 1.21 (br. s., 3H), 1.11-1.04 (m, 3H), 1.02 (s, 3H), 0.94 (s, 3H), 0.93 (br. s., 3H).

Example 18

Preparation of 4-((1R,3aS,5aR,5bR,7aR,11aS,11bR,13aR,13bR)-3a-((2-((1R,4R)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid 11b,12,13,13a,13b-octadecahydro-1H-cyclopenta[a]chrysen-9-yl)benzoate (250 mg, 0.439 mmol) in THF (5 mL) was added N,N-di-iso-propylethylamine (0.535 mL, 3.07 mmol) and (1R,4R)-2-thia-5-azabicyclo[2.2.1]heptane 2,2-dioxide (323 mg, 2.194 mmol). The resulting cloudy reaction mixture was stirred at 100° C. After 71 h, the reaction was cooled to rt. To the reaction mixture was added MeOH (2 mL) and 3N lithium hydroxide (1.462 mL, 4.39 mmol). The mixture was stirred at 75° C. for 4 h, then it was cooled to rt and concentrated in vacuum. The crude material was purified by reverse phase HPLC using HPLC method 14 and concentrated to give product with some ammonium bicarbonate. The material from the above was re-subjected to HPLC method 13, concentrated and dried under vacuum to give the title compound (25.5 mg, 0.026 mmol, 5.99% yield). LC/MS: m/e 703.4 (M+H)+, 3.95 min (method 8). ¹H NMR (400 MHz, 1:1 CDCl₃:METHANOL-d₄) δ 7.90 (d, J=8.3 Hz, 2H), 7.18 (d, J=8.3 Hz, 2H), 5.27 (d, J=4.6 Hz, 1H), 4.80 (s, 1H), 4.71 (s, 1H), 3.81 (br. s., 1H), 3.64 (br. s., 1H), 3.42 (d, J=11.2 Hz, 1H), 3.28 (d, J=2.4 Hz, 1H), 3.22-3.12 (m, 2H), 3.06 (dd, J=13.2, 3.4 Hz, 1H), 3.02-2.88 (m, 3H), 2.84-2.75 (m, 1H), 2.53 (d, J=12.2 Hz, 1H), 2.38 (d, J=10.8 Hz, 1H), 2.20-1.95 (m, 5H), 1.89-1.79 (m, 1H), 1.77 (br. s., 1H), 1.72 (s, 3H), 1.68 (br. s., 1H), 1.65-1.46 (m, 9H), 1.43 (d, J=12.7 Hz, 1H),

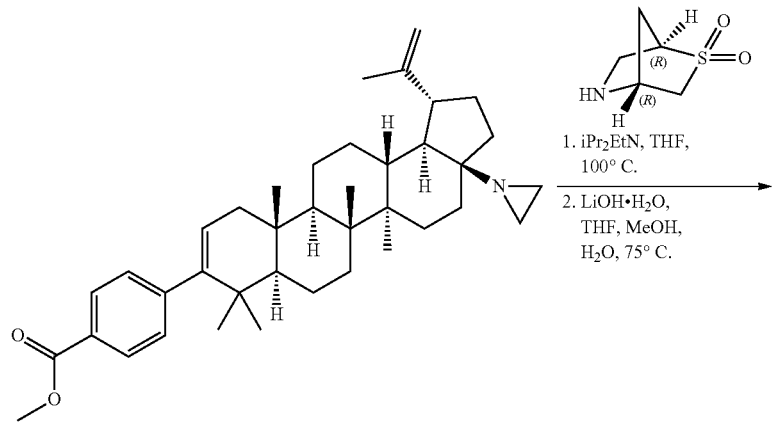

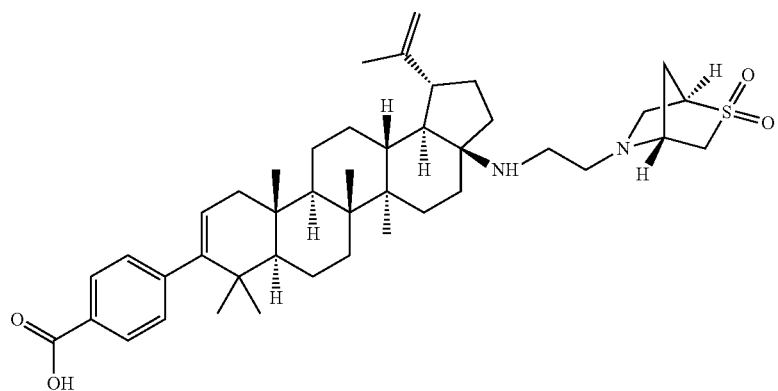

To a solution of methyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a, 1.37 (d, J=3.9 Hz, 1H), 1.25 (d, J=6.6 Hz, 1H), 1.19 (s, 3H), 1.17-1.11 (m, 1H), 1.08 (s, 3H), 1.01 (s, 3H), 0.94 (s, 3H), 0.92 (s, 3H).

Example 19
Preparation of 4-((1R,3aS,5aR,5bR,7aR,11aS,11bR, 13aR,13bR)-3a-((2-((1S,4S)-2-oxa-5-azabicyclo [2.2.1]heptan-5-yl)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid
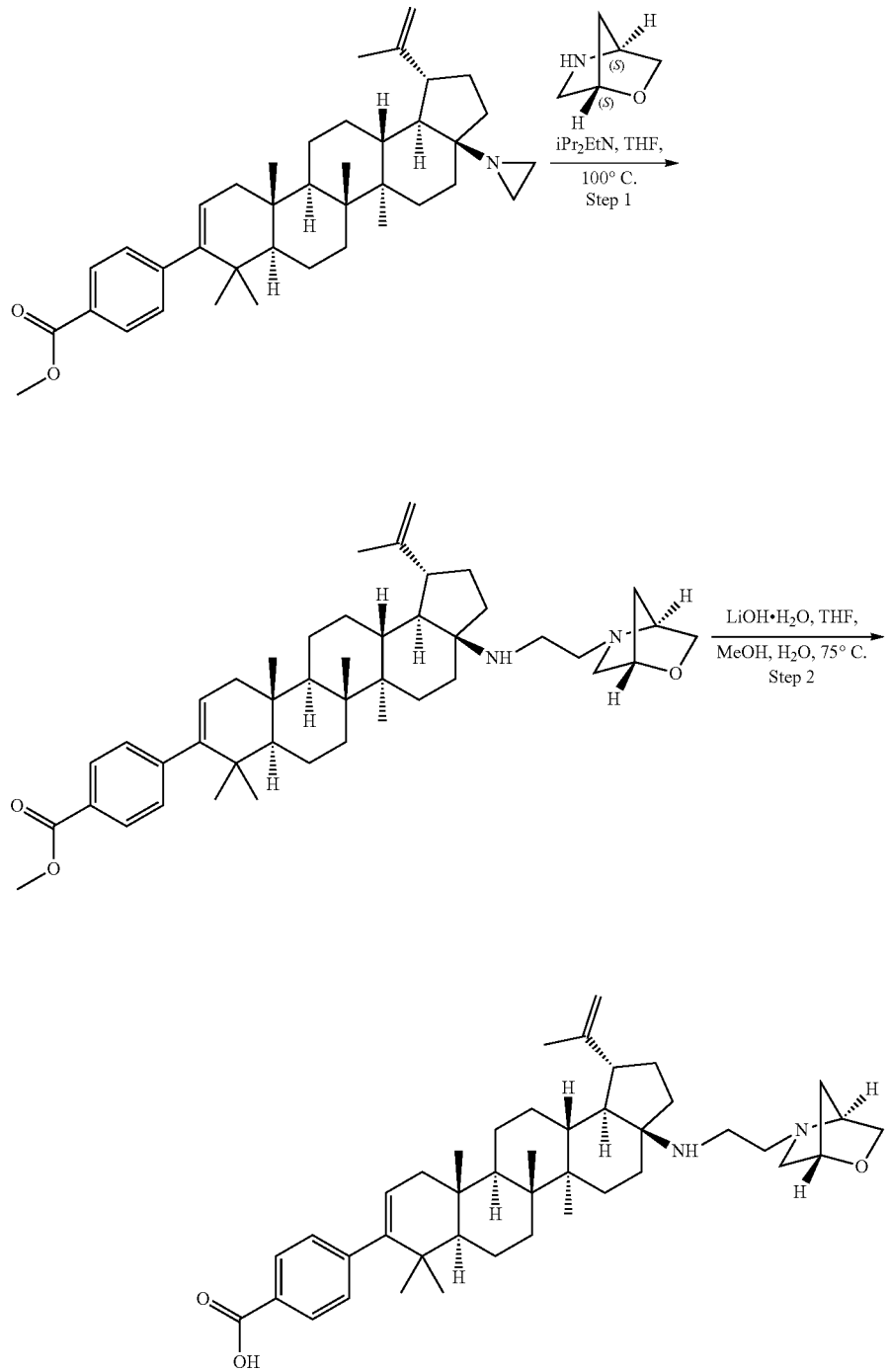
Example 19

Step 1. Preparation of methyl 4-((1R,3aS,5aR,5bR, 7aR,11aS,11bR,13aR,13bR)-3a-((2-((1S,4S)-2-oxa-5-azabicyclo[2.2.1]heptan-5-yl)ethyl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate

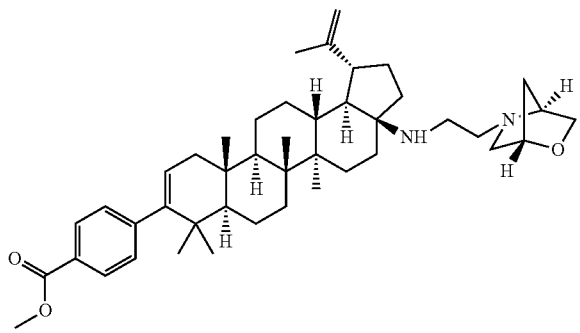

Methyl 4-((1R,3aS,5aR,5bR,7aR,11aS,11bR,13aR, 13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (200 mg, 0.351 mmol), (1S,4S)-2-oxa-5-azabicyclo [2.2.1]heptane, HCl (238 mg, 1.755 mmol), and 4° A molecular sieves (250 mg, 0.351 mmol) were combined in a 20 mL scintillation vial. The mixture was dried in a 50° C. vacuum oven for 1 h. THF (5 mL) and N,N-diisopropylethylamine (0.428 mL, 2.457 mmol) were added. The solution was purged with $N_2$ (g) and stirred at 100° C. After 68 h, reaction was concentrated to a viscous brown oil which was purified by reverse phase HPLC using HPLC method 6 and dried under vacuum to give the title compound (104 mg, 0.114 mmol, 32.4% yield) as a white solid. LC/MS: m/e 669.5 $(M+H)^+$, 4.42 min (method 8). $^1$H NMR (400 MHz, CHLOROFORM-d) δ 7.91 (d, J=8.1 Hz, 2H), 7.18 (d, J=8.1 Hz, 2H), 5.28 (d, J=4.9 Hz, 1H), 4.78 (s, 1H), 4.69 (s, 1H), 4.64 (br. s., 1H), 4.28 (br. s., 1H), 4.17 (d, J=9.8 Hz, 1H), 3.90 (s, 3H), 3.79 (d, J=9.5 Hz, 1H), 3.74-3.61 (m, 1H), 3.44 (br. s., 2H), 3.36 (br. s., 1H), 2.77 (d, J=6.8 Hz, 1H), 2.27-1.99 (m, 6H), 1.98-1.83 (m, 2H), 1.77 (d, J=12.2 Hz, 1H), 1.69 (s, 3H), 1.66-1.61 (m, 1H), 1.59-1.30 (m, 13H), 1.21 (d, J=6.4 Hz, 1H), 1.10 (s, 3H), 1.04 (s, 3H), 0.98 (s, 3H), 0.93 (s, 6H). $^{13}$C NMR (101 MHz, CHLOROFORM-d) δ 167.2, 148.5, 146.8, 146.2, 130.0, 128.5, 127.9, 123.8, 111.9 (br. s., 1C), 74.9, 73.1 (br. s., 1C), 64.3 (br. s., 1C), 61.3 (br. s., 1C), 54.1, 52.8, 51.9, 49.3, 49.0, 45.4, 42.0, 41.7, 40.7, 38.8 (br. s., 1C), 37.4, 37.3, 36.2, 33.5, 32.5, 29.4, 28.0, 27.5, 26.3, 25.0, 20.9, 20.8, 19.6, 18.8, 18.4, 17.2, 16.4, 15.4, 14.5, 11.8.

Step 2

To a solution of methyl 4-((1R,3aS,5aR,5bR,7aR,11aS, 11bR,13aR,13bR)-3a-((2-((1S,4S)-2-oxa-5-azabicyclo [2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate (99 mg, 0.148 mmol) in THF (2 mL) and MeOH (0.5 mL) was added 3N lithium hydroxide (0.197 mL, 0.592 mmol). The reaction mixture was stirred at 75° C. After 3.5 h, the reaction was cooled to rt and concentrated to a white paste which was purified by reverse phase prep-HPLC using prep method 6 and dried under vacuum to give the title compound (81.4 mg, 0.088 mmol, 59.2% yield) as a white solid. LC/MS: m/e 655.5 $(M+H)^+$, 3.76 min (method 8). $^1$H NMR (400 MHz, 1:1 CHLOROFORM-d:METHANOL-$d_4$) δ 7.90 (d, J=8.3 Hz, 2H), 7.18 (d, J=8.3 Hz, 2H), 5.35-5.23 (m, 1H), 4.79 (s, 1H), 4.70 (s, 1H), 4.58 (br. s., 1H), 4.08 (d, J=9.0 Hz, 1H), 4.02 (br. s., 1H), 3.76 (dd, J=9.3, 1.5 Hz, 1H), 3.30-3.21 (m, 2H), 3.16 (d, J=10.3 Hz, 2H), 3.00 (br. s., 1H), 2.74 (td, J=11.1, 5.5 Hz, 1H), 2.18-1.94 (m, 7H), 1.91-1.84 (m, 1H), 1.82-1.75 (m, 1H), 1.71 (s, 3H), 1.70-1.63 (m, 2H), 1.63-1.30 (m, 11H), 1.28-1.17 (m, 2H), 1.14 (s, 3H), 1.07 (s, 3H), 1.00 (s, 3H), 0.93 (s, 3H), 0.92 (br. s., 3H).

Example A1

Preparation of 4-((1R,3aS,5aR,5bR,7aR,11aS,11bR, 13aR,13bR)-3a-((2-((1R,5S)-3-oxa-9-azabicyclo [3.3.1]nonan-9-yl)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid

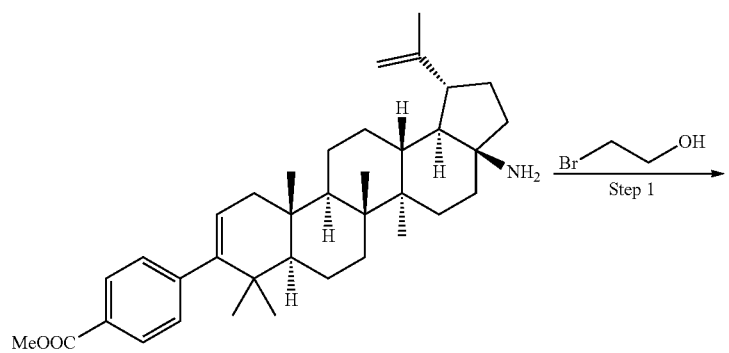

-continued
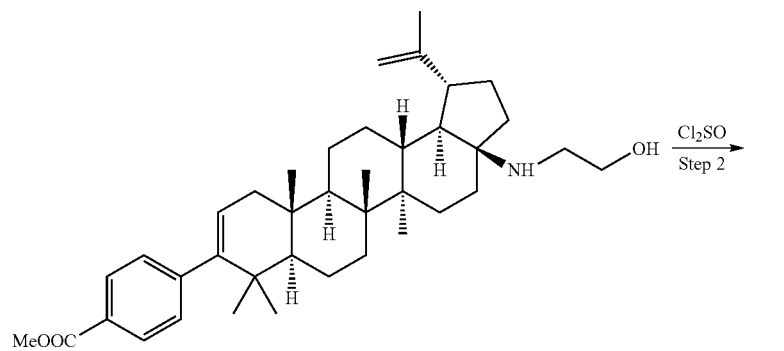
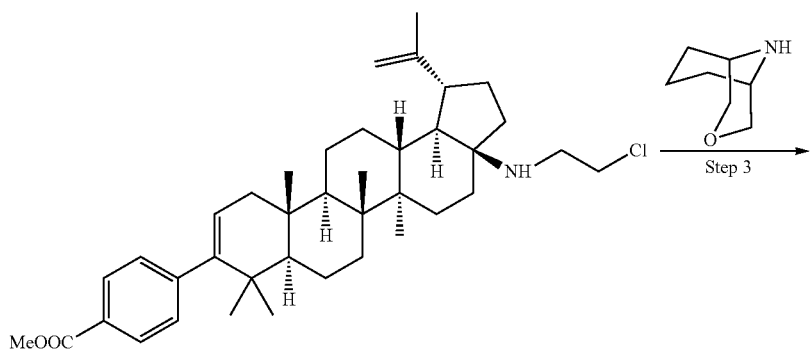
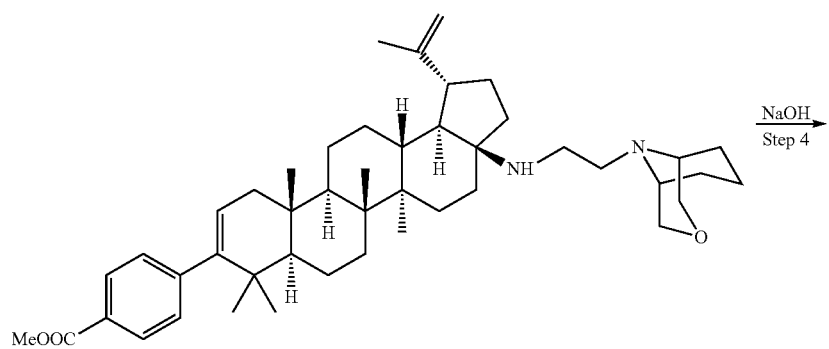
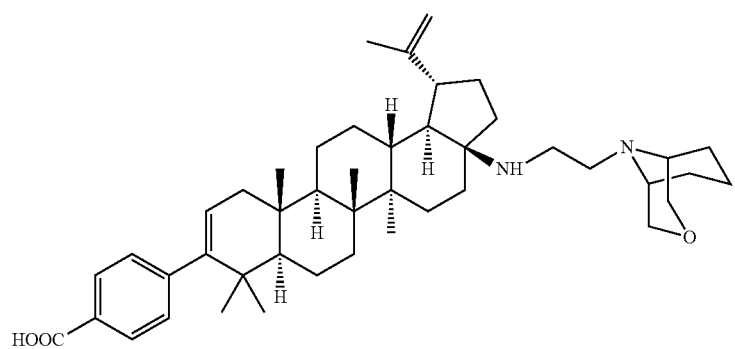
Example A1

Step 1. Preparation of methyl 4-((1R,3aS,5aR,5bR,
7aR,11aS,11bR,13aR,13bR)-3a-((2-hydroxyethyl)
amino)-5a,5b,8,8,11a-pentamethyl-1-(prop-1-en-2-
yl)-2,3,3a,4,5,5a,5b,6,7,7a,8,11,11a,11b,12,13,13a,
13b-octadecahydro-1H-cyclopenta[a]chrysen-9-yl)
benzoate

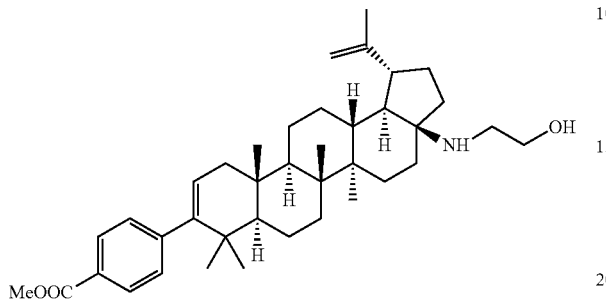

A mixture of methyl 4-((1R,3aS,5aR,5bR,7aR,11aS,
11bR,13aR,13bR)-3a-amino-5a,5b,8,8,11a-pentamethyl-1-
(prop-1-en-2-yl)-2,3,3a,4,5,5a,5b,6,7,7a,8,11,11a,11b,12,
13,13a,13b-octadecahydro-1H-cyclopenta[a]chrysen-9-yl)
benzoate (1500 mg, 2.76 mmol), 2-bromoethanol (1034 mg,
8.27 mmol), potassium phosphate (1756 mg, 8.27 mmol) and
potassium iodide (916 mg, 5.52 mmol) in acetonitrile (10
mL) was heated to 120° C. for 15 h. The reaction mixture was
poured into distilled water (40 mL). The white precipitate was
filtered and washed with distilled water (100 mL). The white
solid was dried under reduced pressure to provide the title
compound (1.4 g, 86%), which was taken to the next step
without further purification. LCMS: m/e 588.5 (M+H)$^+$, 2.40
min (method 5).

Step 2. Preparation of methyl 4-((1R,3aS,5aR,5bR,
7aR,11aS,11bR,13aR,13bR)-3a-((2-chloroethyl)
amino)-5a,5b,8,8,11a-pentamethyl-1-(prop-1-en-2-
yl)-2,3,3a,4,5,5a,5b,6,7,7a,8,11,11a,11b,12,13,13a,
13b-octadecahydro-1H-cyclopenta[a]chrysen-9-yl)
benzoate

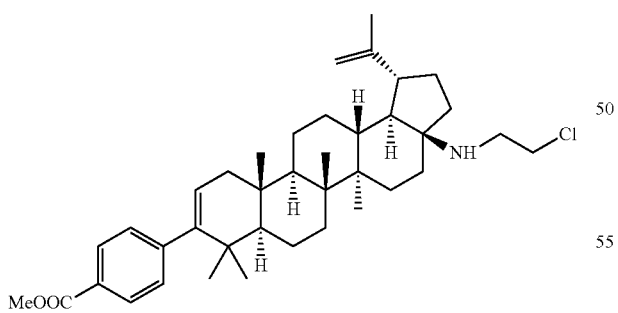

A mixture of methyl 4-((1R,3aS,5aR,5bR,7aR,11aS,
11bR,13aR,13bR)-3a-((2-hydroxyethyl)amino)-5a,5b,8,8,
11a-pentamethyl-1-(prop-1-en-2-yl)-2,3,3a,4,5,5a,5b,6,7,
7a,8,11,11a,11b,12,13,13a,13b-octadecahydro-1H-
cyclopenta[a]chrysen-9-yl)benzoate (1400 mg, 2.381 mmol)
and thionyl chloride (1.738 mL, 23.81 mmol) in dichloroet-
hane (15 mL) was heated to 60° C. for 2 h. The reaction
mixture was concentrated under reduced pressure to provide
the desired product as a brown solid (1.3 g, 90%), which was
taken to the next step without further purification. LCMS: m/e
606.48 (M+H)$^+$, 2.46 min (method 5).

Step 3. Preparation of methyl 4-((1R,3aS,5aR,5bR,
7aR,11aS,11bR,13aR,13bR)-3a-((2-((1R,5S)-3-oxa-
9-azabicyclo[3.3.1]nonan-9-yl)ethyl)amino)-5a,5b,8,
8,11a-pentamethyl-1-(prop-1-en-2-yl)-2,3,3a,4,5,5a,
5b,6,7,7a,8,11,11a,11b,12,13,13a,13b-
octadecahydro-1H-cyclopenta[a]chrysen-9-yl)
benzoate

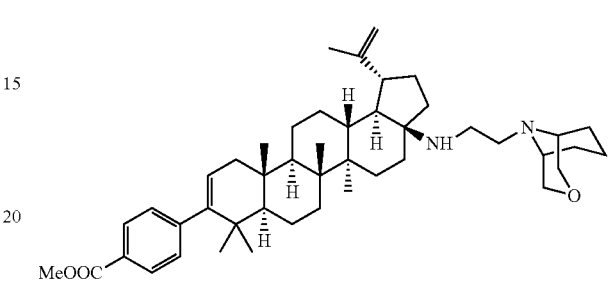

A mixture of methyl 4-((1R,3aS,5aR,5bR,7aR,11aS,
11bR,13aR,13bR)-3a-((2-chloroethyl)amino)-5a,5b,8,8,
11a-pentamethyl-1-(prop-1-en-2-yl)-2,3,3a,4,5,5a,5b,6,7,
7a,8,11,11a,11b,12,13,13a,13b-octadecahydro-1H-
cyclopenta[a]chrysen-9-yl)benzoate (20 mg, 0.033 mmol),
(1R,5S)-3-oxa-9-azabicyclo[3.3.1]nonane (16.78 mg, 0.132
mmol) and Hunig's Base (0.029 mL, 0.165 mmol) in DMSO
(1 mL) was heated to 120° C. for 1 h. The reaction mixture
was quenched with distilled water (2 mL), extracted with
dichloromethane (2×2 mL), dried over sodium sulfate, fil-
tered and concentrated under reduced pressure to provide
methyl 4-((1R,3aS,5aR,5bR,7aR,11aS,11bR,13aR,13bR)-
3a-((2-((1R,5S)-3-oxa-9-azabicyclo[3.3.1]nonan-9-yl)ethyl)
amino)-5a,5b,8,8,11a-pentamethyl-1-(prop-1-en-2-yl)-2,3,
3a,4,5,5a,5b,6,7,7a,8,11,11a,11b,12,13,13a,13b-
octadecahydro-1H-cyclopenta[a]chrysen-9-yl)benzoate as a
brown solid which was taken to the next step without further
purification.

Step 4. Preparation of 4-((1R,3aS,5aR,5bR,7aR,
11aS,11bR,13aR,13bR)-3a-((2-((1R,5S)-3-oxa-9-
azabicyclo[3.3.1]nonan-9-yl)ethyl)amino)-5a,5b,8,8,
11a-pentamethyl-1-(prop-1-en-2-yl)-2,3,3a,4,5,5a,
5b,6,7,7a,8,11,11a,11b,12,13,13a,13b-
octadecahydro-1H-cyclopenta[a]chrysen-9-yl)
benzoic acid

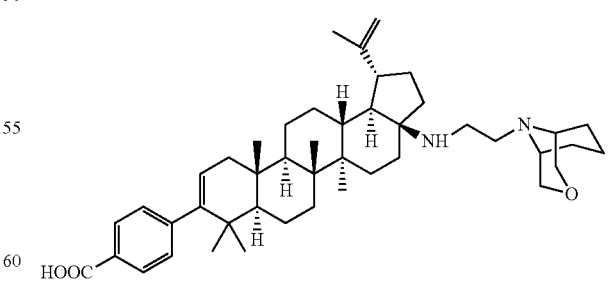

To the ester intermediate from above in 1,4-dioxane (1 mL)
was added 1N NaOH (0.143 mL, 0.143 mmol), the reaction
mixture was heated to 80° C. for 3 h. The mixture was cooled
to rt and purified by Prep. HPLC to provide the title com-
pound as a white solid (3 mg, 13%). LCMS: m/e 683.7
(M+H)$^+$, 2.13 min (method 4). $^1$H NMR (500 MHz, ACETO- NITRILE-d$_3$) δ 7.93 (d, J=8.4 Hz, 2H), 7.28 (d, J=8.4 Hz, 2H), 5.32 (dd, J=6.1, 1.7 Hz, 1H), 4.81 (s, 1H), 4.71 (s, 1H), 4.11 (t, J=14.1 Hz, 2H), 4.01-3.84 (m, 2H), 3.44-2.97 (m, 6H), 2.91-2.73 (m, 1H), 2.45 (qd, J=13.2, 6.2 Hz, 1H), 2.30-1.15 (m, 27H), 1.75 (s, 3H), 1.21 (s, 3H), 1.09 (s, 3H), 1.05 (s, 3H), 0.98 (s, 3H), 0.96 (s, 3H).

Example A2

Preparation of 4-((1R,3aS,5aR,5bR,7aR,11aS,11bR, 13aR,13bR)-3a-((2-(8-oxa-3-azabicyclo[3.2.1]octan-3-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid

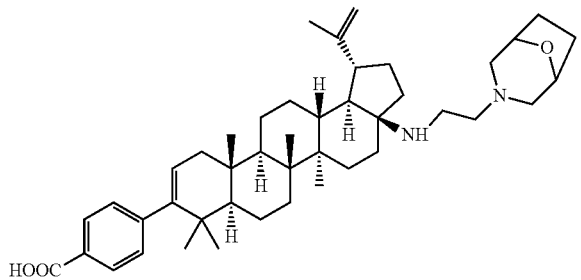

The title compound was prepared following the method described above for the synthesis of 4-((1R,3aS,5aR,5bR, 7aR,11aS,11bR,13aR,13bR)-3a-((2-((1R,5S)-3-oxa-9-azabicyclo[3.3.1]nonan-9-yl)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoic acid using (1R,5S)-8-oxa-3-azabicyclo [3.2.1]octane as the alkylating amine in step 3. The product was isolated as a white solid (8 mg, 28%). LCMS: m/e 669.7 (M+H)$^+$, 2.11 min (method 4). $^1$H NMR (500 MHz, ACETO-NITRILE-d$_3$) δ 8.17-7.83 (m, 2H), 7.43-7.12 (m, 2H), 5.32 (dd, J=6.2, 1.8 Hz, 1H), 4.80 (d, J=1.7 Hz, 1H), 4.72 (d, J=1.4 Hz, 1H), 4.37 (br. s., 2H), 3.14 (br. s., 4H), 2.99 (br. s., 4H), 2.92-2.81 (m, 1H), 2.68-2.44 (m, 2H), 2.27-1.15 (m, 24H), 1.75 (s, 3H), 1.21 (s, 3H), 1.09 (s, 3H), 1.05 (s, 3H), 0.98 (s, 3H), 0.96 (s, 3H).

Example A3

Preparation of 4-((1R,3aS,5aR,5bR,7aR,11aS,11bR, 13aR,13bR)-3a-((2-((1R,5R)-3,7-dioxa-9-azabicyclo [3.3.1]nonan-9-yl)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoic acid

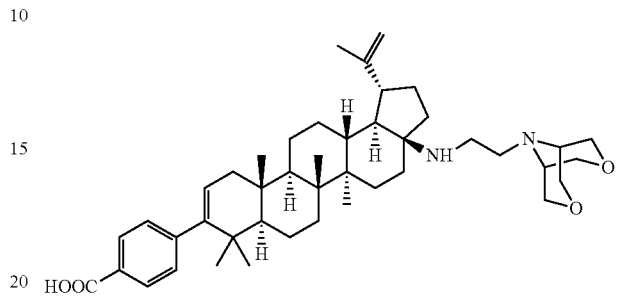

The title compound was prepared following the method described above for the synthesis of 4-((1R,3aS,5aR,5bR, 7aR,11aS,11bR,13aR,13bR)-3a-((2-((1R,5S)-3-oxa-9-azabicyclo[3.3.1]nonan-9-yl)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoic acid using (1s,5s)-3,7-dioxa-9-azabicyclo[3.3.1]nonane as the alkylating amine in step 3. The product was isolated as a white solid (2.4 mg, 7%). LCMS: m/e 685.6 (M+H)$^+$, 2.30 min (method 5). $^1$H NMR (500 MHz, ACETONITRILE-d$_3$) δ 8.04-7.74 (m, 2H), 7.28 (d, J=8.4 Hz, 2H), 5.32 (dd, J=6.2, 1.8 Hz, 1H), 4.81 (s, 1H), 4.73 (s, 1H), 4.11 (d, J=11.7 Hz, 2H), 4.02 (d, J=11.7 Hz, 2H), 3.84 (t, J=12.5 Hz, 4H), 3.56-3.38 (m, 1H), 3.22-2.97 (m, 4H), 2.94 (dd, J=11.1, 5.9 Hz, 2H), 2.70-1.15 (m, 22H), 1.76 (s, 3H), 1.26 (s, 3H), 1.10 (s, 3H), 1.06 (s, 3H), 0.98 (s, 3H), 0.96 (s, 3H).

Example A4

Preparation of 4-((1R,3aS,5aR,5bR,7aR,11aS,11bR, 13aR,13bR)-3a-((2-((1R,3S,5S)-3-hydroxy-3-methyl-8-azabicyclo[3.2.1]octan-8-yl)ethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

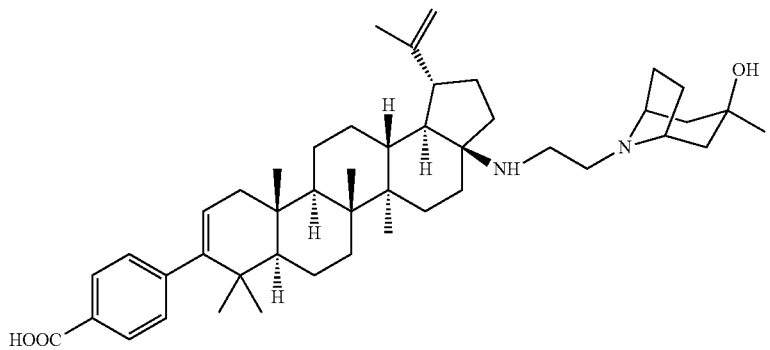

The title compound was prepared following the method described above for the synthesis of 4-((1R,3aS,5aR,5bR,7aR,11aS,11bR,13aR,13bR)-3a-((2-((1R,5S)-3-oxa-9-azabicyclo[3.3.1]nonan-9-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid using (1R,3r,5S)-3-methyl-8-azabicyclo[3.2.1]octan-3-ol as the alkylating amine in step 3. The product was isolated as a white solid (2.5 mg, 30%). LCMS: m/e 697.65 (M+H)+, 1.40 min (method 4). $^1$H NMR (400 MHz, ACETONITRILE-d$_3$) δ 7.89 (d, J=8.0 Hz, 2H), 7.23 (d, J=8.3 Hz, 2H), 5.27 (d, J=4.5 Hz, 1H), 4.74 (s, 1H), 4.63 (br. s., 1H), 3.90 (br. s., 2H), 3.52-2.99 (m, 4H), 2.88-2.64 (m, 1H), 2.53-1.08 (m, 30H), 1.69 (s, 3H), 1.18 (s, 3H), 1.13 (s, 3H), 1.03 (s, 3H), 1.00 (s, 3H), 0.93 (s, 3H), 0.91 (s, 3H).

Example B1

Preparation of 4-((1R,3aS,5aR,5bR,7aR,11aS,11bR,13aR,13bR)-3a-((2-(2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA

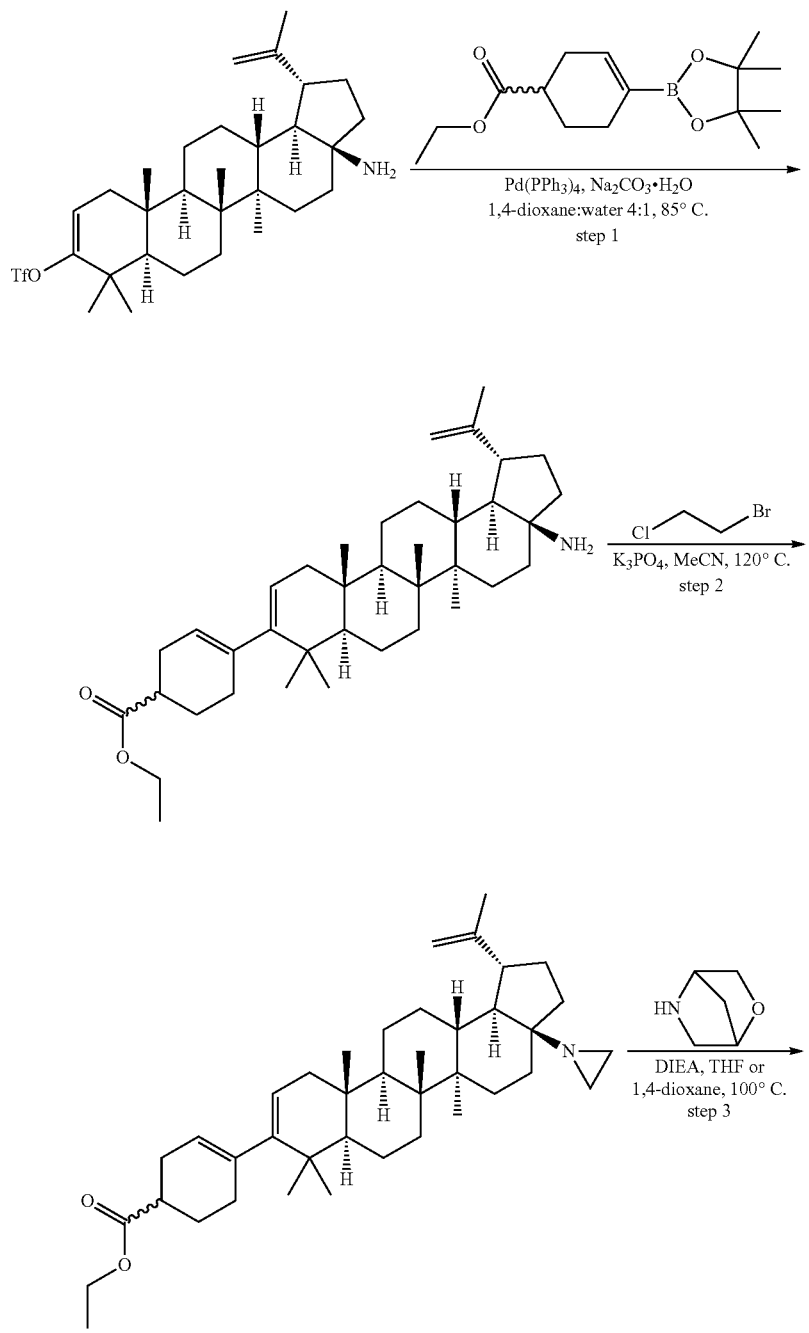

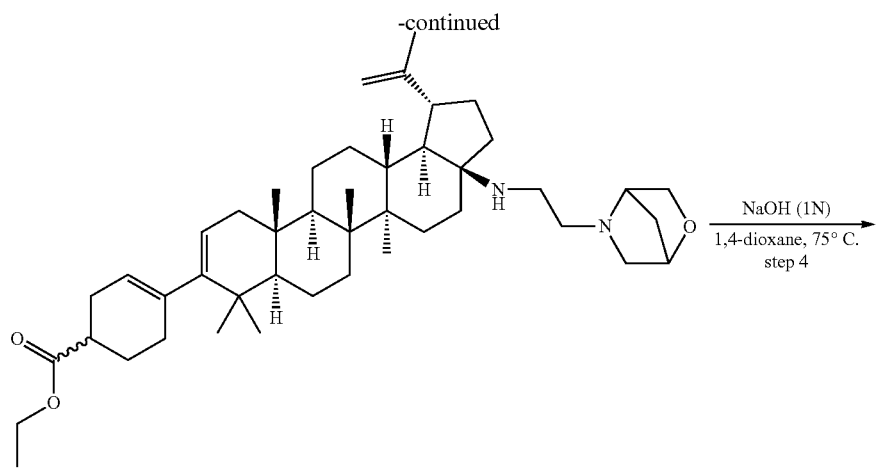

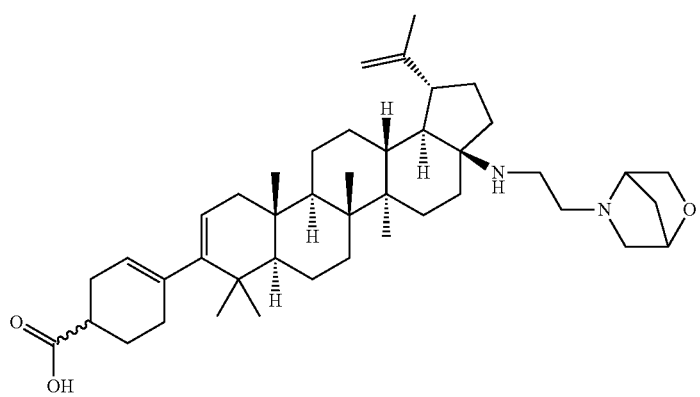

Example B1

Step 1. Preparation of ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

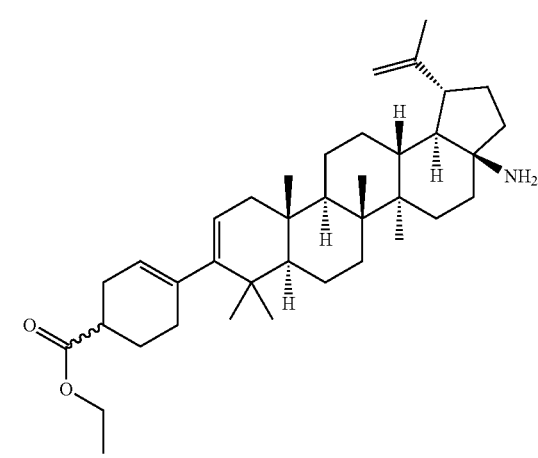

To a flask containing ethyl 4-(4,4,5,5-tetramethyl-1,3,2-dioxaborolan-2-yl)cyclohex-3-enecarboxylate (0.801 g, 2.86 mmol) was added (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (1.45 g, 2.60 mmol), sodium carbonate hydrate (0.967 g, 7.80 mmol) and palladium tetrakis (0.090 g, 0.078 mmol). The mixture was diluted with 1,4-dioxane (20 mL) and water (5 mL). Then it was flushed with nitrogen and heated to 85° C. in an oil bath. After heating the mixture for 16 h, it was cooled to rt, diluted with water (30 mL) and extracted with ethyl acetate (3×30 mL). The combined organic layers were washed with brine, dried over magnesium sulfate, filtered and concentrated under reduced pressure. The residue was purified by flash chromatography using a 10-80% ethyl acetate in hexanes gradient and a 80 g silica gel column. The fractions containing the expected product were combined and concentrated under reduced pressure. Since impurities were still present, a second purification followed using a 20-70% EtOAc in hexanes gradient and an 80 g silica gel column. The factions containing the expected product were combined and concentrated under reduced pressure to give the title compound (0.655 g, 1.17 mmol, 45% yield) as an off-white solid. LCMS: m/e 562.7 (M+H)$^+$, 2.17 min (method 5).

Step 2. Preparation of ethyl 4-((1R,3aS,5aR,5bR, 7aR,11aS,11bR,13aR,13bR)-3a-(aziridin-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)cyclohex-3-enecarboxylate

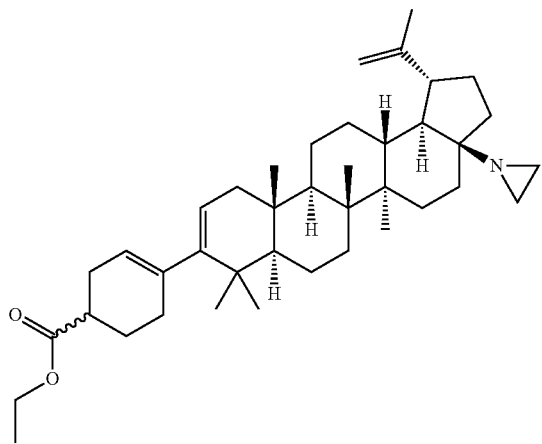

To a sealable vial was added ethyl 4-((1R,3 aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)cyclohex-3-enecarboxylate (0.2 g, 0.356 mmol), 1-bromo-2-chloroethane (0.295 mL, 3.56 mmol) and phosphoric acid, potassium salt (0.378 g, 1.780 mmol). The mixture was diluted with acetonitrile (5 mL), was flushed with nitrogen, then sealed and heated to 120° C. After 24 h of heating, the mixture was cooled to rt. The reaction mixture was filtered to remove solids, then the solids were washed with dichloromethane and the filtrate was concentrated under reduced pressure to give the title compound (0.21 g, 0.357 mmol, 100% yield) as an off-white solid. LCMS: m/e 588.7 (M+H)$^+$, 2.21 min (method 5).

Step 3. Preparation of ethyl 4-((1R,3aS,5aR,5bR, 7aR,11aS,11bR,13aR,13bR)-3a-((2-(2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylate

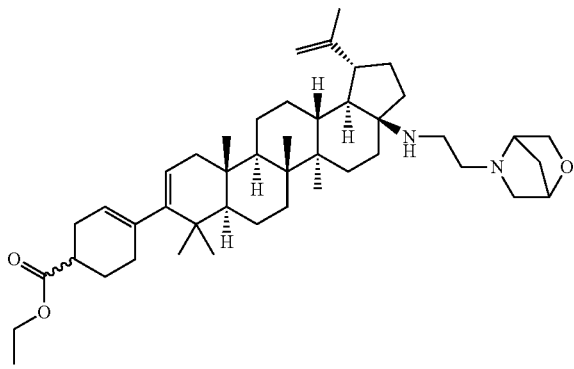

To a vial containing a suspension of ethyl 4-((1R,3 aS,5aR, 5bR,7aR,11aS,11bR,13aR,13bR)-3a-(aziridin-1-yl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylate (0.05 g, 0.085 mmol) in THF (1 mL) was added N,N-diisopropylethylamine (0.089 mL, 0.510 mmol) followed by 2-oxa-5-azabicyclo[2.2.1]heptane, HCl (0.035 g, 0.255 mmol). The vial was sealed and the mixture was heated to 100° C. After 16 h of heating, the mixture was cooled to rt, was diluted with methanol and 1,4-dioxane and was purified by prep HPLC (method 8). The fractions containing the expected product were concentrated under reduced pressure to give ethyl 4-((1R,3aS,5aR,5bR,7aR,11aS,11bR,13aR,13bR)-3a-((2-(2-oxa-5-azabicyclo[2.2.1]heptan-5-yl)ethyl)amino)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylate (0.0152 g, 0.022 mmol, 26.0% yield) as an off-white foam. LCMS: m/e 687.7 (M+H)$^+$, 1.96 min (method 5).

Step 4. Preparation of 4-((1R,3aS,5aR,5bR,7aR, 11aS,11bR,13aR,13bR)-3a-((2-(2-oxa-5-azabicyclo [2.2.1]heptan-5-yl)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)cyclohex-3-enecarboxylic acid, TFA

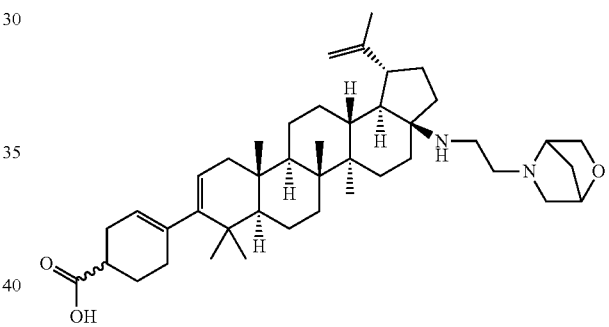

To a solution of ethyl 4-((1R,3aS,5aR,5bR,7aR,11aS, 11bR,13aR,13bR)-3a-((2-(2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylate (0.0152 g, 0.022 mmol) in 1,4-dioxane (1 mL) was added NaOH (1N) (0.2 mL, 0.200 mmol). The mixture was heated to 75° C. for 5 h then was cooled to rt, diluted with methanol and was purified by prep HPLC (method 8). The fractions containing the expected product were combined and concentrated under reduced pressure to give 4-((1R,3aS,5aR,5bR,7aR,11aS,11bR,13aR, 13bR)-3a-((2-(2-oxa-5-azabicyclo[2.2.1]heptan-5-yl)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (9.1 mg, 0.012 mmol, 55% yield). LCMS: m/e 659.7 (M+H)$^+$, 1.59 min (method 5). $^1$H NMR (500 MHz, Acetic Acid-d$_4$) δ=5.41 (br. s., 1H), 5.27-5.23 (m, 1H), 4.86 (s, 1H), 4.77 (s, 1H), 4.75 (s, 1H), 4.64 (s, 1H), 4.23 (d, J=10.2 Hz, 1H), 4.04-3.96 (m, 1H), 3.92-3.82 (m, 2H), 3.77-3.51 (m, 4H), 2.86-2.78 (m, 1H), 2.67-2.58 (m, 1H), 1.76 (s, 3H), 1.15 (s, 3H), 1.10 (s, 3H), 1.05-0.97 (m, 6H), 0.95 (s, 3H), 2.44-0.91 (m, 30H).

Example B2
Preparation of 4-((1R,3aS,5aR,5bR,7aR,11aS,11bR,13aR,13bR)-3a-((2((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA
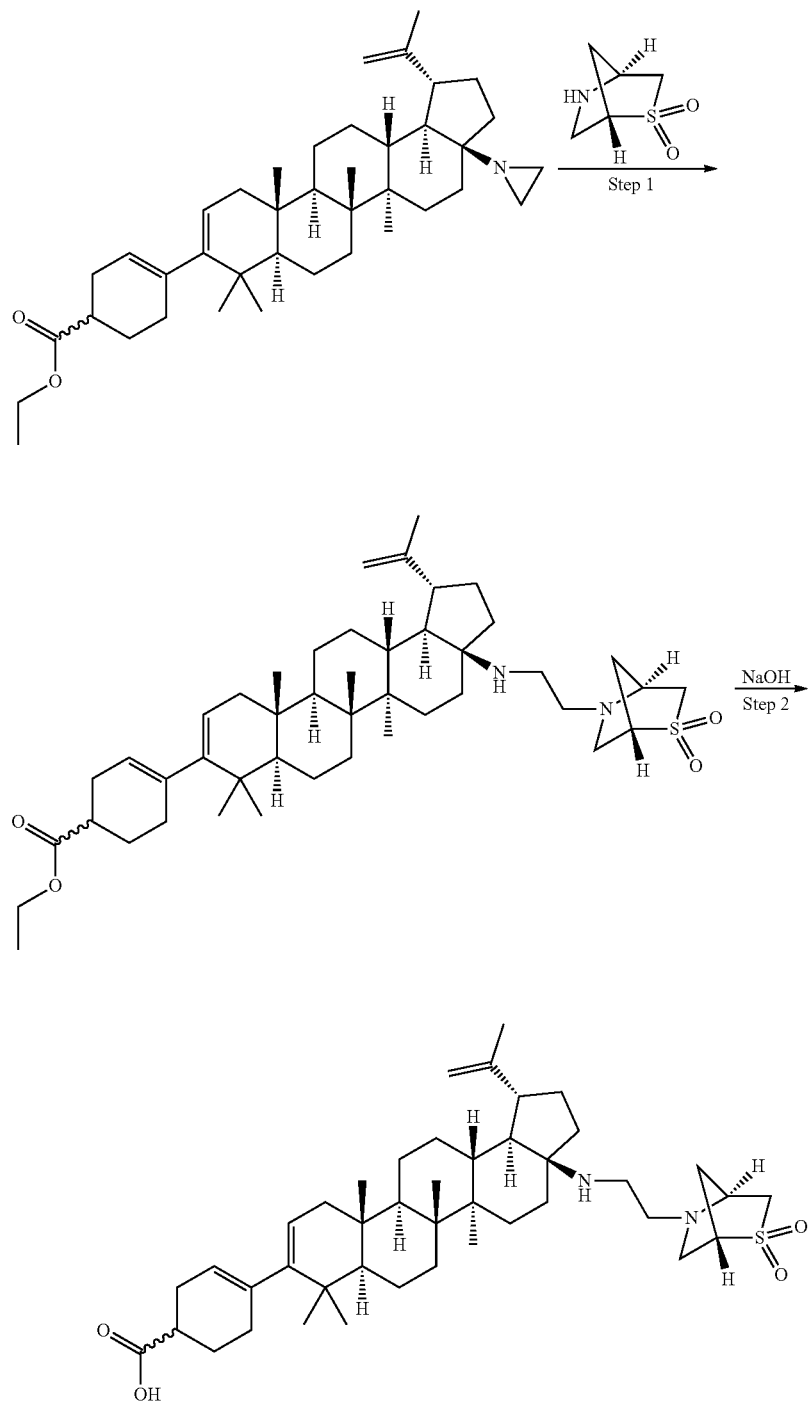

Step 1. Preparation of ethyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

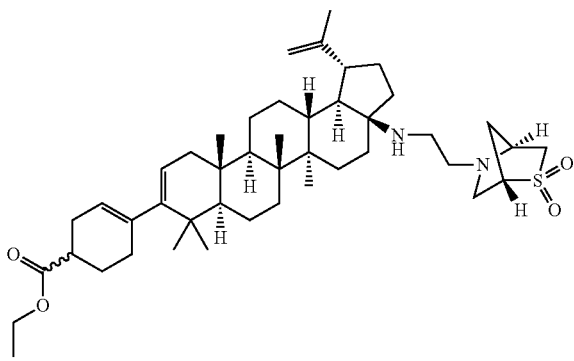

To a sealable vial containing a suspension of ethyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.05 g, 0.085 mmol) in THF (1 mL) was added DIEA (0.089 mL, 0.510 mmol) and (1S,4S)-2-thia-5-azabicyclo[2.2.1]heptane 2,2-dioxide, HCl (0.047 g, 0.255 mmol). The vial was sealed and the suspension was heated to 100° C. After heating the mixture for 16 h, it was cooled to rt, diluted with 1,4-dioxane and methanol and the solids were removed by filtration. The filtrate was purified by prep HPLC (method 8) to give the title compound with remaining impurities (29 mg total) which will be carried to the next step for purification. LCMS: m/e 735 (M+H)$^+$, 2.08 min (method 5).

Step 2

To the crude solution of ethyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (29 mg) in 1,4-dioxane (1 mL) was added NaOH (1N) (0.2 mL, 0.200 mmol). The mixture was heated to 75° C. for 15 h, and then, it was cooled to rt, diluted with 1,4-dioxane and methanol, and purified by prep HPLC (method 9). The fractions containing the product were concentrated under reduced pressure. The compound was purified a second time by prep HPLC (method 10) to give the title compound (4.7 mg, 5.7 μmol, 6.7% yield over 2 steps) as a white solid. LCMS: m/e 707.6 (M+H)$^+$, 1.72 min (method 5). $^1$H NMR (500 MHz, acetic acid-d$_4$) δ=5.38 (br. s., 1H), 5.27-5.19 (m, 1H), 4.81 (s, 1H), 4.71 (s, 1H), 4.12 (br. s., 1H), 3.72 (br. s., 1H), 3.48-3.34 (m, 3H), 3.29-3.18 (m, 2H), 3.16-3.05 (m, 3H), 2.93-2.83 (m, 1H), 2.66-2.54 (m, 2H), 2.50-2.42 (m, 1H), 1.73 (s, 3H), 1.18 (s, 3H), 1.09 (s, 3H), 2.41-0.84 (m, 37H)

Step 4

To a solution of ethyl 3-((1R,3aS,5aR,5bR,7aR,11aS,11bR,13aR,13bR)-3a-((2-((1S)2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate (28 mg, 0.03 mmol) in 1,4-dioxane (2 mL) was added sodium hydroxide (1N) (0.149 mL, 0.149 mmol). The mixture was warmed to 70° C. After heating the mixture for 16 h, it was cooled to rt and was acidified by adding 1 mL of 1N HCl. Then water was added until solids formed. The solids were collected by filtration, dissolved in 1,4-dioxane and methanol and purified by prep HPLC (method 12) to afford 3-((1R,3aS,5aR,5bR,7aR,11aS,11bR,13aR,13bR)-3a-((2-((1R,4R)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid as two different isomers (isomer 1, 16.5% and isomer 2, 11.5%)

Example B4

Isomer 1: MS: m/e 705.6 (M+H)$^+$, 2.393 min (method 6). $^1$H NMR (400 MHz, CHLOROFORM-d) δ 5.83 (s, 1H), 5.46 (m, 1H), 4.79 (s, 1H), 4.73 (s, 1H), 4.09 (br. s., 1H), 3.60 (br. s., 1H), 3.42-3.08 (m, 6H), 3.07-2.71 (m, 4H), 2.69-2.54 (m, 3H), 2.42 (d, J=12.5 Hz, 1H), 2.28 (td, J=6.7, 3.1 Hz, 1H), 2.24-1.84 (m, 7H), 1.72 (s, 4H), 1.65-1.28 (m, 14H), 1.14 (br. s., 1H), 1.11 (s, 3H), 1.05 (m, 9H), 0.86 (s, 3H).

Example B5

Isomer 2: MS: m/e 705.6 (M+H)$^+$, 2.638 min (method 6). $^1$H NMR (400 MHz, CHLOROFORM-d) δ 5.89 (s, 1H), 5.47 (d, J=4.5 Hz, 1H), 4.81 (s, 1H), 4.72 (s, 1H), 4.14 (br. s., 1H), 3.60 (br. s., 1H), 3.47-3.17 (m, 5H), 3.15-2.85 (m, 5H), 2.82-2.57 (m, 3H), 2.44 (d, J=12.3 Hz, 1H), 2.34-2.20 (m, 2H), 2.16-1.90 (m, 6H), 1.77-1.70 (m, 1H), 1.71 (s, 3H), 1.67-1.24 (m, 14H), 1.14 (s, 6H),1.12-1.03 (m, 1H), 1.05 (s, 3H), 1.02 (s, 3H), 0.78 (s, 3H).

Example B6 and Example B7
Preparation of 3-((1R,3aS,5aR,5bR,7aR,11aS,11bR,13aR,13bR)-3a-((2-((1S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid (isomer 1 and isomer 2)
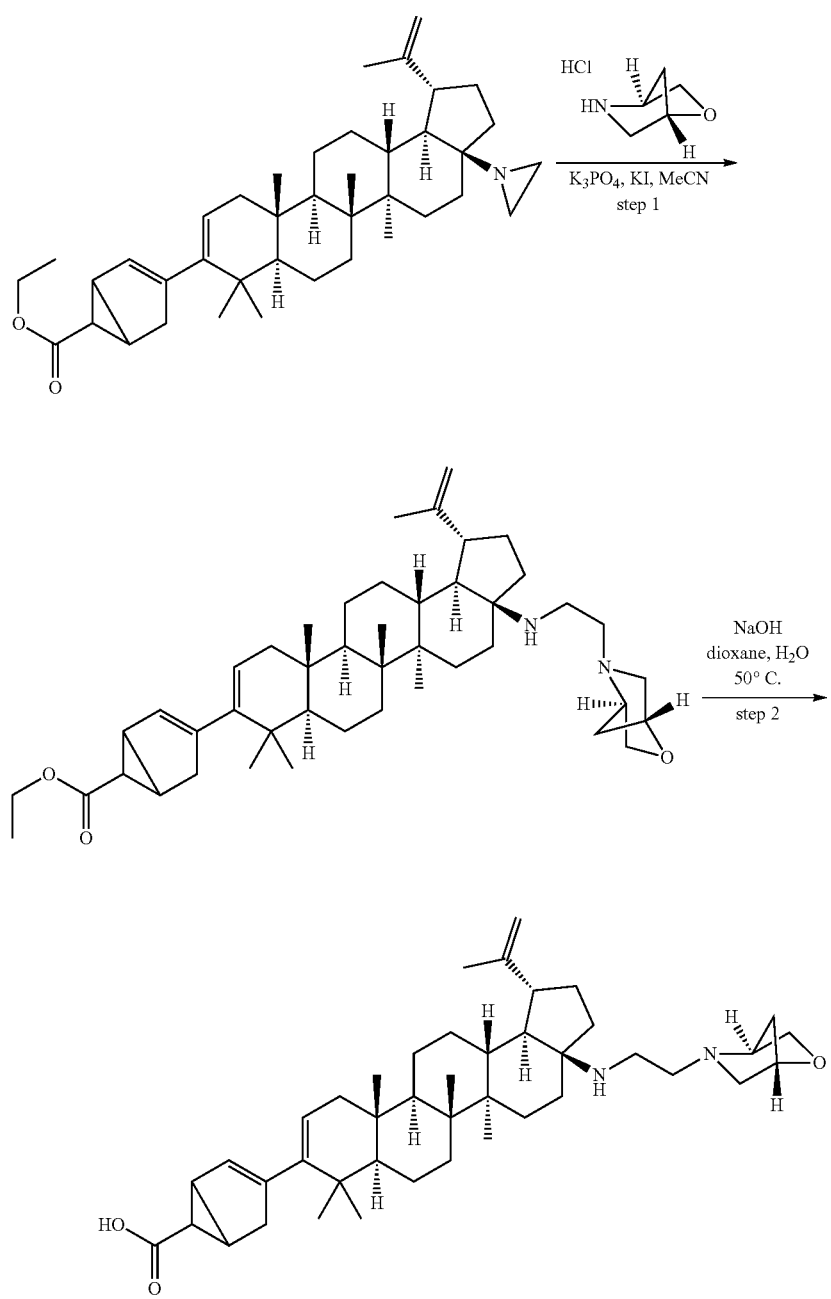
Isomer 1, Example B6
Isomer 2, Example B7

Step 1—Preparation of ethyl 3-((1R,3aS,5aR,5bR,7aR,11aS,11bR,13aR,13bR)-3a-((2-((1S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate

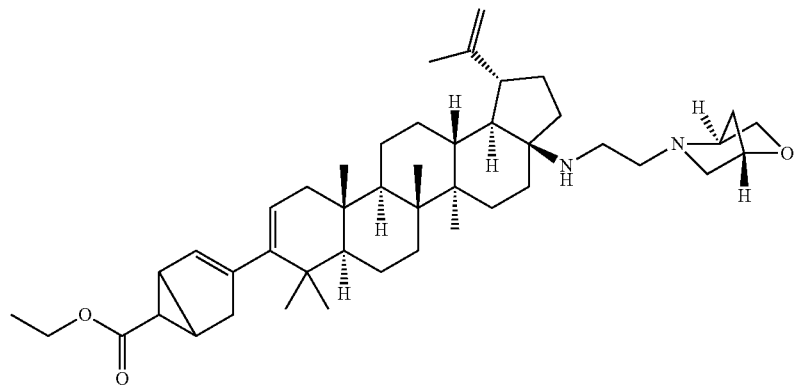

The title compound was prepared quantitative yield following the method described above for the preparation of ethyl 3-((1R,3aS,5aR,5bR,7aR,11aS,11bR,13aR,13bR)-3a-((2-((1S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate, using racemic (1S)-2-oxa-5-azabicyclo[2.2.1]heptane hydrochloride as the reactant. MS: m/e 685.6 (M+H)$^+$, 2.83 min (method 6). $^1$H NMR (400 MHz, CHLOROFORM-d) δ 5.80 (br. s., 1H), 5.51-5.37 (m, 1H), 4.73 (d, J=2.0 Hz, 1H), 4.59 (dd, J=2.3, 1.5 Hz, 1H), 4.42 (s, 1H), 4.18-4.10 (m, 2H), 4.07 (d, J=7.8 Hz, 1H), 3.65 (dd, J=7.7, 1.6 Hz, 1H), 3.50 (s, 1H), 2.95 (dd, J=9.8, 1.5 Hz, 1H), 2.95-2.40 (m, 8H), 2.18 (dt, J=6.5, 3.3 Hz, 1H), 2.09-1.96 (m, 3H), 1.92-1.72 (m, 6H), 1.71 (s, 3H), 1.68-1.31 (m, 9H), 1.30-1.10 (m, 10H), 1.08-0.8 (m, 16).

Step 2

Ethyl 3-((1R,3aS,5aR,5bR,7aR,11aS,11bR,13aR,13bR)-3a-((2-((1S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate was prepared from ethyl 3-((1R,3aS,5aR,5bR,7aR,11aS,11bR,13aR,13bR)-3a-((2-((1S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate using the conditions described above in step 4 of the preparation of 3-((1R,3aS,5aR,5bR,7aR,11aS,11bR,13aR,13bR)-3a-((2-(1R,4R)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid to afford the title compound as a two different isomers (isomer 1, 29.5% and isomer 2, 22.01%) after prep HPLC purification (method 11)

Example B6

Isomer 1: MS: m/e 657.55 (M+H)$^+$, 2.663 min (method 6). $^1$H NMR (400 MHz, CHLOROFORM-d) δ 5.79 (s, 1H), 5.49 (d, J=4.8 Hz, 1H), 4.81 (s, 1H), 4.72 (s, 1H), 4.67 (s, 1H), 4.35 (s, 1H), 4.21 (d, J=10.3 Hz, 1H), 3.84 (d, J=9.3 Hz, 2H), 3.76-3.28 (m, 5H), 2.90 (dd, J=18.2, 5.6 Hz, 1H), 2.73-2.57 (m, 2H), 2.54-2.47 (m, 1H), 2.33 (td, J=6.5, 3.0 Hz, 1H), 2.27-1.93 (m, 7H), 1.91 (m, 2H), 1.79 (d, J=12.0 Hz, 1H), 1.70 (s, 3H), 1.64-1.21 (m, 14H), 1.2-1.16 (m, 1H), 1.14-1.09 (m, 3H), 1.02 (m, 7H), 0.95-0.88 (m, 3H), 0.76 (s, 3H).

Example B7

Isomer 2: MS: m/e 657.55 (M+H)$^+$, 2.696 min (method 6). $^1$H NMR (400 MHz, CHLOROFORM-d) δ 6.01 (s, 1H), 5.53 (d, J=5.0 Hz, 1H), 4.84 (s, 1H), 4.73 (s, 1H), 4.68 (s, 1H), 4.38 (s, 1H), 4.21 (d, J=10.5 Hz, 1H), 3.93-3.79 (m, 2H), 3.74-3.17 (m, 5H), 2.94 (dd, J=17.1, 6.3 Hz, 1H), 2.84-2.32 (m, 2H), 2.28-1.78 (m, 10H), 1.70 (s, 3H), 1.66-1.24 (m, 13H), 1.20 (d, J=3.3 Hz, 6H), 1.16-1.04 (m, 3H), 1.01 (d, J=4.5 Hz, 6H), 0.97-0.93 (m, 1H), 0.65 (s, 3H).

Example B8
Preparation of (S)-4-(((1R,3aS,5aR,5bR,7aR,11aS,11bR,13aR,13bR)-3a-((2-(((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid
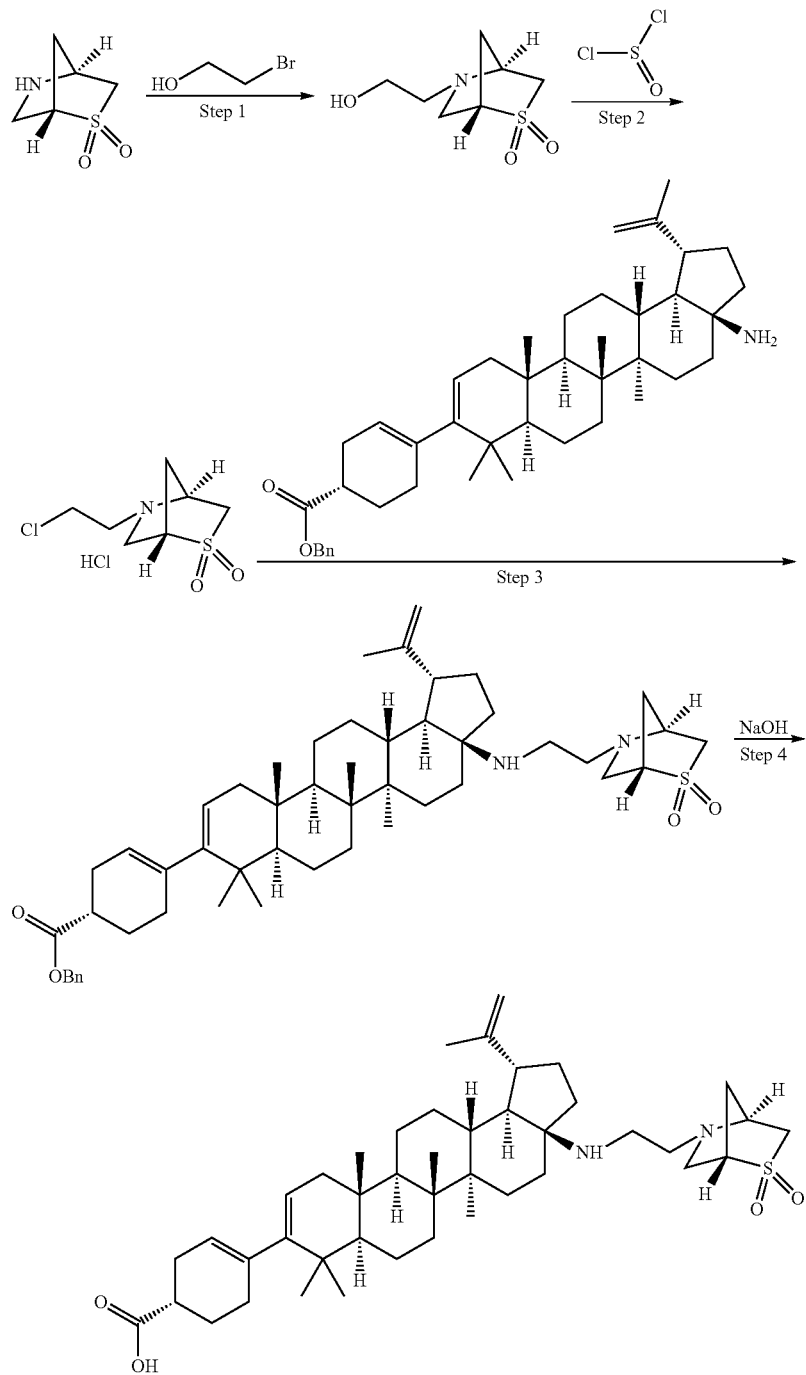
Example B8

Step 1. Preparation of (1S,4S)-5-(2-hydroxyethyl)-2-thia-5-azabicyclo[2.2.1]heptane 2,2-dioxide

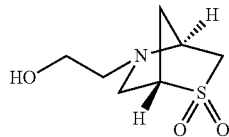

A mixture of (1S,4S)-2-thia-5-azabicyclo[2.2.1]heptane 2,2-dioxide (65 mg, 0.442 mmol), potassium phosphate (375 mg, 1.766 mmol), 2-bromoethanol (221 mg, 1.766 mmol) and potassium iodide (147 mg, 0.883 mmol) in acetonitrile (2 mL) was heated up at 120° C. for 4 hours. The reaction mixture was concentrated under reduced pressure and purified in silica gel with 0-15% methanol/ethyl acetate to provide the title product (60 mg, 71% yield) as a white solid. LCMS: m/e 192.07 (M+H)$^+$, 0.87 min (method 2)

Step 2. Preparation of (1S,4S)-5-(2-chloroethyl)-2-thia-5-azabicyclo[2.2.1]heptane 2,2-dioxide hydrochloride

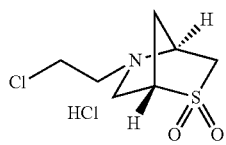

A mixture of (1S,4S)-5-(2-hydroxyethyl)-2-thia-5-azabicyclo[2.2.1]heptane 2,2-dioxide (80 mg, 0.418 mmol) and thionyl chloride (0.153 mL, 2.092 mmol) in dichloromethane (2 mL) was stirred at 20° C. for 16 hours. The reaction mixture was concentrated under reduced pressure to provide the title compound (90 mg, 87% yield) as a yellow solid. LCMS: m/e 210.02 (M+H)$^+$, 1.76 min (method 2).

Step 3. Preparation of (S)-benzyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

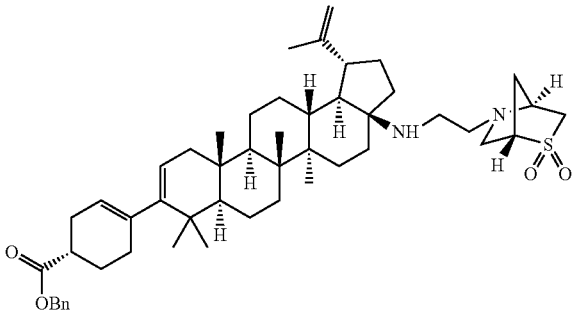

A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (10 mg, 0.016 mmol), (1S,4S)-5-(2-chloroethyl)-2-thia-5-azabicyclo[2.2.1]heptane 2,2-dioxide (3.36 mg, 0.016 mmol), potassium phosphate (17.01 mg, 0.080 mmol) and potassium iodide (5.32 mg, 0.032 mmol) in acetonitrile (1 mL) was heated up at 120° C. for 16 hours. The reaction mixture was then filtered and purified by HPLC to provide the desired product (5 mg, 39% yield) as a white solid. LCMS: m/e 797.8 (M+H)$^+$, 2.31 min (method 5).

Step 4

A mixture of (S)-benzyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (5 mg, 6.27 μmol) and sodium hydroxide (0.063 mL, 0.063 mmol) in acetonitrile (1 mL) was heated up at 80° C. for 3 hours. The reaction mixture was filtered and purified by HPLC to provide (S)-4-((1R,3 aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (2.2 mg, 47% yield) as a white solid. LCMS: m/e 707.8 (M+H)$^+$, 1.82 min (method 5). $^1$H NMR (400 MHz, Acetic) δ 5.37 (br. s., 1H), 5.22 (d, J=4.3 Hz, 1H), 4.80 (s, 1H), 4.70 (s, 1H), 4.10 (br. s., 1H), 3.79-3.65 (m, 1H), 3.50-3.32 (m, 3H), 3.28-3.00 (m, 5H), 2.93-2.75 (m, 1H), 2.56 (d, J=12.3 Hz, 2H), 2.49-2.39 (m, 1H), 2.32 (br. s., 2H), 2.23-1.10 (m, 26H), 1.72 (s, 3H), 1.16 (s, 3H), 1.07 (s, 3H), 1.00 (s, 3H), 0.94 (s, 3H), 0.92 (s, 3H).

Example B9
Preparation of (R)-4-((1R,3aS,5aR,5bR,7aR,11aS,11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid
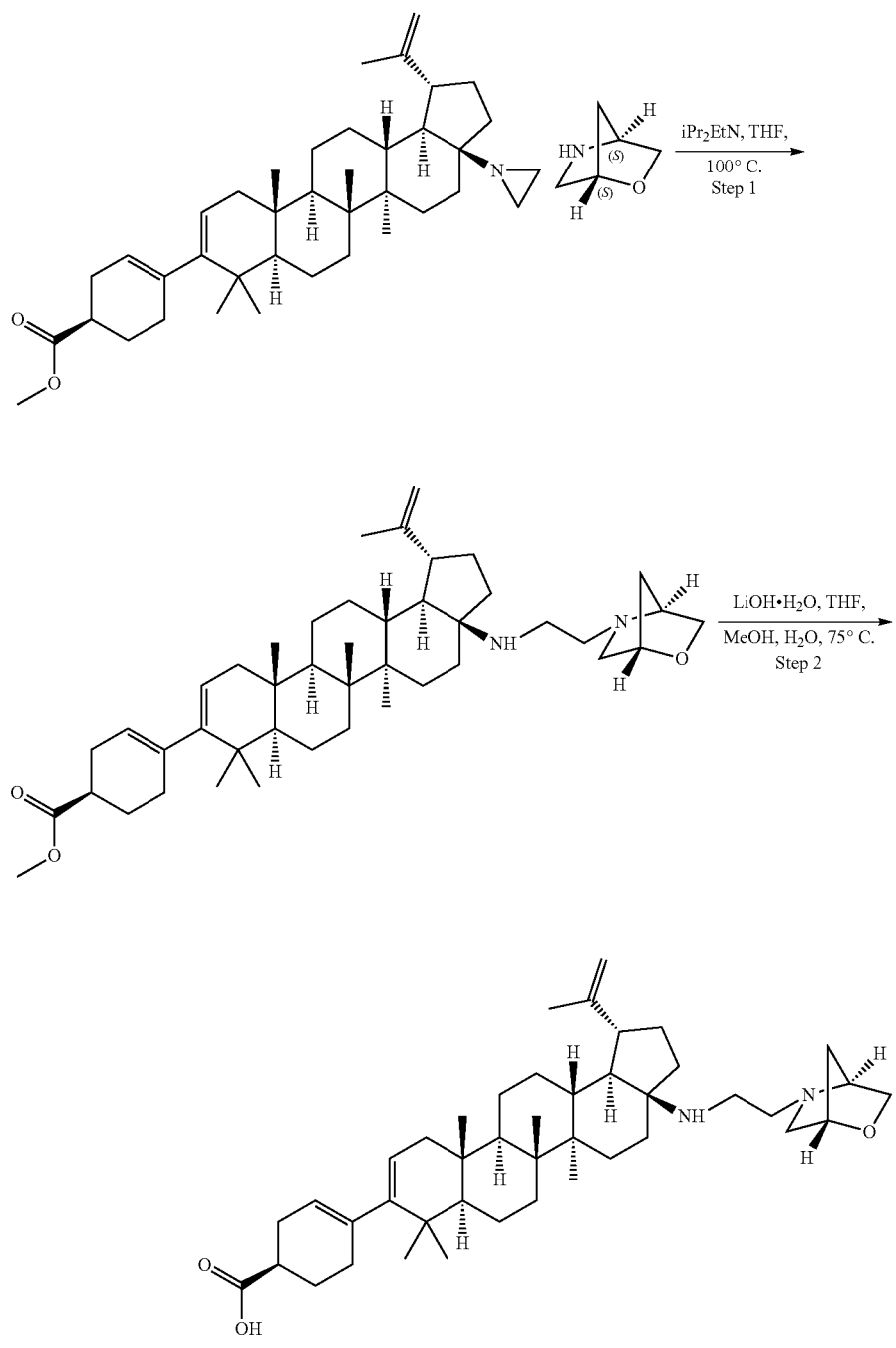
Example B9

Step 1. Preparation of (R)-benzyl 4-((1R,3aS,5aR, 5bR,7aR,11aS,11bR,13aR,13bR)-3a-((2-((1S,4S)-2-oxa-5-azabicyclo[2.2.1]heptan-5-yl)ethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) cyclohex-3-enecarboxylate, 2 TFA

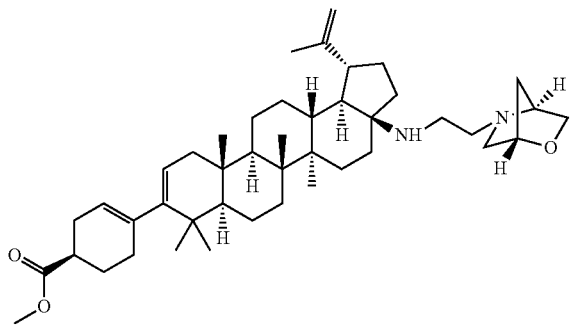

To a mixture of (R)-benzyl 4-((1R,3aS,5aR,5bR,7aR, 11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylate (50 mg, 0.077 mmol), 4° A mol. sieves (100 mg, 0.077 mmol) and N,N-diisopropylethyl amine (0.094 mL, 0.538 mmol) in THF (2 mL) was added (1S,4S)-2-oxa-5-azabicyclo[2.2.1]heptane, HCl (52.2 mg, 0.385 mmol). The reaction was stirred at 100° C. After 70 h, the reaction was cooled to rt, purified by prep-HPLC using prep-HPLC method 15 and dried under vacuum at 50° C. to give the title compound (47.2 mg, 0.048 mmol, 62.8% yield) as a white solid. LC/MS: m/e 749.6 (M+H)+, 4.62 min (method 9). 1H NMR (400 MHz, CHLOROFORM-d) δ 7.75-7.44 (m, 2H), 7.43-7.29 (m, 5H), 5.35 (br. s., 1H), 5.17 (d, J=4.6 Hz, 1H), 5.14 (s, 2H), 4.78 (s, 1H), 4.69 (s, 1H), 4.65 (br. s., 1H), 4.27 (br. s., 1H), 4.18 (d, J=10.3 Hz, 1H), 3.81 (d, J=9.8 Hz, 1H), 3.71 (d, J=16.1 Hz, 2H), 3.51-3.28 (m, 3H), 2.81-2.67 (m, 1H), 2.65-2.54 (m, 1H), 2.34 (br. s., 2H), 2.26-2.10 (m, 4H), 2.10-1.80 (m, 6H), 1.79-1.71 (m, 2H), 1.69 (s, 3H), 1.64-1.23 (m, 12H), 1.07 (s, 3H), 1.01 (s, 3H), 0.93 (s, 3H), 0.92 (s, 3H), 0.86 (s, 3H).

Step 2

To a solution of (R)-benzyl 4-((1R,3aS,5aR,5bR,7aR, 11aS,11bR,13aR,13bR)-3a-((2-((1S,4S)-2-oxa-5-azabicyclo [2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylate (47.2 mg, 0.048 mmol) in THF (1.5 mL) and MeOH (0.5 mL) was added 1N lithium hydroxide (0.193 mL, 0.193 mmol). The reaction was stirred at 75° C. After 3 h the reaction mixture was concentrated and the crude material was dissolved in THF (2 mL)/ H2O (150 µL), purified by reverse phase prep-HPLC using prep-HPLC method 15 and dried under vacuum to give (R)-4-((1R,3aS,5aR,5bR,7aR,11aS,11bR,13aR,13bR)-3a-((2-((1S,4S)-2-oxa-5-azabicyclo[2.2.1]heptan-5-yl)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclohex-3-enecarboxylic acid (32.9 mg, 0.036 mmol, 75% yield) as a white solid. LC/MS: m/e 659.5 (M+H)+, 4.14 min (method 8). 1H NMR (400 MHz, 1:1 CDCl3:METHANOL-d4) δ 5.33 (br. s., 1H), 5.22-5.08 (m, 1H), 4.78 (s, 1H), 4.70 (s, 1H), 4.54 (s, 1H), 4.04 (d, J=8.8 Hz, 1H), 3.84 (br. s., 1H), 3.73 (dd, J=8.8, 1.5 Hz, 1H), 3.23-2.96 (m, 5H), 2.88-2.63 (m, 2H), 2.58-2.40 (m, 1H), 2.35-2.09 (m, 5H), 2.08-1.90 (m, 8H), 1.83-1.75 (m, 1H), 1.71 (s, 3H), 1.70-1.61 (m, 2H), 1.61-1.42 (m, 8H), 1.41-1.36 (m, 1H), 1.35 (s, 1H), 1.33-1.23 (m, 1H), 1.10 (s, 3H), 1.05 (s, 3H), 0.95 (s, 3H), 0.93 (s, 3H), 0.88 (s, 3H)

Example B10

Preparation of (S)-4-((1R,3aS,5aR,5bR,7aR,11aS, 11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylic

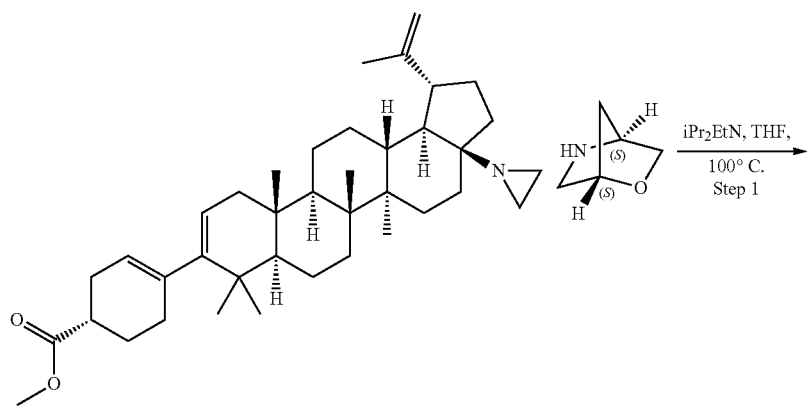

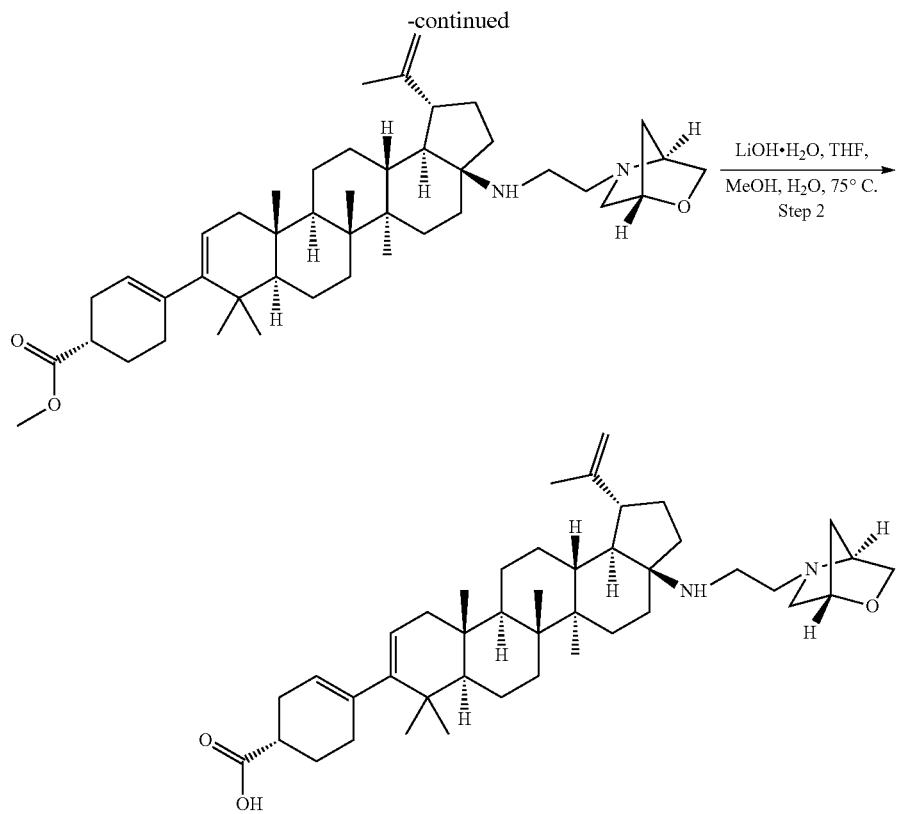

Example B10

Step 1. Preparation of (S)-benzyl 4-((1R,3aS,5aR, 5bR,7aR,11aS,11bR,13aR,13bR)-3a-((2-((1S,4S)-2-oxa-5-azabicyclo[2.2.1]heptan-5-yl)ethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)cyclohex-3-enecarboxylate

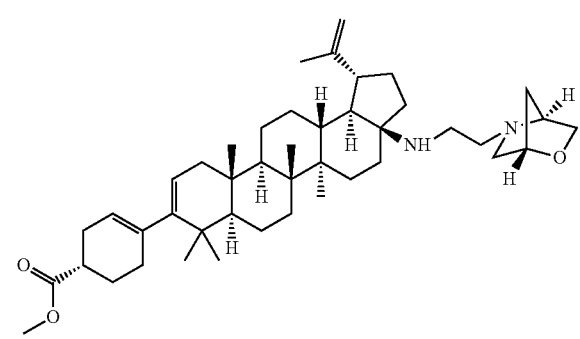

To a mixture of (S)-benzyl 4-((1R,3aS,5aR,5bR,7aR,11aS, 11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarboxylate (50 mg, 0.077 mmol), 4° A mol. sieves (100 mg, 0.077 mmol) and N,N-diisopropylethylamine (0.094 mL, 0.538 mmol) in THF (2 mL) was added (1S,4S)-2-oxa-5-azabicyclo[2.2.1]heptane, HCl (52.2 mg, 0.385 mmol). The reaction mixture was stirred at 100° C. After 70 h, the reaction was cooled to rt, purified by prep-HPLC using prep-HPLC method 15 and dried under vacuum at 50° C. to give the title compound (27.9 mg, 0.029 mmol, 37.1% yield) as a white solid. LC/MS: m/e 749.6 (M+H)$^+$, 4.65 min (method 9). $^1$H NMR (400 MHz, CHLOROFORM-d) δ 7.90 (br. s., 3H), 7.44-7.29 (m, 5H), 5.35 (br. s., 1H), 5.20-5.09 (m, 3H), 4.78 (br. s., 1H), 4.67 (d, J=18.1 Hz, 2H), 4.27 (br. s., 1H), 4.18 (d, J=10.0 Hz, 1H), 3.81 (d, J=9.8 Hz, 1H), 3.71 (d, J=19.8 Hz, 2H), 3.53-3.26 (m, 4H), 2.87-2.67 (m, 1H), 2.64-2.51 (m, 1H), 2.34 (br. s., 2H), 2.15 (br. s., 5H), 2.07-1.89 (m, 5H), 1.88-1.72 (m, 3H), 1.69 (s, 3H), 1.63-1.21 (m, 13H), 1.07 (br. s., 3H), 1.01 (s, 3H), 0.96 (s, 3H), 0.89 (s, 3H), 0.86 (s, 3H).

Step 2

To a solution of (S)-benzyl 4-((1R,3aS,5aR,5bR,7aR, 11aS,11bR,13aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarboxylate in THF (1.5 mL) and MeOH (0.5 mL) was added 1N lithium hydroxide (0.115 mL, 0.115 mmol). The reaction was stirred at 75° C. After 3 h the reaction mixture was concentrated and the crude material was dissolved in THF (2 mL)/H$_2$O (150 μL) and purified by reverse phase prep-HPLC using prep-HPLC method 15 and dried under vacuum to give (S)-4-((1R,3 aS,5aR,5bR,7aR,11aS,11bR,13 aR,13bR)-3a-((2-((1S,4S)-2-oxa-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (21 mg, 0.023 mmol, 80% yield) as a white solid. LC/MS: m/e 659.5 (M+H)$^+$, 34.14 min (method 8). $^1$H NMR (400 MHz, 1:1 CDCl$_3$:METHANOL-d$_4$) δ 5.33 (br. s., 1H), 5.17 (d, J=4.6 Hz, 1H), 4.78 (s, 1H), 4.70 (br. s., 1H), 4.52 (s, 1H), 4.03 (d, J=8.6 Hz, 1H), 3.75 (br. s., 1H), 3.72 (d, J=8.6 Hz, 1H), 3.18-3.09 (m, 2H), 3.09-2.92 (m, 4H), 2.79-2.64 (m, 2H), 2.53-2.42 (m, 1H), 2.31-2.23 (m, 2H), 2.16 (br. s., 2H), 2.04-1.93 (m, 8H), 1.81-1.73 (m, 2H), 1.72 (s, 3H), 1.69-1.63 (m, 1H), 1.61-1.33 (m, 12H), 1.30 (dd, J=12.2, 3.4 Hz, 1H), 1.24 (br. s., 1H), 1.20-1.14 (m, 1H), 1.12-1.09 (m, 3H), 1.05 (s, 3H), 0.97 (s, 3H), 0.90 (s, 3H), 0.88 (s, 3H)

Example B11

Preparation of (R)-4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

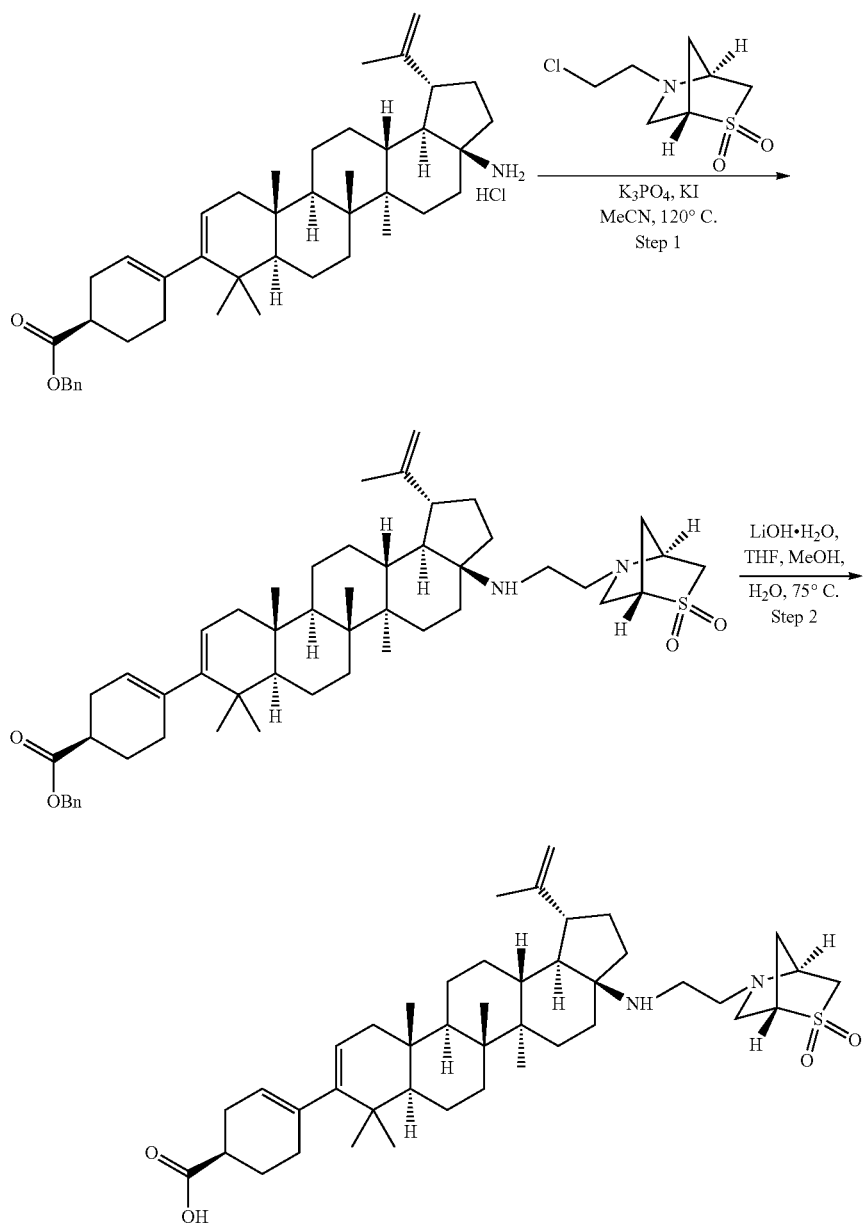

Example B11

Step 1. Preparation of (R)-benzyl 4-((1R,3aS,5aR, 5bR,7aR,11aS,11bR,13aR,13bR)-3a-((2-((1S,4S)-2, 2-dioxido-2-thia-5-azabicyclo[2.2.1]heptan-5-yl) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)cyclohex-3-enecarboxylate

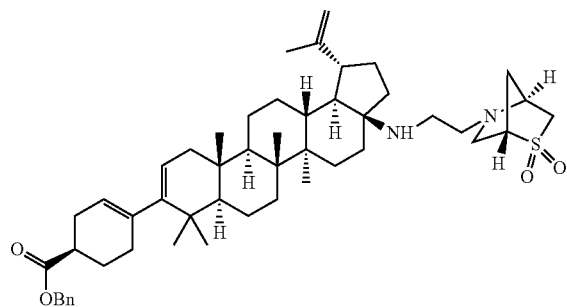

In a 15 mL medium pressure flask was added (R)-benzyl 4-((1R,3 aS,5aR,5bR,7aR,11aS,11bR,13aR,13bR)-3a-amino-5a,5b,8,8,11a-pentamethyl-1-(prop-1-en-2-yl)-2,3, 3a,4,5,5a,5b,6,7,7a,8,11,11a,11b,12,13,13a,13b-octa-decahydro-1H-cyclopenta[a]chrysen-9-yl)cyclohex-3-enecarboxylate (70 mg, 0.112 mmol), phosphoric acid, potassium salt (119 mg, 0.561 mmol), (1S,4S)-5-(2-chloro-ethyl)-2-thia-5-azabicyclo[2.2.1]heptane 2,2-dioxide (70.6 mg, 0.337 mmol) and potassium iodide (55.9 mg, 0.337 mmol). The solid mixture was dried at 50° C. vacuum oven for 15 mins and filled with $N_2$ (g). Acetonitrile (3 mL) was added and the mixture was heated at 120° C. After 22 h, the resulting creamy reaction was cooled to rt and filtered. The light yellow paste obtained was washed with DCM (25 mL). The liquid filtrate was concentrated to give crude product as a light brown solid which was purified by reverse phase HPLC using prep-HPLC method 15 to give the title compound (67.2 mg, 0.062 mmol, 55.5% yield) as a white solid. LC/MS: m/e 797.6 (M+H)$^+$, 4.68 min (method 8). $^1$H NMR (400 MHz, CHLOROFORM-d) δ 7.42-7.32 (m, 5H), 5.35 (br. s., 1H), 5.18 (d, J=4.4 Hz, 1H), 5.14 (s, 2H), 4.78 (s, 1H), 4.70 (s, 1H), 4.18 (br. s., 1H), 3.58 (br. s., 1H), 3.37 (dd, J=13.4, 2.7 Hz, 1H), 3.32-3.22 (m, 2H), 3.21-3.15 (m, 1H), 3.07 (d, J=13.0 Hz, 1H), 3.00 (dd, J=13.2, 3.2 Hz, 1H), 2.93-2.74 (m, 2H), 2.67-2.54 (m, 2H), 2.45-2.29 (m, 8H), 2.27-2.11 (m, 4H), 2.07-1.88 (m, 6H), 1.80-1.73 (m, 1H), 1.70 (s, 3H), 1.67 (br. s., 1H), 1.60-1.42 (m, 8H), 1.38 (d, J=10.8 Hz, 2H), 1.31 (br. s., 1H), 1.10 (s, 3H), 1.04 (s, 3H), 0.94 (s, 3H), 0.93 (s, 3H), 0.87 (s, 3H). $^{13}$C NMR (101 MHz, CHLOROFORM-d) δ 175.7, 148.1, 147.2, 139.3, 136.2, 128.5, 128.1, 128.0, 122.6, 121.0, 111.4, 77.2, 70.5, 66.1, 61.5, 60.7, 56.2, 53.0, 52.7, 49.3, 49.2, 48.8, 44.8, 42.1, 41.7, 40.83-40.72, 40.7, 39.0, 37.5, 36.9, 36.1, 33.8, 32.8, 31.6, 29.6, 28.3, 27.7 (br. s., 1C), 27.70-27.57, 25.9, 25.8, 25.2, 21.5, 20.9, 19.6, 19.4, 16.4, 16.1, 14.5.

Step 2

To a solution of (R)-benzyl 4-((1R,3aS,5aR,5bR,7aR, 11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylate (65.2 mg, 0.082 mmol) in THF (1.5 mL) and MeOH (0.5 mL) was added 3N lithium hydroxide (0.136 mL, 0.409 mmol). The reaction mixture was stirred at 75° C. for 3 h and then cooled to rt. The reaction content was subjected to reverse phase HPLC purification using prep-HPLC method 6 and dried under vacuum to give (R)-4-((1R,3aS,5aR,5bR,7aR,11aS,11bR,13aR, 13bR)-3a-((2-((1S,4S)-2,2-dioxido-2-thia-5-azabicyclo [2.2.1]heptan-5-yl)ethyl)amino)-5a,5b,8,8,11a-pentam-ethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylic acid (48.2 mg, 0.049 mmol, 59.9% yield) as a white solid. LC/MS: m/e 707.5 (M+H)$^+$, 4.07 min (method 8). $^1$H NMR (400 MHz, 1:1 CDCl$_3$:METHANOL-d$_4$) δ 5.33 (br. s., 1H), 5.21-5.13 (m, 1H), 4.77 (s, 1H), 4.70 (s, 1H), 3.98 (br. s., 1H), 3.64 (br. s., 1H), 3.40-3.34 (m, 1H), 3.30-3.24 (m, 1H), 3.16 (dd, J=11.4, 3.8 Hz, 2H), 3.11-3.05 (m, 2H), 3.05-2.94 (m, 2H), 2.83-2.70 (m, 1H), 2.58 (d, J=12.2 Hz, 1H), 2.48 (ddt, J=17.4, 6.1, 2.9 Hz, 1H), 2.44-2.36 (m, 1H), 2.32-2.22 (m, 2H), 2.21-2.12 (m, 2H), 2.11-2.04 (m, 2H), 2.03-1.91 (m, 5H), 1.87-1.72 (m, 3H), 1.71 (s, 3H), 1.68-1.53 (m, 5H), 1.52-1.37 (m, 7H), 1.34 (s, 1H), 1.32-1.23 (m, 1H), 1.09 (s, 3H), 1.05 (s, 3H), 0.95 (s, 3H), 0.93 (s, 3H), 0.87 (s, 3H).

Example B12

Preparation of 4-(((1R,3aS,5aR,5bR,7aR,9S,11aR, 11bR,13aR,13bR)-3a-((2-((1S,4S)-2,2-dioxido-2-thia-5-azabicyclo[2.2.1]heptan-5-yl)ethyl)amino)-5a, 5b,8,8,11a-pentamethyl-1-(prop-1-en-2-yl) icosahydro-1H-cyclopenta[a]chrysen-9-yl)oxy)-2,2-dimethyl-4-oxobutanoic acid

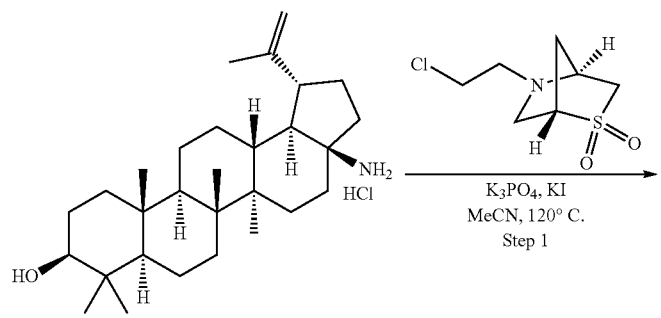

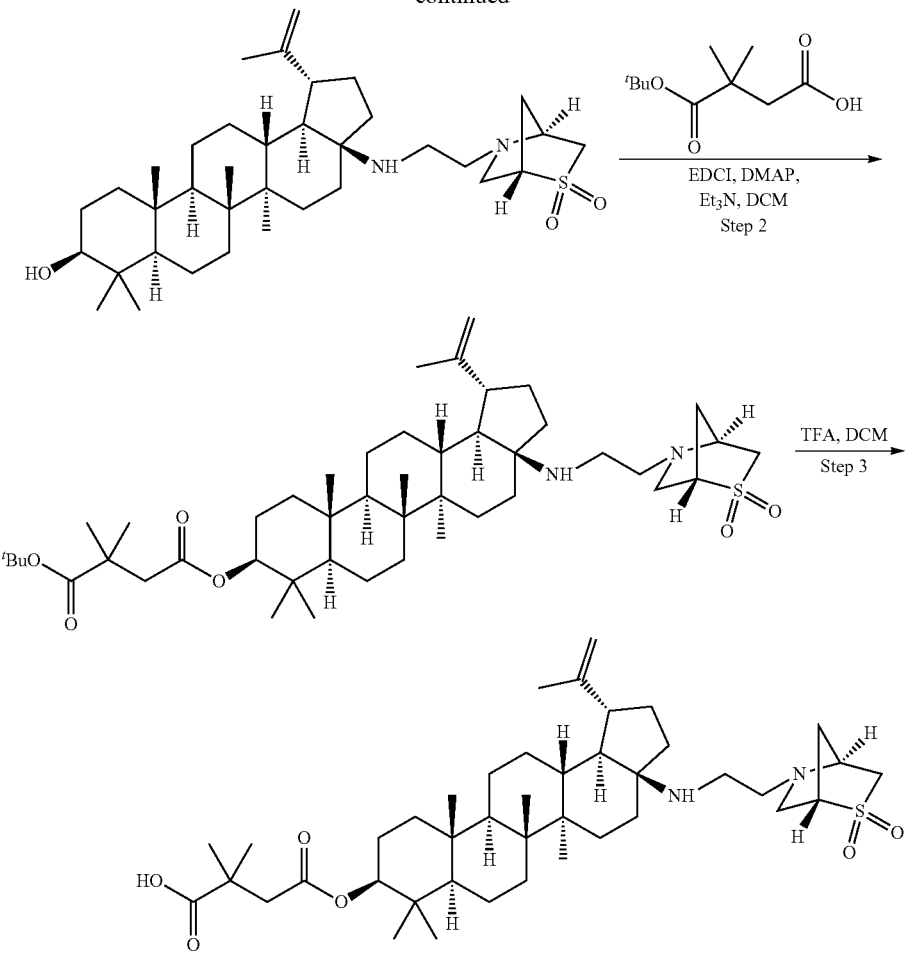

Example B12

Step 1. Preparation of (1S,4S)-5-(2-(((1R,3aS,5aR, 5bR,7aR,9S,11aR,11bR,13 aR,13bR)-9-hydroxy-5a, 5b,8,8,11a-pentamethyl-1-(prop-1-en-2-yl)icosahydro-1H-cyclopenta[a]chrysen-3a-yl)amino)ethyl)-2-thia-5-azabicyclo[2.2.1]heptane 2,2-dioxide

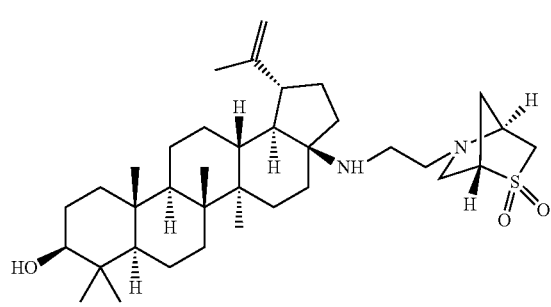

(1R,3aS,5aR,5bR,7aR,9S,11aR,11bR,13aR,13bR)-3a-Amino-5a,5b,8,8,11a-pentamethyl-1-(prop-1-en-2-yl) icosahydro-1H-cyclopenta[a]chrysen-9-ol, HCl (350 mg, 0.754 mmol), (1S,4S)-5-(2-chloroethyl)-2-thia-5-azabicyclo[2.2.1]heptane 2,2-dioxide, HCl (278 mg, 1.131 mmol), phosphoric acid, potassium salt (800 mg, 3.77 mmol), and potassium iodide (376 mg, 2.262 mmol) were combined in a medium pressure flask. The reaction flask was evacuated in the vacuum oven at 50° C. for 15 mins and filled with $N_2$ (g) then it was charged with acetonitrile (10 mL). The resulting slurry was stirred at 120° C. After 48 h, the reaction was cooled to rt. The solid formed was removed by filtration and washed several times with DCM (100 mL). The liquid filtrate was washed with $H_2O$ (25 mL). The aqueous layer was extracted with DCM (50 mL). The combined organic layer was dried over $MgSO_4$, filtered and concentrated to a brown solid. The crude material was purified by flash column chromatography (40 g, eluted with 0% B to 50% B over 5 column volume and then hold at 50% for 20 column volume; solvent A=hex, solvent B=EtOAc) and dried under vacuum to give the title compound (0.25 g, 0.416 mmol, 55.2% yield) as a white solid. LC/MS: m/e 601.4 $(M+H)^+$, 3.00 min (method 8). $^1$H NMR (400 MHz, CHLOROFORM-d) δ 4.70 (d, J=1.7 Hz, 1H), 4.59 (s, 1H), 3.82 (br. s., 1H), 3.51 (br. s., 1H), 3.41 (dd, J=12.8, 2.8 Hz, 1H), 3.28-3.23 (m, 1H), 3.22-3.15 (m, 2H), 2.90 (dd, J=13.0, 3.4 Hz, 1H), 2.87-2.82 (m, 1H), 2.80-2.72 (m, 1H), 2.60 (td, J=10.9, 5.1 Hz, 1H), 2.56-2.48 (m, 2H), 2.47-2.41 (m, 1H), 2.41-2.34 (m, 1H), 2.02-1.93 (m, 1H), 1.87 (d, J=13.4 Hz, 1H), 1.76 (dd, J=12.0, 8.3 Hz, 2H), 1.69 (s, 3H), 1.67-1.64 (m, 1H), 1.62 (dd, J=8.7, 3.8 Hz, 2H), 1.59-1.48 (m, 8H), 1.47-1.36 (m, 5H), 1.33-1.25 (m, 4H), 1.22 (dd, J=13.4, 3.9 Hz, 2H), 1.13-1.05 (m, 2H), 1.02 (s, 3H), 0.98 (s, 3H), 0.97 (s, 3H), 0.91 (d, J=4.2 Hz, 1H), 0.84 (s, 3H). $^{13}$C NMR (101 MHz, CHLOROFORM-d) δ 150.9, 109.3, 78.9, 77.2 (br. s., 1C), 62.6, 60.9, 55.7, 55.3, 53.6, 51.7, 50.5, 49.8, 47.4, 42.0, 40.9, 40.1, 38.9, 38.7, 37.2, 36.7, 35.5, 34.3, 30.1, 28.4, 28.0, 27.4, 26.7, 25.1, 21.0, 19.6, 18.3, 16.1, 15.4, 14.4.

Step 2. Preparation of 1-tert-butyl 4-((1R,3aS,5aR, 5bR,7aR,9S,11aR,11bR,13aR,13bR)-3a-((2-((1S, 4S)-2,2-dioxido-2-thia-5-azabicyclo[2.2.1]heptan-5-yl)ethyl)amino)-5a,5b,8,8,11a-pentamethyl-1-(prop-1-en-2-yl)icosahydro-1H-cyclopenta[a]chrysen-9-yl) 2,2-dimethylsuccinate

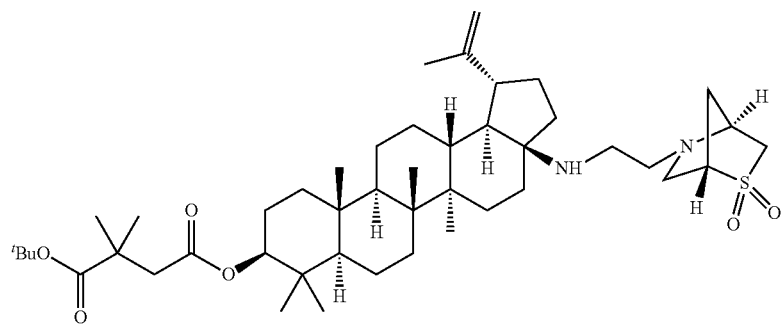

To a solution of (1S,4S)-5-(2-(((1R,3aS,5aR,5bR,7aR,9S, 11aR,11bR,13aR,13bR)-9-hydroxy-5a,5b,8,8,11a-pentamethyl-1-(prop-1-en-2-yl)icosahydro-1H-cyclopenta[a]chrysen-3a-yl)amino)ethyl)-2-thia-5-azabicyclo[2.2.1]heptane 2,2-dioxide (73 mg, 0.121 mmol) in DCM (2 mL) was added N,N-diisopropylethylamine (0.063 mL, 0.364 mmol), 4-(tert-butoxy)-3,3-dimethyl-4-oxobutanoic acid (49.1 mg, 0.243 mmol) (prepared as described in WO 2004014881), 1-(3-dimethylaminopropyl)-3-ethylcarbodiimide hydrochloride (47.5 mg, 0.243 mmol) and 4-dimethylaminopyridine (29.7 mg, 0.243 mmol). The resulting solution mixture was stirred at rt. After 3.5 h, the reaction mixture was diluted with DCM (30 mL) and washed with 0.1N HCl (5 mL). The aqueous layer was extracted with DCM (25 mL). The combined organic layer was washed with 10% NaHCO$_3$, brine, dried over MgSO$_4$, filtered and concentrated. The crude material was purified by flash column chromatography (12 g, eluted with 97:3 DCM:MeOH) and dried under vacuum to give the title compound (83.2 mg, 87% yield) as a white solid. LC/MS: m/e 785.6 (M+H)$^+$, 4.15 min (method 8). $^1$H NMR (400 MHz, CHLOROFORM-d) δ 4.71 (br. s., 1H), 4.59 (s, 1H), 4.48 (dd, J=10.6, 5.5 Hz, 1H), 3.89 (br. s., 1H), 3.51 (br. s., 1H), 3.40 (dd, J=13.0, 2.7 Hz, 1H), 3.27-3.21 (m, 1H), 3.20 (d, J=3.9 Hz, 1H), 2.90 (dd, J=13.1, 3.1 Hz, 1H), 2.86 (br. s., 1H), 2.74-2.60 (m, 1H), 2.53 (s, 3H), 2.51 (d, J=7.3 Hz, 2H), 2.41-2.32 (m, 1H), 2.02 (d, J=17.4 Hz, 1H), 1.86 (d, J=13.4 Hz, 1H), 1.82-1.73 (m, 2H), 1.68 (s, 3H), 1.66-1.50 (m, 7H), 1.43 (s, 11H), 1.42-1.30 (m, 6H), 1.26 (d, J=8.1 Hz, 2H), 1.23 (s, 3H), 1.22 (s, 3H), 1.12-1.04 (m, 2H), 1.01 (s, 3H), 0.95 (s, 3H), 0.84 (s, 6H), 0.83 (s, 3H), 0.78 (d, J=9.5 Hz, 1H).

Step 3

To a solution of 1-tert-butyl 4-((1R,3 aS,5aR,5bR,7aR,9S, 11aR,11bR,13 aR,13bR)-3a-((2-((1S,4S)-2,2-dioxido-2-thia-5-azabicyclo[2.2.1]heptan-5-yl)ethyl)amino)-5a,5b,8,8, 11a-pentamethyl-1-(prop-1-en-2-yl)icosahydro-1H-cyclopenta[a]chrysen-9-yl) 2,2-dimethylsuccinate (55.2 mg, 0.070 mmol) in DCM (1 mL) was added TFA (0.3 ml, 3.89 mmol). The reaction mixture was stirred rt and turned purple/red. After 1 h, TLC (95:5 DCM:MeOH) showed the reaction was completed. The reaction mixture was diluted with DCE (2 mL) and concentrated to a red solid. The crude material was redissolved in DCM (0.5 mL). Et$_2$O was added to produce ad precipitate which was filtered and washed with Et$_2$O to give 4-(((1R,3aS,5aR,5bR,7aR,9S,11aR,11bR,13aR, 13bR)-3a-((2-((1S,4S)-2,2-dioxido-2-thia-5-azabicyclo [2.2.1]heptan-5-yl)ethyl)amino)-5a,5b,8,8,11a-pentamethyl-1-(prop-1-en-2-yl)icosahydro-1H-cyclopenta[a] chrysen-9-yl)oxy)-2,2-dimethyl-4-oxobutanoic acid as off-white solid (9.5 mg, 18.8% yield). LC/MS: m/e 729.5 (M+H)$^+$, 3.49 min (method 8). $^1$H NMR (400 MHz, CHLOROFORM-d) δ 4.79 (br. s., 1H), 4.68 (s, 1H), 4.54-4.43 (m, 1H), 4.23 (br. s., 1H), 3.58 (br. s., 1H), 3.49-3.31 (m, 2H), 3.29-3.13 (m, 3H), 3.11-2.91 (m, 4H), 2.79 (br. s., 1H), 2.72-2.64 (m, 1H), 2.59 (s, 1H), 2.56 (d, J=6.4 Hz, 1H), 2.39 (d, J=11.5 Hz, 1H), 2.28 (br. s., 1H), 1.93 (br. s., 4H), 1.70 (s, 3H), 1.69-1.49 (m, 9H), 1.48-1.40 (m, 3H), 1.35 (br. s., 2H), 1.31 (br. s., 3H), 1.30 (br. s., 3H), 1.09 (br. s., 3H), 1.03 (s, 3H), 1.00-0.89 (m, 2H), 0.86 (br. s., 3H), 0.85 (s, 3H), 0.83 (s, 3H), 0.79-0.73 (m, 1H)

Preparation of ethyl 3-(4,4,5,5-tetramethyl-1,3,2-dioxaborolan-2-yl)bicyclo[3.1.0]hex-2-ene 6-carboxylate

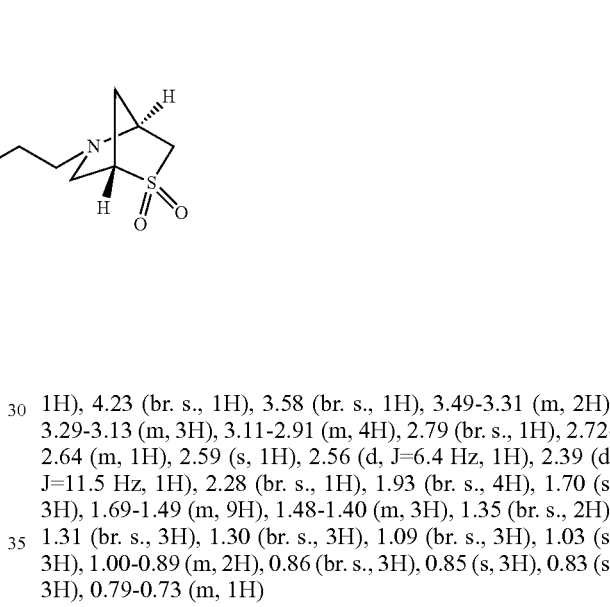

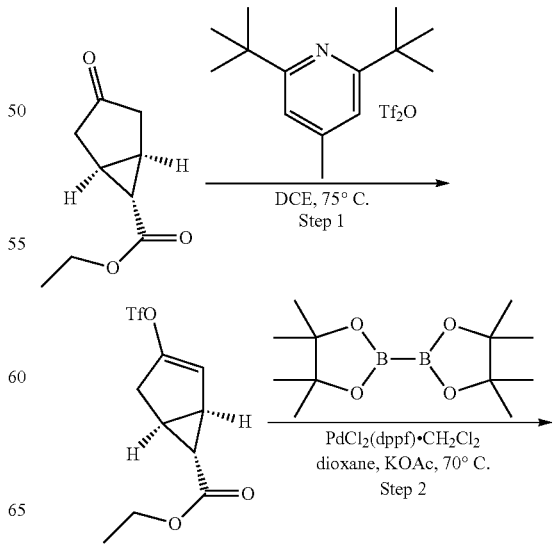

-continued

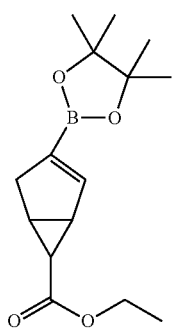

Step 1: Preparation of (1S,5S,6R)-ethyl 3-(((trifluoromethyl)sulfonyl)oxy)bicyclo[3.1.0]hex-2-ene-6-carboxylate

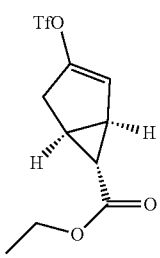 [SMILES: CCOC(=O)[C@H]1[C@@H]2C=C(OS(=O)(=O)C(F)(F)F)C[C@@H]21]

The title compound was prepared in 34.5% yield following the procedure described in WO 2012/003497, using (±)-(1R,5S,6R)-ethyl 3-oxobicyclo[3.1.0]hexane-6-carboxylate (racemic fragment unless otherwise noted) as the reactant. And (±)-(1R,5S,6R)-ethyl 3-oxobicyclo[3.1.0]hexane-6-carboxylate was prepared following procedures described in WO 2011/075515. MS: m/e 301.05 (M+H)$^+$, 2.689 min (method 8) $^1$H NMR (400 MHz, CHLOROFORM-d) δ 5.89 (d, J=1.8 Hz, 1H), 4.24-4.05 (m, 2H), 3.01 (ddd, J=18.1, 7.2, 1.8 Hz, 1H), 2.70 (d, J=18.3 Hz, 1H), 2.41 (dq, J=7.1, 2.6 Hz, 1H), 2.19 (td, J=7.2, 3.3 Hz, 1H), 1.41-1.33 (m, 1H), 1.30-1.20 (m, 3H), $^{19}$F NMR (376 MHz, CHLOROFORM-d) δ −73.22 (s, 3F).

Step 2

The title compound was prepared in quantitative yield following the method described in step 2 for the preparation of methyl 6-(4,4,5,5-tetramethyl-1,3,2-dioxaborolan-2-yl)spiro[3.3]hept-5-ene-2-carboxylate, using (±)-(1S,5S,6R)-ethyl 3-(((trifluoromethyl)sulfonyl)oxy)bicyclo[3.1.0]hex-2-ene-6-carboxylate as the reactant. $^1$H NMR (500 MHz, CHLOROFORM-d) δ 6.67 (q, J=2.0 Hz, 1H), 4.27-3.98 (m, 2H), 2.89-2.72 (m, 1H), 2.63-2.53 (m, 1H), 2.54-2.41 (m, 1H), 2.28 (td, J=6.2, 3.3 Hz, 1H), 1.33-1.15 (m, 16H).

Biology Data for the Examples

"µM" means micromolar;
"mL" means milliliter;
"µl" means microliter;
"mg" means milligram;
"µg" means microgram;

The materials and experimental procedures used to obtain the results reported in Tables 1-2 are described below.

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 µg/mL penicillin G and up to 100 units/mL streptomycin. The 293T cells were propagated in DMEM media supplemented with 10% heat inactivated fetal bovine serum (FBS), 100 units/mL penicillin G and 100 µg/mL streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) µL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 2. Table 1 is the key for the data in Table 2.

Results

TABLE 1

Biological Data Key for $EC_{50}$

| Compounds with $EC_{50}$ >0.1 µM | Compounds with $EC_{50}$ <0.1 µM |
|---|---|
| Group "B" | Group "A" |

TABLE 2

| Example # | Structure | EC$_{50}$ (µM) |
|---|---|---|
| 1 | 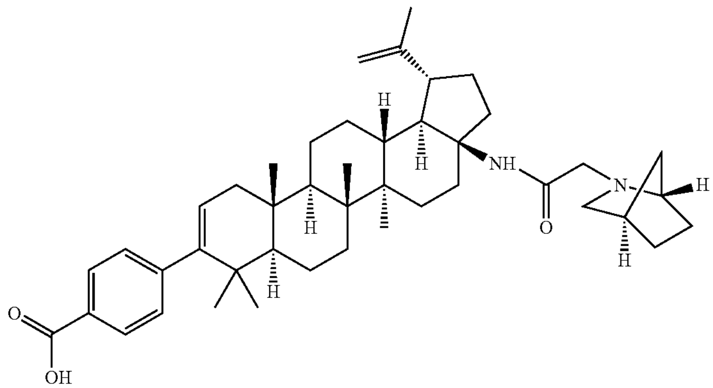 | 3.65E−03 |
| 2 | 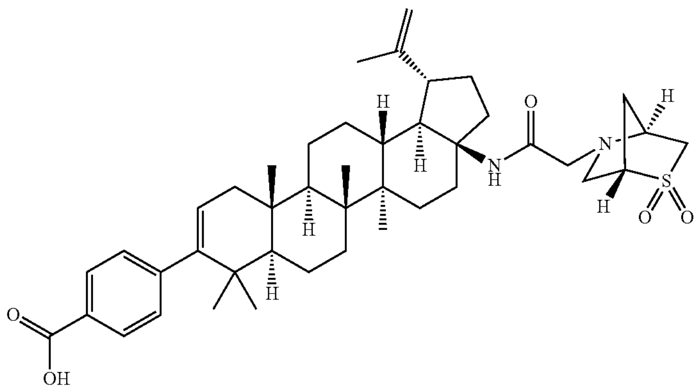 | 1.93E−03 |
| 3 | 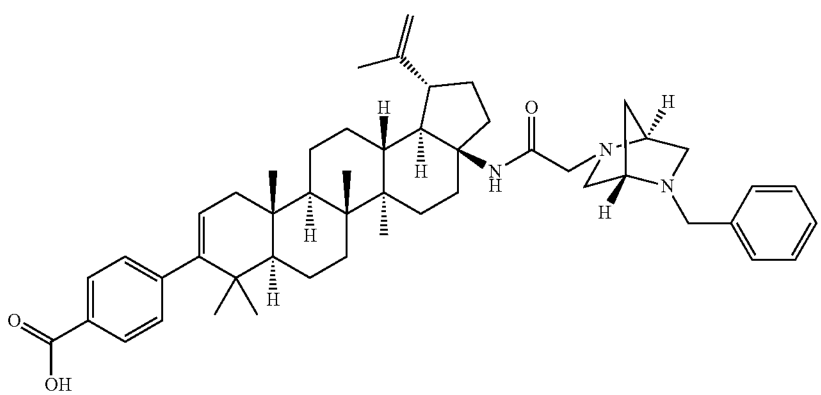 | A |
| 4 | 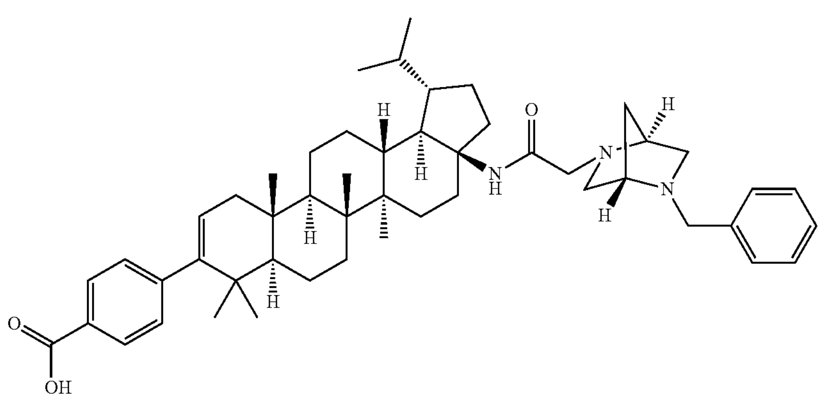 | A |

TABLE 2-continued

| Example # | Structure | EC$_{50}$ (μM) |
|---|---|---|
| 5 | 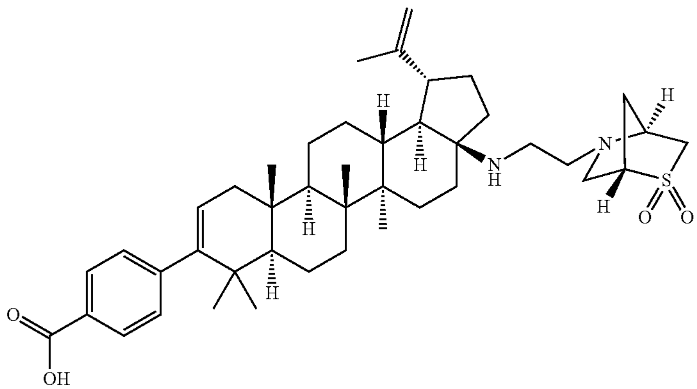 | A |
| 6 | 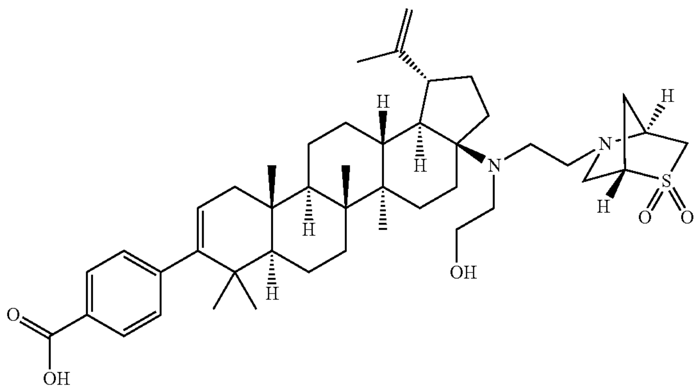 | A |
| 7 | 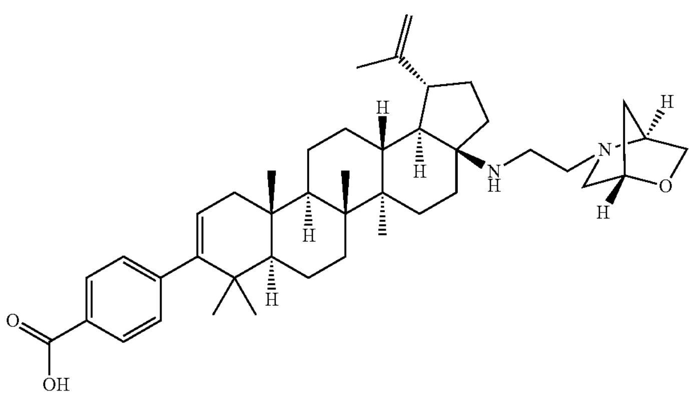 | A |
| 8 | 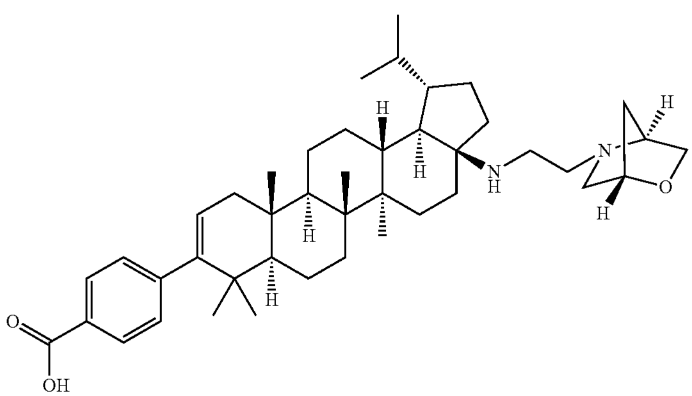 | A |

TABLE 2-continued

| Example # | Structure | EC$_{50}$ (μM) |
|---|---|---|
| 9 | 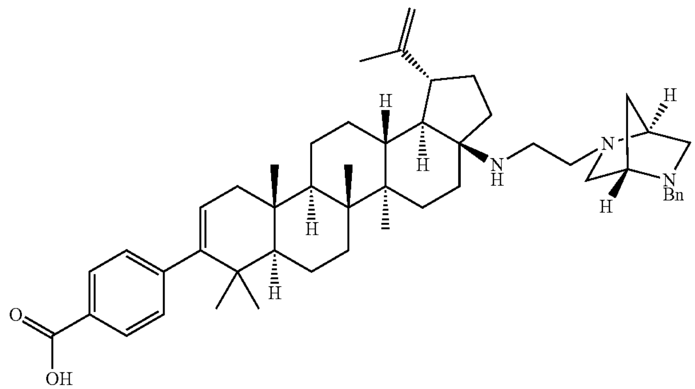 | 6.09E−03 |
| 10 | 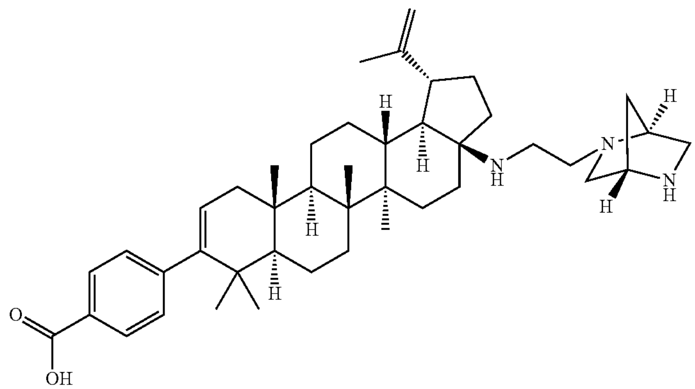 | 1.21E−03 |
| 11 | 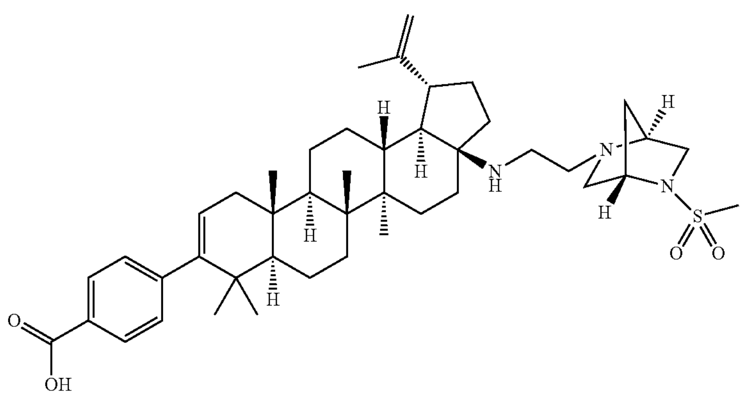 | A |
| 12 | 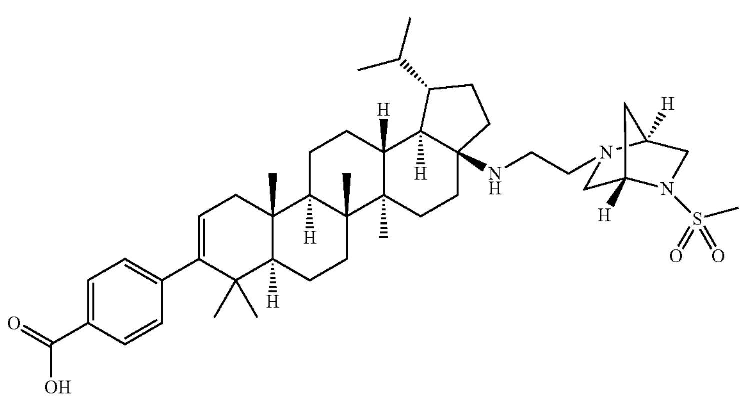 | A |

TABLE 2-continued

| Example # | Structure | EC$_{50}$ (µM) |
|---|---|---|
| 13 | 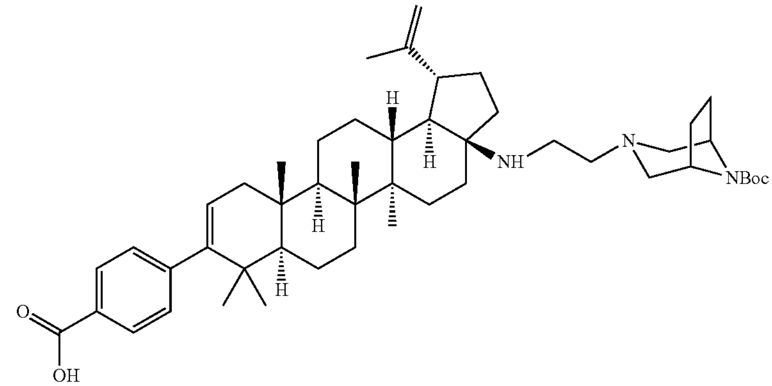 | B |
| 14 | 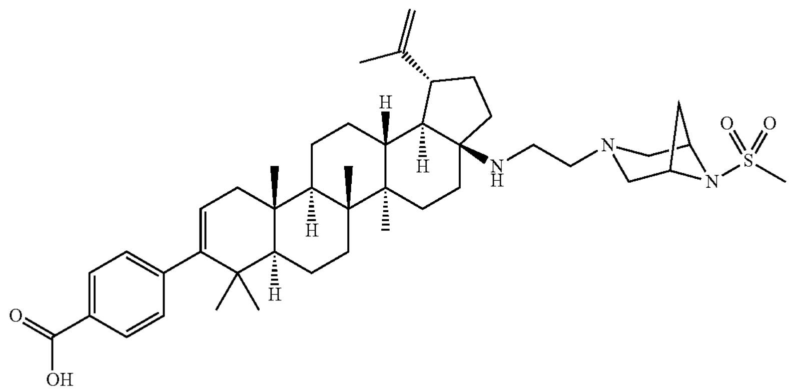 | 3.24E−03 |
| 15 | 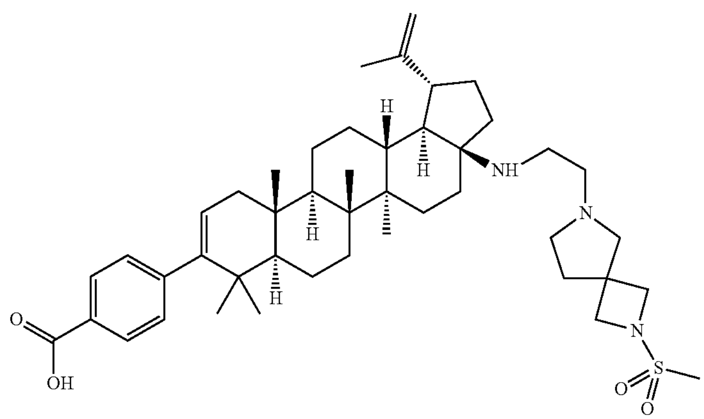 | 1.65E−03 |
| 16 | 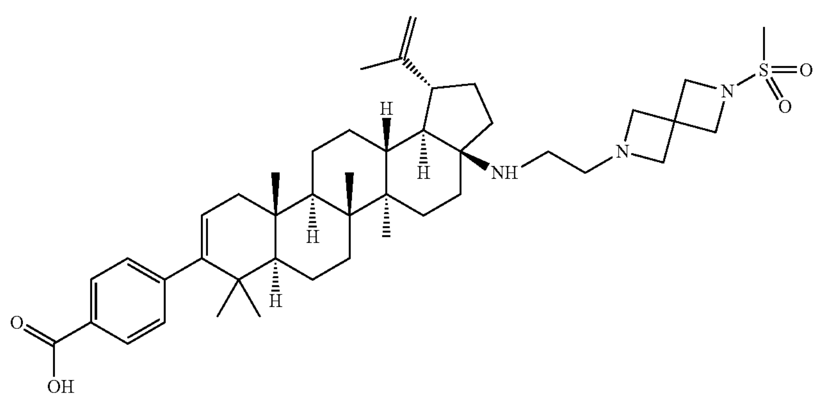 | 1.64E−03 |

TABLE 2-continued

| Example # | Structure | EC$_{50}$ (μM) |
|---|---|---|
| 17 | 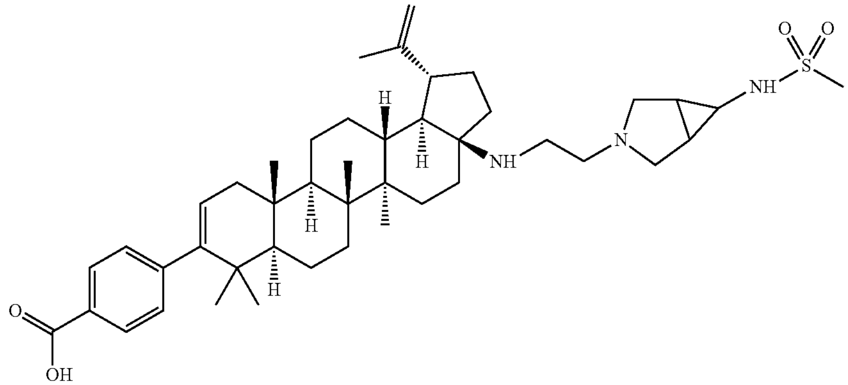 | A |
| 18 | 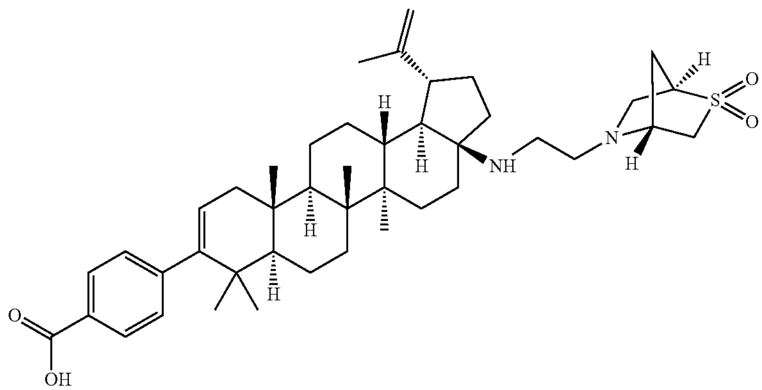 | A |
| 19 | 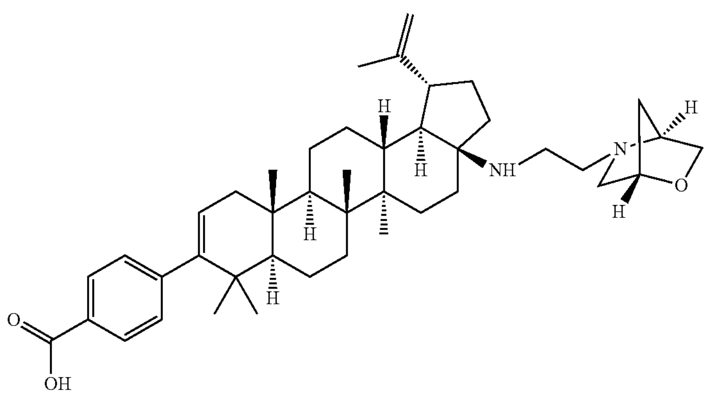 | A |
| A1 | 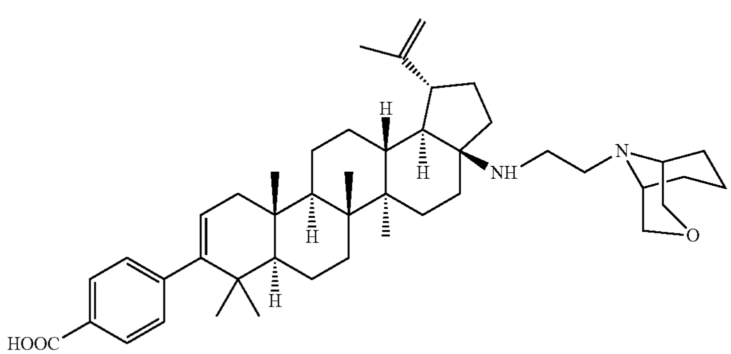 | 0.03 |

TABLE 2-continued
| Example # | Structure | EC$_{50}$ (μM) |
|---|---|---|
| A2 | 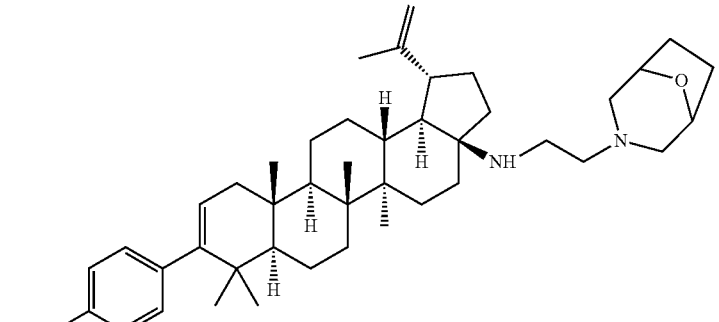 | 0.071 |
| A3 | 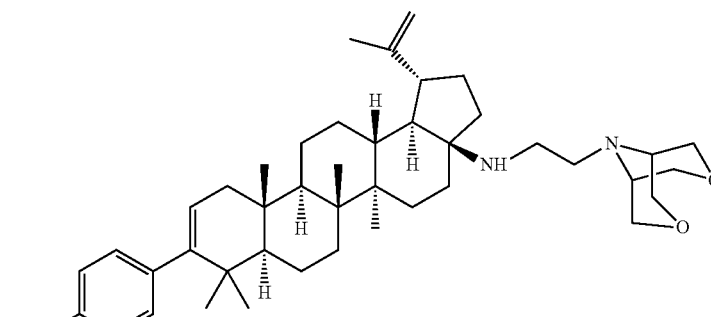 | 0.083 |
| A4 | 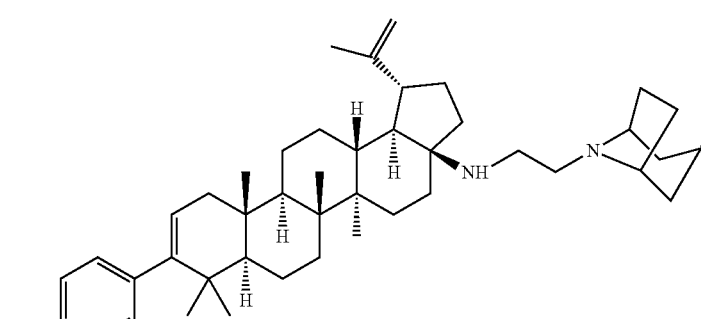 | 8.80E−03 |
| B1 | 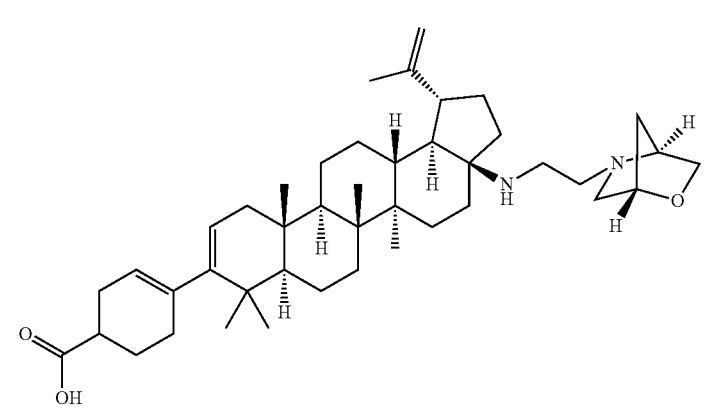 | A |

TABLE 2-continued

| Example # | Structure | EC$_{50}$ (μM) |
|---|---|---|
| B2 | 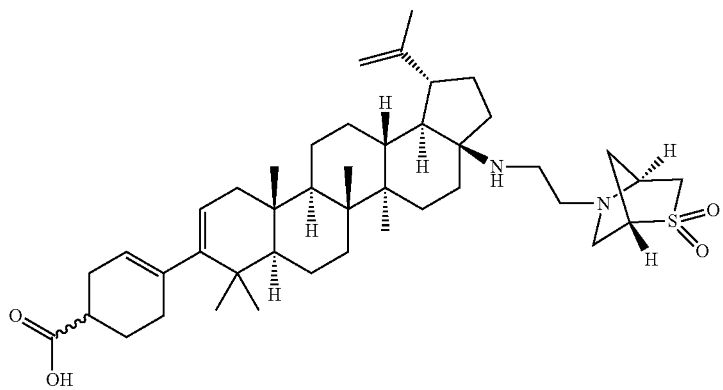 | 1.18E−03 |
| B3 | 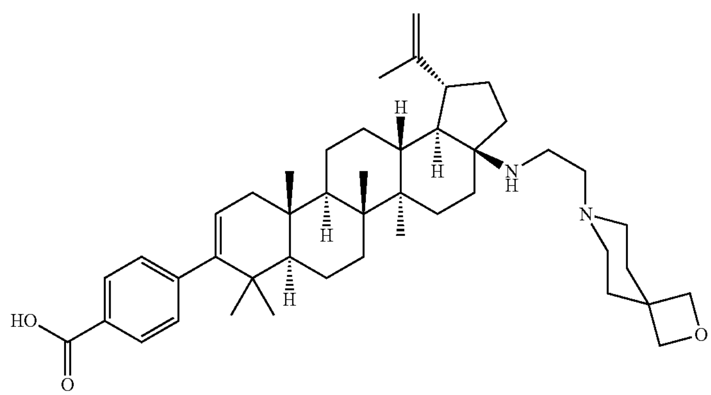 | 3.82E−03 |
| B4 | 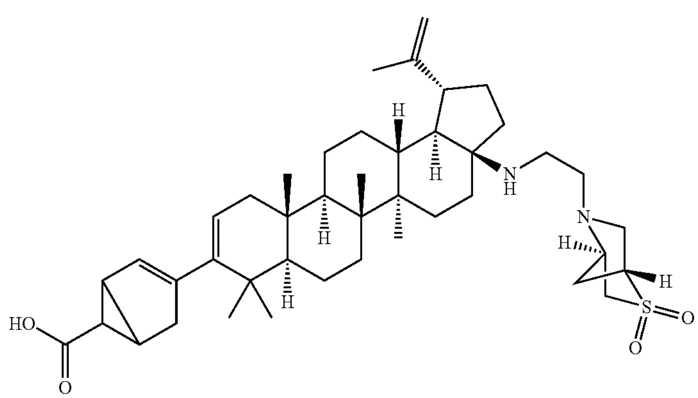 | A |

Isomer 1

TABLE 2-continued
| Example # | Structure | EC$_{50}$ (μM) |
|---|---|---|
| B5 | 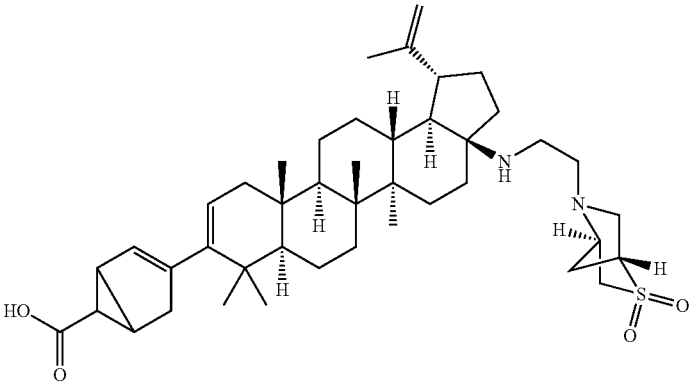<br>Isomer 2 | A |
| B6 | 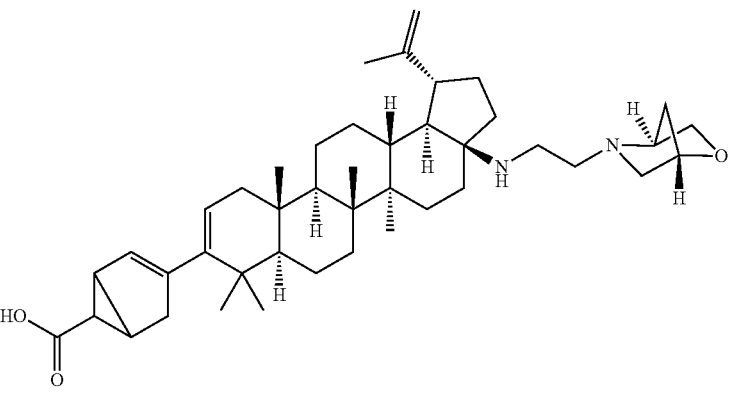<br>Isomer 1 | 1.42E−03 |
| B7 | 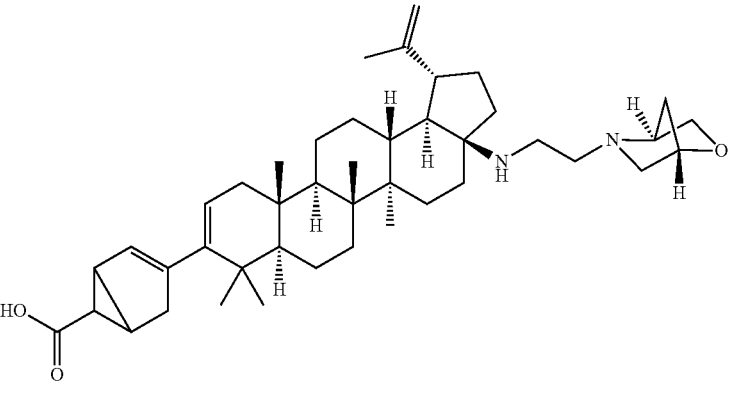<br>Isomer 2 | 2.28E−03 |

TABLE 2-continued

| Example # | Structure | EC$_{50}$ (μM) |
|---|---|---|
| B8 | 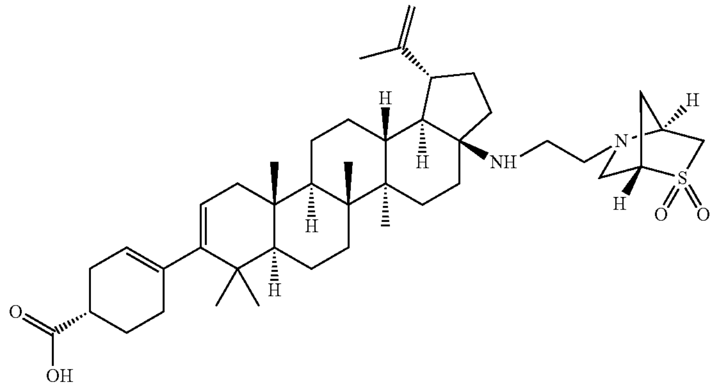 | 1.30E−03 |
| B9 | 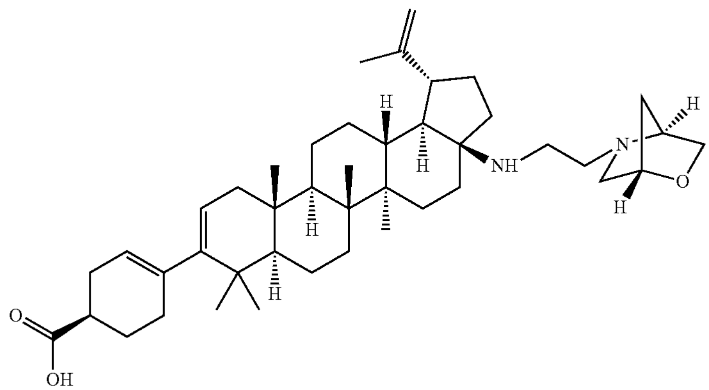 | 1.69E−03 |
| B10 | 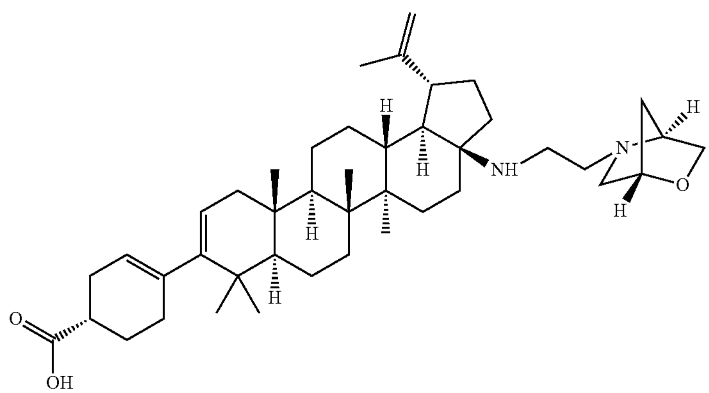 | A |
| B11 | 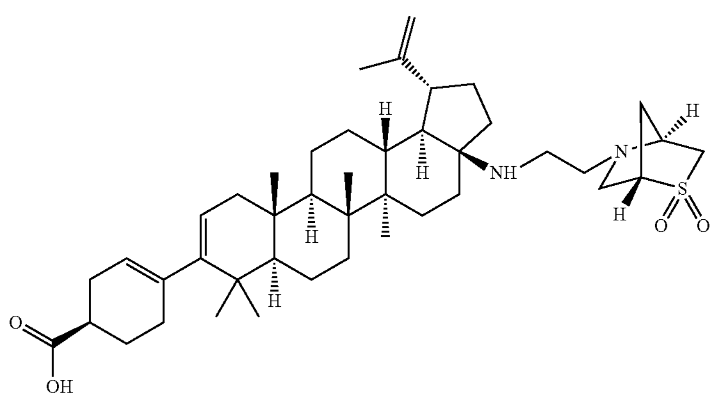 | A |

TABLE 2-continued

| Example # | Structure | EC$_{50}$ (μM) |
|---|---|---|
| B12 | 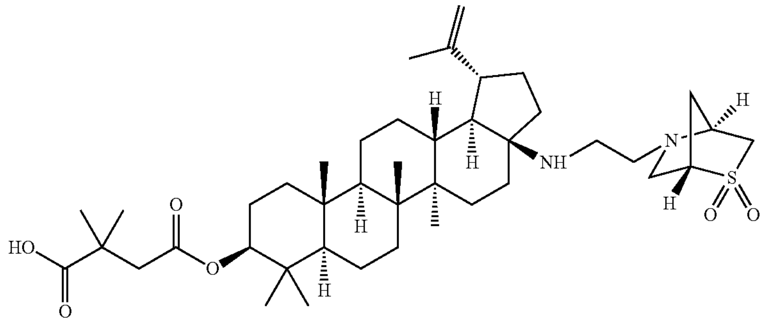 | A |

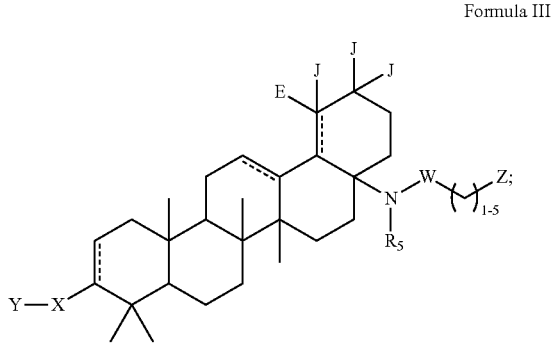

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group consisting of:

a compound of Formula I

Formula I

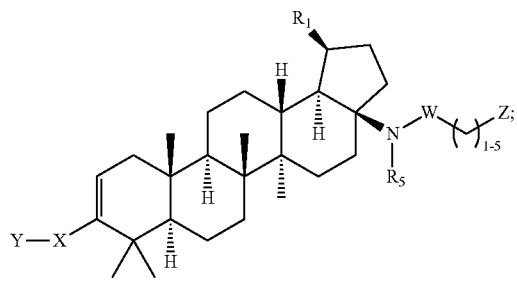

a compound of Formula II

Formula II

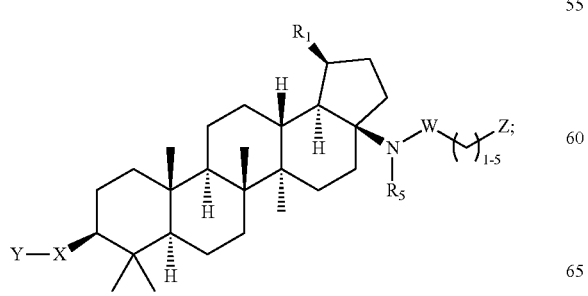

and
a compound of Formula III

Formula III

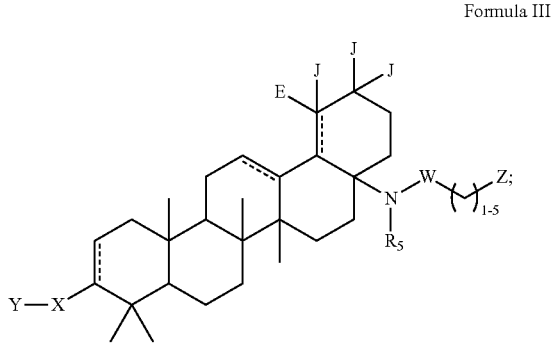

wherein $R_1$ is isopropenyl or isopropyl;

J and E are each independently —H or —CH$_3$, and E is absent when the double bond is present;

X is selected from the group of phenyl, heteroaryl ring, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring;

X is also selected from the group of:

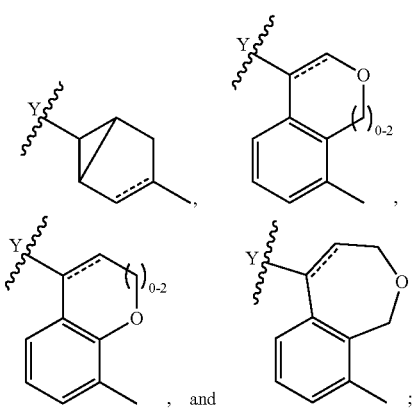

and for compounds of formula II and III, X is also selected from

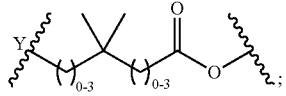

wherein X is substituted with A, and A is at least one member selected from the group of —H, -halo, -hydroxyl, —$C_{1-6}$ alkyl, —$C_{1-6}$ alkoxy, —$C_{1-6}$ haloalkyl, —$NR_2R_2$, —$COOR_2$, —$C(O)NR_2R_2$, —$C(O)NR_2SO_2R_3$, —$SO_2NR_2R_2$, —$NR_2SO_2R_2$, —$SO_2NR_2R_2$, —$C_{1-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and -bicyclic heteroaryl-$COOR_2$;

Y is selected from the group of —$COOR_2$, —$C(O)NR_2SO_2R_3$, —$C(O)NHSO_2NR_2R_2$, —$NR_2SO_2R_3$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, —$NHC(O)(CH_2)_n$—$COOR_2$, —$SO_2NR_2C(O)R_2$, tetrazole, and —CONHOH, wherein n=1-6;

W is —$CH_2$ or —CO;

Z is selected from the group of:

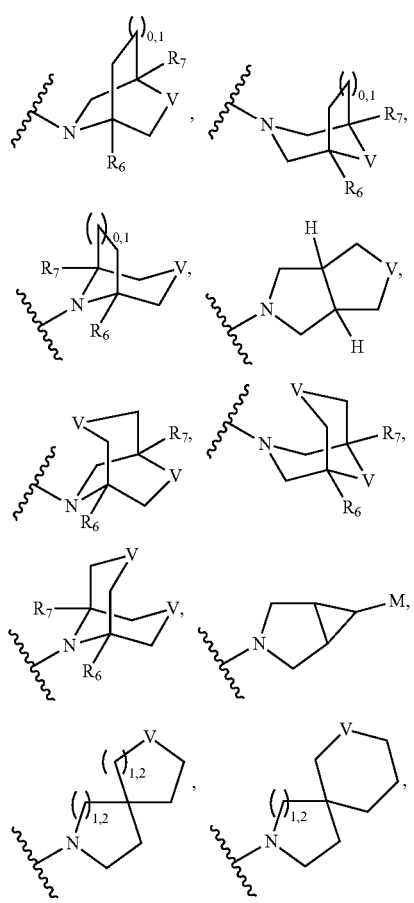

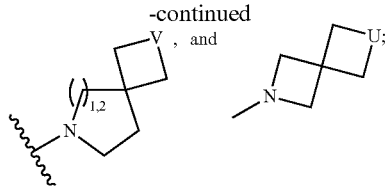

V is selected from the group of —$CR_8R_9$—, —$SO_2$—, —O— and —$NR_{10}$—;

U is selected from the group of —$CR_8R_9$—, —$SO_2$— and —$NR_{10}$—;

M is selected from the group of —$CHR_8R_9$, —$SO_2R_4$, —$SO_2NR_3R_3$, —OH and —$NR_{10}R_{11}$—;

$R_2$ is —H, —$C_{1-6}$ alkyl, -alkylsubstituted $C_{1-6}$ alkyl or -arylsubstituted $C_{1-6}$ alkyl;

$R_3$ is —$C_{1-6}$ alkyl or -alkylsubstituted $C_{1-6}$ alkyl;

$R_4$ is selected from the group of —$C_{1-6}$ alkyl, -alkylsubstituted $C_{1-6}$ alkyl, —$C_{3-6}$ cycloalkl, -aryl and -heteroaryl;

$R_5$ is selected from the group of —H, —$C_{1-6}$ alkyl, -alkylsubstituted $C_{1-6}$ alkyl and —$C_{1-6}$ alkyl-OH;

$R_6$ and $R_7$ are each independently selected from the group of —H, —$C_{1-6}$ alkyl, -alkylsubstituted $C_{1-6}$ alkyl, —$CO_2R_2$, —$CH_2OH$, —$CHF_2$ and —$CF_3$;

$R_8$ and $R_9$ are each independently selected from the group of —H, —$C_{1-6}$ alkyl, -alkylsubstituted $C_{1-6}$ alkyl, —$SO_2R_3$, —$SO_2NR_2R_2$ or —OH, —$NR_2R_2$, —$NR_2SO_2R_3$, —$NR_2COR_3$ and —$NR_2CONR_2R_2$;

with the proviso that only one of $R_8$ and $R_9$ is selected from the group of —OH, —$NR_2R_2$, —$NR_2SO_2R_3$, —$NR_2COR_3$ and —$NR_2CONR_2R_2$; and $R_{10}$ and $R_{11}$ are each independently selected from the group of —H, —$C_{1-6}$ alkyl, -alkylsubstituted $C_{1-6}$ alkyl, —$C_{1-3}$ alkylaryl, $C_{1-3}$ alkylheteroaryl, —$CO_2R_2$ and —$SO_2R_3$;

with the proviso that only one of $R_{10}$ and $R_{11}$ is selected from the group of —$CO_2R_2$ and —$SO_2R_3$;

and pharmaceutically acceptable salts thereof.

2. The compound of claim 1, wherein said compound is of the Formula I.

3. The compound of claim 2, wherein X is -phenyl or —$C_{4-8}$ cycloalkenyl.

4. The compound of claim 3, wherein A is —H.

5. The compound of claim 1, wherein $R_5$ is —H.

6. The compound of claim 1, wherein Y is —$COOR_2$.

7. The compound of claim 6, wherein Y is —COOH.

8. The compound of claim 1, wherein $R_{10}$ is —$C_{1-3}$ alkylaryl.

9. The compound of claim 8, wherein said alkylaryl is alkylphenyl.

10. The compound of claim 9, wherein alkyl is methyl.

11. The compound of claim 1, wherein Z is

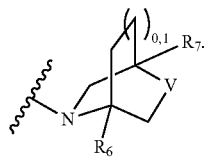

12. The compound of claim 6, wherein Z is
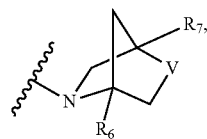
and further wherein $R_6$ is —H and $R_7$ is —H.
13. The compound of claim 1 of the formula:
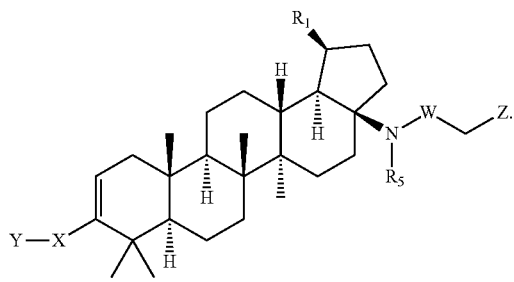
14. The compound of claim 1 of the formula:
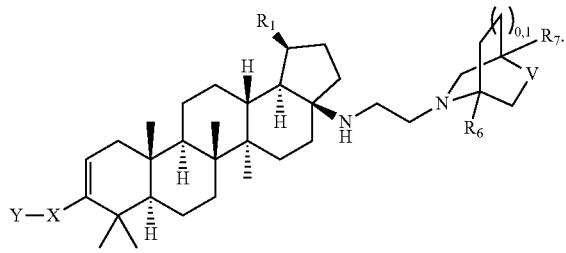
15. The compound of claim 1 of the formula:
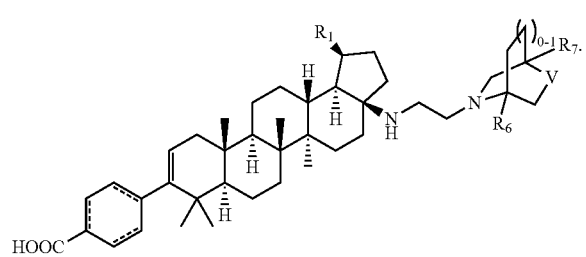
16. A compound which is selected from the group consisting of:
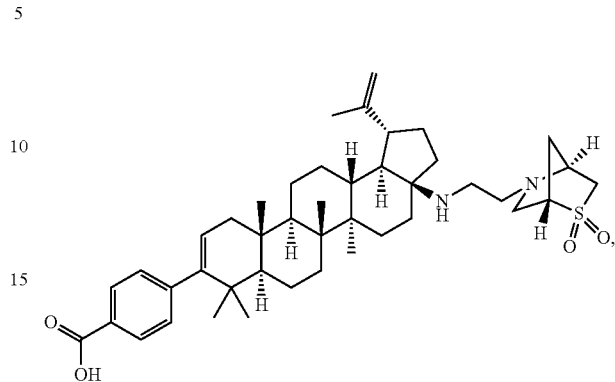
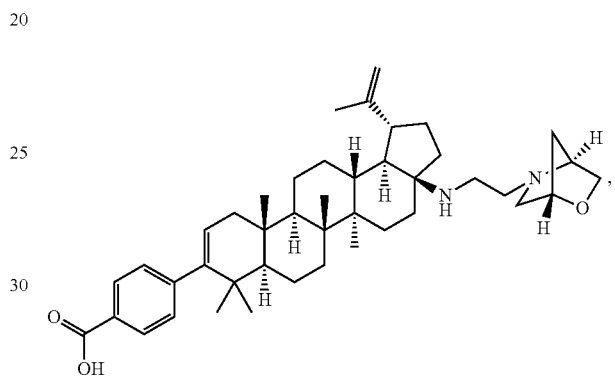
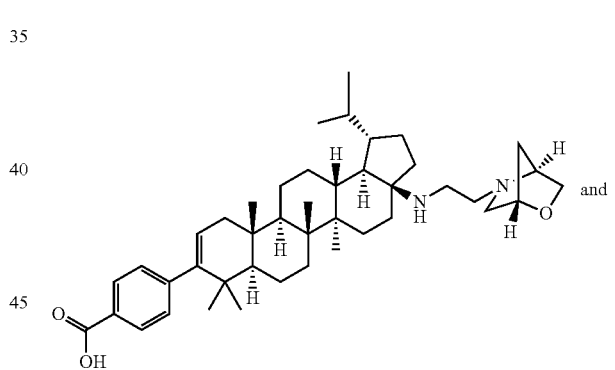
and
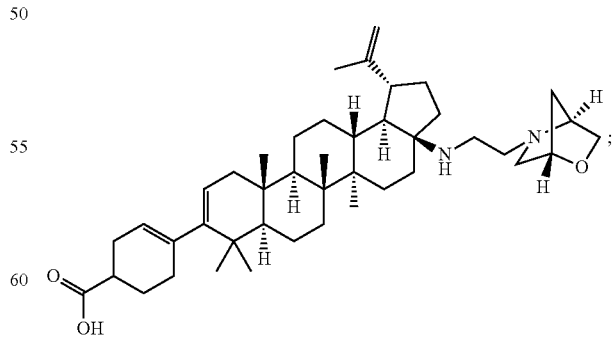
and pharmaceutically acceptable salts thereof.

17. A compound which is selected from the group consisting of:
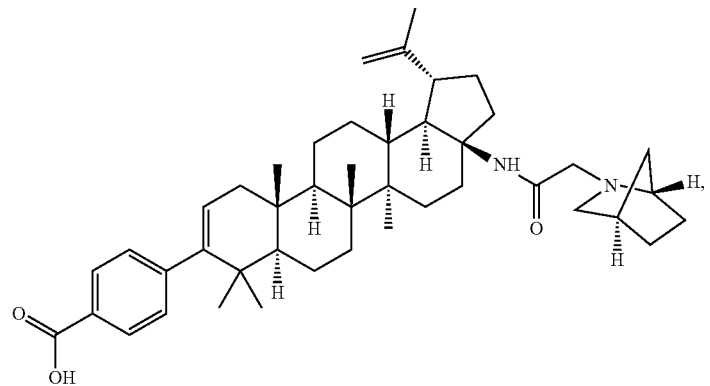
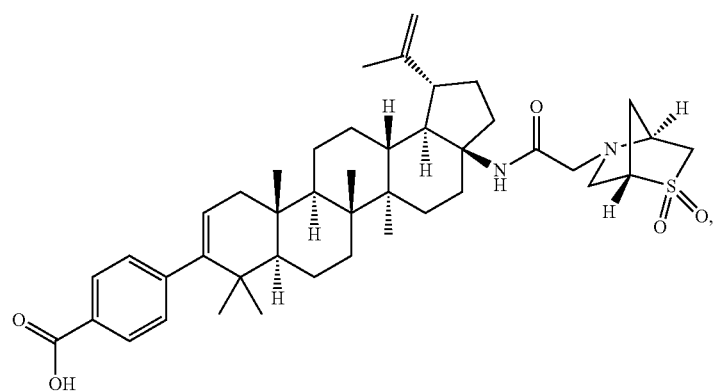
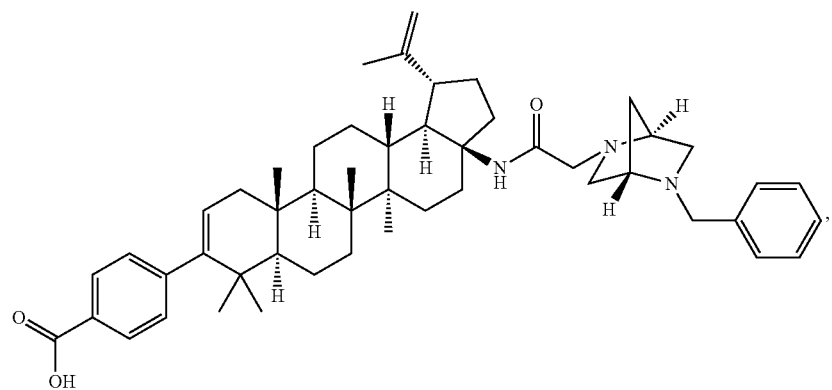
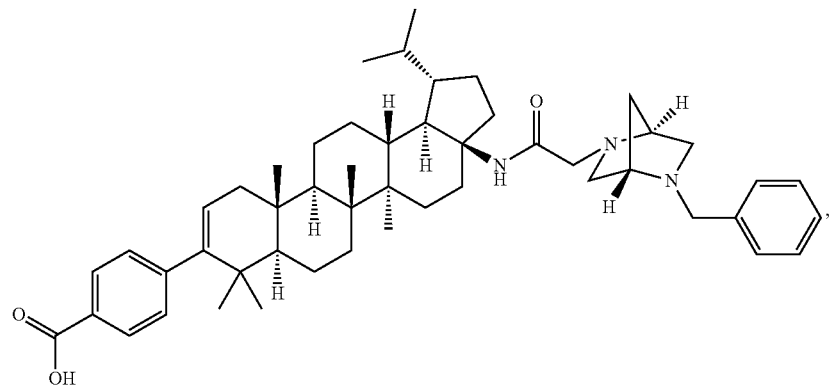

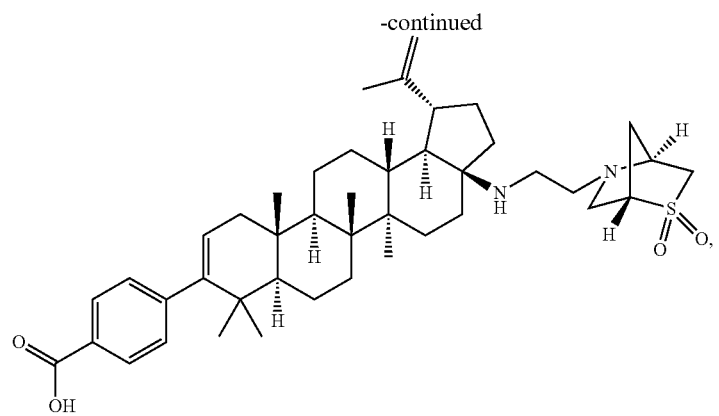
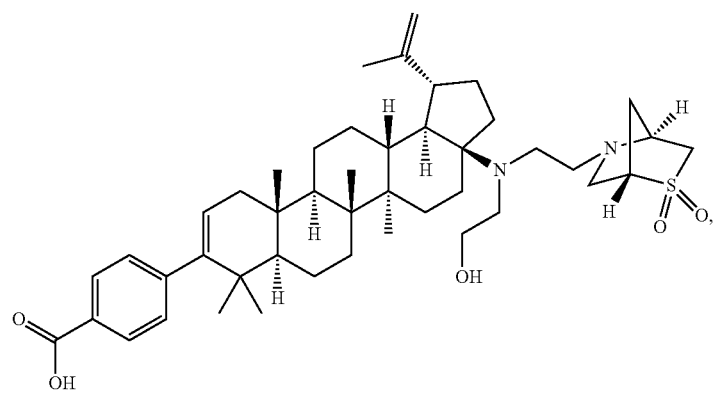
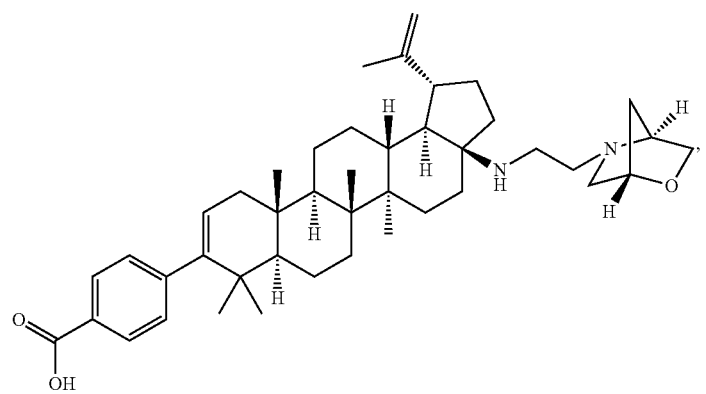
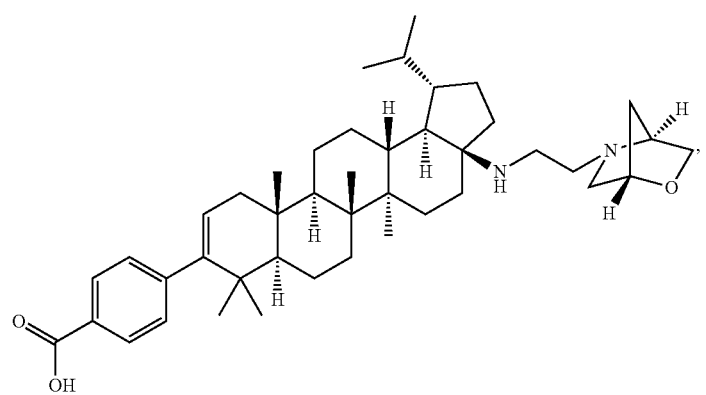

-continued
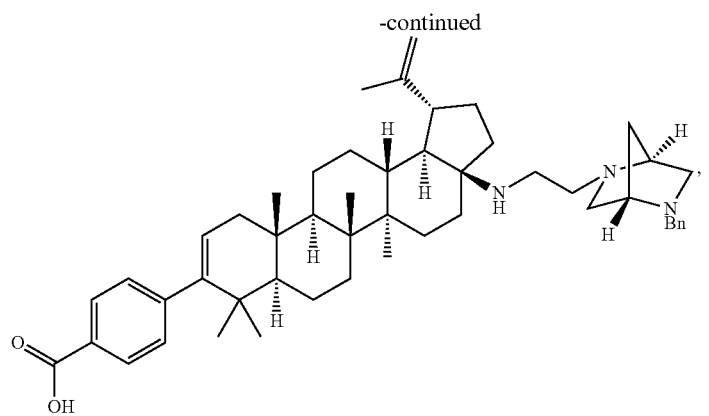
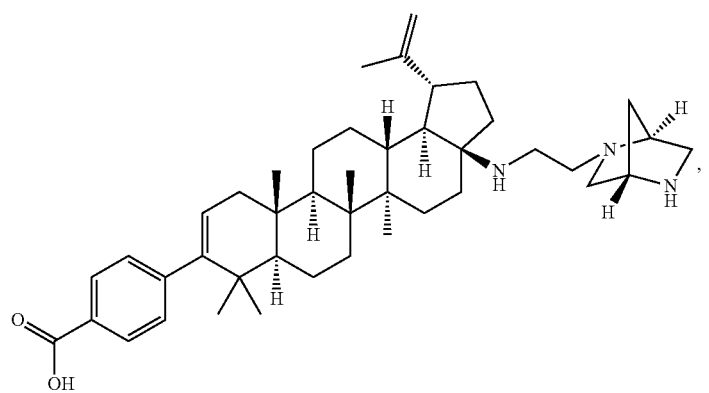
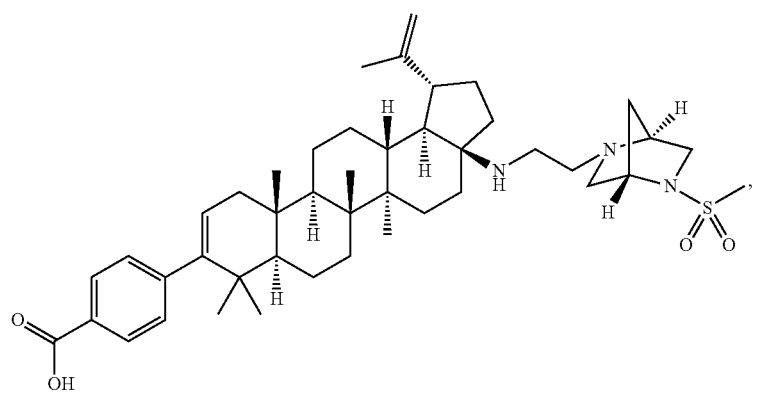
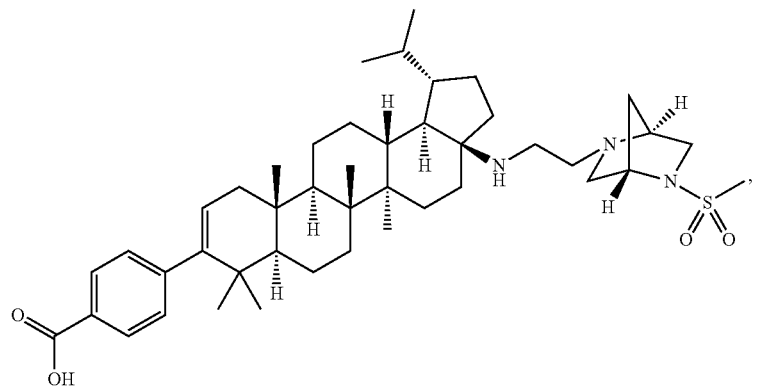

-continued
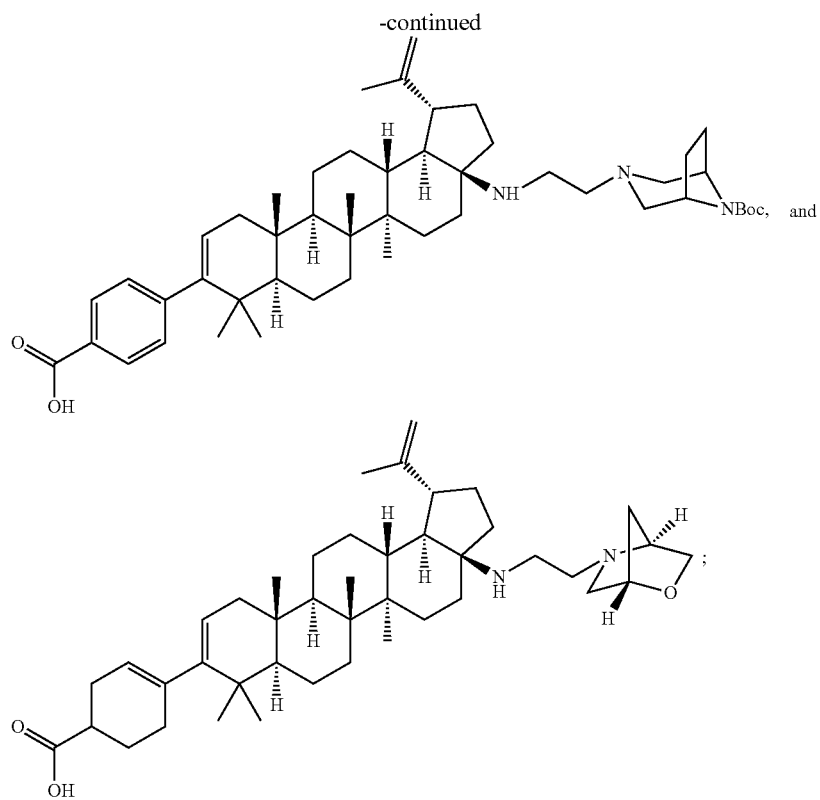
and pharmaceutically acceptable salts thereof.
18. A compound which is selected from the group consisting of:
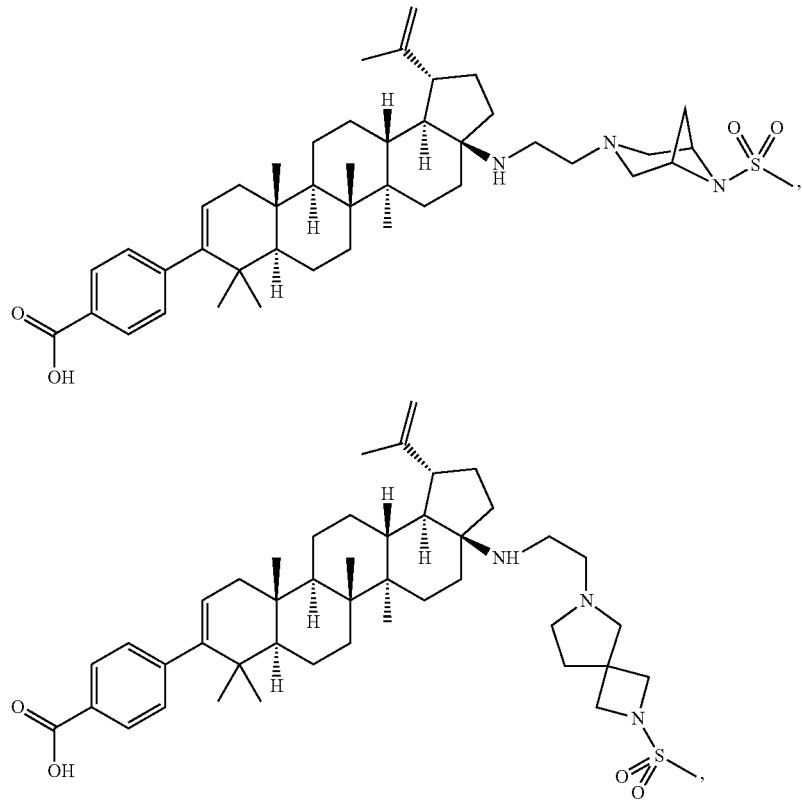

-continued
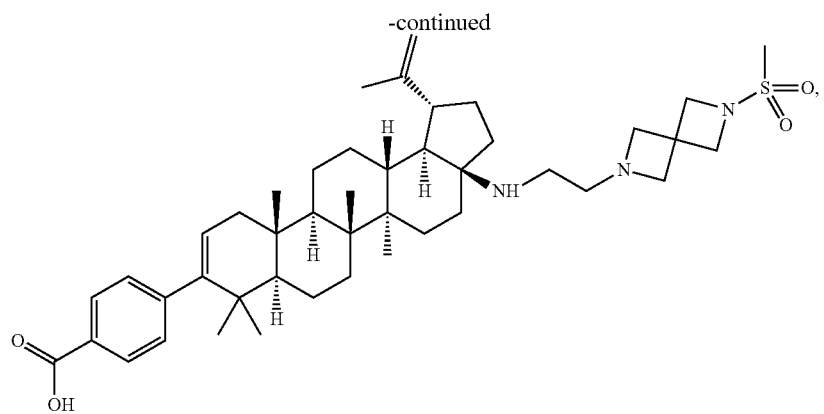
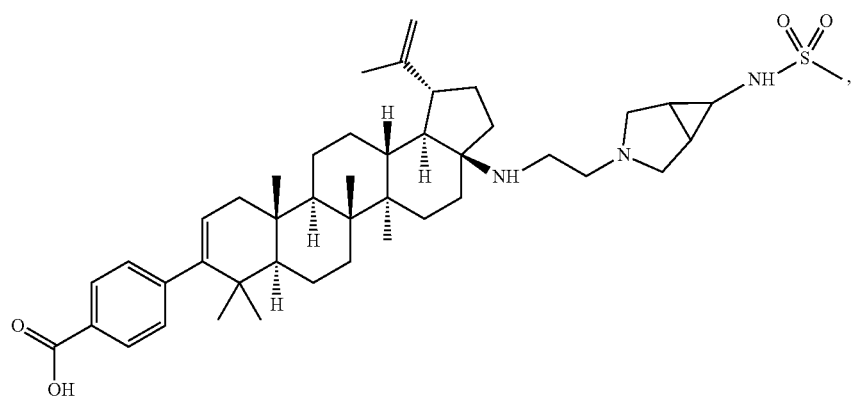
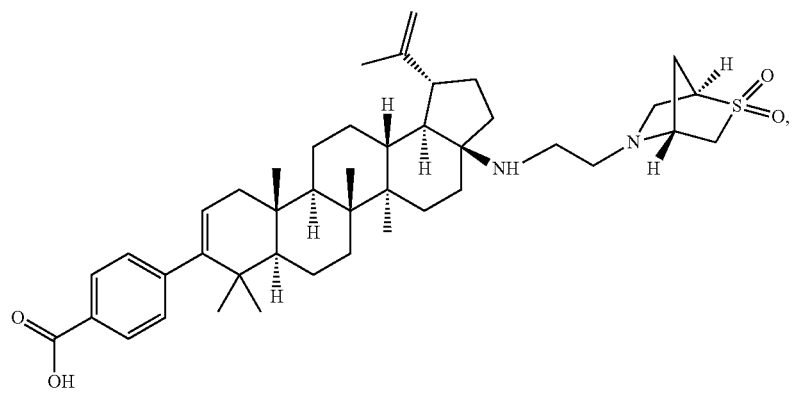
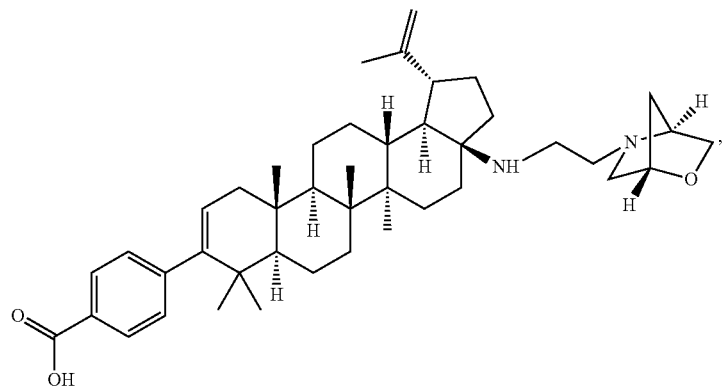

-continued
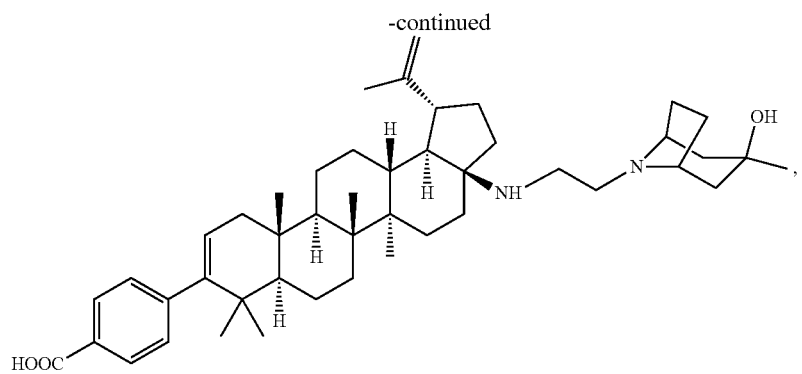
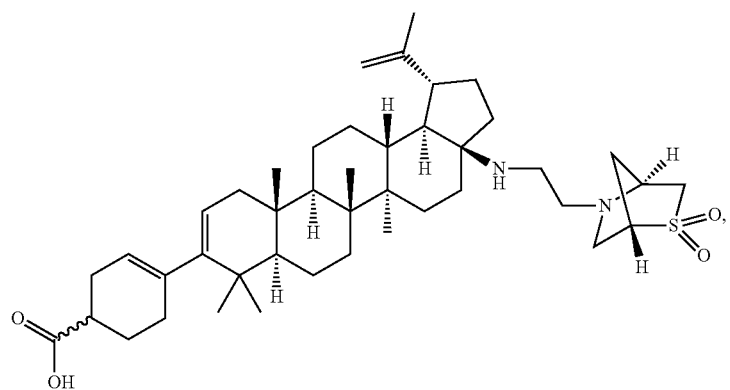
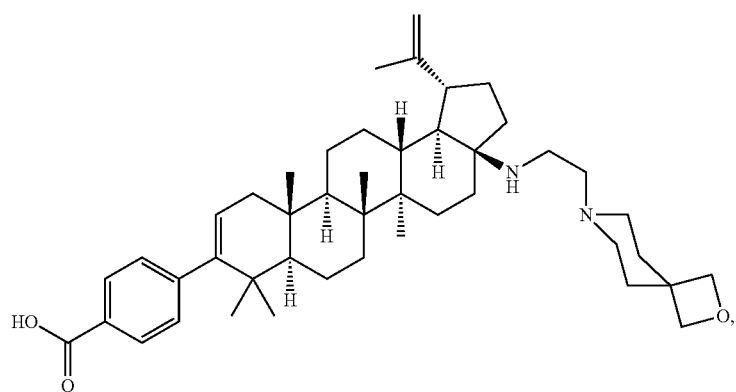
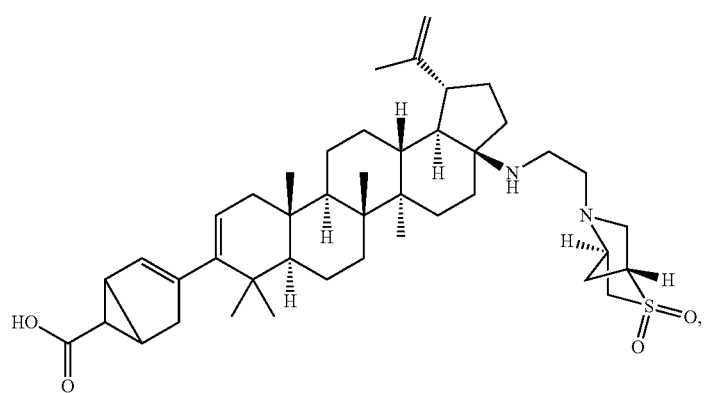
Isomer 1

-continued
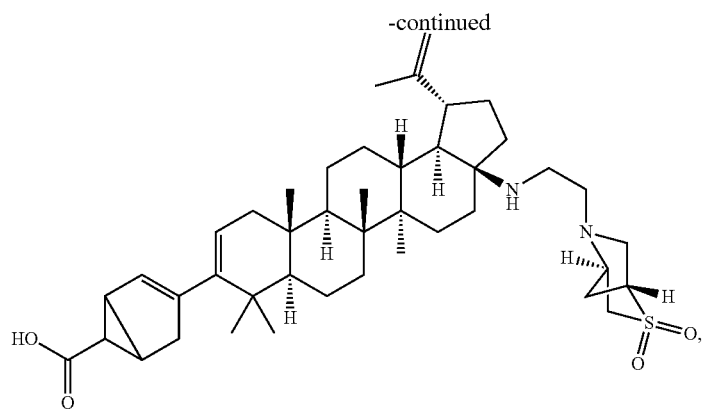
Isomer 2
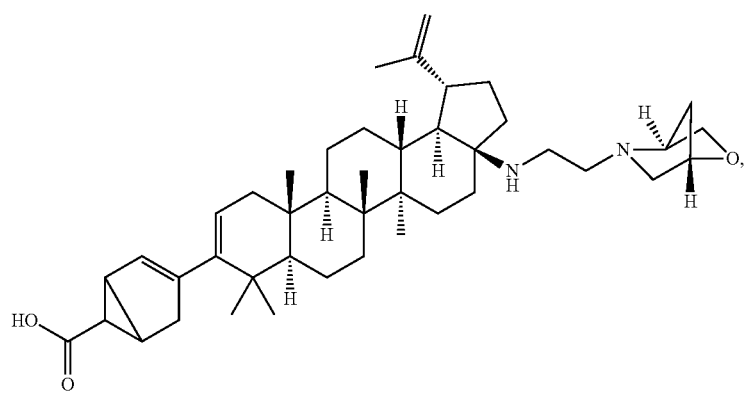
Isomer 1
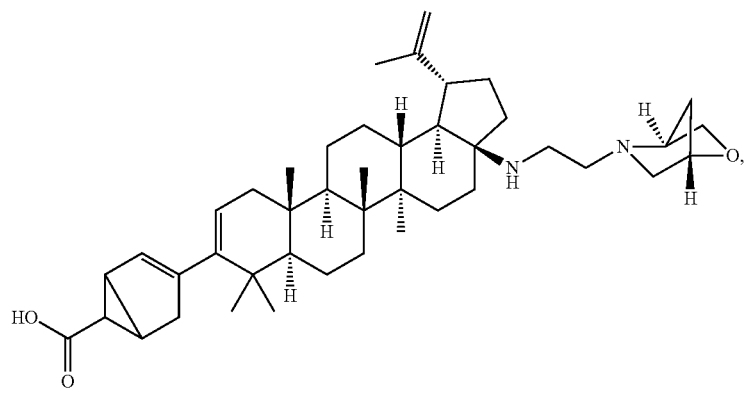
Isomer 2
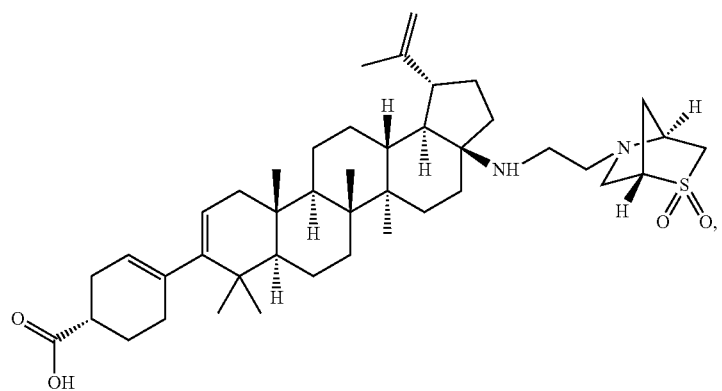

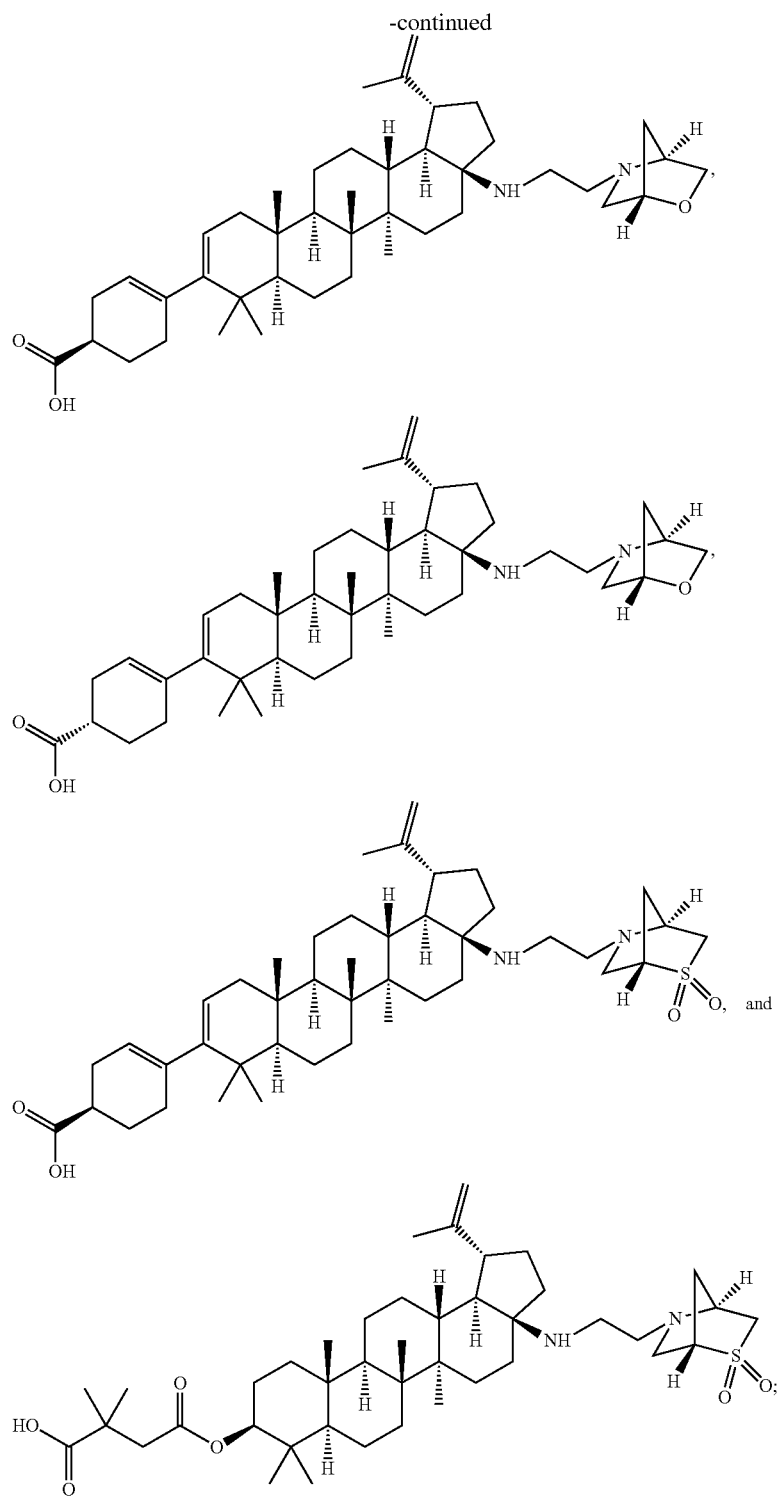
and pharmaceutically acceptable salts thereof.